(12) United States Patent
Ahlijanian et al.

(10) Patent No.: US 11,142,570 B2
(45) Date of Patent: Oct. 12, 2021

(54) ANTIBODIES TO ALPHA-SYNUCLEIN AND USES THEREOF

(71) Applicant: BRISTOL-MYERS SQUIBB COMPANY, Princeton, NJ (US)

(72) Inventors: Michael K. Ahlijanian, Madison, CT (US); Jere Ernest Meredith, Jr., Haddam, CT (US); Nino Devidze, Madison, CT (US); John David Graef, Hingham, MA (US); Edward L. Halk, Sunnyvale, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 16/486,238

(22) PCT Filed: Feb. 16, 2018

(86) PCT No.: PCT/US2018/000032
§ 371 (c)(1),
(2) Date: Aug. 15, 2019

(87) PCT Pub. No.: WO2018/151821
PCT Pub. Date: Aug. 23, 2018

(65) Prior Publication Data
US 2020/0231661 A1 Jul. 23, 2020

Related U.S. Application Data

(60) Provisional application No. 62/460,416, filed on Feb. 17, 2017.

(51) Int. Cl.
*C07K 16/18* (2006.01)
*A61K 39/395* (2006.01)

(52) U.S. Cl.
CPC .......... *C07K 16/18* (2013.01); *A61K 39/3955* (2013.01); *C07K 2317/21* (2013.01); *C07K 2317/24* (2013.01); *C07K 2317/31* (2013.01); *C07K 2317/33* (2013.01); *C07K 2317/565* (2013.01); *C07K 2317/92* (2013.01)

(58) Field of Classification Search
CPC combination set(s) only.
See application file for complete search history.

(56) References Cited

U.S. PATENT DOCUMENTS

| | | |
|---|---|---|
| 4,399,216 A | 8/1983 | Axel et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,634,665 A | 1/1987 | Axel et al. |
| 4,790,824 A | 12/1988 | Morrow et al. |
| 4,816,567 A | 3/1989 | Cabilly et al. |
| 4,881,175 A | 11/1989 | Ladner |
| 4,941,880 A | 7/1990 | Burns |
| 4,946,778 A | 8/1990 | Ladner et al. |
| 5,013,653 A | 5/1991 | Huston et al. |
| 5,064,413 A | 11/1991 | McKinnon et al. |
| 5,091,513 A | 2/1992 | Huston et al. |
| 5,132,405 A | 7/1992 | Huston et al. |
| 5,179,017 A | 1/1993 | Axel et al. |
| 5,223,409 A | 6/1993 | Ladner et al. |
| 5,225,539 A | 7/1993 | Winter |
| 5,258,498 A | 11/1993 | Huston et al. |
| 5,260,203 A | 11/1993 | Ladner et al. |
| 5,312,335 A | 5/1994 | McKinnon et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,403,484 A | 4/1995 | Ladner et al. |
| 5,416,016 A | 5/1995 | Low et al. |
| 5,427,908 A | 6/1995 | Dower et al. |
| 5,455,030 A | 10/1995 | Ladner et al. |
| 5,476,786 A | 12/1995 | Huston |
| 5,476,996 A | 12/1995 | Wilson et al. |
| 5,482,858 A | 1/1996 | Huston et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,677,425 A | 10/1997 | Bodmer et al. |

(Continued)

FOREIGN PATENT DOCUMENTS

| | | |
|---|---|---|
| AR | 114808 A1 | 10/2020 |
| CA | 2453344 A1 | 1/2003 |

(Continued)

OTHER PUBLICATIONS

Lindstrom et al., Immunotherapy 6(2), 141-153 (Year: 2014).*

(Continued)

*Primary Examiner* — Christina M Borgeest
*Assistant Examiner* — Stacey N MacFarlane
(74) *Attorney, Agent, or Firm* — Nelson Mullins Riley & Scarborough LLP; Jane E. Remillard, Esq.; Jill Gorny Sloper, Esq.

(57) ABSTRACT

Disclosed herein are anti-α-synuclein antibodies which preferentially bind to oligomeric α-synuclein over monomeric α-synuclein, therapeutic compositions comprising the antibodies, and methods of using the antibodies to treat synucleinopathies.

28 Claims, 52 Drawing Sheets
Specification includes a Sequence Listing.

(56) References Cited

U.S. PATENT DOCUMENTS

| | | |
|---|---|---|
| 5,693,762 A | 12/1997 | Queen et al. |
| 5,698,767 A | 12/1997 | Wilson et al. |
| 5,714,350 A | 2/1998 | Co et al. |
| 5,767,135 A | 6/1998 | Fernandez-Pol |
| 5,770,429 A | 6/1998 | Lonberg et al. |
| 5,789,650 A | 8/1998 | Lonberg et al. |
| 5,814,318 A | 9/1998 | Lonberg et al. |
| 5,869,046 A | 2/1999 | Presta et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,121,022 A | 9/2000 | Presta et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,172,197 B1 | 1/2001 | McCafferty et al. |
| 6,180,370 B1 | 1/2001 | Queen et al. |
| 6,194,551 B1 | 2/2001 | Idusogie et al. |
| 6,277,375 B1 | 8/2001 | Ward |
| 6,350,861 B1 | 2/2002 | Co et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,737,056 B1 | 5/2004 | Presta |
| 6,890,535 B1 | 5/2005 | Schenk |
| 6,989,452 B2 | 1/2006 | Ng et al. |
| 7,001,720 B1 | 2/2006 | Polymeropoulous et al. |
| 7,087,600 B2 | 8/2006 | Ng et al. |
| 7,129,261 B2 | 10/2006 | Ng et al. |
| 7,317,091 B2 | 1/2008 | Lazar et al. |
| 7,919,088 B2 | 4/2011 | Schenk et al. |
| 8,092,801 B2 | 1/2012 | Schenk et al. |
| 8,101,720 B2 | 1/2012 | Lazar et al. |
| 8,147,833 B2 | 4/2012 | Schenk et al. |
| 8,506,959 B2 | 8/2013 | Schenk et al. |
| 8,673,593 B2 | 3/2014 | Chilcote et al. |
| 8,968,734 B2 | 3/2015 | Nordstrom et al. |
| 9,034,337 B2 | 5/2015 | Schenk et al. |
| 9,493,553 B2 | 11/2016 | Kaluza et al. |
| 9,534,044 B2 | 1/2017 | El-Agnaf |
| 9,732,148 B2 | 8/2017 | Ayalon et al. |
| 10,208,111 B2 | 2/2019 | El-Agnaf |
| 10,766,954 B2 | 9/2020 | Griswold-Prenner et al. |
| 2002/0137139 A1 | 9/2002 | Byatt et al. |
| 2002/0151464 A1 | 10/2002 | Wolozin et al. |
| 2002/0162129 A1 | 10/2002 | Lannfelt et al. |
| 2002/0197258 A1 | 12/2002 | Ghanbari et al. |
| 2003/0073610 A1 | 4/2003 | Lindquist et al. |
| 2003/0104633 A1 | 6/2003 | Orser et al. |
| 2003/0125522 A1 | 7/2003 | Kim |
| 2003/0152923 A1 | 8/2003 | Yakhini et al. |
| 2003/0153043 A1 | 8/2003 | Carr et al. |
| 2003/0166558 A1 | 9/2003 | Frangione et al. |
| 2004/0014142 A1 | 1/2004 | VanMechelen et al. |
| 2004/0048249 A1 | 3/2004 | Tang et al. |
| 2004/0101876 A1 | 5/2004 | Mintz et al. |
| 2004/0136993 A1 | 7/2004 | Schenk et al. |
| 2004/0248156 A1 | 12/2004 | Hu et al. |
| 2005/0071088 A1 | 3/2005 | Landfield et al. |
| 2005/0240352 A1 | 10/2005 | Liang |
| 2006/0004081 A1 | 1/2006 | Chen et al. |
| 2006/0024317 A1 | 2/2006 | Boyd et al. |
| 2006/0057671 A1 | 3/2006 | Orser et al. |
| 2006/0127350 A1 | 6/2006 | Heegaard et al. |
| 2006/0134663 A1 | 6/2006 | Harkin et al. |
| 2006/0241074 A1 | 10/2006 | Woolf et al. |
| 2006/0247295 A1 | 11/2006 | Gangwar et al. |
| 2006/0280733 A1 | 12/2006 | Kayed et al. |
| 2008/0038761 A1 | 2/2008 | Beernink et al. |
| 2008/0131907 A1 | 6/2008 | Wang et al. |
| 2008/0146504 A1 | 6/2008 | Bonnin |
| 2008/0160011 A1 | 7/2008 | Chilcote et al. |
| 2008/0248565 A1 | 10/2008 | Katzen et al. |
| 2009/0054300 A1 | 2/2009 | Abbas et al. |
| 2009/0169549 A1 | 7/2009 | Chang |
| 2009/0170069 A1 | 7/2009 | Ghosh et al. |
| 2009/0186018 A1 | 7/2009 | Abbas et al. |
| 2009/0258794 A1 | 10/2009 | Chaudhuri |
| 2010/0031377 A1 | 2/2010 | Schenk et al. |
| 2010/0069614 A1 | 3/2010 | Houtzager et al. |
| 2010/0105134 A1 | 4/2010 | Quay et al. |
| 2011/0020237 A1 | 1/2011 | Glabe et al. |
| 2011/0124010 A1 | 5/2011 | Fladby et al. |
| 2011/0135660 A1 | 6/2011 | Schenk et al. |
| 2011/0150892 A1 | 6/2011 | Thudium et al. |
| 2011/0159527 A1 | 6/2011 | Schlossmacher et al. |
| 2011/0190166 A1 | 8/2011 | Wong et al. |
| 2011/0201686 A1 | 8/2011 | Al-Abed |
| 2011/0293520 A1 | 12/2011 | Giese et al. |
| 2012/0070861 A1 | 3/2012 | Macdonald et al. |
| 2012/0073004 A1 | 3/2012 | MacDonald et al. |
| 2012/0142902 A1 | 6/2012 | Schenk et al. |
| 2012/0148591 A1 | 6/2012 | Kayed |
| 2012/0190652 A1 | 7/2012 | El-Agnaf |
| 2012/0201842 A1 | 8/2012 | Schenk et al. |
| 2013/0011922 A1 | 1/2013 | Quay et al. |
| 2013/0022544 A1 | 1/2013 | Wisniewski et al. |
| 2013/0022620 A1 | 1/2013 | Schmidt et al. |
| 2013/0029998 A1 | 1/2013 | Mayanil et al. |
| 2013/0052200 A1 | 2/2013 | Dodel et al. |
| 2013/0289022 A1 | 10/2013 | Ringe et al. |
| 2013/0316384 A1 | 11/2013 | Ringe et al. |
| 2014/0010861 A1 | 1/2014 | Bancel et al. |
| 2014/0017713 A1 | 1/2014 | Lee et al. |
| 2014/0018250 A1 | 1/2014 | Abbas et al. |
| 2014/0056901 A1 | 2/2014 | Agadjanyan et al. |
| 2014/0186294 A1 | 7/2014 | Gardai et al. |
| 2014/0241984 A1 | 8/2014 | El-Agnaf |
| 2014/0241987 A1 | 8/2014 | El-Agnaf |
| 2014/0271669 A1 | 9/2014 | Hofbauer et al. |
| 2014/0295465 A1 | 10/2014 | Weihofen et al. |
| 2014/0349308 A1 | 11/2014 | West et al. |
| 2015/0024419 A1 | 1/2015 | Sharon |
| 2015/0079074 A1 | 3/2015 | Garidel et al. |
| 2015/0093431 A1 | 4/2015 | Mandler et al. |
| 2015/0093432 A1 | 4/2015 | Mandler et al. |
| 2015/0139937 A1 | 5/2015 | Gendelman et al. |
| 2015/0175685 A1 | 6/2015 | Grueninger et al. |
| 2015/0219579 A1 | 8/2015 | Davis |
| 2015/0276771 A1 | 10/2015 | Madasamy |
| 2016/0054333 A1 | 2/2016 | Staffler et al. |
| 2016/0060331 A1 | 3/2016 | Schenk et al. |
| 2016/0077112 A1 | 3/2016 | Jara et al. |
| 2016/0108113 A1 | 4/2016 | Ayalon et al. |
| 2016/0161481 A1 | 6/2016 | Willbold et al. |
| 2016/0184416 A1 | 6/2016 | Schenk et al. |
| 2016/0220649 A1 | 8/2016 | Roodveldt Catellani et al. |
| 2016/0279238 A1 | 9/2016 | Neumann et al. |
| 2017/0010212 A1 | 1/2017 | Gerwert et al. |
| 2017/0174777 A1 | 6/2017 | Barbour et al. |
| 2017/0184612 A1 | 6/2017 | Sulzer et al. |
| 2017/0190765 A1 | 7/2017 | El-Agnaf |
| 2017/0192017 A1 | 7/2017 | Barbour et al. |
| 2017/0196948 A1 | 7/2017 | Cao et al. |
| 2017/0261521 A1 | 9/2017 | Lee et al. |
| 2017/0320940 A1 | 11/2017 | Ayalon et al. |
| 2017/0349651 A1 | 12/2017 | Schenk et al. |
| 2017/0354669 A1 | 12/2017 | McIntire |
| 2018/0126191 A1 | 5/2018 | Loike et al. |
| 2018/0128840 A1 | 5/2018 | Yang |
| 2018/0134775 A1 | 5/2018 | El-Agnaf et al. |
| 2018/0134776 A1 | 5/2018 | El-Agnaf et al. |
| 2018/0134777 A1 | 5/2018 | El-Agnaf et al. |
| 2018/0194833 A1 | 7/2018 | Kallunki et al. |
| 2018/0238908 A1 | 8/2018 | Nithiyanandam |
| 2018/0256748 A1 | 9/2018 | Angel et al. |
| 2018/0339065 A1 | 11/2018 | Wilson et al. |
| 2018/0344869 A1 | 12/2018 | Fischer et al. |

(56) References Cited

U.S. PATENT DOCUMENTS

| | | |
|---|---|---|
| 2019/0079077 A1 | 3/2019 | Co et al. |
| 2019/0137490 A1 | 5/2019 | Abou-Donia |
| 2019/0153102 A1 | 5/2019 | Soto et al. |
| 2019/0170771 A1 | 6/2019 | Limgala et al. |
| 2019/0192691 A1 | 6/2019 | Barrett et al. |
| 2019/0194324 A1 | 6/2019 | Dawson et al. |
| 2019/0225699 A1 | 7/2019 | Lannfelt et al. |
| 2019/0227082 A1 | 7/2019 | Barbour et al. |
| 2019/0277863 A1 | 9/2019 | Barbour |
| 2019/0300598 A1 | 10/2019 | Schenk et al. |
| 2019/0315846 A1 | 10/2019 | Martinez et al. |
| 2019/0330315 A1 | 10/2019 | Griswold-Prenner et al. |
| 2019/0330318 A1 | 10/2019 | Bennett et al. |
| 2020/0062835 A1 | 2/2020 | Luk et al. |
| 2020/0095296 A1 | 3/2020 | Sulzer et al. |
| 2020/0101146 A1 | 4/2020 | Hubbell et al. |
| 2020/0132268 A1 | 4/2020 | Zhang et al. |
| 2020/0132683 A1 | 4/2020 | Wasserman et al. |
| 2020/0141866 A1 | 5/2020 | Gerwert |
| 2020/0179421 A1 | 6/2020 | Wassenaar et al. |
| 2020/0255507 A1 | 8/2020 | Narasimhan et al. |
| 2020/0277390 A1 | 9/2020 | Legname |
| 2020/0309796 A1 | 10/2020 | Malik et al. |
| 2020/0332265 A1 | 10/2020 | Abeliovich et al. |
| 2020/0362347 A1 | 11/2020 | Olson et al. |
| 2020/0369752 A1 | 11/2020 | Luk et al. |
| 2020/0385450 A1 | 12/2020 | Griswold-Prenner et al. |
| 2021/0032318 A1 | 2/2021 | Schenk et al. |
| 2021/0032369 A1 | 2/2021 | Lasmezas et al. |
| 2021/0041461 A1 | 2/2021 | Sharon |

FOREIGN PATENT DOCUMENTS

| | | |
|---|---|---|
| CA | 2677068 A1 | 3/2011 |
| CN | 101570575 A | 11/2009 |
| CN | 101692092 A | 4/2010 |
| CN | 104215777 A | 12/2014 |
| CN | 104215779 A | 12/2014 |
| CN | 109001452 A | 12/2018 |
| CN | 109490542 A | 3/2019 |
| CN | 110172098 A | 8/2019 |
| DE | 102007024382 A1 | 11/2008 |
| EP | 0154316 A2 | 9/1985 |
| EP | 338841 A1 | 10/1989 |
| EP | 0401384 A1 | 12/1990 |
| EP | 1074563 A1 | 2/2001 |
| EP | 1176195 A1 | 1/2002 |
| EP | 1578253 A2 | 9/2005 |
| EP | 1793855 A2 | 6/2007 |
| EP | 2118300 A2 | 11/2009 |
| EP | 2361928 A1 | 8/2011 |
| EP | 2450056 A1 | 5/2012 |
| EP | 2583978 A2 | 4/2013 |
| EP | 2949666 A1 | 12/2015 |
| EP | 3067066 A1 | 9/2016 |
| EP | 3470079 A1 | 4/2019 |
| EP | 3369433 A1 | 9/2019 |
| GB | 201720978 | 1/2018 |
| JP | 2014012700 A | 1/2014 |
| JP | 2014159439 A | 9/2014 |
| JP | 2016145211 A | 8/2016 |
| JP | 2018091735 A | 6/2018 |
| JP | 2020034353 A | 6/2020 |
| KR | 20120090672 A | 8/2012 |
| WO | 2021028452 A1 | 0/2202 |
| WO | 87/04462 A1 | 7/1987 |
| WO | 89/01036 A1 | 2/1989 |
| WO | 92/03918 A1 | 3/1992 |
| WO | 93/12227 A1 | 6/1993 |
| WO | 94/25585 A1 | 11/1994 |
| WO | 94/29351 A2 | 12/1994 |
| WO | 9506407 A1 | 3/1995 |
| WO | 95/17886 A1 | 7/1995 |
| WO | 95064077 A1 | 9/1995 |
| WO | 96/32478 A1 | 10/1996 |
| WO | 97/13852 A1 | 4/1997 |
| WO | 97/34631 A1 | 9/1997 |
| WO | 98/24884 A1 | 6/1998 |
| WO | 99/45962 A1 | 9/1999 |
| WO | 99/54342 A1 | 10/1999 |
| WO | 20003203 A1 | 1/2000 |
| WO | 00/42072 A2 | 7/2000 |
| WO | 01/14424 A2 | 3/2001 |
| WO | 0121836 A2 | 3/2001 |
| WO | 01/58957 A2 | 8/2001 |
| WO | 02/06919 A2 | 1/2002 |
| WO | 19023809 A1 | 1/2002 |
| WO | 02/43478 A2 | 6/2002 |
| WO | 0250121 A1 | 6/2002 |
| WO | 02/096910 A1 | 12/2002 |
| WO | 03/035835 A2 | 5/2003 |
| WO | 20079113 A2 | 1/2004 |
| WO | 04/016750 A2 | 2/2004 |
| WO | 04/029207 A2 | 4/2004 |
| WO | 04/035752 A2 | 4/2004 |
| WO | 04041067 A2 | 5/2004 |
| WO | 04/063351 A2 | 7/2004 |
| WO | 04/074455 A2 | 9/2004 |
| WO | 04/099249 A2 | 11/2004 |
| WO | 050113889 A2 | 2/2005 |
| WO | 05/040217 A2 | 5/2005 |
| WO | 05047860 A2 | 5/2005 |
| WO | 05/070963 A1 | 8/2005 |
| WO | 05/092925 A2 | 10/2005 |
| WO | 06/020114 A2 | 2/2006 |
| WO | 06020581 A2 | 2/2006 |
| WO | 06125195 A2 | 11/2006 |
| WO | 01011907 A2 | 1/2007 |
| WO | 07012061 A2 | 1/2007 |
| WO | 20073121 A1 | 1/2007 |
| WO | 20079113 A2 | 1/2007 |
| WO | 07021255 A1 | 2/2007 |
| WO | 07/038658 A2 | 4/2007 |
| WO | 07/059404 A2 | 5/2007 |
| WO | 2007/051081 A1 | 5/2007 |
| WO | 08053358 A2 | 5/2008 |
| WO | 08/083312 A2 | 7/2008 |
| WO | 08/103693 A2 | 8/2008 |
| WO | 08103472 A2 | 8/2008 |
| WO | 20073121 A1 | 1/2009 |
| WO | 2009/15777 A1 | 2/2009 |
| WO | 09/045957 A1 | 4/2009 |
| WO | 09/054863 A2 | 4/2009 |
| WO | 2009/059278 A1 | 5/2009 |
| WO | 09/073546 A2 | 6/2009 |
| WO | 2009073533 A2 | 6/2009 |
| WO | 09133521 A2 | 11/2009 |
| WO | 2010/069603 A1 | 6/2010 |
| WO | 1107544 A1 | 1/2011 |
| WO | 11027308 A1 | 3/2011 |
| WO | 2011/072204 A1 | 6/2011 |
| WO | 2011/097603 A1 | 8/2011 |
| WO | 2011/104696 A1 | 9/2011 |
| WO | 2011/163311 A1 | 12/2011 |
| WO | 2011/163314 A1 | 12/2011 |
| WO | 20123330 A2 | 1/2012 |
| WO | 12032519 A2 | 3/2012 |
| WO | 2012148873 A2 | 11/2012 |
| WO | 12177639 A2 | 12/2012 |
| WO | 12177972 A1 | 12/2012 |
| WO | 13063516 A1 | 5/2013 |
| WO | 13151665 A2 | 10/2013 |
| WO | 2014/058924 A9 | 4/2014 |
| WO | 10458924 A2 | 4/2014 |
| WO | 14055925 A1 | 4/2014 |
| WO | 2014/089113 A1 | 6/2014 |
| WO | 2014/132210 A1 | 9/2014 |
| WO | 15075011 A1 | 5/2015 |
| WO | 16061389 A2 | 4/2016 |
| WO | 17009312 A1 | 1/2017 |
| WO | 17032871 A1 | 3/2017 |
| WO | 17103266 A1 | 6/2017 |
| WO | 17176835 A2 | 10/2017 |
| WO | 17178685 A1 | 10/2017 |

(56) References Cited

FOREIGN PATENT DOCUMENTS

| | | |
|---|---|---|
| WO | 17207739 A1 | 12/2017 |
| WO | 18006092 A1 | 1/2018 |
| WO | 18109058 A1 | 6/2018 |
| WO | 18111670 A2 | 6/2018 |
| WO | 18115225 A1 | 6/2018 |
| WO | 18128454 A1 | 6/2018 |
| WO | 18128454 A1 | 7/2018 |
| WO | 2018/151821 A1 | 8/2018 |
| WO | 18178950 A1 | 10/2018 |
| WO | 18204352 A1 | 11/2018 |
| WO | 18204764 A1 | 11/2018 |
| WO | 18232369 A1 | 12/2018 |
| WO | 18236986 A1 | 12/2018 |
| WO | 18237338 A1 | 12/2018 |
| WO | 2019040617 A1 | 2/2019 |
| WO | 2019064053 A1 | 4/2019 |
| WO | 2019094679 A1 | 5/2019 |
| WO | 2019098763 A2 | 5/2019 |
| WO | 2019115671 A1 | 6/2019 |
| WO | 2019115674 A1 | 6/2019 |
| WO | 2019117684 A1 | 6/2019 |
| WO | 2019138057 A1 | 7/2019 |
| WO | 2019161386 A1 | 8/2019 |
| WO | 2019169448 A1 | 9/2019 |
| WO | 2019215590 A1 | 11/2019 |
| WO | 2019217628 A1 | 11/2019 |
| WO | 2019222840 A1 | 11/2019 |
| WO | 2019224275 A1 | 11/2019 |
| WO | 2020009482 A1 | 1/2020 |
| WO | 2020033756 A1 | 2/2020 |
| WO | 2020073121 A1 | 4/2020 |
| WO | 2020146497 A1 | 4/2020 |
| WO | 2020146497 A1 | 7/2020 |
| WO | 2020185632 A1 | 9/2020 |
| WO | 2020190970 A1 | 9/2020 |
| WO | 2020219868 | 10/2020 |
| WO | 2020219868 A1 | 10/2020 |
| WO | 2020251316 A1 | 12/2020 |
| WO | 2020254697 A1 | 12/2020 |
| WO | 20212593 A1 | 1/2021 |
| WO | 2021028452 A1 | 2/2021 |

OTHER PUBLICATIONS

Emadi, S. et al., "Isolation of a Human Single Chain Antibody Fragment Against Oligomeric alpha-Synuclein that Inhibits Aggregation and Prevents alpha-Synuclein-induced Toxicity," Journal of Molecular Biology, vol. 368 (4):1132-1144 (2007).

International Preliminary Report on Patentability, PCT/US2018/000032, dated Aug. 20, 2019, 9 pages.

International Search Report and Written Opinion, PCT/US2018/000032, dated Jun. 19, 2018, 13 pages.

Masliah, E. et al., "Passive Immunization Reduces Behavioral and Neuropathological Deficits in an Alpha-Synuclein Transgenic Model of Lewy Body Disease," PLOS ONE, vol. 6(4): e19338-e19338 (2011).

Paleologou, K. E. "Detection of elevated levels of soluble alpha-synuclein oligomers in post-mortem brain extracts from patients with dementia with Lewy bodies," Brain, A Journal of Neurology, vol. 132: 1093-1101 (2009).

Kuroiwa, Y. et al., "Cloned transchromosomic calves producing human immunoglobulin," Nature Biotechnology, vol. 20:889-894 (2002).

Liu, Ma et al.,"Heteroantibody duplexes target cells for lysis by cytotoxic T lymphocytes," Proc. Natl. Acad. Sci., vol. 82:8648 (1985).

Lonberg, N. "Human antibodies from transgenic animals," Nature Biotech., vol. 23(9):1117-1125 (2005).

Lonberg, N. et al., "Antigen-specific human antibodies from mice comprising four distinct genetic modifications.," Nature, vol. 368(6474): 856-859 (1994).

Lonberg, N. et al., "Human antibodies from transgenic mice," Intern. Rev. ImmunoL, vol. 13 65-93 (1995).

Lonberg, N., "Transgenic Approaches to Human Monoclonal Antibodies," Handbook of Experimental Pharmacology, vol. 113:49-101 (1994).

Luk, K. et al., "Exogenous alpha-synuclein fibrils seed the formation of Lewy body-like intracellular inclusions in cultured cells," PNAS, vol. 106(47):20051-6 (2009).

Luk, K. et al., "Pathological alph-synuclein transmission initiates Parkinson-like neurodegeneration in nontransgenic mice," Science, vol. 338: 949-953 (2012).

McCafferty, J. et al., "Phage antibodies: filamentous phage displaying antibody variable domains," Nature, vol. 348:552-554 (1990).

Miller, D. et al., "Absence of alpha-synuclein mRNA expression in normal and multiple system atrophy oligodendroglia," J Neural Transm (Vienna), vol. 112:1613-24 (2005).

Moldenhauer, G. et al., "Identity of HML-1 Antigen on Intestinal Intraepithelial T Cells and of B-ly7 Antigen on Hairy Cell Leukaemia," Scand. J. Immunol., vol. 32:77 (1990).

Morel, G. et al., "Monoclonal antibodies to bovine serum albumin: Affinity and specificity determinations," Mol. Immunol., vol. 25(1):7 (1988).

Morrison, S., "Transfectomas provide novel chimeric antibodies," Science, vol. 229:1202 (1985).

Myers, E. et al., "Optimal alignments in linear space ," CABIOS, vol. 4:11-17 (1989).

Nails, M. et al., "Large-scale meta-analysis of genome-wide association data identifies six new risk loci for Parkinson's disease," Nature Genetics, vol. 46(9): 989-993 (2014).

Needleman and Wunsch, "A general method applicable to the search for similarities in the amino acid sequence of two proteins," J. Mol. Biol., vol. 48:444-453 (1970).

Oueslati, A., "Implication of Alpha-Synuclein Phosphorylation at S129 in Synucleinopathies: What Have We Learned in the Last Decade?," J Parkinsons Dis., ,vol. 6:39-51 (2016).

Owais, M. et al., "Chloroquine encapsulated in malaria-infected erythrocyte-specific antibody-bearing liposomes effectively controls chloroquine-resistant Plasmodium berghei infections in mice," Antimicrob. Agents Chemother., vol. 39:180 (1995).

Ozawa, T. et al., "Analysis of the expression level of alpha-synuclein mRNA using postmortem brain samples from pathologically confirmed cases of multiple system atrophy," Acta Neuropathologica, vol. 102:188-190 (2001).

Prusiner, E. et al., "Evidence for alpha-synuclein prions causing multiple system atrophy in humans with parkinsonism," PNAS, vol. 112:E5308-17 (2015).

Queen, C. et al., "A humanized antibody that binds to the interleukin 2 receptor," Proc. Natl. Acad. See., vol. 86:10029-10033 (1989).

Ranade, V.V. "Drug delivery systems. 1. site-specific drug delivery using liposomes as carriers," J. Clin. Pharmacol., vol. 29(8):685-94 (1989).

Recasens et al., "Lewy body extracts from Parkinson disease brains trigger alpha-synuclein pathology and neurodegeneration in mice and monkeys," Annals Neurology, vol. 75:351-62 (2014).

Ren, H. et al., "A biocompatible condensation reaction for the labeling of terminal cysteine residues on proteins," Angew. Chem. Int. Ed. Engl., vol. 48: 9658-9662 (2009).

Reyes, J. et al., "Alpha-synuclein transfers from neurons to oligodendrocytes," Glia, vol. 62:387-98 (2014).

Riechmann, L. et al., "Reshaping human antibodies for therapy," Nature, vol. 332:323-327 (1998).

Sarmay, G. et al., "Mapping and comparison of the interaction sites on the Fc region of IgG responsible for triggering antibody dependent cellular cytotoxicity (ADCC) through different types of human Fcγ receptor," Molec. Immunol., vol. 29 (5): 633-9 (1992).

Schreier et al., "Targeting of liposomes to cells expressing CD4 using glycosylphosphatidylinositol-anchored gp120. Influence of liposome composition on intracellular trafficking," J. Biol. Chem., vol. 269(12):9090-9098(1994).

Senter, P. D., "Potent antibody drug conjugates for cancer therapy," Curr. Opin. Chem. Biol., vol. 13:235-244 (2009).

Shields, R. et al, "High resolution mapping of the binding site on human IgG1 for Fc gamma RI, Fc gamma RII, Fc gamma RIII, and

(56) References Cited

OTHER PUBLICATIONS

FcRn and design of IgG1 variants with improved binding to the Fc gamma R," Journal of Biological Chemistry, vol. 276(9):6591-6604 (2001).
Shields, R.L. et al., "Lack of fucose on human IgG1 N-linked oligosaccharide improves binding to human Fcgamma RIII and antibody-dependent cellular toxicity," J. Biol. Chem., vol. 277:26733-26740 (2002).
Songsivilai & Lachmann, "Bispecific antibody: a tool for diagnosis and treatment of disease," Clin. Exp. Immunol., vol. 79:315-321 (1990).
Stahli et al., "Distinction of epitopes by monoclonal antibodies," Methods in Enzymology, vol. 92: 242-253 (1983).
Strohl, W., "Optimization of Fc-mediated effector functions of monoclonal antibodies," Current Opinion in Biotechnology, vol. 20:685-691 (2009).
Sunbul, M. et al., "Site specific protein labeling by enzymatic posttranslational modification," Org. Biomol.Chem., vol. 7:3361-3371 (2009).
Takebe, Y. et al., "SR alpha promoter: an efficient and versatile mammalian cDNA expression system composed of the simian virus 40 early promoter and the R-U5 segment of human T-cell leukemia virus type 1 long terminal repeat," Mol. Cell. Biol., vol. 8:466-472 (1988).
Taki, M. et al., "Transglutaminase-mediated N-and C-terminal fluorescein labeling of a protein can support the native activity of the modified protein," Prot. Eng. Des. Sel., vol. 17:119-126 (2004).
Taylor, E, "Native Chemical Ligation: SemiSynthesis of Post-translationally Modified Proteins and Biological Probes," Nucleic Acids and Molecular Biology Protein Engineering, vol. 22: 65-96 (2009).
Taylor, L. et al., "A transgenic mouse that expresses a diversity of human sequence heavy and light chain immunoglobulins," Nucleic Acids Research, vol. 20: 6287-6295 (1992).
Taylor, L. et al., "Human immunoglobulin transgenes undergo rearrangement, somatic mutation and class switching in mice that lack endogenous IgM," International Immunology, vol. 6: 579-591 (1994).
Tomizuka, K. et al., "Double trans-chromosomic mice: maintenance of two individual human chromosome fragments containing Ig heavy and kappa loci and expression of fully human antibodies," Proc. Natl. Acad. Sci., vol. 97:722-727 (2000).
Tomlinson, I. M., et al., "The Repertoire of Human Germline VH Sequences Reveals about Fifty Groups of VH Segments with Different Hypervariable Loops" J. Mol. Biol., vol. 227:776-798 (1992).
Tran, H. et al., "alpha-synuclein immunotherapy blocks uptake and templated propagation of misfolded alpha-synuclein and neurodegeneration," Cell Reports, vol. 7(6):2054-65 (2014).
Tuaillon, N. et al., "Biased utilization of DHQ52 and JH4 gene segments in a human Ig transgenic minilocus is independent of antigenic selection," J. Immunol., vol. 152:2912-2920 (1994).
Tuaillon, N. et al., "Human immunoglobulin heavy-chain minilocus recombination in transgenic mice: gene-segment use in mu and gamma transcripts," Proc. Natl. Acad. Sci., vol. 90:3720-3724 (1993).
Umana, P. et al., "Engineered glycoforms of an antineuroblastoma IgG1 with optimized antibody-dependent cellular cytotoxic activity," Nat. Biotech., vol. 17:176-180 (1999).
Umezawa, F. et al., "Liposome targeting to mouse brain: mannose as a recognition marker," Biochem. Biophys. Res. Commun., vol. 153(3):1038-44 (1988).
Urlaub, G. et al., "Isolation of Chinese hamster cell mutants deficient in dihydrofolate reductase activity," Proc. Natl. Acad. Sci. USA 77:4216-4220 (1980).
Volpicelli-Daley, L. et al., "Exogenous alpha-synuclein fibrils induce Lewy body pathology leading to synaptic dysfunction and neuron death," Neuron, vol. 72:57-71 (2011).
Wang, W. et al., "A soluble alpha-synuclein construct forms a dynamic tetramer" PNAS, vol. 108:17797-802 (2011).

Ward, E. et al. "Binding activities of a repertoire of single immunoglobulin variable domains secreted from *Escherichia coli*," Nature, vol. 341:544-546 (1989).
Watts, J. et al., "Transmission of multiple system atrophy prions to transgenic mice," PNAS, vol. 110:19555-60 (2013).
Waxman, E. et al., "Specificity and regulation of casein kinase-mediated phosphorylation of alpha-synuclein," J Neuropath Exp Neurol., vol. 67(5):402-16 (2008).
Yeung et al., "Engineering human IgG1 affinity to human neonatal Fc receptor: impact of affinity improvement on pharmacokinetics in primates," J Immunol, vol. 182:7663-7671 (2010).
Altschul, S. et al., "Basic local alignment search tool," J Mol Biol., vol. 215:403-410 (1990).
Altschul, S. et al., "Gapped BLAST and PSI-BLAST: a new generation of protein database search programs," Nucleic Acids Res., vol. 25(17):3389-3402 (1997).
Asi, Y. et al., "Alpha-synuclein mRNA expression in oligodendrocytes in MSA," Glia, vol. 62(6):964-970 (2014).
Baba, M. et al., "Aggregation of alpha-synuclein in Lewy bodies of sporadic Parkinson's disease and dementia with Lewy bodies," Am J Path., vol. Am J Pathol, vol. 152(4):879-884 (1998).
Bartels, T. et al., "alpha-Synuclein occurs physiologically as a helically folded tetramer that resists aggregation," Nature, vol. 477:107-110 (2011).
Bendor et al., "The Function of alpha-Synuclein," Neuron, vol. 79:1044-1066 (2013).
Berge, S.M., et al., "Pharmaceutical Salts," J. Pharm. Sci., vol. 66(1):1-19 (1977).
Beyer, K. et al., "alpha-Synuclein posttranslational modification and alternative splicing as a trigger for neurodegeneration," Mol Neurobiol., vol. 47:509-524 (2013).
Bird, R. et al., "Single-chain antigen-binding proteins," Science, vol. 242:423-426 (1988).
Bloeman, P.G. et al., "Adhesion molecules: a new target for immunoliposome-mediated drug delivery," FEBS Lett., vol. 357:140-144 (1995).
Boss, M. A. et al., "Genetically engineered antibodies," Immunology Today, vol. 6:12-13 (1985).
Braak, H., et al., "Staging of brain pathology related to sporadic Parkinson's disease," Neurobiol Aging, vol. 24 (2):197-211 (2003).
Brennan, M. et al., "Preparation of bispecific antibodies by chemical recombination of monoclonal immunoglobulin G1 fragments," Science, vol. 229:81-83 (1985).
Briscoe, P. et al. , "Delivery of superoxide dismutase to pulmonary epithelium via pH-sensitive liposomes," Am. J. Physiol., vol. 1233:134:370-380 (1995).
Brummell, D. et al., "Probing the combining site of an anti-carbohydrate antibody by saturation-mutagenesis: role of the heavy-chain CDR3 residues," Biochem., vol. 32:1180-1187 (1993).
Burks, E. et al., "In vitro scanning saturation mutagenesis of an antibody binding pocket," Proc. Natl. Acad. Sci., vol. 94:412-417 (1997).
Chen, J. et al. "B cell development in mice that lack one or both immunoglobulin kappa light chain genes", EMBO J. 12: 821-830 (1993).
Chen, J. et al., "Immunoglobulin gene rearrangement in B cell deficient mice generated by targeted deletion of the JH locus," International Immunology, vol. 5: 647-656 (1993).
Cheung, R. et al., "Epitope-specific antibody response to the surface antigen of duck hepatitis B virus in infected ducks," Virology, vol. 176:546-552 (1990.
Choi, T. et al., "Transgenic mice containing a human heavy chain immunoglobulin gene fragment cloned in a yeast artificial chromosome," Nature Genetics, vol. 4:117-123 (1993).
Cox, J. P. L. et al., "A Directory of Human Germ-line VH Segments Reveals a Strong Bias in their Usage," Eur. Immunol., vol. 24:827-836 (1994).
Dall Acqua, W. et al., "Increasing the affinity of a human IgG1 for the neonatal Fc receptor: biological consequences," Journal of Immunology, vol. 169:5171-5180 (2002).
Dall Acqua, W. et al., "Properties of human IgG1s engineered for enhanced binding to the neonatal Fc receptor (FcRn)," Journal of Biological Chemistry, vol. 281:23514-23524 (2006).

(56) References Cited

OTHER PUBLICATIONS de Graaf, A. J. et al., "Nonnatural amino acids for site-specific protein conjugation," Bioconjug. Chem., vol. 20:1281-1295 (2009).

Duda, et al., "Novel antibodies to synuclein show abundant striatal pathology in Lewy body diseases," Ann Neurol., vol. 52(2):205-10 (2002).

Fauvet, B. et al., "alpha-Synuclein in central nervous system and from erythrocytes, mammalian cells, and *Escherichia coli* exists predominantly as disordered monomer," JBC, vol. 287:15345-64 (2012).

Fishwild, D. et al "High-avidity human IgG kappa monoclonal antibodies from a novel strain of minilocus transgenic mice," Nature Biotechnology, vol. 14: 845-851 (1996).

Frese, M. A., et al., "Formylglycine aldehyde Tag—protein engineering through a novel post-translational modification," ChemBioChem., vol. 10:425-427 (2009).

Galvin, J. et al., "Synucleinopathies: clinical and pathological implications," Arch Neurol, vol. 58:186-90 (2001).

Gautier, A. et al., "An engineered protein tag for multiprotein labeling in living cells," Chem. Biol., vol. 15: 128-136 (2008).

Glennie, M. et al., "Preparation and performance of bispecific F(ab' gamma)2 antibody containing thioether-linked Fab' gamma fragments," J. Immunol., vol. 139: 2367-2375 (1987).

Hackenberger, C., et al., "Chemoselective ligation and modification strategies for peptides and proteins," Angew. Chem. Int. Ed. Engl., vol. 47:10030-10074 (2008).

Harding, F. and Lonberg, N., "Class switching in human immunoglobulin transgenic mice," Ann. N.Y. Acad.Sci., vol. 764:536-546 (1995).

Hernandez et al., "Genetics in Parkinson disease: Mendelial versus non-Medndelian inheritance," Journal of Neurochemistry, 10.1111/jnc.13593 (2016).

Hinton, P. et al., "An engineered human IgG1 antibody with longer serum half-life," Journal of Immunology, vol. 176:346-356 (2006).

Hinton, P. et al., "Engineered human IgG antibodies with longer serum half-lives in primates ," J. Biol. Chem., vol. 279 (8): 6213-6216 (2004).

Huston, J. et al., "Protein engineering of antibody binding sites: recovery of specific activity in an anti-digoxin single-chain Fv analogue produced in *Escherichia coli*," Proc. Natl. Acad. Sci., vol. 85:5879-5883 (1988).

Jakes, R. et al., "Epitope mapping of LB509, a monoclonal antibody directed against human alpha-synuclein," Neurosci Letts, vol. 269(1):13-6.

Jefferis, R. et al., "Human immunoglobulin allotypes: possible implications for immunogenicity," mAbs, 1(4):332-8 (2009).

Jin, H. et al., "Analyses of copy number and mRNA expression level of the 1-synuclein gene in multiple system atrophy," Journal of Medical and Dental Sciences, vol. 555:145-53 (2008).

Jones, P. et al., "Replacing the complementarity-determining regions in a human antibody with those from a mouse," Nature, vol. 321:522-525 (1986).

Karpovsky, B. et al., "Production of Target-Specific Effector Cells Using Hetero-Cross-Linked Aggregates Containing Anti-Target Cell and Anti-Fc3, Receptor Antibodies," vol. 160:1686 (1984).

Kaufman, R. J., et al., "Amplification and expression of sequences cotransfected with a modular dihydrofolate reductase complementary dna gene," Mol. Biol., vol. 159:601-621(1982).

Keinanen, M.L., et al., "Biosynthetic lipid-tagging of antibodies," FEBS Lett., vol. 346:123 (1994).

Killion; I., et al., "Systemic targeting of liposome-encapsulated immunomodulators to macrophages for treatment of cancer metastasis," Immunomethods, vol. 4:273 (1994).

Kirkland, T. et al., "Analysis of the fine specificity and cross-reactivity of monoclonal anti-lipid A antibodies," J. Immunol., vol. 137(11):3614-9 (1986).

Kobayashi, H. et al., "Tryptophan H33 plays an important role in pyrimidine (6-4) pyrimidone photoproduct binding by a high-affinity antibody," Protein Eng., vol. 12(10):879-884 (1999).

Kohler and Milstein, "Continuous cultures of fused cells secreting antibody of predefined specificity," Nature, vol. (5517):495-7 (1975).

Kostelny, S.A., et al., "Formation of a bispecific antibody by the use of leucine zippers," J. Immunol., vol. 148: 1547-1553 (1992).

Kuo, Y-M., et al, "Extensive enteric nervous system abnormalities in mice transgenic for artificial chromosomes containing Parkinson disease-associated alpha-synuclein gene mutations precede central nervous system changes," Human Molecular Genetics, vol. 19:1633-50 (2010).

\* cited by examiner

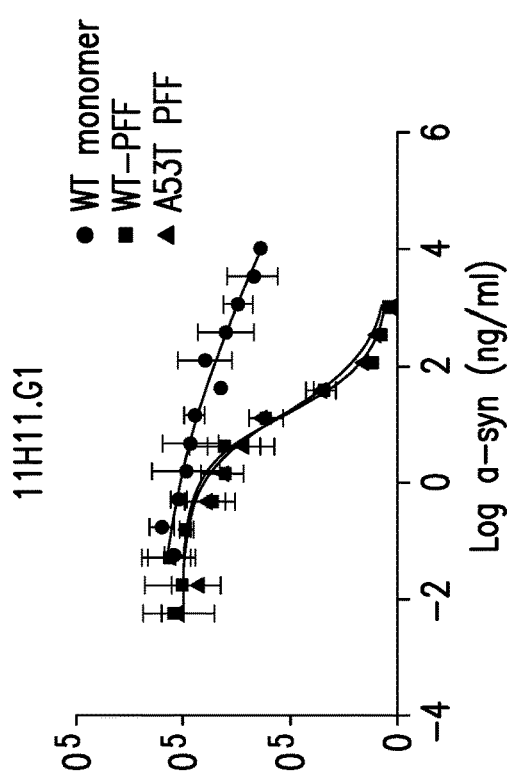
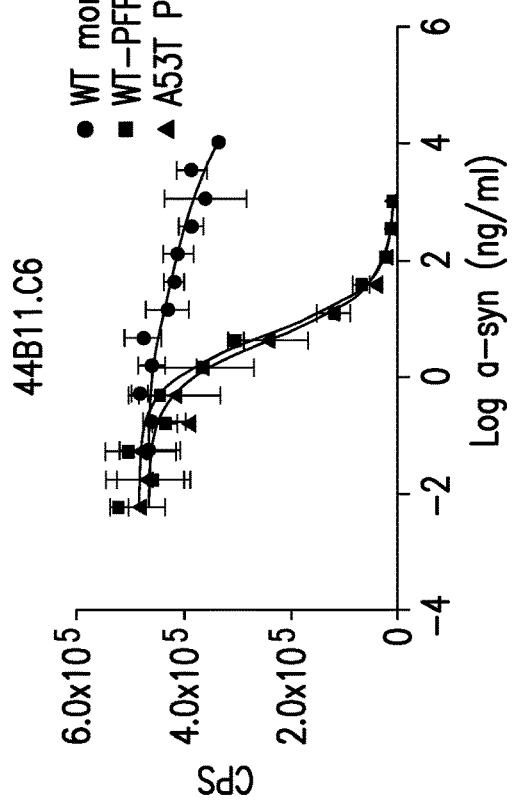
FIG.2F
FIG.2E

```
7A10_VH   QVQLQESGPGLVKPSETLSLTCTVSGGSVS SGRYYWS WIR
                5        10       15       20      25      30      35AB
          000000000000000000000000000000 0000011 112
                              FW1             CDR1

7A10_VH   QPPGKGLEWIG YIYYSGRTKYNPSLKSR VTISVDTSKNQF
                40      45        50       55       60       65       70      75
          0000000000 0001122121112233 000000000000
                     FW2         CDR2                                   FW3

7A10_VH   SLKLSSVTAADTAVYYCT REGYLDY WGQGTLVTVSS
              82ABC    85        90        95       100      105      110
          000000000000021000002 2110011 00000000111
                     FW3                CDR3

7A10_VK   EIVLTQSPGTLSLSPGERATLSC RASQSVSSSYLA WYQQK
                5       10       15       20      25       30      35       40
          00000000000000000000000 000000000000 00000
                            FW1                  CDR1

7A10_VK   PGQAPRLLIY GASSRAT GIPDRFSGSGSGTDFTLTISRLE
                45       50       55       60      65       70      75      80
          0000000000 0000000 00000000000000000000000
                 FW2     CDR2                       FW3

7A10_VK   PEDFAVYYC QQYGSSPLT FGGGTKVEIK
                85       90       95       100     105     110
          000000000 000000011 0000000011
                FW3       CDR3
```

FIG.4

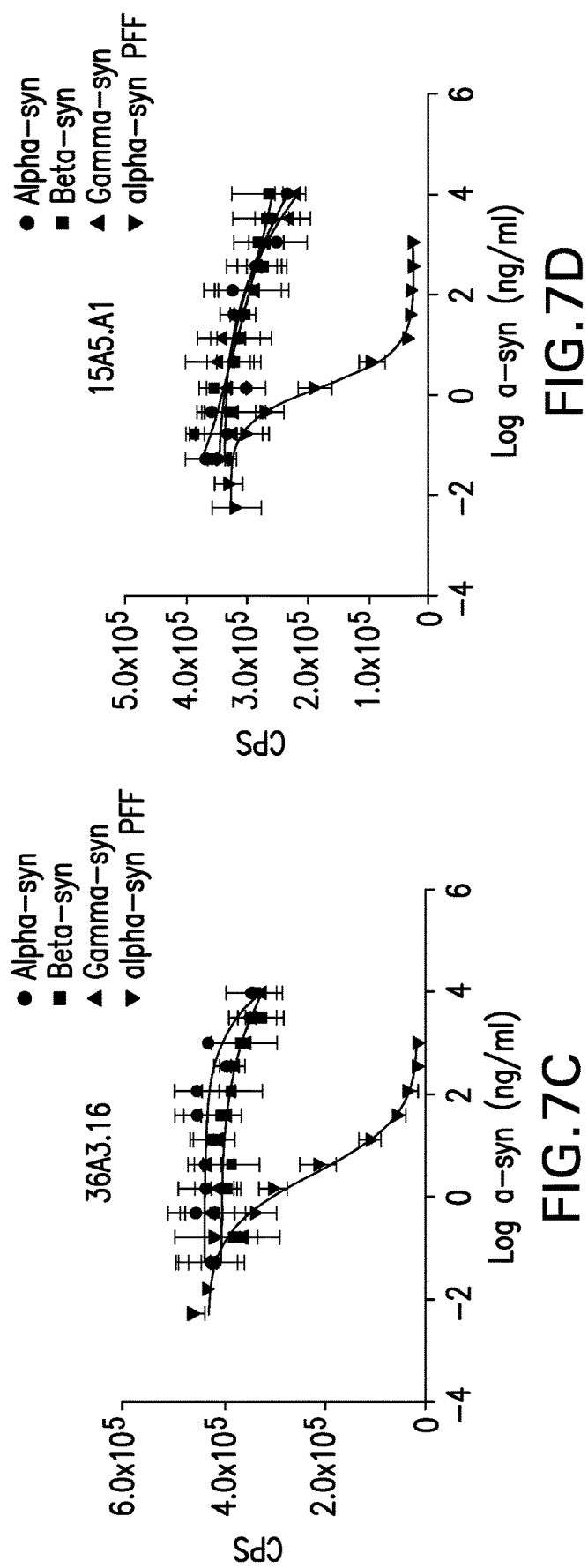

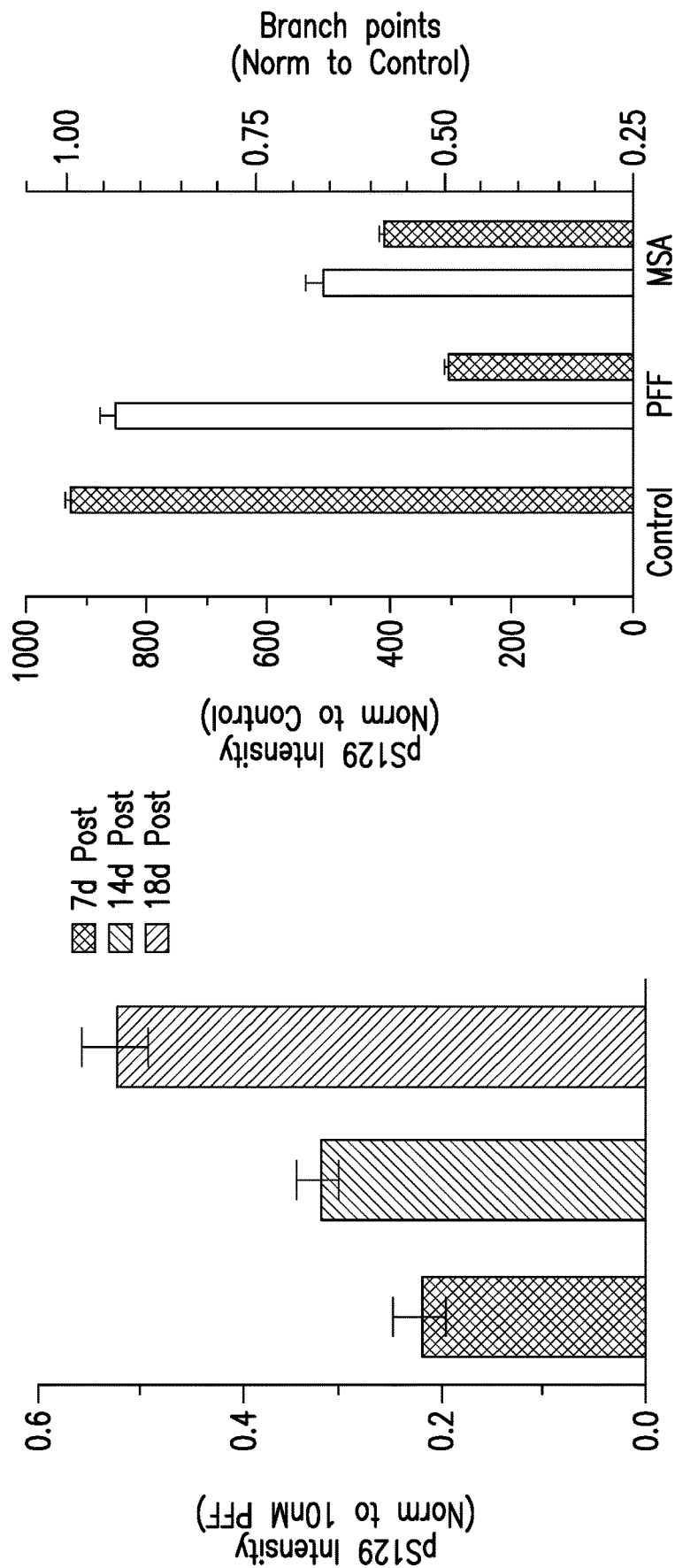

ANTIBODIES TO ALPHA-SYNUCLEIN AND USES THEREOF

RELATED APPLICATIONS

This application is a 35 U.S.C. 371 national stage filing of International Application No. PCT/US2018/000032, filed on Feb. 16, 2018, which claims priority to U.S. Provisional Application No. 62/460,416, filed Feb. 17, 2017, each of which are incorporated herein by reference in their entirely.

SEQUENCE LISTING

The instant application contains a Sequence Listing which has been submitted electronically in ASCII format and is hereby incorporated by reference in its entirety. Said ASCII copy, created on Aug. 13, 2019, is named SL_MXI-554US.txt and is 139712 bytes in size.

BACKGROUND

α-synuclein (αSyn) is a 140 amino acid protein preferentially expressed in neurons at pre-synaptic terminals where it is thought to play a role in regulating synaptic transmission (Bendor et al., *Neuron* 2013; 79:1044-66). It has been proposed to exist natively as both an unfolded monomer (Fauvet et al., *JBC* 2012; 287:15345-64) and a stable tetramer of α-helices (Bartels et al., *Nature* 2011; 477:107-10; Wang et al., *PNAS* 2011; 108:17797-802) and has been shown to undergo several posttranslational modifications (Beyer and Ariza, *Mol Neurobiol* 2013; 47:509-24). One modification that has been extensively studied is phosphorylation of αSyn at amino acid residue serine 129 (S129). Normally, only a small percentage of αSyn is constitutively phosphorylated at S129 (pS129), whereas the vast majority of αSyn found in pathological intracellular inclusions is pS129 αSyn (Oueslati, *J Parkinsons Dis* 2016; 6:39-51). These pathological inclusions consist of aggregated, insoluble accumulations of misfolded αSyn proteins and are a characteristic feature of a group of neurodegenerative diseases collectively known as synucleinopathies (Galvin et al., *Arch Neurol* 2001; 58:186-90).

In synucleinopathies, αSyn can form pathological aggregates in neurons know as Lewy bodies, which are characteristic of both Parkinson's Disease (PD) and dementia with Lewy bodies (DLB). Additionally, abnormal αSyn-rich lesions called glial cytoplasmic inclusions (GCIs) are found in oligodendrocytes, and represent the pathologic hallmark of a rapidly progressing, fatal synucleinopathy known as multiple systems atrophy (MSA). The initial evidence for the propagation of pathologic αSyn throughout the brain comes from the stereotypical progression of brain pathology described in PD (Braak et al., 2003) and from evidence of host-to-graft spreading of αSyn aggregates in PD patients (Kordower et al., 2008). Intriguingly, reports of either undetectable (Ozawa et al., *Acta Neuropathologica* 2001; 102:188-190; Miller et al., *J Neural Transm (Vienna)* 2005; 112:1613-24; Jin et al., *Journal of Medical and Dental Sciences* 2008; 555:145-53) or low levels (Asi et al., *Glia* 2014; 62:964-70) of αSyn mRNA expression in oligodendrocytes suggests that some pathological form of αSyn is propagated from neurons, where it is highly expressed, to oligodendrocytes. Recent work supports this idea of αSyn propagation, demonstrating that αSyn is taken up by oligodendrocytes (Reyes et al., *Glia* 2014; 62:387-98) and by neurons (Volpicelli-Daley et al., *Neuron* 2011; 72:57-71; Luk et al., *Science* 2012; 338: 949-953). Moreover, inoculation of human brain homogenates from MSA patients into αSyn transgenic mice or purified LB extracts from PD brains into mice and nonhuman primates results in neurological dysfunction and extensive pS129 neuronal deposits (Watts et al., *PNAS* 2013; 110:19555-60; Prusiner et al., *PNAS* 2015; 112:E5308-17; Recasens et al., *Annals Neurology* 2014; 75:351-62).

There is currently a lack of therapeutics that target synucleinopathies from the perspective of αSyn propagation. Accordingly, therapeutic agents that preferentially target the pathological form of αSyn would be desirable in the treatment of patients with synucleinopathies such as PD, DLB, and MSA.

SUMMARY

Provided herein are isolated antibodies, such as monoclonal antibodies, that specifically bind to α-synuclein and have desirable functional properties. These properties include binding preferentially to oligomeric α-synuclein compared to monomeric α-synuclein, and the ability to inhibit the generation of soluble or insoluble α-synuclein aggregates (e.g., serine-129 phosphorylated α-synuclein aggregates) in vitro and in vivo. The anti-α-synuclein antibodies described herein can be used to treat, lessen the severity of, delay the progression of, reducing the risk of developing, dealying the onset of, and diagnosing synucleinopathies, a family of diseases characterized by the presence of Lewy bodies or pathological aggregates of α-synuclein in the brain.

In one aspect, provided herein are antibodies, or antigen-binding portions thereof, which bind to α-synuclein and exhibit one or more of the following properties:

(a) binds to mouse and rat α-synuclein;
(b) binds to human β-synuclein and human γ-synuclein;
(c) has a greater affinity for α-synuclein oligomers over α-synuclein monomers;
(d) inhibits the generation of α-synuclein oligomer-induced insoluble α-synuclein aggregates (e.g., serine-129 phosphorylated α-synuclein aggregates);
(e) depletes the molecular species that produces soluble or insoluble α-synuclein aggregates (e.g., serine-129 phosphorylated α-synuclein aggregates) from PFF and/or brain lysate prepared from patients with pathological aggregates of α-synuclein in the brain;
(f) binds to all or a portion of amino acid positions 123-128 of human α-synuclein (SEQ ID NO: 1);
(g) binds to all or a portion of amino acid positions 125-128 of human α-synuclein (SEQ ID NO: 1);
(h) hinds to all or a portion of amino acid positions 130-139 of human α-synuclein (SEQ ID NO: 1);
(i) binds to all or a portion of amino acid positions 119-126 of human α-synuclein (SEQ ID NO: 1); and
(j) binds to all or a portion of amino acid positions 130-138 of human α-synuclein (SEQ ID NO: 1).

In certain embodiments, the α-synuclein oligomer is PFF, for example, prepared as described in Example 3. In some embodiments, the α-synuclein oligomers are soluble α-synuclein oligomers. In other embodiments, the α-synuclein oligomers are insoluble α-synuclein oligomers.

In some embodiments, the anti-α-synuclein antibodies, or antigen-binding portions thereof, have a greater affinity for α-synuclein PFF, soluble aggregates (oligomers) or insoluble aggregates over α-synuclein monomers, as assessed by, e.g., an α-synuclein monomer/α-synuclein PFF binding ratio, for example, as described in Example 3. In some embodiments, the anti-α-synuclein antibodies, or antigen-binding portions thereof, have an α-synuclein monomer/α-synuclein PFF binding ratio of 100 or greater, for example, 500 or greater, 700 or greater, 1500 or greater 3000 or greater, or 5000 or greater.

In some embodiments, the anti-α-synuclein antibodies, or antigen-binding portions thereof, bind to monomeric α-synuclein with an EC50 of 500 nM or greater, and binds to PFF with an $EC_{50}$ of 0.5 nM or less. In some embodiments, the anti-α-synuclein antibodies, or antigen-binding portions thereof, inhibit PFF-induced α-synuclein serine-129 phosphorylation with an $IC_{50}$ of 0.1 nM or less, as assessed, e.g., using the assay described in Example 10.

In another aspect, provided herein are isolated monoclonal antibodies, or antigen-binding portions thereof, which specifically bind to α-synuclein and comprise the three variable heavy chain CDRs and the three variable light chain CDRs that are in the variable heavy chain and variable light chain pairs selected from the group consisting of SEQ ID NOs: 8 and 9, 18 and 19, 28 and 29, 38 and 39, 48 and 49, 58 and 59, 68 and 69, 78 and 79, 94 and 95, 94 and 96, 94 and 97, and 106 and 107.

In another aspect, provided herein are isolated monoclonal antibodies, or antigen-binding portions thereof, which bind to α-synuclein, comprising:

(a) heavy chain variable region CDR1, CDR2, and CDR3 comprising SEQ ID NOs: 2-4, respectively, and the light chain variable region CDR1, CDR2, and CDR3 comprising SEQ ID NOs: 5-7, respectively;

(b) heavy chain variable region CDR1, CDR2, and CDR3 comprising SEQ ID NOs: 22-24, respectively, and the light chain variable region CDR1, CDR2, and CDR3 comprising SEQ ID NOs: 25-27, respectively;

(c) heavy chain variable region CDR1, CDR2, and CDR3 comprising SEQ ID NOs: 22-24, respectively, and the light chain variable region CDR1, CDR2, and CDR3 comprising SEQ ID NOs: 28-30, respectively;

(d) heavy chain variable region CDR1, CDR2, and CDR3 comprising SEQ ID NOs: 37-39, respectively, and the light chain variable region CDR1, CDR2, and CDR3 comprising SEQ ID NOs: 40-42, respectively;

(e) heavy chain variable region CDR1, CDR2, and CDR3 comprising SEQ ID NOs: 47-49, respectively, and the light chain variable region CDR1, CDR2, and CDR3 comprising SEQ ID NOs: 50-52, respectively;

(f) heavy chain variable region CDR1, CDR2, and CDR3 comprising SEQ ID NOs: 57-59, respectively, and the light chain variable region CDR1, CDR2, and CDR3 comprising SEQ ID NOs: 60-62, respectively;

(g) heavy chain variable region CDR1, CDR2, and CDR3 comprising SEQ ID NOs: 67-69, respectively, and the light chain variable region CDR1, CDR2, and CDR3 comprising SEQ ID NOs: 70-72, respectively;

(h) heavy chain variable region CDR1, CDR2, and CDR3 comprising SEQ ID NOs: 77-79, respectively, and the light chain variable region CDR1, CDR2, and CDR3 comprising SEQ ID NOs: 80-82, respectively;

(i) heavy chain variable region CDR1, CDR2, and CDR3 comprising SEQ ID NOs: 87-89, respectively, and the light chain variable region CDR1, CDR2, and CDR3 comprising SEQ ID NOs: 90-92, respectively;

(j) heavy chain variable region CDR1, CDR2, and CDR3 comprising SEQ ID NOs: 87-89, respectively, and the light chain variable region CDR1, CDR2, and CDR3 comprising SEQ ID NOs: 93-95, respectively;

(k) heavy chain variable region CDR1, CDR2, and CDR3 comprising SEQ ID NOs: 87-89, respectively, and the light chain variable region CDR1, CDR2, and CDR3 comprising SEQ ID NOs: 96-98, respectively; or (l) heavy chain variable region CDR1, CDR2, and CDR3 comprising SEQ ID NOs: 107-109, respectively, and the light chain variable region CDR1, CDR2, and CDR3 comprising SEQ ID NOs: 110-112, respectively.

In another aspect, provided herein are isolated monoclonal antibodies, or antigen-binding portions thereof, which bind to to α-synuclein and comprises heavy and light chain variable regions, wherein the heavy chain variable region comprises an amino acid sequence which is at least 90% identical to the amino acid sequence selected from the group consisting of SEQ ID NOs: 8, 18, 31, 43, 53, 63, 73, 83, 99, and 113.

In another aspect, provided herein are isolated monoclonal antibodies, or antigen-binding portions thereof, which bind to to α-synuclein and comprises heavy and light chain variable regions, wherein the light chain variable region comprises an amino acid sequence which is at least 90% identical to the amino acid sequence selected from the group consisting of SEQ ID NOs: 9, 19, 32, 33, 44, 54, 64, 74, 84, 100, 101, 102, and 114.

In another aspect, provided herein are isolated monoclonal antibodies, or antigen-binding portions thereof, which bind to to α-synuclein and comprise heavy and light chain variable region sequences at least 90%, 95%, 98%, 99%, or 100% identical to the amino acid sequences selected from the group consisting of: (a) SEQ ID NOs: 8 and 9, 18 and 19, 31 and 32, 31 and 33, 43 and 44, 53 and 54, 63 and 64, 73 and 74, 83 and 84, 99 and 100, 99 and 101, 99 and 102; and SEQ ID NOs: 113 and 114.

In another aspect, provided herein are isolated monoclonal antibodies, or antigen-binding portions thereof, which bind to α-synuclein and comprises heavy chain and light chain sequences at least 80%, 85%, 90%, 95%, 96%, 97%, 98% 99%, or 100% identical to the amino acid sequences selected from the group consisting of SEQ ID NOs: 10 and 11, 20 and 21, 34 and 35, 34 and 36, 45 and 46, 55 and 56, 65 and 66, 75 and 76, 85 and 86, 103 and 104, 103 and 105, 103 and 106, and 115 and 116. In some embodiments, the anti-α-synuclein antibodies, or antigen-binding portions thereof, bind to all or a portion of amino acid positions 123-128 of human α-synuclein (SEQ ID NO: 1). In some embodiments, the anti-α-synuclein antibodies, or antigen-binding portions thereof, bind to all or a portion of amino acid positions 125-128 of human α-synuclein (SEQ ID NO: 1). the anti-α-synuclein antibodies, or antigen-binding portions thereof, bind to all or a portion of amino acid positions 130-139 of human α-synuclein (SEQ ID NO: 1). the anti-α-synuclein antibodies, or antigen-binding portions thereof, bind to all or a portion of amino acid positions 119-126 of human α-synuclein (SEQ ID NO: 1). the anti-α-synuclein antibodies, or antigen-binding portions thereof, bind to all or a portion of amino acid positions 130-138 of human α-synuclein (SEQ ID NO: 1).

In some embodiments, the anti-α-synuclein antibodies, or antigen-binding portions thereof, bind to rat and mouse α-synuclein. In some embodiments, the anti-α-synuclein antibodies, or antigen-binding portions thereof, bind to human β-synuclein and human γ-synuclein. In some embodiments, the anti-α-synuclein antibodies, or antigen-binding portions thereof, have greater affinity for α-synuclein PFF, soluble aggregates (oligomers) or insoluble aggregates than α-synuclein monomers, as assessed by an α-synuclein monomer/α-synuclein PFF binding ratio (monomer:PFF binding ratio), as described, e.g., in Example 3. In some embodiments, the monomer:PFF binding ratio is 100 or greater, 500 or greater, 700 or greater, 1500 or greater, 3000 or greater, or 5000 or greater.

In some embodiments, the anti-α-synuclein antibodies, or antigen-binding portions thereof, bind to the same epitope as the anti-α-synuclein antibodies described herein (e.g., antibodies 7A10, 7A10-T93A, 11H11-1, 11H11-2, 15A5, 21A3, 36A3, 44B11, 2E2, 23H8-1, 23H8-2, 23H8-3, and 1E8). In some embodiments, the anti-α-synuclein antibodies, or antigen-binding portions thereof, compete for binding to to human α-synuclein with the anti-α-synuclein antibodies described herein (e.g., antibodies 7A10, 7A10-T93A, 11H11-1, 11H11-2, 15A5, 21A3, 36A3, 44B11, 2E2, 23H8-1, 23H8-2, 23H8-3, and 1E8).

In some embodiments, the anti-α-synuclein antibodies, or antigen-binding portions thereof, are igG1, IgG2, IgG3, or IgG4 antibodies, or variants thereof. In some embodiments, the anti-α-synuclein antibodies comprise an Fc region with reduced or no effector function, for example, an effectorless IgG1 Fc with the following mutations: L234A, L235E, and G257A.

In some embodiments, the anti-α-synuclein antibodies, or antigen-binding portions thereof, are chimeric, humanized, or human antibodies. In some embodiments, the anti-α-synuclein antibodies, or antigen-binding portions thereof, are modified to reduce immunogenicity in humans. In one embodiment, the anti-α-synuclein antibody, or antigen-binding portion thereof, comprises heavy and light chain variable regions set forth in SEQ ID NOs: 18 and 19, respectively.

In another aspect, provided herein are bispecific molecules comprising an anti-α-synuclein antibody linked to a molecule having a second binding specificity.

In another aspect, provided herein are nucleic acids encoding the CDRs, or the heavy and/or light chain variable regions, or the heavy and/or light chains of the anti-α-synuclein antibodies, or antigen-binding portions thereof, described herein, expression vectors comprising the nucleic acid molecules, and cells transformed with the expression vectors.

In another aspect, provided herein are immunoconjugates comprising anti-α-synuclein antibodies linked to a moiety, such as a binding moiety, a labeling moiety, a biologically active moiety, or a therapeutic agent.

In another aspect, provided herein are compositions comprising anti-α-synuclein antibodies, or antigen-binding portions thereof, and a carrier. Also provided herein are kits comprising the anti-α-synuclein antibodies, or antigen-binding portions thereof, and instructions for use.

In another aspect, provided herein is a method of preparing an anti-α-synuclein antibody, or antigen-binding portion thereof, comprising expressing the antibody, or antigen binding portion thereof, in a cell and isolating the antibody, or antigen binding portion thereof, from the cell.

In another aspect, provided herein is a method of detecting α-synuclein in a sample comprising contacting the sample with a anti-α-synuclein antibody, or antigen-binding portion thereof, bispecific antibody, or immunoconjugate described herein under conditions that allow for formation of a complex between the antibody, or antigen-binding portion thereof, and α-synuclein, and detecting the formation of the complex.

In another aspect, provided herein is a method of inhibiting the generation of insoluble or soluble α-synuclein aggregates (e.g., serine-129 phosphorylated α-synuclein aggregates) in a cell comprising contacting the cell with an effective amount of the anti-α-synuclein antibody, or antigen-binding portion thereof, bispecific antibody, or immunoconjugate described herein. In some embodiments, the antibodies inhibit the generation of insoluble or soluble α-synuclein aggregates that do not contain serine-129 phosphorylated α-synuclein. In some embodiments, phosphorylation of serine-129 is induced by α-synuclein oligomers. In some embodiments, α-synuclein oligomers are pre-formed α-synuclein fibrils. In other embodiments, the α-synuclein oligomers are derived from brain samples from patients with synucleinopathies.

In another aspect, provided herein is a method of treating, lessening the severity of, delaying the progression of, reducing the risk of developing, and/or delaying the onset of, a disease characterized by the presence of Lewy bodies or pathological aggregates of α-synuclein in the brain comprising administering to a subject with the disease an effective amount of the anti-α-synuclein antibody, or antigen-binding portion thereof, bispecific antibody, or immunoconjugate described herein.

In another aspect, provided herein is a method of diagnosing a disease characterized by the presence of Lewy bodies or pathological aggregates of α-synuclein in a subject comprising:
 (a) contacting a sample from the subject with the anti-α-synuclein antibody, or antigen-binding portion thereof, bispecific antibody, or immunoconjugate described herein such that an antibody-antigen complex is formed;
 (b) measuring the amount of the complex formed; and
 (c) comparing the amount of the complex in the sample with the amount in a control wherein an elevated level of the complex in the sample relative to the control indicates the subject has a disease characterized by the presence of Lewy bodies or pathological aggregates of α-synuclein. In some embodiments, the sample is cerebrospinal fluid, brain tissue extract, urine, or blood.

In some embodiments, the disease in the methods described above is Parkinson's disease, Parkinson's disease dementia, dementia with Lewy bodies, Lewy body disease, multiple system atrophy, or pure autonomic failure. In some embodiments, the methods described above further comprise administering one or more additional therapeutic agents.

BRIEF DESCRIPTION OF THE FIGURES

FIG. 4 shows the immunogenicity hotspot analysis of the heavy (VH) and light (VK) chains of 7A10. The numbering of the amino acids follows the Kabat convention. The three CDR regions are indicated by the rectangular boxes for each of the two chains, whereas the framework residues are indicated by FW1, FW2 and FW3. The number below each amino acid denotes the proportion of alleles that bind a 15-mer peptide centered at that amino acid. For example, "5" at Y52 in 7A10_VH refers to the 15-mer peptide centered at Y52, i.e., LEWIGYIYYSGRTKY and denotes that (i) this peptide does not have a human germline match (therefore non-self), and (ii) between 50-60% of the 27 alleles show high binding affinity to this peptide. The numbers are assigned a color on a grayscale from light (least likely to be immunogenic) to dark (most likely immunogenic hotspot) which varying degrees of color as seen in the figure. The 3 bold arrows show the choices for the mutant selections: R56S, K58N, T93A.

FIG. 8A shows binding of monomeric wt αSyn to surface captured 7A10 as the lower curve, and enhanced binding of multimeric PFF (upper curve) to 7A10. In particular, the dissociation rate of wt αSyn is very rapid, whereas PFF dissociation is very slow. FIG. 8B shows the same format of data for Antibody 1 (lower curve corresponds to PFF and upper curve to wt αSyn). In contrast to 7A10, Antibody 1 shows no discernible selectivity in binding the wt αSyn versus the PFF form.

FIG. 9A shows avidity-influenced binding kinetics of several concentrations (3-fold dilutions 100 nM to 0.4 nM) of 7A10-IgG1.3f to PFF immobilized on the surface (ka (1/Ms): 5.811E+7, kd (1/s): 0.009834, $K_D$: 1.692E-10 M). FIG. 9B shows same format of data for 7A10-T93A-IgG1.3f (ka (1/Ms): 8.946E+7, kd (1/s): 0.03873, $K_D$: 4.329E-10 M).

FIG. 10G is a graph showing the time-dependent induction of pS129 αSyn (normalized to a 10 nM PFF positive control) following treatment with re-suspended pellet from a MSA brain tissue lysate. Bars from left to right correspond to 7 days after incubation, 14 days after incubation, and 18 days after incubation. FIG. 10H is a graph showing pS129 induction (normalzied to untreated control) and branch points (normalzied to untreated control) 11d post treatment with both 10 nM PFF and MSA brain tissue lysates. The pair of bars presented for each of Control (the pS129 induction bar is absent, given the lack of induction), PFF, and MSA are in the order of pS129 induction and branch points.

Figure 31:
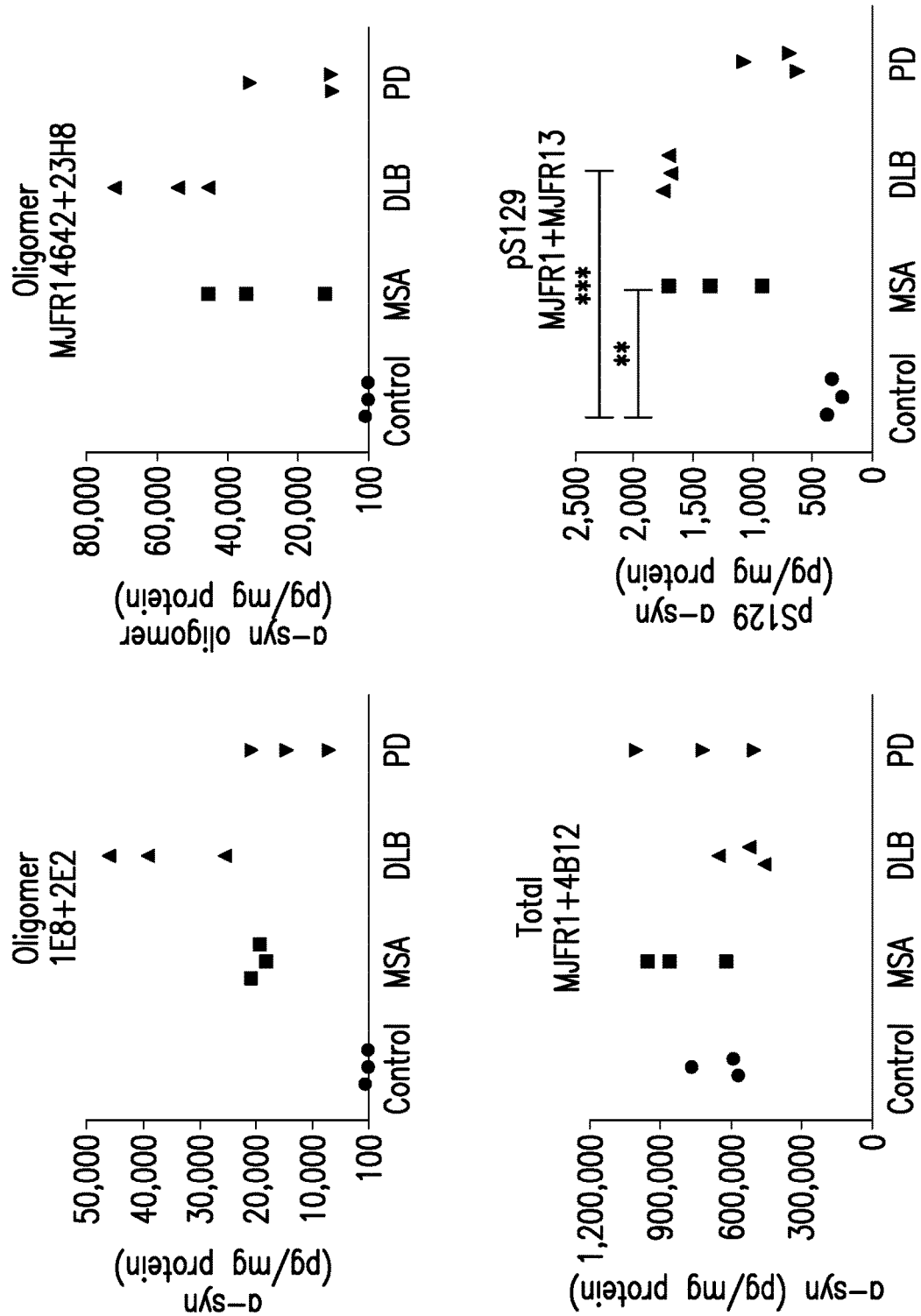

FIG. 31 is a series of graphs showing αSyn levels measured in control, MSA, DLB and PD extracts using 1E8.10+2E2.2 oligomer ELISA, MJFR14642+23H8.G3 oligomer ELISA, MJFR1+4B12 total ELISA and MJFR1+MJFR13 (pS129) ELISA. Capture antibody is the first antibody listed, the detection antibody the second listed. Levels are expressed as αSyn monomer equivalent or pS129 peptide equivalent (MJFR1+MJFR13) normalized to total protein (pg/mg protein). Statistics based on 1-way ANOVA with Dunnett's multiple comparisons relative to the control group. Note that statistics were not performed on oligomer assay results since the majority of control samples were <LLQ. p<0.01, *p<0.001.

Figure 32:
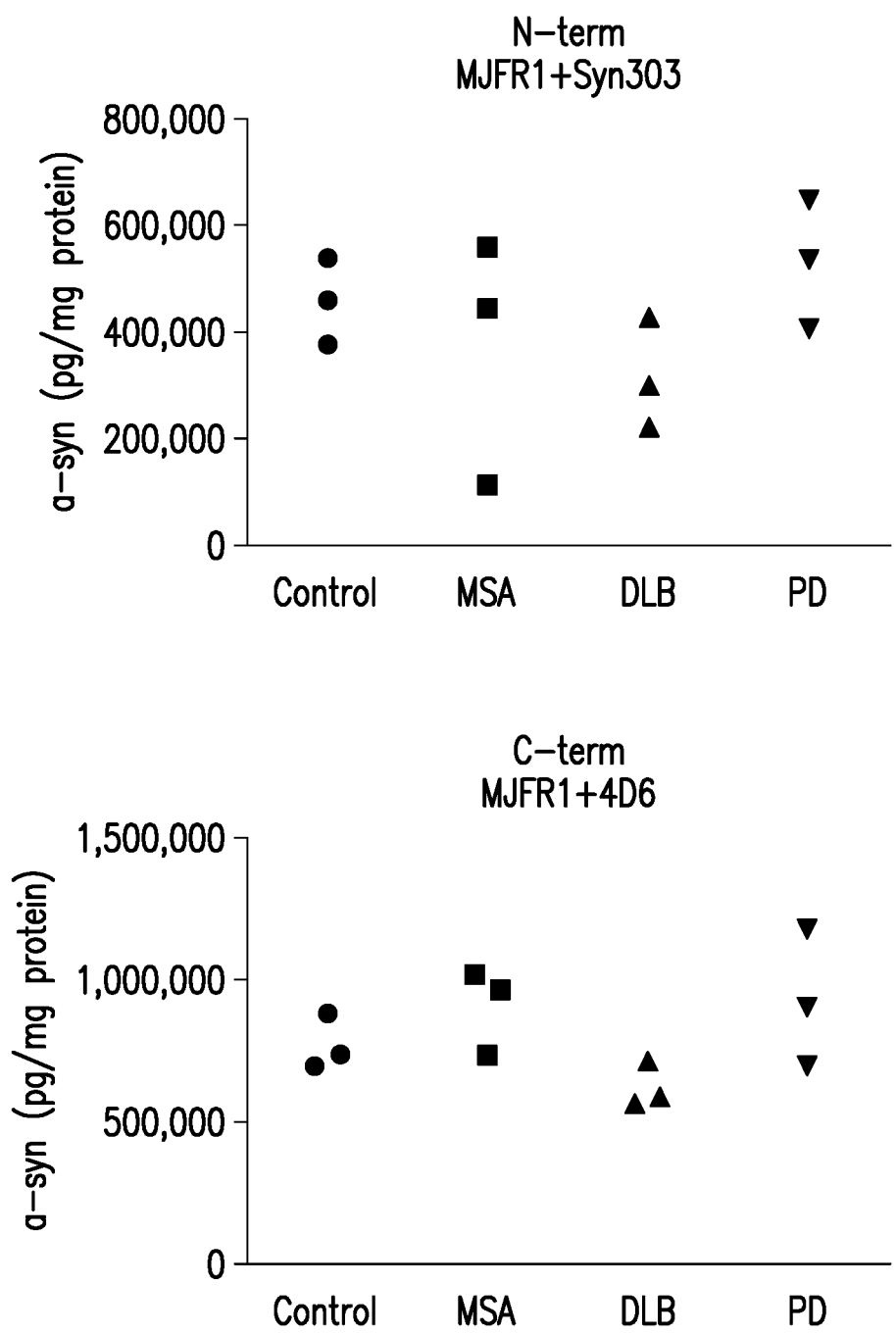

FIG. 32 is a series of graphs showing αSyn levels measured in control, MSA, DLB and PD extracts using, MJFR1+Syn303 N-terminal ELISA and MJFR1+4D6 C-terminal ELISA. Capture antibody is the first antibody listed, the detection antibody the second listed. Levels are expressed as αSyn monomer equivalent normalized to total protein (pg/mg protein). No significant differences were observed (statistics based on 1-way ANOVA with Dunnett's multiple comparisons relative to the control group).

Figure 33:
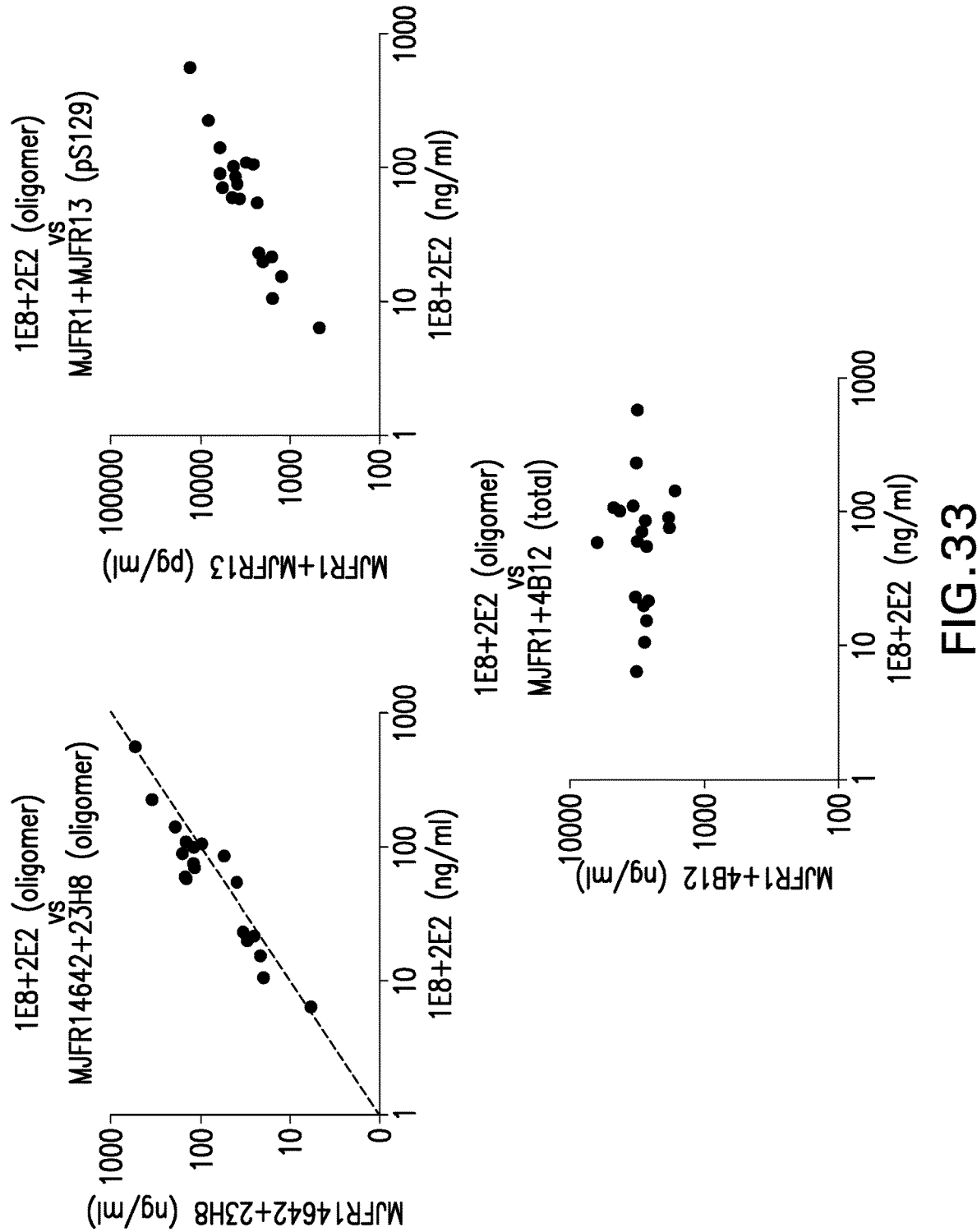

FIG. 33 is a series of graphs showing the correlation of αSyn levels measured in MSA, DLB and PD extracts using 1E8+2E2 oligomer ELISA, MJFR14642+23H8 oligomer ELISA, MJFR1+4B12 total ELISA and MJFR1+MJFR13 (pS129) ELISAs. Capture antibody is the first antibody listed, the detection antibody the second listed. Levels are expressed as αSyn monomer equivalent or pS129 peptide equivalent (MJFR1+MJFR13). Note that units in the 1E8+2E2, MJFR14642+23H8, MJFR1+4B12 assays are expressed as ng/ml. Dashed line represents 1:1 correlation.

Figure 34:
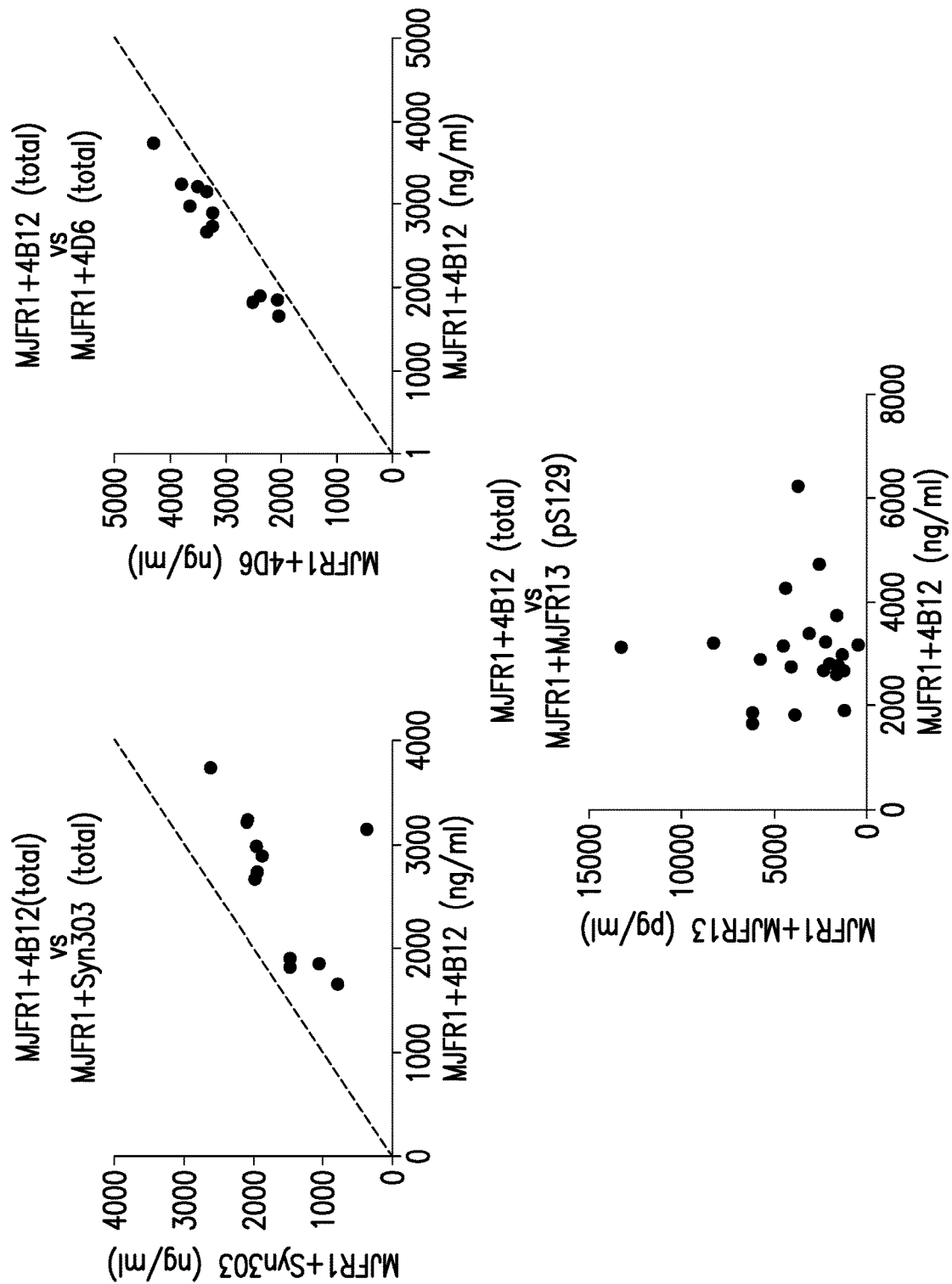

FIG. 34 is a series of graphs showing the correlation of αSyn levels measured in control, MSA, DLB and PD extracts using, MJFR1+4B12 total ELISA, MJFR1+Syn303 N-terminal ELISA, MJFR1+4D6 C-terminal ELISA and MJFR1+MJFR13 (pS129) ELISAs. Capture antibody is the first antibody listed, the detection antibody the second listed. Levels are expressed as αSyn monomer equivalent or pS129 peptide equivalent (MJFR1+MJFR13). Note that units in the MJFR1+4B12, MJFR1+Syn303, MJFR1+4D6 assays are expressed as ng/ml. Dashed line represents 1:1 correlation.

Figure 35:
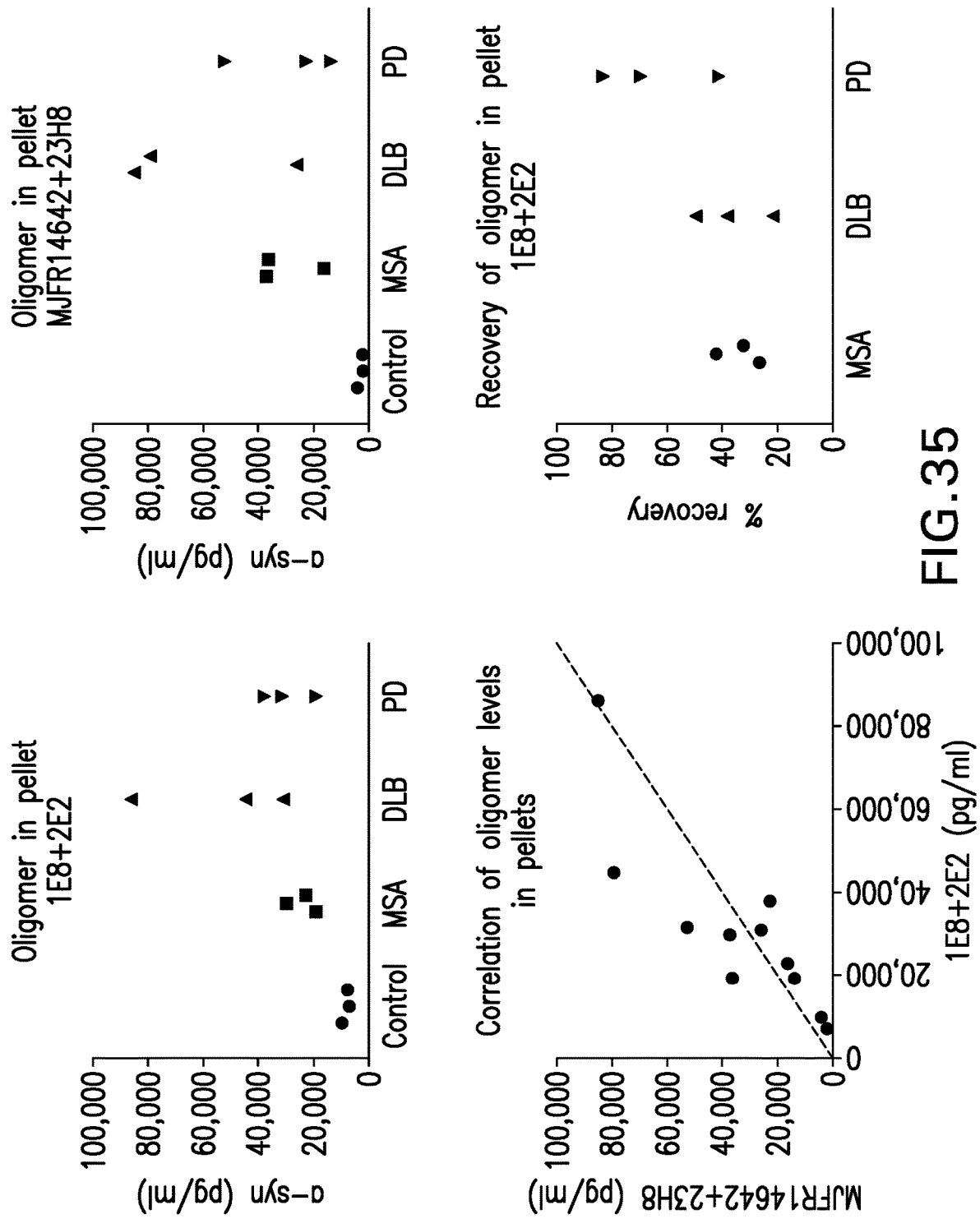

FIG. 35 is a series of graphs showing the detection and recovery of oligomers in high-speed pellets isolated from control, MSA, DLB and PD extracts. Levels are measured using 1E8+2E2 oligomer ELISA and MJFR14642+23H8 oligomer ELISA, and are expressed as αSyn monomer equivalent. Capture antibody is the first antibody listed, the detection antibody the second listed. Dashed line represents 1:1 correlation. % recovery calculated based on starting oligomer levels and is shown for 1E8+2E2 assay.

Figure 36:
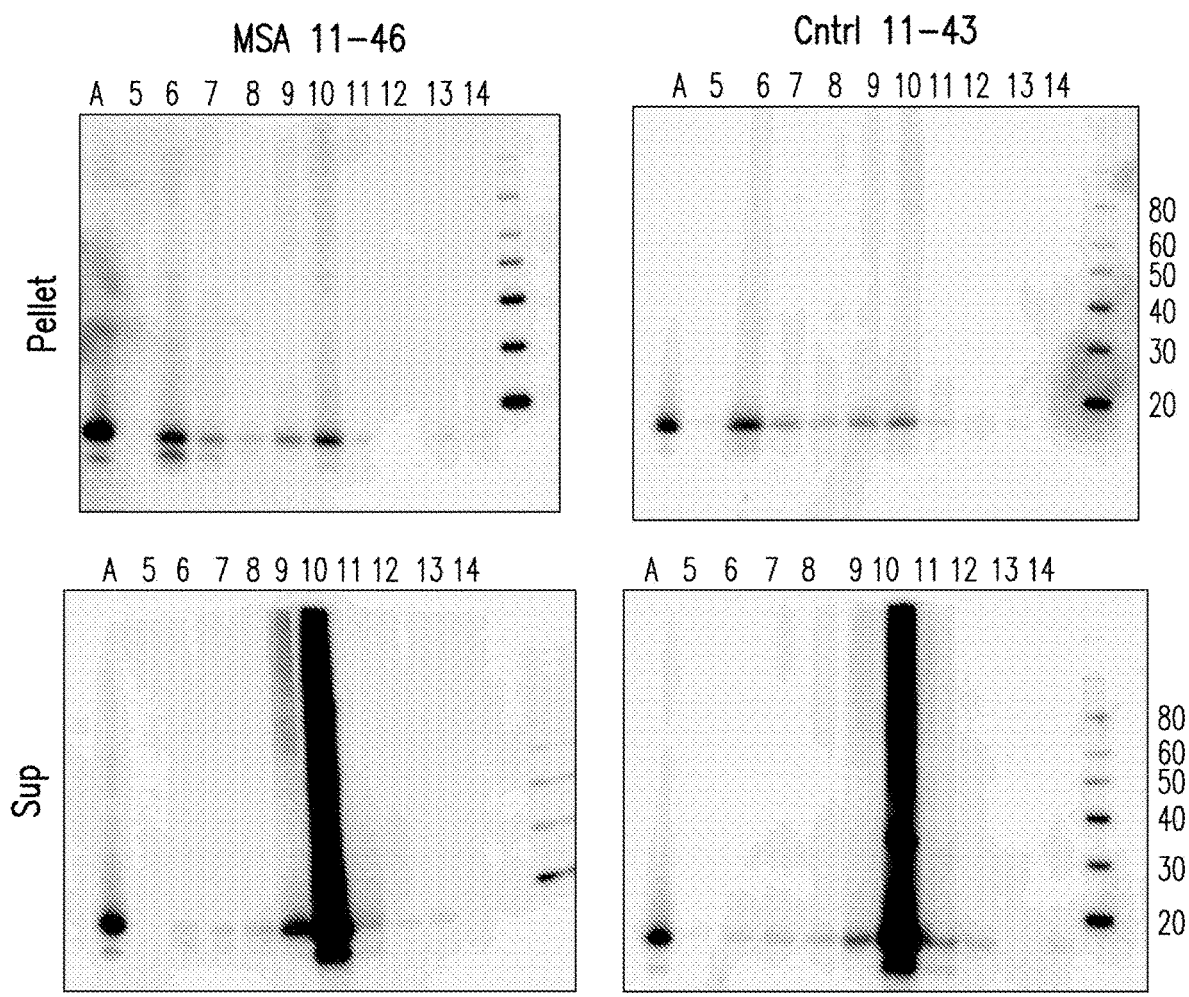
Figure 37:
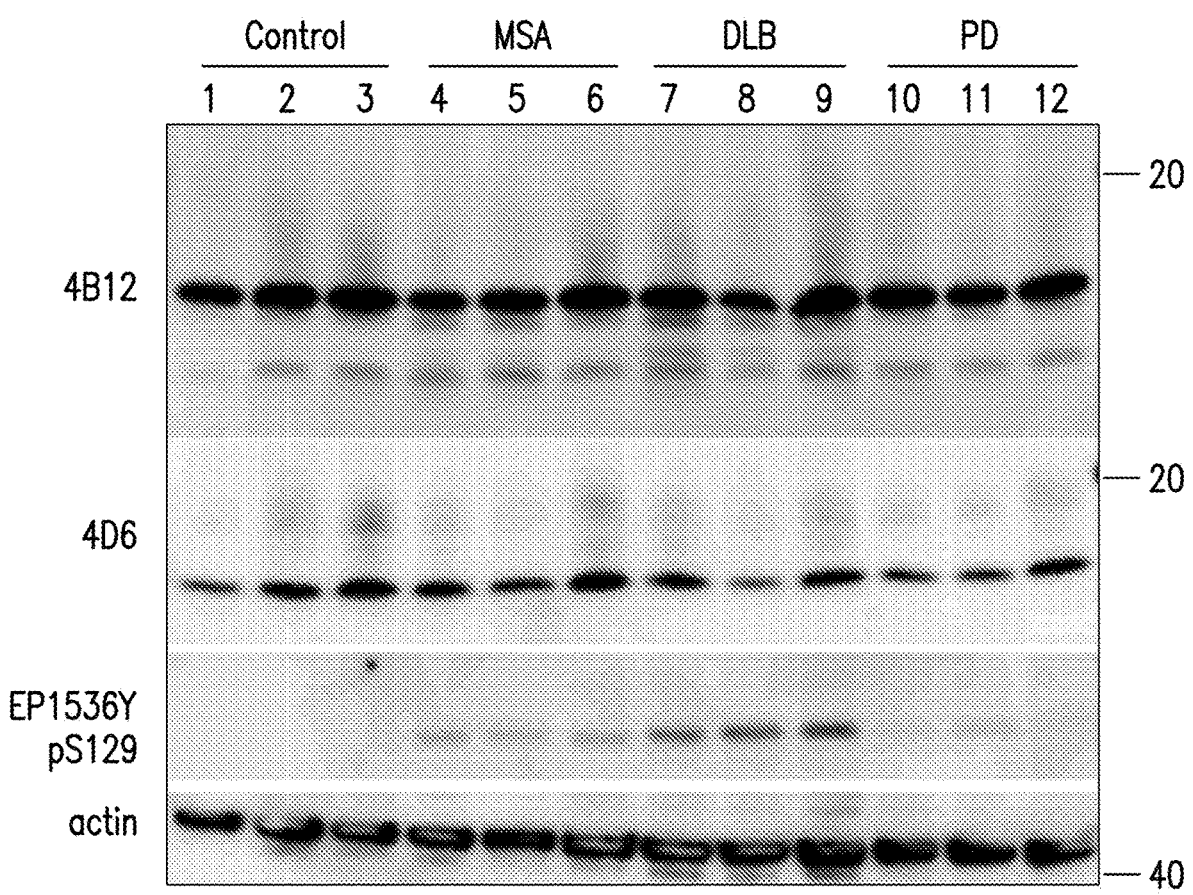

FIG. 36 shows immunoblots of pellet and supernatant (sup) fractions isolated from extracts generated from control subject (11-46) and MSA patient (11-46) brain tissue samples. Brain extracts were subjected to SEC and then fractions 5-14 analyzed by SDS-PAGE/immunoblot. αSyn monomer standard (Lane A) and molecular weight standards were also included on each immunoblot. The majority of αSyn in the supernatant fractions eluted in fraction 10, corresponding to a molecular radius of ~60 kDa, and resolved to a monomer and cleavage fragment by SDS-PAGE/immunoblot. Similar results were observed for both control and MSA samples. The majority of the αSyn in the pellet eluted in the void volume (fraction 6), corresponding to a molecular radius of >670 kDa, resolved into a monomer and cleavage fragment by SDS-PAGE/immunoblot. aSyn antibody 4B12 was used for immunoblot FIG. 37 shows an immunoblot of brain extract pellets isolated from control, MSA, DLB and PD patient brain tissue samples. Results for the <20 kDa molecular weight region are shown. Samples were analyzed using the αSyn antibodies 4B12, 4D6, EP1536Y and an anti-actin antibody control.

Figure 38:
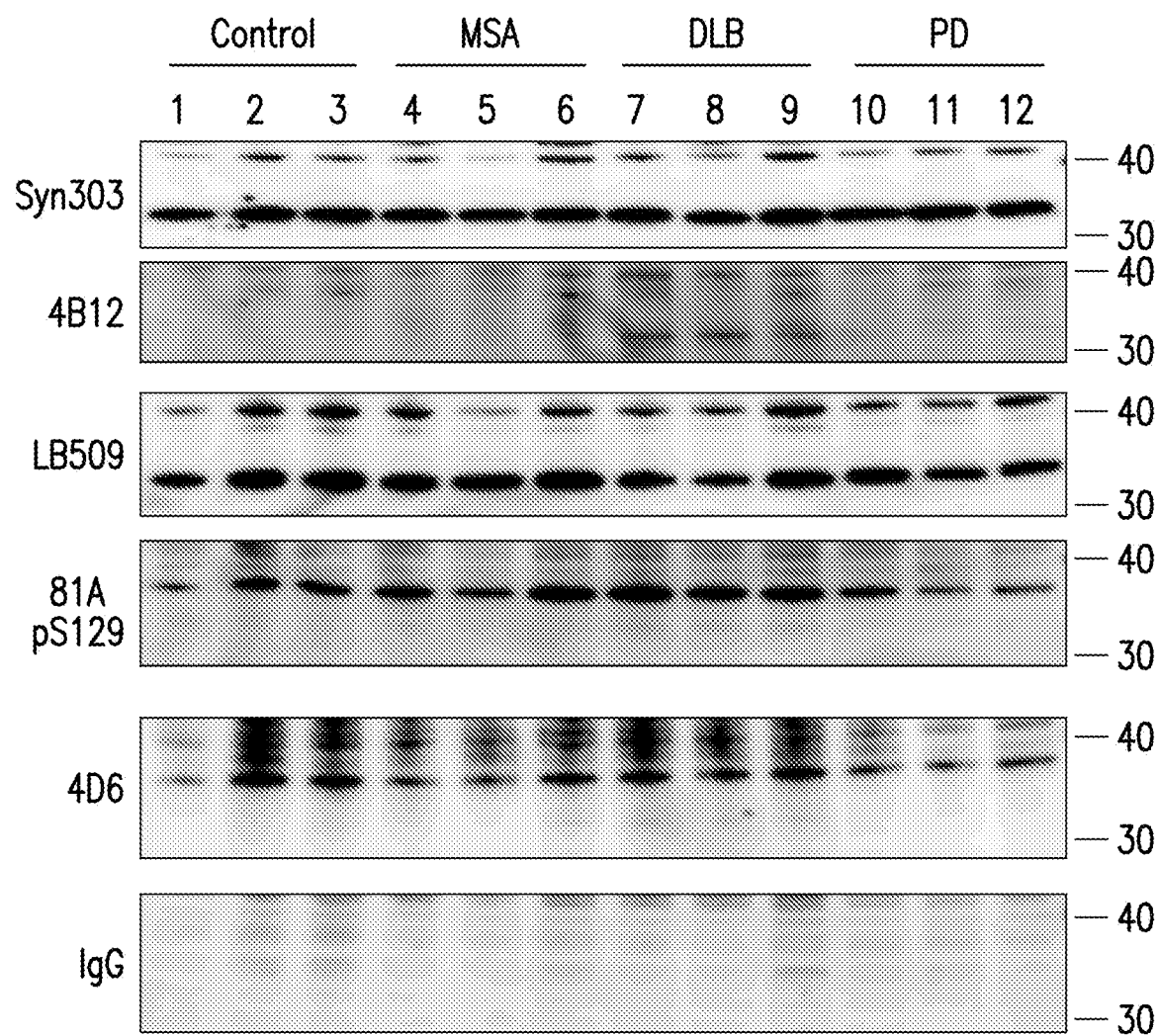

FIG. 38 shows an immunoblot of brain extract pellets isolated from control, MSA, DLB and PD patient brain tissue samples. Results for the 30-40 kDa molecular weight region shown. Samples were analyzed using the αSyn antibodies Syn303, 4B12, LB509, 81A, 4D6 and an IgG antibody control.

Figure 39:
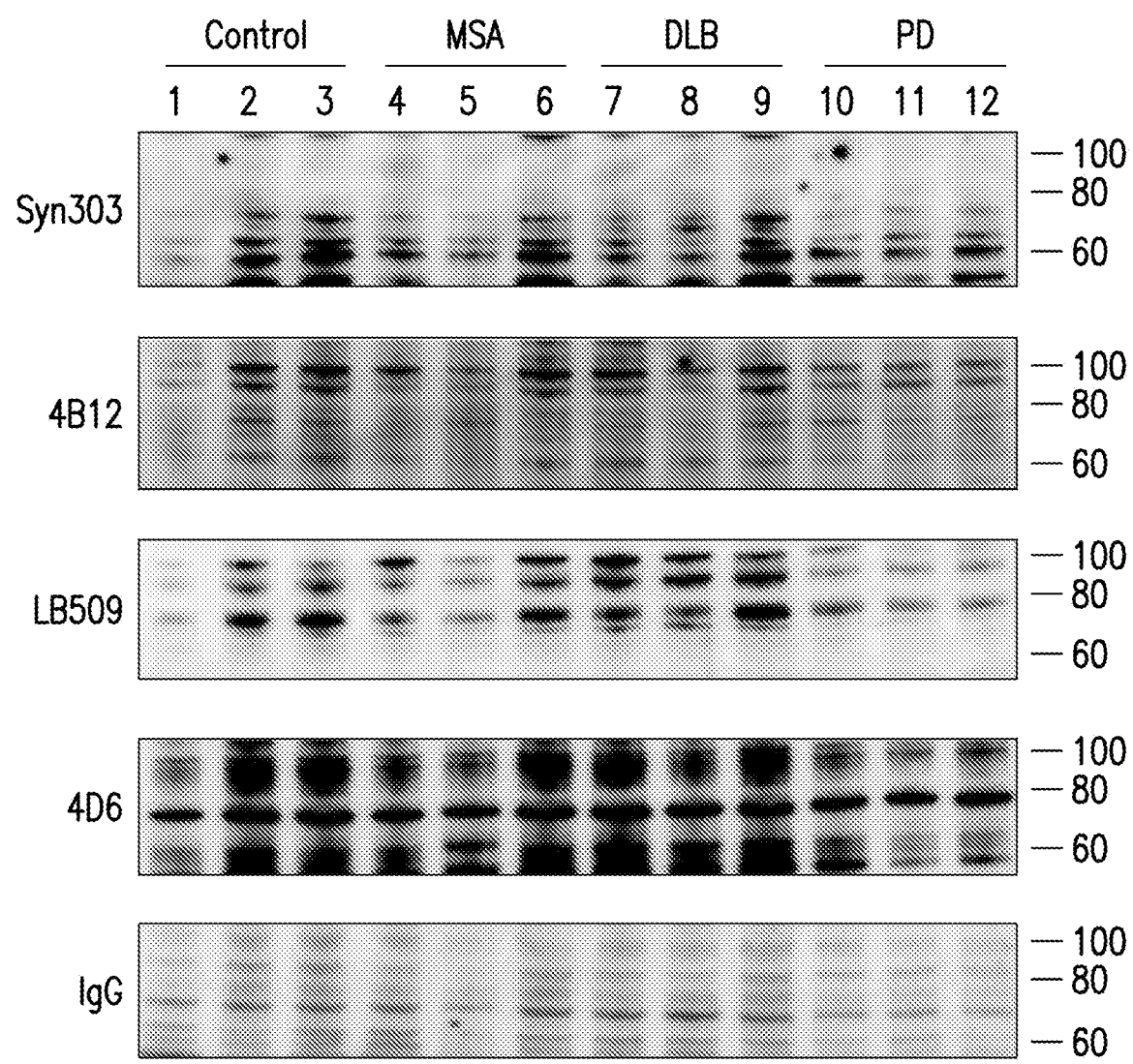

FIG. 39 shows an immunoblot of brain extract pellets isolated from control, MSA, DLB and PD patient brain tissue samples. Results for the 60-100 kDa molecular weight region shown. Samples were analyzed using the αSyn antibodies Syn303, 4B12, LB509, 4D6 and an IgG antibody control.

Figure 40:
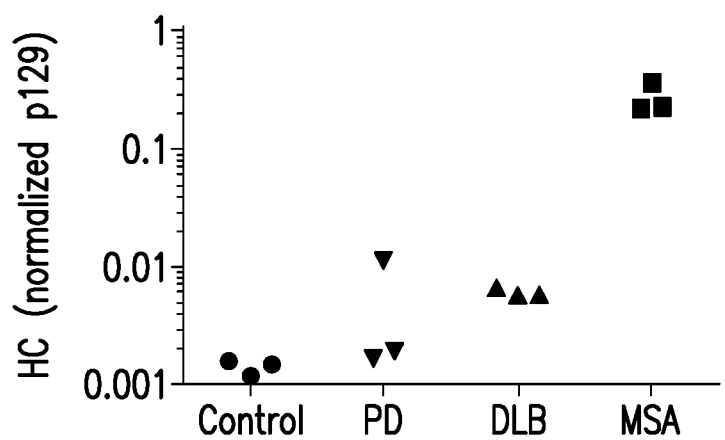
Figure 40:
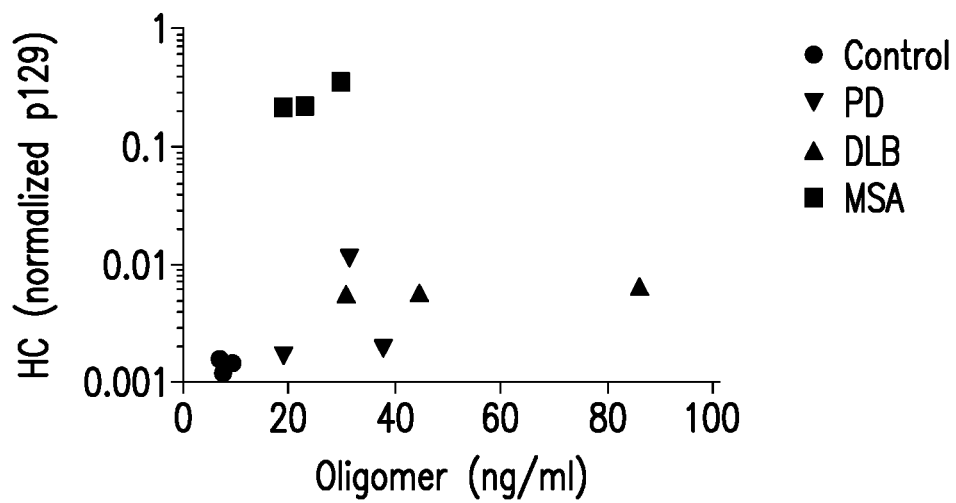

FIG. 40 is a series of graphs showing induction of pS129 αSyn in transduced (AAV-hA53T-αSyn 3K MOI) primary rat hippocampal neurons. Neurons were treated with brain extract pellets from control, PD, DLB and MSA brain extracts for 11 days prior to extraction and fixation. Insoluble pS129 signal was measured by high content (HC) analysis and normalized to PFF treatment control (10 nM). HC signal detected with control extract pellets was similar to background signal. The level of HC signal for each pellet was correlated with the oligomer signal as measured using 1E8+2E2 ELISA. Levels are expressed as αSyn monomer equivalent.

Figure 41:
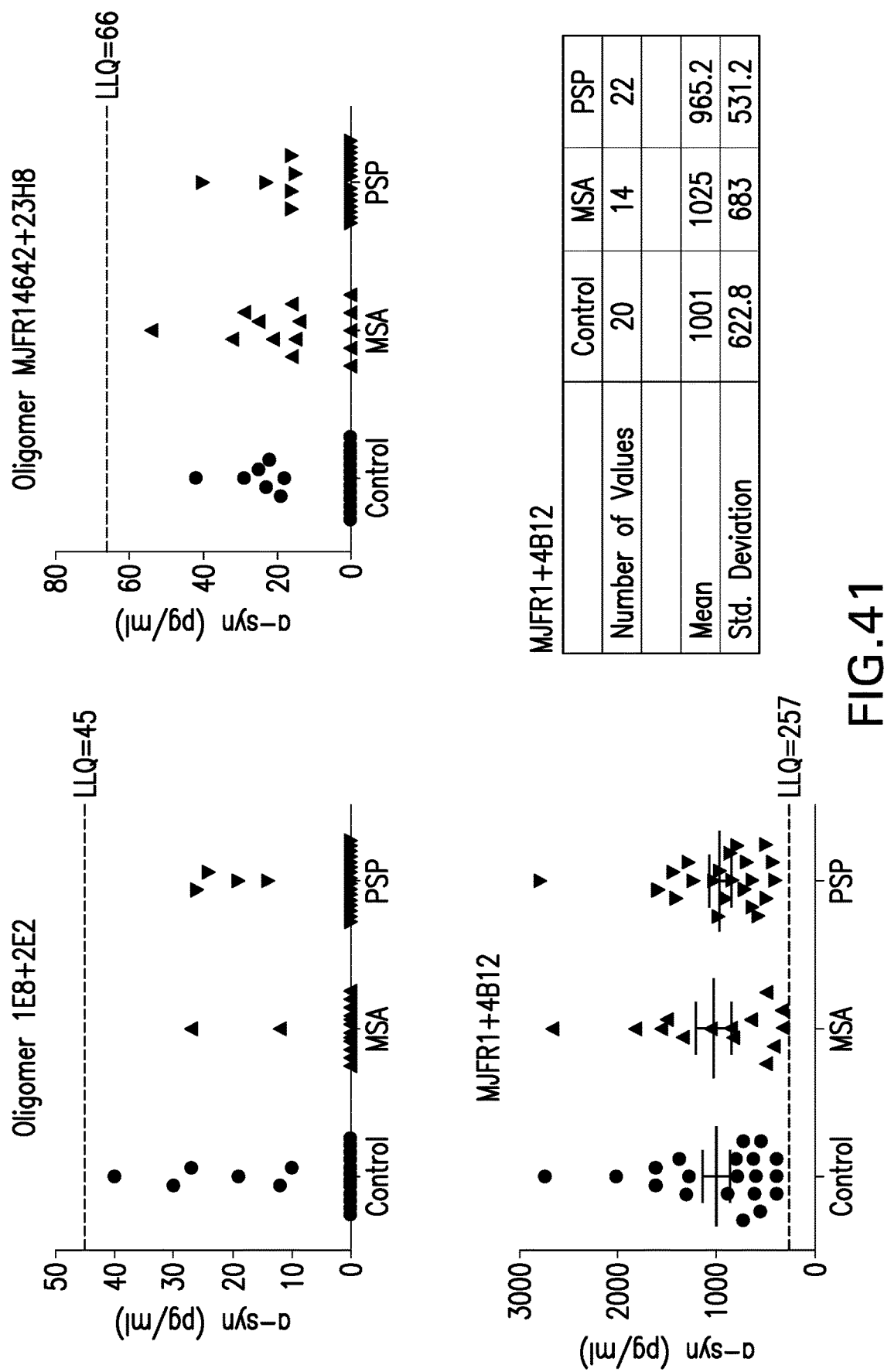

FIG. 41 is a series of graphs showing aSyn oligomer (1E8+2E2 and MJFR14642+23H8) and total aSyn (MJFR1+4B12) levels from human CSF samples from MSA, progressive supranuclear palsy (PSP) and healthy controls. Capture antibody is the first antibody listed, the detection antibody the second listed. CSF was diluted 4-fold (1E8+2E2 and MJFR14642+23H8) and 20-fold (MJFR1+4B12) prior to analysis. Data expressed as dilution corrected and αSyn monomer equivalent (pg/ml). LLQ defined as 2× assay background and dilution corrected LLQ indicated for each assay. Mean and SD for MJFR1+4B12 levels shown in the table.

Figure 42:
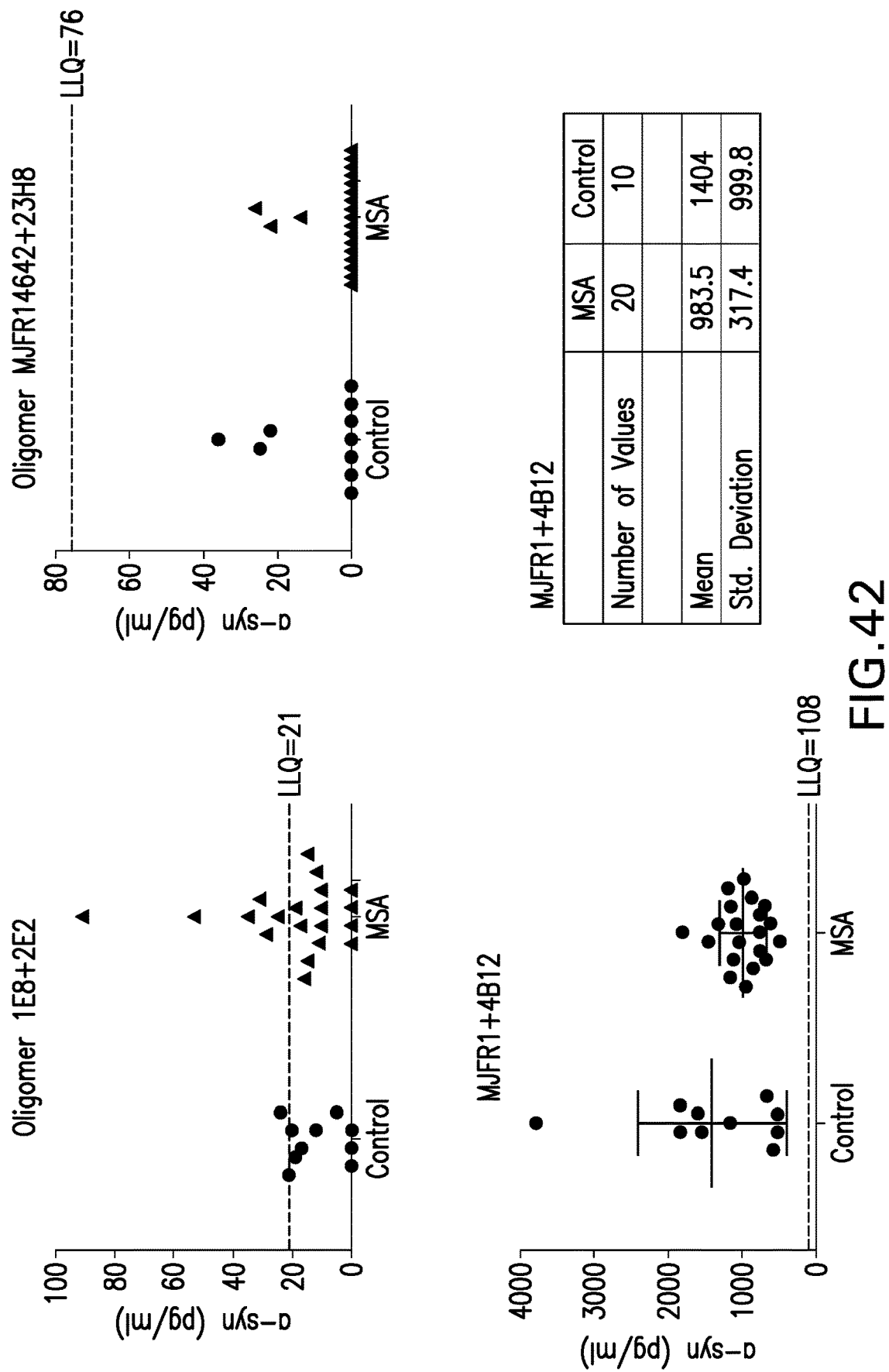

FIG. 42 is a series of graphs showing aSyn oligomer (1E8+2E2 and MJFR14642+23H8) and total aSyn (MJFR1+4B12) levels from human CSF samples from MSA and healthy controls. CSF was diluted 4-fold (1E8+2E2 and MJFR14642+23H8) and 20-fold (MJFR1+4B12) prior to analysis. Data expressed as dilution corrected and αSyn monomer equivalent (pg/ml). LLQ defined as 2× assay background and dilution corrected LLQ indicated for each assay. Mean and SD for MJFR1+4B12 levels shown in the table.

DETAILED DESCRIPTION

Described herein are isolated antibodies, particularly monoclonal antibodies, e.g., human moncloncal antibodies, which preferentially bind to oligomeric α-synuclein over monomeric α-synuclein. In certain embodiments, the antibodies described herein are derived from particular heavy and light chain germline sequences and/or comprise particular structural features such as CDR regions comprising particular amino acid sequences. Provided herein are isolated antibodies, methods of making such antibodies, immunoconjugates, and bispecific molecules comprising such antibodies, and pharmaceutical compositions formulated to contain the antibodies. Also provided herein are methods of using the antibodies to inhibit the generation of insoluble aggregates of α-synuclein. Accordingly, the α-synuclein antibodies described herein may be used in a treatment in a wide variety of therapeutic applications, including, for example, the treatment of Lewy body diseases and synucleinopathies, and diagnostic assays.

Definitions

In order that the present description may be more readily understood, certain terms are first defined. Additional definitions are set forth throughout the detailed description.

The terms "α-synuclein" and "αSyn" are used interchangeably herein and refer to a 140 amino acid polypeptide with the following amino acid sequence (wild-type human α-synuclein):

```
       (SEQ ID NO: 1; GenBank Accession No. P37840)
MDVFMKGLSKAICEGVVAAAEKTKQGVAEAAGKTKEGVLYVGSKT

KEGVVHGVATVAEKTKEQVTNVGGAVVTGVTAVAQKTVEGAGSIA

AATGFVICKDQLGKNEEGAPQEGILEDMPVDPDNEAYEMPSEEGY

QDYEPEA
```

The protein has three recognized domains, a KTKE repeat domain covering amino acids 1-61, a NAC (Non-amyloid component) domain running from about amino acids 60-95, and a C-terminal acidic domain running from about amino acid 98 to 140. Unless specified otherwise, α-synuclein or its fragments includes the natural human wildtype amino acid sequence above and allelic variants thereof. For example, also encompassed are variants associated with Lewy body disease (e.g., E46K, A30P and A53T). The induced mutations E83Q, A90V, A76T, which enhance α-synuclein aggregation, can also be present individually or in combination with each other and/or human allelic variants E46K, A30P and A53T.

As used herein, "synucleinopathy" refers to neurodegenerative disorders characterized by the presence of abnormal, accumulation of α-synuclein aggregates in neurons and glia, and include, for example, Parkinson's Disease (PD), PD with Demenita (PDD), Dementia with Lewy Bodies (DLB), Multiple System Atrophy (MSA), Gaucher's disease (GD), neurodegeneration with brain iron accumulation (NBIA), Alzheimer's disease (AD), and lysosomal storage disorders (LSD) including Sanfilippo syndrome, Hunter's syndrome, Tay-Sachs and Sandhoff disease and Niemann-Pick type C. Accumulations of α-synuclein aggregates found in the cell bodies or neurites of neurons are called Lewy Bodies and Lewy Neurites, respectively, and are the pathological hallmarks of PD and DLB. The presence of glial cyoplasmic inclusions of α-synuclein (GCIs) found in oligodendrocytes is the pathological hallmark of MSA.

"Multiple system atrophy" or "MSA" is a neurodegenerative disease marked by a combination of symptoms; affecting movement, blood pressure, and other body functions. Symptoms of MSA vary in distribution of onset and severity from person to person. Because of this, three different diseases were initially described to accomplish this range of symptoms; Shy-Drager syndrome, striatonigral degeneration (SD), and olivopontocerebellar atrophy (OPCA).

As used herein, the term "α-synuclein oligomer" refers to an aggregate of two or more α-synuclein monomers, and can have a range of molecular weights. In general oligomers are understood to be a soluble species of aggregates compared to less soluble fibrils. Soluble oligomers are believed to comprise in part the so-called "transmissible species" of α-synuclein responsible for cell-to-cell propagation of α-synuclein pathology. Unless specified otherwise, "pre-formed fibrils" or "PFF" is a species of α-synuclein oligomers, for example, α-synuclein oligomers prepared as described in Example 3. PFF are understood to be manufactured from recombinant human monomeric α-synuclein under conditions that favor aggregation and fibrillization.

As used herein, "monomer/PFF binding ratio" refers to the ratio of binding affinity of anti-α-synuclein antibodies for α-synuclein monomers to the binding affinity of the antibodies to PFF. Ratios greater than 1 indicate a greater preference for binding to PFF than monomeric α-synuclein. For example, if an antibody binds to monomeric α-synuclein with an EC50 of 291 nM and PFF with an $EC_{50}$ of 0.16 nM using, e.g., the ELISA described in Example 3, the monomer/PFF binding ratio of that antibody would be 291/0.16=1819. In some embodiments, assays other than ELISA can be used to generate a monomer/PFF binding ratio. In some embodiments, PFF is prepared using the method described in Example 3. In some embodiments, α-synuclein oligomers other than PFF are used to generate a ratio of monomer to oligomer binding affinity.

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen (e.g., human α-synuclein). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The term "monoclonal antibody," as used herein, refers to an antibody that displays a single binding specificity and affinity for a particular epitope or a composition of antibodies in which antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al. (2009) mAbs 1:1). Antibodies described herein may be of any allotype. As used herein, antibodies referred to as "IgG1f" or "IgG1.3f" isotype are IgG1 and effectorless IgG1.3 antibodies, respectively, of the allotype "f," i.e., having L234A, L235E, and G237A according to the EU index as in Kabat, as shown, e.g., in SEQ ID NO: 119.

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to α-synuclein is substantially free of antibodies that specifically bind antigens other than α-synuclein). An isolated antibody that specifically binds to an epitope of α-synuclein may, however, have cross-reactivity to other α-synuclein proteins from different species (e.g., α-synuclein from mouse or rat).

An "effector function" refers to the interaction of an antibody Fc region with an Fc receptor or ligand, or a biochemical event that results therefrom. Exemplary "effector functions" include Clq binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (Clq) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second ($C_{H2}$) and third ($C_{H3}$) constant domains of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

The term "epitope" or "antigenic determinant" refers to a site on an antigen to which an immunoglobulin or antibody specifically binds. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides are tested for reactivity with a given antibody. Methods of determining spatial conformation of epitopes include techniques in the art and those described herein, for example, x-ray crystallography, 2-dimensional nuclear magnetic resonance and HDX-MS (see, e.g., *Epitope Mapping Protocols in Methods in Molecular Biology*, Vol. 66, G. E. Morris, Ed. (1996)).

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on α-synuclein" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope, or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 instrument using the predetermined antigen as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system or flow cytometry and Scatchard analysis.

The term "EC50" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or disulfide bond formation. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" of the sequences set forth herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-α-synuclein antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIQS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the) (BLAST program, score=50, wordlength=3 to obtain amino acid sequences homologous to the protein molecules described herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be α-synuclein or a fragment thereof.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

As used herein, the term "subject" includes any human or non-human animal. For example, the methods and compositions described herein can be used to treat a subject having a disease characterized by the presence of Lewy bodies or aggregated α-synuclein in the brain.

The term "patient" includes human and other mammalian subjects that receive either prophylactic or therapeutic treatment.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to a subjective evidence of a disease, such as altered gait, as perceived by the patient. A "sign" refers to objective evidence of a disease as observed by a physician.

Statistical significance means p≤0.05.

The term "sample" refers to tissue, body fluid, or a cell (or a fraction of any of the foregoing) taken from a patient or a subject. Normally, the tissue or cell will be removed from the patient, but in vivo diagnosis is also contemplated.

As used herein, the term "about" means plus or minus 10% of a specified value.

As used herein, the term "and/or" includes any and all combinations of one or more of the associated listed items.

As used in the description of the invention and the appended claims, the singular forms "a," "an" and "the" are intended to include the plural forms as well, unless the context clearly indicates otherwise.

Various aspects of the disclosure are described in further detail in the following subsections.

I. Anti-α-synuclein (αSyn) Antibodies

Described herein are antibodies, e.g., isolated antibodies, e.g., fully human isolated antibodies, which are characterized by particular functional features or properties. For example, the antibodies specifically bind to human α-synuclein, i.e., both monomeric human α-synuclein and oligomeric human α-synuclein. Additionally, antibodies may cross react with α-synuclein from one or more non-human species, such as mouse or rat α-synuclein, or different isoforms of synuclein, such as β-synuclein and γ-synuclein.

Accordingly, the anti-α-synuclein antibodies described herein exhibit one or more of the following functional properties:

(a) binds to mouse and rat α-synuclein;
(b) binds to β-synuclein and γ-synuclein;
(c) has a greater affinity for α-synuclein oligomers (e.g., PFF) over α-synuclein monomers;
(d) inhibits the generation of α-synuclein oligomer (e.g., PFF)-induced soluble or insoluble α-synuclein aggregates (e.g., serine-129 phosphorylated α-synuclein aggregates);
(e) depletes the molecular species that produces soluble or insoluble α-synuclein aggregates (e.g., serine-129 phosphorylated α-synuclein aggregates) from PFF and/or brain lysate prepared from patients with pathological aggregates of α-synuclein in the brain;
(f) binds to all or a portion of amino acid positions 123-128 of human α-synuclein (SEQ ID NO: 1);
(g) binds to all or a portion of amino acid positions 125-128 of human α-synuclein (SEQ ID NO: 1);
(h) binds to all or a portion of amino acid positions 130-139 of human α-synuclein (SEQ ID NO: 1);
(i) binds to all or a portion of amino acid positions 119-126 of human α-synuclein (SEQ ID NO: 1); and
(j) binds to all or a portion of amino acid positions 130-138 of human α-synuclein (SEQ ID NO: 1).

In some embodiments, the α-synuclein oligomer is PFF. In some embodiments, PFF is prepared using the method described in Example 3. In some embodiments, the α-synuclein oligomer is soluble. In other embodiments, the α-synuclein oligomer is insoluble. In some embodiments, the antibodies inhibit the generation of insoluble or soluble serine-129 phosphorylated α-synuclein aggregates. In other embodiments, the antibodies inhibit the generation of insoluble or soluble α-synuclein aggregates that do not contain serine-129 phosphorylated α-synuclein.

In some embodiments, the anti-α-synuclein antibodies described herein preferentially bind to α-synuclein oligomers (e.g., PFF) over α-synuclein monomers, which can be presented as a ratio of binding affinity for α-synuclein monomers to the binding affinity for α-synuclein oligomers (e.g., PFF), also referred to herein as α-synuclein monomer/α-synuclein oligomer binding ratio. When PFF is the α-synuclein oligomer species, the ratio is referred to as α-synuclein monomer/PFF binding ratio, or "M/P ratio," and can be determined as described in Example 3.

In some embodiments, the anti-α-synuclein antibodies described herein have an M/P ratio of 10 or greater, 20 or greater, 30 or greater, 40 or greater, 50 or greater, 75 or greater 100 or greater, 150 or greater 200 or greater, 250 or greater, 300 or greater, 350 or greater, 400 or greater, 450 or greater, 500 or greater, 600 or greater, 700 or greater, 800 or greater, 900 or greater, 1000 or greater, 1500 or greater, 2000 or greater, 2500 or greater, 3000 or greater, 3500 or greater, 4000 or greater, 5000 or greater, 6000 or greater, 7000 or greater, 8000 or greater, 9000 or greater, 10000 or greater, 10 to 10000, 50 to 10000, 100 to 10000, 500 to 10000, 700 to 10000, 1500 to 10000, 3000 to 10000, 5000 to 10000, 7000 to 10000, 100 to 7000, 500 to 7000, 700 to 7000, 1500 to 7000, 3000 to 7000, 5000 to 7000, 100 to 5000, 500 to 5000, 700 to 5000, 700 to 1500, 700 to 3000, 700 to 5000, 100 to 3000, 500 to 3000, 700 to 3000, 1500 to 3000, 100 to 1500, 500 to 1500, 700 to 1500, 100 to 700, 500 to 700, or 100 to 500. In some embodiments, the binding affinities of the antibodies for monomeric and oligomeric α-synuclein are determined using ELISA, e.g., as described in Example 3, to calculate the M/P ratio.

In some embodiments, the anti-α-synuclein antibodies bind to monomeric α-synuclein with an $EC_{50}$ of 100 nM or greater, and binds to PFF with an $EC_{50}$ of 2 nM or less. In some embodiments, the anti-α-synuclein antibodies bind to monomeric α-synuclein with an EC50 of 500 nM or greater, and binds to PFF with an $EC_{50}$ of 1 nM or less. In some embodiments, the anti-α-synuclein antibodies bind to monomeric α-synuclein with an $EC_{50}$ of 500 nM or greater, and binds to PFF with an $EC_{50}$ of 0.5 nM or less. In some embodiments, the anti-α-synuclein antibodies bind to monomeric α-synuclein with an $EC_{50}$ of 500 nM or greater, and binds to PFF with an $EC_{50}$ of 0.3 nM or less. In some embodiments, the anti-α-synuclein antibodies bind to monomeric α-synuclein with an $EC_{50}$ of 500 nM or greater, and binds to PFF with an $EC_{50}$ of 0.2 nM or less. In some embodiments, the anti-α-synuclein antibodies bind to monomeric α-synuclein with an $EC_{50}$ of 700 nM or greater, and binds to PFF with an $EC_{50}$ of 1 nM or less. In some embodiments, the anti-α-synuclein antibodies bind to monomeric α-synuclein with an $EC_{50}$ of 700 nM or greater, and binds to PFF with an $EC_{50}$ of 0.5 nM or less. In some embodiments, the anti-α-synuclein antibodies bind to monomeric α-synuclein with an $EC_{50}$ of 700 nM or greater, and binds to PFF with an $EC_{50}$ of 0.3 nM or less. In some embodiments, the anti-α-synuclein antibodies bind to monomeric α-synuclein with an EC50 of 700 nM or greater, and binds to PFF with an $EC_{50}$ of 0.2 nM or less. In some embodiments, the $EC_{50}$ values for oligomeric and monomeric α-synuclein are determined using ELISA, for example, as described in Example 3.

In some embodiments, the anti-α-synuclein antibodies described herein bind to oligomeric α-synuclein, e.g., PFF (e.g., PFF prepared as described in Example 3), with an $EC_{50}$ of 50 nM or less, 40 nM or less, 30 nM or less, 20 nM or less, 10 nM or less, 5 nM or less, 4 nM or less, 3 nM or less, 2 nM or less, 1 nM or less, 0.9 nM or less, 0.8 nM or less, 0.7 nM or less, 0.6 nM or less, 0.5 nM or less, 0.4 nM or less, 0.3 nM or less, 0.2 nM or less, 0.1 nM or less, 0.07 nM or less, 0.05 nM or less, 0.03 nM or less, or 0.01 or less, as determined by ELISA, for example, as described in Example 3.

In some embodiments, the anti-α-synuclein antibodies described herein may inhibit the generation of PFF-induced insoluble α-synuclein aggregates (e.g., serine-129 phosphorylated α-synuclein aggregates). Accordingly, in some embodiments, the antibodies inhibit PFF-induced α-synuclein serine-129 phosphorylation with an IC50 of 0.2 nM or less, 0.15 nM or less, 0.1 nM or less, 0.09 nM or less, 0.08 nM or less, 0.07 nM or less, 0.06 nM or less, 0.05 nM or less, 0.04 nM or less, 0.03 nM or less, 0.02 nM or less, 0.01 nM or less, or 0.005 nM or less, as assessed using, e.g., the high content immunofluorescence assay described in Example 10.

In some embodiments, the anti-α-synuclein antibodies described herein may deplete α-synuclein serine-129 phosphorylation inducing activity of PFF and/or brain lysate prepared from patients with Lewy bodies or α-synuclein aggregation in the brain.

In some embodiments, the anti-α-synuclein antibodies described herein may bind to an epitope at the C-terminal region of α-synuclein. For instance, anti-α-synuclein antibodies may bind to all or a portion of amino acids 123-128 of human α-synuclein (SEQ ID NO: 1), as determined, e.g., by binding of the antibodies to overlapping peptides of human α-synuclein (see Example 2). In another embodiment, the anti-α-synuclein antibodies may bind to all or a portion of amino acids 125-128 of human α-synuclein (SEQ ID NO: 1), as determined, e.g., by binding of the antibodies to overlapping peptides of human α-synuclein (see Example 2). In another embodiment, the anti-α-synuclein antibodies may bind to all or a portion of amino acids 130-139 of human α-synuclein (SEQ ID NO: 1), as determined, e.g., by binding of the antibodies to overlapping peptides of human α-synuclein (see Example 2). In another embodiment, the anti-α-synuclein antibodies may bind to all or a portion of amino acids 119-126 of human α-synuclein (SEQ ID NO: 1), as determined, e.g., by binding of the antibodies to overlapping peptides of human α-synuclein (see Example 2). In another embodiment, the anti-α-synuclein antibodies may bind to all or a portion of amino acids 130-138 of human α-synuclein (SEQ ID NO: 1), as determined, e.g., by binding of the antibodies to overlapping peptides of human α-synuclein (see Example 2).

An antibody that exhibits one or more of the functional properties described above (e.g., biochemical, immunochemical, cellular, physiological or other biological activities, or the like) as determined according to methodologies known in the art and described herein, will be understood to relate to a statistically significant difference in the particular activity relative to that seen in the absence of the antibody (e.g., or when a control antibody of irrelevant specificity is present). Preferably, the anti-α-synuclein antibody-induced increases in a measured parameter is an increase by at least 10%, more preferably by at least 20%, 30%, 40%, 50%, 60%, 70%, 80%, 90%, 95%, or 100% (i.e., 2 fold), 3 fold, 5 fold or 10 fold. Conversely, anti-α-synuclein antibody-induced decreases in a measured parameter is a decrease by at least 10%, 20%, 30%, 40%, 50%, 60%, 70%, 80%, 90%, 95%, 97%, 98%, 99%, or 100%.

Standard assays to evaluate the binding ability of the antibodies toward α-synuclein (e.g., monomeric α-synuclein and oligomeric α-synuclein) are known in the art, including for example, ELISAs, Western blots, and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of α-synuclein are described in further detail infra and in the Examples.

In certain embodiments, the α-synuclein antibodies described herein are not native antibodies or are not naturally-occurring antibodies.

II. Exemplary Anti-α-Synuclein (αSyn) Antibodies

Particular antibodies described herein are antibodies, e.g., monoclonal antibodies, having the CDR and/or variable region sequences of antibodies 7A10, 7A10-T93A, 11H11 (11H11-1 and 11H11-2), 15A5, 21A3, 36A3, 44B11, 2E2, 23H8 (23H8-1, 23H8-2, 23H8-3), and 1E8, isolated and structurally characterized as described in Example 1, as well as antibodies having at least 80% identity (e.g., at least 85%, at least 90%, at least 95%, or at least 99% identity) to their variable region or CDR sequences. The $V_H$ amino acid sequences of 7A10, 7A10-T93A, 11H11 (11H11-1 and 11H11-2), 15A5, 21A3, 36A3, 44B11, 2E2, 23H8, and 1E8 are set forth in SEQ ID NOs: 8, 18, 31, 43, 53, 63, 73, 83, 99, and 113, respectively. The $V_L$ amino acid sequences of 7A10, 7A10-T93A, 11H11-1, 11H11-2, 15A5, 21A3, 36A3, 44B11, 2E2, 23H8-1, 23H8-2, 23H8-3, and 1E8 are set forth in SEQ ID NOs: 9, 19, 32, 33, 44, 54, 64, 74, 84, 100, 101, 102, and 114, respectively.

Accordingly, provided herein are isolated antibodies, or antigen binding portion thereof, comprising heavy and light chain variable regions, wherein the heavy chain variable region comprises an amino acid sequence selected from the group consisting of SEQ ID NOs: 8, 18, 31, 43, 53, 63, 73, 83, 99, and 113.

Also provided are isolated antibodies, or antigen binding portions thereof, comprising heavy and light chain variable regions, wherein the light chain variable region comprises an amino acid sequence selected from the group consisting of SEQ ID NOs: 9, 19, 32, 33, 44, 54, 64, 74, 84, 100, 101, 102, and 114.

Also provided herein are isolated antibodies, or antigen-binding portion thereof, comprising:
(a) heavy and light chain variable region sequences comprising SEQ ID NOs: 8 and 9, respectively;
(b) heavy and light chain variable region sequences comprising SEQ ID NOs: 18 and 19, respectively;
(c) heavy and light chain variable region sequences comprising SEQ ID NOs: 31 and 32, respectively;
(d) heavy and light chain variable region sequences comprising SEQ ID NOs: 31 and 33, respectively;
(e) heavy and light chain variable region sequences comprising SEQ ID NOs: 43 and 44, respectively;
(f) heavy and light chain variable region sequences comprising SEQ ID NOs: 53 and 54, respectively;
(g) heavy and light chain variable region sequences comprising SEQ ID NOs: 63 and 64, respectively;
(h) heavy and light chain variable region sequences comprising SEQ ID NOs: 73 and 74, respectively;
(i) heavy and light chain variable region sequences comprising SEQ ID NOs: 83 and 84, respectively;
(j) heavy and light chain variable region sequences comprising SEQ ID NOs: 99 and 100, respectively;
(k) heavy and light chain variable region sequences comprising SEQ ID NOs: 99 and 101, respectively;
(l) heavy and light chain variable region sequences comprising SEQ ID NOs: 99 and 102, respectively; and
(m) heavy and light chain variable region sequences comprising SEQ ID NOs: 113 and 114, respectively.

Anti-α-synuclein antibodies may comprise the heavy and light chain CDR1s, CDR2s and CDR3s of 7A10 (and 7A10-T93A, which shares VHCDR1-3 and VLCDR1-3 sequences with 7A10), 11H11 (11H11-1 and 11H11-2 share a common VH but have different VLs), 15A5, 21A3, 36A3, 44B11, 2E2, 23H8 (23H8-1, 23H8-2, 23H8-3, which share a common VH but have different VLs), and 1E8, or combinations thereof. The amino acid sequences of the $V_H$ CDR1s of 7A10 (and 7A10-T93A), 11H11, 15A5, 21A3, 36A3, 44B11, 2E2, 23H8, and 1E8 are set forth in SEQ ID NOs: 2, 22, 37, 47, 57, 67, 77, 87, and 107, respectively. The amino acid sequences of the $V_H$ CDR2s of 7A10 (and 7A10-T93A), 11H11, 15A5, 21A3, 36A3, 44B11, 2E2, 23H8, and 1E8 are set forth in SEQ ID NOs: 3, 23, 38, 48, 58, 68, 78, 88, and 108, respectively. The amino acid sequences of the $V_H$ CDR3s of 7A10 (and 7A10-T93A), 11H11, 15A5, 21A3, 36A3, 44B11, 2E2, 23H8, and 1E8 are set forth in SEQ ID NOs: 4, 24, 39, 49, 59, 69, 79, 89, and 109. The amino acid sequences of the $V_L$ CDR1s of 7A10 (and 7A10-T93A), 11H11-1, 11H11-2, 15A5, 21A3, 36A3, 44B11, 2E2, 23H8-1, 23H8-2, 23H8-3, and 1E8 are set forth in SEQ ID NOs: 5, 25, 28, 40, 50, 60, 70, 80, 90, 93, 96, and 110, respectively. The amino acid sequences of the $V_L$ CDR2s of 7A10 (and 7A10-T93A), 11H11-1, 11H11-2, 15A5, 21A3, 36A3, 44B11, 2E2, 23H8-1, 23H8-2, 23H8-3, and 1E8 are set forth in SEQ ID NOs: 6, 26, 29, 41, 51, 61, 71, 81, 91, 94, 97, and 111, respectively. The amino acid sequences of the $V_L$ CDR3s of 7A10 (and 7A10-T93A), 11H11-1, 11H11-2, 15A5, 21A3, 36A3, 44B11, 2E2, 23H8-1, 23H8-2, 23H8-3, and 1E8 are set forth in SEQ ID NOs: 7, 27, 30, 42, 52, 62, 72, 82, 92, 95, 98, and 112, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies bind to α-synuclein and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, although each antibody must contain a $V_H$ CDR1, 2 and 3 and a $V_L$ CDR1, 2 and 3) to create other anti-α-synuclein binding molecules described herein. α-synuclein binding of such "mixed and matched" antibodies can be tested using the binding assays described above and in the Examples (e.g., ELISAs). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 7A10 (and 7A10-T93A), 11H11-1, 11H11-2, 15A5, 21A3, 36A3, 44B11, 2E2, 23H8-1, 23H8-2, 23H8-3, and 1E8.

Accordingly, provided herein are isolated antibodies, or antigen binding portion thereof comprising:
(a) a heavy chain variable region CDR1 comprising an amino acid sequence selected from the group consisting of SEQ ID NOs: 2, 22, 37, 47, 57, 67, 77, 87, and 107;
(b) a heavy chain variable region CDR2 comprising an amino acid sequence selected from the group consisting of SEQ ID NOs: 3, 23, 38, 48, 58, 68, 78, 88, and 108;
(c) a heavy chain variable region CDR3 comprising an amino acid sequence selected from the group consisting of SEQ ID NOs: 4, 24, 39, 49, 59, 69, 79, 89, and 109;
(d) a light chain variable region CDR1 comprising an amino acid sequence selected from the group consisting of SEQ ID NOs: 5, 25, 28, 40, 50, 60, 70, 80, 90, 93, 96, and 110;
(e) a light chain variable region CDR2 comprising an amino acid sequence selected from the group consisting of SEQ ID NOs: 6, 26, 29, 41, 51, 61, 71, 81, 91, 94, 97, and 111; and
(f) a light chain variable region CDR3 comprising an amino acid sequence selected from the group consisting of SEQ ID NOs: 7, 27, 30, 42, 52, 62, 72, 82, 92, 95, 98, and 112;
wherein the antibody specifically binds to human α-synuclein.

In one embodiment, the antibody comprises heavy and light chain variable regions, wherein the heavy chain variable region CDR1, CDR2, and CDR3 regions comprise:
(a) SEQ ID NOs: 2-4;

(b) SEQ ID NOs: 22-24;
(c) SEQ ID NOs: 37-39;
(d) SEQ ID NOs: 47-49;
(e) SEQ ID NOs: 57-59;
(f) SEQ ID NOs: 67-69;
(g) SEQ ID NOs: 77-79;
(h) SEQ ID NOs: 87-89; or
(i) SEQ ID NOs: 107-109,
wherein the antibody specifically binds to human α-synuclein.

In another embodiment, the antibody comprises heavy and light chain variable regions, wherein the light chain variable region CDR1, CDR2, and CDR3 regions comprise:
(a) SEQ ID NOs: 5-7;
(b) SEQ ID NOs: 25-27;
(c) SEQ ID NOs: 28-30;
(d) SEQ ID NOs: 40-42;
(e) SEQ ID NOs: 50-52;
(f) SEQ ID NOs: 60-62;
(g) SEQ ID NOs: 70-72;
(h) SEQ ID NOs: 80-82;
(i) SEQ ID NOs: 90-92;
(j) SEQ ID NOs: 93-92
(k) SEQ ID NOs: 96-98; or
(l) SEQ ID NOs: 110-112,
wherein the antibody specifically binds to human α-synuclein.

In a particular embodiment, the antibody comprises heavy and light chain variable regions, wherein:
(a) the heavy chain variable region CDR1, CDR2, and CDR3 comprises SEQ ID NOs: 2-4, respectively, and the light chain variable region CDR1, CDR2, and CDR3 comprises SEQ ID NOs: 5-7, respectively;
(b) the heavy chain variable region CDR1, CDR2, and CDR3 comprises SEQ ID NOs: 22-24, respectively, and the light chain variable region CDR1, CDR2, and CDR3 comprises SEQ ID NOs: 25-27, respectively;
(c) the heavy chain variable region CDR1, CDR2, and CDR3 comprises SEQ ID NOs: 22-24, respectively, and the light chain variable region CDR1, CDR2, and CDR3 comprises SEQ ID NOs: 28-30, respectively;
(d) the heavy chain variable region CDR1, CDR2, and CDR3 comprises SEQ ID NOs: 37-39, respectively, and the light chain variable region CDR1, CDR2, and CDR3 comprises SEQ ID NOs: 40-42, respectively;
(e) the heavy chain variable region CDR1, CDR2, and CDR3 comprises SEQ ID NOs: 47-49, respectively, and the light chain variable region CDR1, CDR2, and CDR3 comprises SEQ ID NOs: 50-52, respectively;
(f) the heavy chain variable region CDR1, CDR2, and CDR3 comprises SEQ ID NOs: 57-59, respectively, and the light chain variable region CDR1, CDR2, and CDR3 comprises SEQ ID NOs: 60-62, respectively;
(g) the heavy chain variable region CDR1, CDR2, and CDR3 comprises SEQ ID NOs: 67-69, respectively, and the light chain variable region CDR1, CDR2, and CDR3 comprises SEQ ID NOs: 70-72, respectively;
(h) the heavy chain variable region CDR1, CDR2, and CDR3 comprises SEQ ID NOs: 77-79, respectively, and the light chain variable region CDR1, CDR2, and CDR3 comprises SEQ ID NOs: 80-82, respectively;
(i) the heavy chain variable region CDR1, CDR2, and CDR3 comprises SEQ ID NOs: 87-89, respectively, and the light chain variable region CDR1, CDR2, and CDR3 comprises SEQ ID NOs: 90-92, respectively;
(j) the heavy chain variable region CDR1, CDR2, and CDR3 comprises SEQ ID NOs: 87-89, respectively, and the light chain variable region CDR1, CDR2, and CDR3 comprises SEQ ID NOs: 93-95, respectively;
(k) the heavy chain variable region CDR1, CDR2, and CDR3 comprises SEQ ID NOs: 87-89, respectively, and the light chain variable region CDR1, CDR2, and CDR3 comprises SEQ ID NOs: 96-98, respectively; or
(l) the heavy chain variable region CDR1, CDR2, and CDR3 comprises SEQ ID NOs: 107-109, respectively, and the light chain variable region CDR1, CDR2, and CDR3 comprises SEQ ID NOs: 110-112, respectively,
wherein the antibody specifically binds to human α-synuclein.

A VH domain, or one or more CDRs thereof, described herein may be linked to a constant domain for forming a heavy chain, e.g., a full length heavy chain. Similarly, a VL domain, or one or more CDRs thereof, described herein may be linked to a constant domain for forming a light chain, e.g., a full length light chain. A full length heavy chain (with the exception of the C-terminal lysine (K) or with the exception of the C-terminal glycine and lysine (GK), which may be absent) and full length light chain combine to form a full length antibody.

A VH domain described herein may be fused to the constant domain of a human IgG, e.g., IgG1, IgG2, IgG3 or IgG4, which are either naturally-occurring or modified, e.g., as further described herein. For example, a VH domain may comprise the amino acid sequence of any VH domain described herein fused to the following human IgG1 amino acid sequence:

```
                                         (SEQ ID NO: 117)
    ASTKGP SVFPLAPSSK STSGGTAALG

CLVKDYFPEP VTVSWNSGAL TSGVHTFPAV

LQSSGLYSLS SVVTVPSSSL GTQTYICNVN

HKPSNTKVDK RVEPKSCDKT HTCPPCPAPE

LLGGPSVFLF PPKPKDTLMI SRTPEVTCVV

VDVSHEDeEV KFNWYVDOVE VHNAKTKPRE

EQYNSTYRVV SVLTVLHQDW LNGKEYKCKV

SNKALPAPIE KTISKAKGQP REPQVYTLPP

SREEMTKNQV SLTCLVKGFY PSDIAVEWES

NGQPENNYKT TPPVLDSDGS FFLYSKLTVD

KSRWQQGNVF SCSVMHEALH NHYTQKSLSL SPG
```

The human IgG1 constant domain may also be that of an allotypic variant. For example, an allotypic variant of IgG1 comprises an R107K, E189D and M191L (underlined above). Within the full length heavy region, these amino acid substitutions are numbered R214K, E356D and M358L.

A VL domain described herein may be fused to the constant domain of a human Kappa or Lambda light chain. For example, a VL domain may comprise the amino acid sequence of any VL domain described herein fused to the following human IgG1 kappa light chain amino acid sequence:

(SEQ ID NO: 120)
RTV AAPSVFIFPP SDEQLKSGTA SVVCLLNNFY
PREAKVQWKV DNALQSGNSQ ESVTEQDSKD STYSLSSTLT
LSKADYEKHK VYACEVTHQG LSSPVTKSFN RGEC

In certain embodiments, the heavy chain constant region comprises a lysine or another amino acid at the C-terminus. In certain embodiments, the heavy chain constant region is lacking one or more amino acids at the C-terminus, and has, e.g., the C-terminal sequence LSPG (SEQ ID NO: 127) or LSP.

The amino acid sequences of exemplary heavy and light chains of the anti-α-synuclein antibodies described herein are set forth in Table 22.

In some embodiments, the anti-α-synuclein antibody comprises heavy and light chains, wherein the heavy chain comprises an amino acid sequence set forth in SEQ ID NOs: 10, 20, 34, 45, 55, 65, 75, 85, 103, and 115.

In some embodiments, the anti-α-synuclein antibody comprises heavy and light chains, wherein the light chain comprises an amino acid sequence set forth in SEQ ID NOs: 11, 21, 35, 36, 46, 56, 66, 76, 86, 104, 105, 106, and 116.

In some embodiments, the anti-α-synuclein antibody comprises heavy and light chains, wherein the heavy and light chains comprise amino acid sequences selected from the group consisting of:
(a) 10 and 11,
(b) 20 and 21,
(c) 34 and 35,
(d) 34 and 36,
(e) 45 and 46,
(f) 55 and 56,
(g) 65 and 66,
(h) 75 and 76,
(i) 85 and 86,
(j) 103 and 104,
(k) 103 and 105,
(l) 103 and 106, and
(m) 115 and 116.

Heavy and light chains comprising an amino acid sequence that is at least 99%, 98%, 97%, 96%, 95%, 90%, 85%, 80%, 75% or 70% identical to any of the heavy or light chains set forth in Table 22 (or their variable regions), e.g., SEQ ID NOs: 10, 11, 20, 21, 34, 35, 36, 45, 46, 55, 56, 65, 66, 75, 76, 85, 86, 103, 104, 105, 106, 115, and 116 may be used for forming anti-human α-synuclein antibodies having the desired characteristics, e.g., those further described herein. Exemplary variants are those comprising an allotypic variation, e.g., in the constant domain, and/or a mutation in the variable or constant regions, such as the mutations disclosed herein. Heavy and light chains comprising an amino acid sequence that differs in at most 1-30, 1-25, 1-20, 1-15, 1-10, 1-5, 1-4, 1-3, 1-2 or 1 amino acid (by substitution, addition or deletion) from any of the heavy or light chains set forth in Table 22 (or their variable regions) may be used for forming anti-α-synuclein antibodies having the desired characteristics, e.g., those further described herein.

In various embodiments, the antibodies described above exhibit one or more of the following functional properties:
(a) binds to mouse and rat α-synuclein;
(b) binds to β-synuclein and γ-synuclein;
(c) has a greater affinity for α-synuclein oligomers (e.g., PFF) over α-synuclein monomers;
(d) inhibits the generation of α-synuclein oligomer (e.g., PFF)-induced insoluble α-synuclein aggregates (e.g., serine-129 phosphorylated α-synuclein aggregates);
(e) depletes the molecular species that produces soluble or insoluble α-synuclein aggregates (e.g., serine-129 phosphorylated α-synuclein aggregates) from PFF and/or brain lysate prepared from patients with pathological aggregates of α-synuclein in the brain;
(f) binds to all or a portion of amino acid positions 123-128 of human α-synuclein (SEQ ID NO: 1);
(g) binds to all or a portion of amino acid positions 125-128 of human α-synuclein (SEQ ID NO: 1);
(h) binds to all or a portion of amino acid positions 130-139 of human α-synuclein (SEQ ID NO: 1);
(i) binds to all or a portion of amino acid positions 119-126 of human α-synuclein (SEQ ID NO: 1); and
(j) binds to all or a portion of amino acid positions 130-138 of human α-synuclein (SEQ ID NO: 1).

In some embodiments, the α-synuclein oligomer is PFF. In some embodiments, PFF is prepared using the method described in Example 3. In some embodiments, the α-synuclein oligomer is soluble. In other embodiments, the α-synuclein oligomer is insoluble.

Such antibodies include, for example, human antibodies, humanized antibodies, or chimeric antibodies.

In one embodiment, the anti-α-synuclein antibodies described herein bind to all or a portion of the following sequence of human α-synuclein (SEQ ID NO: 1):
EAYEMP (SEQ ID NO: 121),
corresponding to amino acid residues 123-128 of human α-synuclein (SEQ ID NO: 1).

In another embodiment, the anti-α-synuclein antibodies described herein bind to all or a portion of the following sequence of human α-synuclein (SEQ ID NO: 1):
YEMP (SEQ ID NO: 122),
corresponding to amino acid residues 125-128 of human α-synuclein (SEQ ID NO: 1).

In another embodiment, the anti-α-synuclein antibodies described herein bind to all or a portion of the following sequence of human α-synuclein (SEQ ID NO: 1):
EEGYQDYEPE (SEQ ID NO: 124),
corresponding to amino acid residues 130-139 of human α-synuclein (SEQ ID NO: 1).

In another embodiment, the anti-α-synuclein antibodies described herein bind to all or a portion of the following sequence of human α-synuclein (SEQ ID NO: 1):
DPDNEAYE (SEQ ID NO: 125),
corresponding to amino acid residues 119-126 of human α-synuclein (SEQ ID NO: 1).

In another embodiment, the anti-α-synuclein antibodies described herein bind to all or a portion of the following sequence of human α-synuclein (SEQ ID NO: 1):
EEGYQDYEP (SEQ ID NO: 123),
corresponding to amino acid residues 130-138 of human α-synuclein (SEQ ID NO: 1).

Also provided herein are anti-α-synuclein antibodies that compete for binding to α-synuclein with anti-α-synuclein antibodies comprising CDRs or variable regions described herein, e.g., those of any of 7A10, 7A10-T93A, 11H11-1, 11H11-2, 15A5, 21A3, 36A3, 44B11, 2E2, 23H8-1, 23H8-2, 23H8-3, and 1E8. In some embodiments, anti-α-synuclein antibodies inhibit binding of any of 7A10, 7A10-T93A, 11H11-1, 11H11-2, 15A5, 21A3, 36A3, 44B11, 2E2, 23H8-1, 23H8-2, 23H8-3, and 1E8 to human α-synuclein (e.g., monomeric α-synuclein or oligomeric α-synuclein) by at least 10%, 20%, 30%, 40%, 50%, 60%, 70%, 80%, 90% or by 100%. Competing antibodies can be identified based on their ability to competitively inhibit binding to α-synuclein using standard binding assays known in the art (e.g., competitive ELISA assay).

Also provided herein are anti-α-synuclein antibodies which bind to the same epitope on α-synuclein with anti-α-synuclein antibodies comprising CDRs or variable regions described herein, e.g., those of any of 7A10, 7A10-T93A, 11H11-1, 11H11-2, 15A5, 21A3, 36A3, 44B11, 2E2, 23H8-1, 23H8-2, 23H8-3, and 1E8. Methods for determining whether antibodies bind to the same epitope on α-synuclein with the antibodies described herein include, for example, epitope mapping methods, monitoring the binding of the antibody to antigen fragments or mutated variations of the antigen where loss of binding due to a modification of an amino acid residue within the antigen sequence is considered an indication of an epitope component (e.g., alanine scanning); MS-based protein footprinting, and assessing the ability of an antibody of interest to affinity isolate specific short peptides (either in native three dimensional form or in denatured form) from combinatorial phage display peptide libraries.

Antibodies disclosed herein include all known forms of antibodies and other protein scaffolds with antibody-like properties. For example, the antibody can be a human antibody, a humanized antibody, a bispecific antibody, an immunoconjugate, a chimeric antibody, or a protein scaffold with antibody-like properties, such as fibronectin or ankyrin repeats. The antibody also can be a Fab, Fab'2, seFv, Affibody®, avimer, nanobody, or a domain antibody. The antibody also can have any isotype, including any of the following isotypes: IgG1, IgG2, IgG3, IgG4, IgM, IgA1, IgA2, IgAsec, IgD, and IgE. IgG antibodies are preferred. Full-length antibodies can be prepared from $V_H$ and $V_L$ sequences using standard recombinant DNA techniques and nucleic acid encoding the desired constant region sequences to be operatively linked to the variable region sequences.

III. Antibodies Having Particular Germline Sequences

In certain embodiments, the anti-α-synuclein antibodies described herein comprise a heavy chain variable region from a particular germline heavy chain immunoglobulin gene and/or a light chain variable region from a particular germline light chain immunoglobulin gene.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

IV. Homologous Antibodies

Encompassed herein are anti-α-synuclein antibodies having heavy and light chain variable regions comprising amino acid sequences that are homologous to the amino acid sequences of the preferred antibodies described herein, and wherein the antibodies retain the desired functional properties of the anti-α-synuclein antibodies described herein.

For example, an isolated anti-α-synuclein antibody, or antigen binding portion thereof, may comprise a heavy chain variable region and a light chain variable region, wherein:

(a) the heavy chain variable region comprises an amino acid sequence that is at least 80%, 85%, 90%, 95%, 96%, 97%, 98% or 99% identical to an amino acid sequence selected from the group consisting of SEQ ID NOs: 8, 18, 31, 43, 53, 63, 73, 83, 99, and 113, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 8, 18, 31, 43, 53, 63, 73, 83, 99, and 113;

(b) the light chain variable region comprises an amino acid sequence that is at least 80%, 85%, 90%, 95%, 96%, 97%, 98% or 99% identical to an amino acid sequence selected from the group consisting of SEQ ID NOs: 9, 19, 32, 33, 44, 54, 64, 74, 84, 100, 101, 102, and 114, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 9, 19, 32, 33, 44, 54, 64, 74, 84, 100, 101, 102, and 114;

(c) the antibody specifically binds to α-synuclein, and (d) the antibody exhibits one or more of the following functional properties:

(1) binds to mouse and rat α-synuclein;
(2) binds to β-synuclein and γ-synuclein;
(3) has a greater affinity for α-synuclein oligomers (e.g., PFF) over α-synuclein monomers;
(4) inhibits the generation of α-synuclein oligomer (e.g., PFF)-induced insoluble α-synuclein aggregates (e.g., serine-129 phosphorylated α-synuclein aggregates);
(5) depletes the molecular species that produces insoluble α-synuclein aggregates (e.g., serine-129 phosphorylated α-synuclein aggregates) from PFF and/or brain lysate prepared from patients with pathological aggregates of α-synuclein in the brain;
(6) binds to all or a portion of amino acid positions 123-128 of human α-synuclein (SEQ ID NO: 121);
(7) binds to all or a portion of amino acid positions 125-128 of human α-synuclein (SEQ ID NO: 122);
(8) binds to all or a portion of amino acid positions 130-139 of human α-synuclein (SEQ ID NO: 124);

(9) binds to all or a portion of amino acid positions 119-126 of human α-synuclein (SEQ ID NO: 125); and
(10) binds to all or a portion of amino acid positions 130-138 of human α-synuclein (SEQ ID NO: 123).

In some embodiments, the α-synuclein oligomer is PFF. In some embodiments, PFF is prepared using the method described in Example 3. In some embodiments, the α-synuclein oligomer is soluble. In other embodiments, the α-synuclein oligomer is insoluble.

In some embodiments, provided is an isolated monoclonal antibody, or antigen binding portion thereof, comprising heavy and light chain variable region sequences at least 80%, 85%, 90%, 95%, 96%, 97%, 98% or 99% identical to the heavy and light chain variable region sequences selected from the group consisting of:
(a) SEQ ID NOs: 8 and 9;
(b) SEQ ID NOs: 18 and 19;
(c) SEQ ID NOs: 31 and 32;
(d) SEQ ID NOs: 31 and 33;
(e) SEQ ID NOs: 43 and 44;
(f) SEQ ID NOs: 53 and 54;
(g) SEQ ID NOs: 63 and 64;
(h) SEQ ID NOs: 73 and 74;
(i) SEQ ID NOs: 83 and 84;
(j) SEQ ID NOs: 99 and 100;
(k) SEQ ID NOs: 99 and 101;
(l) SEQ ID NOs: 99 and 102; and
(m) SEQ ID NOs: 113 and 114,
wherein the antibody binds to α-synuclein.

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 8 and 9, respectively, wherein:
the heavy chain variable region of the antibody comprises the following CDRs:
  i. CDR1 having the amino acid sequence of SEQ ID NO: 2;
  ii. CDR2 having the amino acid sequence of SEQ ID NO: 3; and
  iii. CDR3 having the amino acid sequence of SEQ ID NO: 4; and
the light chain variable region of the antibody comprises the following CDRs:
  i. CDR1 having the amino acid sequence of SEQ TD NO: 5;
  ii. CDR2 having the amino acid sequence of SEQ ID NO: 6; and
  iii. CDR3 having the amino acid sequence of SEQ ID NO: 7; and
wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 18 and 19, respectively, wherein:
the heavy chain variable region of the antibody comprises the following CDRs:
  i. CDR1 having the amino acid sequence of SEQ ID NO: 12;
  ii. CDR2 having the amino acid sequence of SEQ ID NO: 13; and
  iii. CDR3 having the amino acid sequence of SEQ ID NO: 14; and
the light chain variable region of the antibody comprises the following CDRs:
  i. CDR1 having the amino acid sequence of SEQ ID NO: 15;
  ii. CDR2 having the amino acid sequence of SEQ ID NO: 16; and
  iii. CDR3 having the amino acid sequence of SEQ ID NO: 17; and
wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 31 and 32, respectively, wherein:
the heavy chain variable region of the antibody comprises the following CDRs:
  i. CDR1 having the amino acid sequence of SEQ ID NO: 22;
  ii. CDR2 having the amino acid sequence of SEQ ID NO: 23; and
  iii. CDR3 having the amino acid sequence of SEQ ID NO: 24; and
the light chain variable region of the antibody comprises the following CDRs:
  i. CDR1 having the amino acid sequence of SEQ ID NO: 25;
  ii. CDR2 having the amino acid sequence of SEQ ID NO: 26; and
  iii. CDR3 having the amino acid sequence of SEQ ID NO: 27; and
wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 31 and 33, respectively, wherein:
the heavy chain variable region of the antibody comprises the following CDRs:
  i. CDR1 having the amino acid sequence of SEQ ID NO: 22;
  ii. CDR2 having the amino acid sequence of SEQ ID NO: 23; and
  iii. CDR3 having the amino acid sequence of SEQ ID NO: 24; and
the light chain variable region of the antibody comprises the following CDRs:
  i. CDR1 having the amino acid sequence of SEQ ID NO: 28;
  ii. CDR2 having the amino acid sequence of SEQ ID NO: 29; and
  iii. CDR3 having the amino acid sequence of SEQ ID NO: 30; and
wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 43 and 44, respectively, wherein:
the heavy chain variable region of the antibody comprises the following CDRs:

i. CDR1 having the amino acid sequence of SEQ ID NO: 37;
ii. CDR2 having the amino acid sequence of SEQ ID NO: 38; and
iii. CDR3 having the amino acid sequence of SEQ ID NO: 39; and the light chain variable region of the antibody comprises the following CDRs:
i. CDR1 having the amino acid sequence of SEQ ID NO: 40;
ii. CDR2 having the amino acid sequence of SEQ ID NO: 41; and
iii. CDR3 having the amino acid sequence of SEQ ID NO: 42; and wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 53 and 54, respectively, wherein:

the heavy chain variable region of the antibody comprises the following CDRs:
i. CDR1 having the amino acid sequence of SEQ ID NO: 47;
ii. CDR2 having the amino acid sequence of SEQ ID NO: 48; and
iii. CDR3 having the amino acid sequence of SEQ ID NO: 49; and the light chain variable region of the antibody comprises the following CDRs:
i. CDR1 having the amino acid sequence of SEQ ID NO: 50;
ii. CDR2 having the amino acid sequence of SEQ ID NO: 51; and
iii. CDR3 having the amino acid sequence of SEQ ID NO: 52; and wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 63 and 64, respectively, wherein:

the heavy chain variable region of the antibody comprises the following CDRs:
i. CDR1 having the amino acid sequence of SEQ ID NO: 57;
ii. CDR2 having the amino acid sequence of SEQ ID NO: 58; and
iii. CDR3 having the amino acid sequence of SEQ ID NO: 59; and the light chain variable region of the antibody comprises the following CDRs:
i. CDR1 having the amino acid sequence of SEQ ID NO: 60;
ii. CDR2 having the amino acid sequence of SEQ ID NO: 61; and
iii. CDR3 having the amino acid sequence of SEQ ID NO: 62; and wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 73 and 74, respectively, wherein:

the heavy chain variable region of the antibody comprises the following CDRs:
i. CDR1 having the amino acid sequence of SEQ ID NO: 67;
ii. CDR2 having the amino acid sequence of SEQ ID NO: 68; and
iii. CDR3 having the amino acid sequence of SEQ ID NO: 69; and the light chain variable region of the antibody comprises the following CDRs:
i. CDR1 having the amino acid sequence of SEQ ID NO: 70;
ii. CDR2 having the amino acid sequence of SEQ ID NO: 71; and
iii. CDR3 having the amino acid sequence of SEQ ID NO: 72; and wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 83 and 84, respectively, wherein:

the heavy chain variable region of the antibody comprises the following CDRs:
i. CDR1 having the amino acid sequence of SEQ ID NO: 77;
ii. CDR2 having the amino acid sequence of SEQ ID NO: 78; and
iii. CDR3 having the amino acid sequence of SEQ ID NO: 79; and the light chain variable region of the antibody comprises the following CDRs:
i. CDR1 having the amino acid sequence of SEQ ID NO: 80;
ii. CDR2 having the amino acid sequence of SEQ ID NO: 81; and
iii. CDR3 having the amino acid sequence of SEQ ID NO: 82; and wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 99 and 100, respectively, wherein:

the heavy chain variable region of the antibody comprises the following CDRs:
i. CDR1 having the amino acid sequence of SEQ ID NO: 87;
ii. CDR2 having the amino acid sequence of SEQ ID NO: 88; and
iii. CDR3 having the amino acid sequence of SEQ ID NO: 89; and the light chain variable region of the antibody comprises the following CDRs:
i. CDR1 having the amino acid sequence of SEQ ID NO: 90;
ii. CDR2 having the amino acid sequence of SEQ ID NO: 91; and
iii. CDR3 having the amino acid sequence of SEQ ID NO: 92; and wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 99 and 101, respectively, wherein:

the heavy chain variable region of the antibody comprises the following CDRs:
  i. CDR1 having the amino acid sequence of SEQ ID NO: 87;
  ii. CDR2 having the amino acid sequence of SEQ ID NO: 88; and
  iii. CDR3 having the amino acid sequence of SEQ ID NO: 89; and
the light chain variable region of the antibody comprises the following CDRs:
  i. CDR1 having the amino acid sequence of SEQ ID NO: 93;
  ii. CDR2 having the amino acid sequence of SEQ ID NO: 94; and
  iii. CDR3 having the amino acid sequence of SEQ ID NO: 95; and
wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 99 and 102, respectively, wherein:

the heavy chain variable region of the antibody comprises the following CDRs:
  i. CDR1 having the amino acid sequence of SEQ ID NO: 87;
  ii. CDR2 having the amino acid sequence of SEQ ID NO: 88; and
  iii. CDR3 having the amino acid sequence of SEQ ID NO: 89; and
the light chain variable region of the antibody comprises the following CDRs:
  i. CDR1 having the amino acid sequence of SEQ ID NO: 96;
  ii. CDR2 having the amino acid sequence of SEQ ID NO: 97; and
  iii. CDR3 having the amino acid sequence of SEQ ID NO: 98; and
wherein the antibody binds to human α-synuclein (SEQ ID NO:1).

In one embodiment, provided is an antibody (e.g., isolated monoclonal antibody) comprising heavy and light chain variable region sequences which are at least 80%, 85%, 90%, 95%, 96%, 97%, 98% or 99% identical to the amino acid sequences set forth in SEQ ID NOs: 113 and 114, respectively, wherein:

the heavy chain variable region of the antibody comprises the following CDRs:
  i. CDR1 having the amino acid sequence of SEQ ID NO: 107;
  ii. CDR2 having the amino acid sequence of SEQ ID NO: 108; and
  iii. CDR3 having the amino acid sequence of SEQ ID NO: 109; and
the light chain variable region of the antibody comprises the following CDRs:
  i. CDR1 having the amino acid sequence of SEQ ID NO: 110;
  ii. CDR2 having the amino acid sequence of SEQ ID NO: 111; and
  iii. CDR3 having the amino acid sequence of SEQ ID NO: 112; and
wherein the antibody binds to human α-synuclein (SEQ ID NO:1).

In some embodiments, the antibody is a human antibody, a humanized antibody or a chimeric antibody.

In some embodiments, an isolated anti-α-synuclein antibody, or antigen binding portion thereof, may comprise a heavy chain and a light chain, wherein:

(a) the heavy chain comprises an amino acid sequence that is at least 80%, 85%, 90%, 95%, 96%, 97%, 98% or 99% identical to an amino acid sequence selected from the group consisting of SEQ ID NOs: 10, 20, 34, 45, 55, 65, 75, 85, 103, and 115, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 10, 20, 34, 45, 55, 65, 75, 85, 103, and 115, with the proviso that, in certain embodiments, if the sequence is that of an effectorless heavy chain, the mutations rendering the heavy chain effectorless are not modified;

(b) the light chain comprises an amino acid sequence that is at least 80%, 85%, 90%, 95%, 96%, 97%, 98% or 99% identical to an amino acid sequence selected from the group consisting of SEQ ID NOs: 11, 21, 35, 36, 46, 56, 66, 76, 86, 104, 105, 106, and 116, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 11, 21, 35, 36, 46, 56, 66, 76, 86, 104, 105, 106, and 116;

(c) the antibody specifically binds to α-synuclein, and (d) the antibody exhibits one or more of the following functional properties:
  (1) binds to mouse and rat α-synuclein;
  (2) binds to β-synuclein and γ-synuclein;
  (3) has a greater affinity for α-synuclein oligomers (e.g., PFF) over α-synuclein monomers;
  (4) inhibits the generation of α-synuclein oligomer (e.g., PFF)-induced insoluble α-synuclein aggregates (e.g., serine-129 phosphorylated α-synuclein aggregates);
  (5) depletes the molecular species that produces insoluble α-synuclein aggregates (e.g., serine-129 phosphorylated α-synuclein aggregates) from PFF and/or brain lysate prepared from patients with pathological aggregates of α-synuclein in the brain;
  (6) binds to all or a portion of amino acid positions 123-128 of human α-synuclein (SEQ ID NO: 121);
  (7) binds to all or a portion of amino acid positions 125-128 of human α-synuclein (SEQ ID NO: 122);
  (8) binds to all or a portion of amino acid positions 130-139 of human α-synuclein (SEQ ID NO: 124);
  (9) binds to all or a portion of amino acid positions 119-126 of human α-synuclein (SEQ ID NO: 125); and
  (10) binds to all or a portion of amino acid positions 130-138 of human α-synuclein (SEQ ID NO: 123).

In some embodiments, the α-synuclein oligomer is PFF. In some embodiments, PFF is prepared using the method described in Example 3. In some embodiments, the α-synuclein oligomer is soluble. In other embodiments, the α-synuclein oligomer is insoluble.

In some embodiments, provided is an antibody, or antigen binding portion thereof, comprising heavy chain and light chain sequences at least 80%, 85%, 90%, 95%, 96%, 97%, 98%, or 99% identical to the amino acid sequences selected from the group consisting of:
(a) SEQ ID NOs: 10 and 11,
(b) SEQ ID NOs: 20 and 21,
(c) SEQ ID NOs: 34 and 35,
(d) SEQ ID NOs: 34 and 36,
(e) SEQ ID NOs: 45 and 46,
(f) SEQ ID NOs: 55 and 56,
(g) SEQ ID NOs: 65 and 66,
(h) SEQ ID NOs: 75 and 76,
(i) SEQ ID NOs: 85 and 86,
(j) SEQ ID NOs: 103 and 104,
(k) SEQ ID NOs: 103 and 105,
(l) SEQ ID NOs: 103 and 106, and
(m) SEQ ID NOs: 115 and 116,
wherein the antibody binds to α-synuclein.

Also provided are anti-α-synuclein antibodies comprising a VHCDR1, VHCDR2, VHCDR3, VLCDR1, VLCDR2, and/or VLCDR3 that differs from the corresponding CDR of 7A10, 7A10-T93A, 11H11-1, 11H11-2, 15A5, 21A3, 36A3, 44B11, 2E2, 23H8-1, 23H8-2, 23H8-3, and/or 1E8, in 1, 2, 3, 4, 5, 1-2, 1-3, 1-4, or 1-5 amino acid changes (i.e., amino acid substitutions, additions or deletions). In certain embodiments, an anti-α-synuclein antibody comprises 1-5 amino acid changes in each of 1, 2, 3, 4, 5 or 6 of the CDRs relative to the corresponding sequence in 7A10, 7A10-T93A, 11H11-1, 11H11-2, 15A5, 21A3, 36A3, 44B11, 2E2, 23H8-1, 23H8-2, 23H8-3, and/or 1E8. In certain embodments, an anti-α-synuclein antibody comprises at total of 1-5 amino acid changes across all CDRs relative to the CDRs in 7A10, 7A10-T93A, 11H11-1, 11H11-2, 15A5, 21A3, 36A3, 44B11, 2E2, 23H8-1, 23H8-2, 23H8-3, and/or 1E8. These altered antibodies can be tested, using the in vitro and in vivo assays described herein and in the Examples, to determine whether they retain one or more of the functional properties listed above.

Antibodies having sequences with homology to those of 7A10, 11H11 (11H11-1 and 11H11-2), 15A5, 21A3, 36A3, 44B11, 2E2, 23H8 (23H8-1, 23H8-2, and 23H8-3), and/or 1E8, e.g., the $V_H$ and $V_L$ regions of SEQ ID NOs: 8, 18, 31, 43, 53, 63, 73, 83, 99, and 113, and SEQ ID NOs: 9, 19, 32, 33, 44, 54, 64, 74, 84, 100, 101, 102, and 114, respectively, or heavy and light chains of SEQ ID NOs: 10, 20, 34, 45, 55, 65, 75, 85, 103, and 115, and SEQ ID NOs: 11, 21, 35, 36, 46, 56, 66, 76, 86, 104, 105, 106, and 116, respectively, or CDRs can be obtained by mutagenesis (e.g., site-directed or PCR-mediated mutagenesis) of nucleic acid molecules encoding the amino acid sequences, followed by testing of the encoded altered antibody for retained function using the functional assays described herein.

V. Antibodies with Conservative Modifications

Anti-α-synuclein antibodies may comprise a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties of the anti-α-synuclein antibodies described herein. Accordingly, an isolated anti-α-synuclein antibody, or antigen binding portion thereof, may comprise a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of SEQ ID NOs: 4, 24, 39, 49, 59, 69, 79, 89, and 109, and conservative modifications thereof, e.g., 1, 2, 3, 4, 5, 1-2, 1-3, 1-4 or 1-5 conservative amino acid substitutions;

(b) the light chain variable region CDR3 sequence comprises an amino acid sequence selected from the group consisting of SEQ ID NOs: 7, 27, 30, 42, 52, 62, 72, 82, 92, 95, 98, and 102, and conservative modifications thereof, e.g., 1, 2, 3, 4, 5, 1-2, 1-3, 1-4 or 1-5 conservative amino acid substitutions;

(c) the antibody specifically binds to α-synuclein, and (d) the antibody exhibits one or more of the following functional properties:
(1) binds to mouse and rat α-synuclein;
(2) binds to β-synuclein and γ-synuclein;
(3) has a greater affinity for α-synuclein oligomers (e.g., PFF) over α-synuclein monomers;
(4) inhibits the generation of α-synuclein oligomer (e.g., PFF)-induced insoluble α-synuclein aggregates (e.g., serine-129 phosphorylated α-synuclein aggregates);
(5) depletes the molecular species that produces insoluble α-synuclein aggregates (e.g., serine-129 phosphorylated α-synuclein aggregates) from PFF and/or brain lysate prepared from patients with pathological aggregates of α-synuclein in the brain;
(6) binds to all or a portion of amino acid positions 123-128 of human α-synuclein (SEQ ID NO: 121);
(7) binds to all or a portion of amino acid positions 125-128 of human α-synuclein (SEQ ID NO: 122);
(8) binds to all or a portion of amino acid positions 130-139 of human α-synuclein (SEQ ID NO: 124);
(9) binds to all or a portion of amino acid positions 119-126 of human α-synuclein (SEQ ID NO: 125); and
(10) binds to all or a portion of amino acid positions 130-138 of human α-synuclein (SEQ ID NO: 123).

In some embodiments, the α-synuclein oligomer is PFF. In some embodiments, PFF is prepared using the method described in Example 3. In some embodiments, the α-synuclein oligomer is soluble. In other embodiments, the α-synuclein oligomer is insoluble.

In a preferred embodiment, the heavy chain variable region CDR2 sequence comprises an amino acid sequence selected from the group consisting of SEQ ID NOs: 3, 23, 38, 48, 58, 68, 78, 88, and 108, and conservative modifications thereof, e.g., 1, 2, 3, 4, 5, 1-2, 1-3, 1-4 or 1-5 conservative amino acid substitutions; and the light chain variable region CDR2 sequence comprises an amino acid sequence selected from the group consisting of SEQ ID NOs: 6, 26, 29, 41, 51, 61, 71, 81, 91, 94, 97, and 111, and conservative modifications thereof, e.g., 1, 2, 3, 4, 5, 1-2, 1-3, 1-4 or 1-5 conservative amino acid substitutions. In another preferred embodiment, the heavy chain variable region CDR1 sequence comprises an amino acid sequence selected from the group consisting of SEQ ID NOs: 2, 22, 37, 47, 57, 67, 77, 87, and 107, and conservative modifications thereof, e.g., 1, 2, 3, 4, 5, 1-2, 1-3, 1-4 or 1-5 conservative amino acid substitutions; and the light chain variable region CDR1 sequence comprises an amino acid sequence selected from the group consisting of SEQ ID NOs: 5, 25, 28, 40, 50, 60, 70, 80, 90, 93, 96, and 110, and conservative modifications thereof, e.g., 1, 2, 3, 4, 5, 1-2, 1-3, 1-4 or 1-5 conservative amino acid substitutions.

In various embodiments, the antibody may exhibit one or more of the functional properties listed above. Such antibodies can be, for example, human antibodies, humanized antibodies or chimeric antibodies.

Conservative amino acid substitutions may also be made in portions of the antibodies other than, or in addition to, the CDRs. For example, conservative amino acid modifications may be made in a framework region or in the Fc region. A variable region or a heavy or light chain may comprise 1, 2, 3, 4, 5, 1-2, 1-3, 1-4, 1-5, 1-10, 1-15, 1-20, 1-25, or 1-50 conservative amino acid substitutions relative to the anti-α-synuclein antibody sequences provided herein. In certain embodiments, an anti-α-synuclein antibody comprises a combination of conservative and non-conservative amino acid modification.

VI. Engineered and Modified Antibodies

VH and VL Regions

Also provided are engineered and modified antibodies that can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment described herein pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 2, 22, 37, 47, 57, 67, 77, 87, and 107; SEQ ID NOs: 3, 23, 38, 48, 58, 68, 78, 88, and 108; and SEQ ID NOs: 4, 24, 39, 49, 59, 69, 79, 89, and 109, respectively, and a light chain variable region comprising CDR1, CDR2, and CDR3 sequences comprising an amino acid sequence selected from the group consisting of SEQ ID NOs: 5, 25, 28, 40, 50, 60, 70, 80, 90, 93, 96, and 110; SEQ ID NOs: 6, 26, 29, 41, 51, 61, 71, 81, 91, 94, 97, and 111; and SEQ ID NOs: 7, 27, 30, 42, 52, 62, 72, 82, 92, 95, 98, and 102, respectively. Thus, such antibodies contain the $V_H$ and $V_L$ CDR sequences of monoclonal antibodies 7A10, 7A10-T93A, 11H11-1, 11H11-2, 15A5, 21A3, 36A3, 44B11, 2E2, 23H8-1, 23H8-2, 23H8-3, and 1E8, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Engineered antibodies described herein include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, also provided are isolated anti-α-synuclein monoclonal antibodies, or antigen binding portions thereof, comprising a heavy chain variable region comprising: (a) a $V_H$ CDR1 region comprising an amino acid sequence selected from the group consisting of SEQ ID NOs: 2, 22, 37, 47, 57, 67, 77, 87, and 107, or an amino acid sequence having one, two, three, four or five amino acid substitutions, deletions or additions as compared to SEQ ID NOs: 2, 22, 37, 47, 57, 67, 77, 87, and 107; (b) a $V_H$ CDR2 region comprising an amino acid sequence selected from the group consisting of SEQ ID NOs: 3, 23, 38, 48, 58, 68, 78, 88, and 108, or an amino acid sequence having one, two, three, four or five amino acid substitutions, deletions or additions as compared to SEQ ID NOs: 3, 23, 38, 48, 58, 68, 78, 88, and 108; (c) a $V_H$ CDR3 region comprising an amino acid sequence selected from the group consisting of SEQ ID NOs: 4, 24, 39, 49, 59, 69, 79, 89, and 109, or an amino acid sequence having one, two, three, four or five amino acid substitutions, deletions or additions as compared to SEQ ID NOs: 4, 24, 39, 49, 59, 69, 79, 89, and 109; (d) a $V_L$ CDR1 region comprising an amino acid sequence selected from the group consisting of SEQ ID NOs: 5, 25, 28, 40, 50, 60, 70, 80, 90, 93, 96, and 110, or an amino acid sequence having one, two, three, four or five amino acid substitutions, deletions or additions as compared to SEQ ID NOs: 5, 25, 28, 40, 50, 60, 70, 80, 90, 93, 96, and 110; (e) a $V_L$ CDR2 region comprising an amino acid sequence selected from the group consisting of SEQ ID NOs: 6, 26, 29, 41, 51, 61, 71, 81, 91, 94, 97, and 111, or an amino acid sequence having one, two, three, four or five amino acid substitutions, deletions or additions as compared to SEQ ID NOs: 6, 26, 29, 41, 51, 61, 71, 81, 91, 94, 97, and 111; and (f) a $V_L$ CDR3 region comprising an amino acid sequence selected from the group consisting of SEQ ID NOs: 7, 27, 30, 42, 52, 62, 72, 82, 92, 95, 98, and 102, or an amino acid sequence having one, two, three, four or five amino acid substitutions, deletions or additions as compared to SEQ ID NOs: 7, 27, 30, 42, 52, 62, 72, 82, 92, 95, 98, and 102.

Methionine residues in CDRs of antibodies can be oxidized, resulting in potential chemical degradation and consequent reduction in potency of the antibody. Accordingly, also provided are anti-α-synuclein antibodies which have one or more methionine residues in the heavy and/or light chain CDRs replaced with amino acid residues which do not undergo oxidative degradation.

Similarly, deamidation sites may be removed from anti-α-synuclein antibodies, particularly in the CDRs.

Fcs and Modified Fcs

Anti-α-synuclein antibody variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16(t), G3m6(c3), G3m24(c5), G3m26(u), G3m27(v); and for K: Km, Km1, Km2, Km3 (see, e.g., Jefferies et al. (2009) mAbs 1:1).

In certain embodiments, anti-α-synuclein antibodies have an Fc receptor with no, or with reduced, FcR binding, e.g., reduced binding to activating FcRs.

In certain embodiments, anti-α-synuclein antibody variable regions described herein are linked to an effectorless or mostly effectorless Fc, e.g., IgG2 or IgG4.

Generally, variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

The Fc region encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

The constant region of an immunoglobulin is responsible for many important antibody functions including Fc receptor (FcR) binding and complement fixation. There are five major classes of heavy chain constant region, classified as IgA, IgG, IgD, IgE, IgM, each with characteristic effector functions designated by isotype. For example, IgG is separated into four subclasses known as IgG1, IgG2, IgG3, and IgG4.

Ig molecules interact with multiple classes of cellular receptors. For example IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR).

In certain embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

For example, one may make modifications in the Fc region in order to generate an Fc variant that (a) has decreased antibody-dependent cell-mediated cytotoxicity (ADCC), (b) has decreased complement mediated cytotoxicity (CDC), (c) has decreased affinity for C1q and/or (d) has decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc substitutions therein, e.g. of the specific Fc region positions identified herein.

A variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other embodiments, the Fc region may be modified to make it more compatible with a selected host cell. For example, one may remove the PA sequence near the N-terminus of a typical native Fc region, which may be recognized by a digestive enzyme in E. coli such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the Clq binding site, may be removed from the Fc region. For example, one may delete or substitute the EKK sequence of human IgG1. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317, 091; 8,101,720; PCT Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

The affinities and binding properties of an Fc region for its ligand may be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In certain embodiments, the antibody is modified to increase its biological half-life. Various approaches are possible. For example, this may be done by increasing the binding affinity of the Fc region for FcRn. For example, one or more of more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 31 1A, 312A, 376A, 378Q, 380A, 382A, 434A (Shields et al, Journal of Biological Chemistry, 2001, 276 (9):6591-6604), 252F, 252T, 252Y, 252W, 254T, 256S, 256R, 256Q, 256E, 256D, 256T, 309P, 31 1 S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-

23524). Other modifications for modulating FcRn binding are described in Yeung et al., 2010, J Immunol, 182:7663-7671. In certain embodiments, hybrid IgG isotypes with particular biological characteristics may be used. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A.

In certain embodiments, an Fc is chosen that has reduced binding to FcγRs. An exemplary Fc, e.g., IgG1 Fc, with reduced FcγR binding comprises the following three amino acid substitutions: L234A, L235E and G237A. This triple mutant IgG1 Fc is referred to herein as "IgG1.3f".

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

When using an IgG4 constant domain, it is usually preferable to include the substitution S228P, which mimics the hinge sequence in IgG1 and thereby stabilizes IgG4 molecules.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180).

Another modification of the antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0 154 316 by Nishimura et al. and EP 0 401 384 by Ishikawa et al.

VII. Nucleic Acid Molecules

Another aspect described herein pertains to nucleic acid molecules that encode the anti-α-synuclein antibodies described herein. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules described herein are those encoding the VH and VL sequences of the 7A10, 7A10-T93A, 11H11-1, 11H11-2, 15A5, 21A3, 36A3, 44B11, 2E2, 23H8-1, 23H8-2, 23H8-3, and 1E8 monoclonal antibodies (see, e.g., Table 22).

A method for making anti-α-synuclein antibodies may comprise expressing the heavy chain and the light chains in a cell line comprising the nucleotide sequences encoding the heavy and light chains, respectively. Host cells comprising these nucleotide sequences (e.g., or vectors comprising these nucleotide sequences) are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Also provided herein are nucleic acid molecules encoding VH and VL sequences that are homologous to those of the 7A10, 7A10-T93A, 11H11-1, 11H11-2, 15A5, 21A3, 36A3, 44B11, 2E2, 23H8-1, 23H8-2, 23H8-3, and 1E8 monoclonal antibodies (for example, those shown in Table 22). Exemplary nucleic acid molecules encode VH and VL sequences that are at least 70% identical, for example, at least 75%, at least 80%, at least 85%, at least 90%, at least 95%, or at least 99% identical, to nucleic acid molecules encoding the VH and VL sequences of the 7A10, 7A10-T93A, 11H11-1, 11H11-2, 15A5, 21A3, 36A3, 44B11, 2E2, 23H8-1, 23H8-2, 23H8-3, and 1E8 monoclonal antibodies (for example, those shown in Table 22). Also provided herein are vectors, e.g., expression vectors encoding the nucleic acids, as well as host cells that comprise the vectors or nucleic acids described above. Also provided herein are nucleic acid molecules with silent substitutions (i.e., substitutions that do not alter the resulting amino acid sequence upon translation of nucleic acid molecule), e.g., for codon optimization.

VIII. Antibody Production

Monoclonal antibodies described herein can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al.).

In one embodiment, the antibodies described herein are human monoclonal antibodies. Such human monoclonal antibodies directed against α-synuclein can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In certain embodiments, antibodies described herein are raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-α-synuclein antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-α-synuclein antibodies described herein. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-α-synuclein antibodies described herein.

Additional mouse systems described in the art for raising human antibodies include (i) the VelocImmune® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunizations

To generate fully human antibodies to α-synuclein, transgenic or transchromosomal mice containing human immunoglobulin genes (e.g., HCo12, HCo7 or KM mice) can be immunized with a purified or enriched preparation of the α-synuclein antigen and/or cells expressing α-synuclein or fragment thereof, as described for other antigens, for example, by Lonberg et al. (1994) *Nature* 368(6474): 856-859; Fishwild et al. (1996) *Nature Biotechnology* 14: 845-851 and WO 98/24884. For example, in one embodiment, mice are immunized with recombinant human αSyn WT. In another embodiment, mice are immunized with αSyn A53T-PFF mutant protein. In another embodiment, mice are immunized with αSyn WT-PFF. In another embodiment, mice are immunized with crosslinked αSyn WT. In another embodiment, mice are immunized with crosslinked A53T PFF. In another embodiment, mice are immunized with a mixture of αSyn WT-PFF, αSyn A53T-PFF, crosslinked αSyn WT-PFF, and crosslinked αSyn A53T-PFF. Alternatively, mice can be immunized with DNA encoding human α-synuclein or fragment thereof. Preferably, the mice will be 6-16 weeks of age upon the first infusion. For example, a purified or enriched preparation (5-50 µg) of the recombinant α-synuclein antigen can be used to immunize the HuMAb mice intraperitoneally. In the event that immunizations using a purified or enriched preparation of the α-synuclein antigen do not result in antibodies, mice can also be immunized with cells expressing α-synuclein, e.g., a cell line, to promote immune responses. Exemplary cell lines include α-synuclein-overexpressing stable CHO and Raji cell lines.

Cumulative experience with various antigens has shown that the HuMAb transgenic mice respond best when initially immunized intraperitoneally (IP) or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-α-synuclein human immunoglobulin can be used for fusions. Mice can be boosted intravenously with antigen 3 days before sacrifice and removal of the spleen and lymph nodes. It is expected that 2-3 fusions for each immunization may need to be performed. Between 6 and 24 mice are typically immunized for each antigen. Usually, HCo7, HCo12, and KM strains are used. In addition, both HCo7 and HCo12 transgene can be bred together into a single mouse having two different human heavy chain transgenes (HCo7/HCo12).

Generation of Hybridomas Producing Monoclonal Antibodies to α-Synuclein

To generate hybridomas producing human monoclonal antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 nonsecreting mouse myeloma cells (ATCC, CRL 1581) with 50% PEG. Cells are plated at approximately $2 \times 10^5$ in flat bottom microtiter plate, followed by a two week incubation in selective medium containing 10% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/nil penicillin, 50 mg/ml streptomycin, 50 mg/ml gentamycin and 1×HAT (Sigma). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies to α-Synuclein

Antibodies can be produced in a host cell transfectoma using, for example, a combination of recombinant DNA techniques and gene transfection methods as is well known in the art (Morrison, S. (1985) Science 229:1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector.

Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies described herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

IX. Assays

Antibodies described herein can be tested for binding to α-synuclein by, for example, standard ELISA, using standard techniques, such as those described in the Examples.

An ELISA assay as described above can be used to screen for antibodies and, thus, hybridomas that produce antibodies that show positive reactivity with the α-synuclein immunogen. Hybridomas that produce antibodies that bind, preferably with high affinity, to α-synuclein can then be subcloned and further characterized. One clone from each hybridoma, which retains the reactivity of the parent cells (by ELISA), can then be chosen for making a cell bank, and for antibody purification.

To determine if the selected anti-α-synuclein monoclonal antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using α-synuclein coated-ELISA plates as described above.

Techniques for assessing competition between antibodies include, for example, an immunoassay, which shows the ability of one antibody to block (or not block) the binding of another antibody to a target antigen, i.e., a competitive binding assay. Competitive binding is determined in an assay in which the immunoglobulin under test inhibits specific binding of a reference antibody to a common antigen, such as α-synuclein. Numerous types of competitive binding assays are known, for example: solid phase direct or indirect radioimmunoassay (RIA), solid phase direct or indirect enzyme immunoassay (EIA), sandwich competition assay; solid phase direct biotin-avidin EIA; solid phase direct labeled assay, solid phase direct labeled sandwich assay; solid phase direct $^{125}$I labeled RIA; solid phase direct biotin-avidin EIA; and direct labeled RIA. Surface plasmon resonance can also be used for this purpose. Typically, such an assay involves the use of purified antigen bound to a solid surface or cells bearing either of these, an unlabeled test immunoglobulin, and a labeled reference immunoglobulin. Competitive inhibition is measured by determining the amount of label bound to the solid surface or cells in the presence of the test immunoglobulin. The test immunoglobulin is typically present in excess. Usually, when a competing antibody is present in excess, it will inhibit specific binding of a reference antibody to a common antigen by at least 30%, at least 40%, at least 50%, at least 60%, at least 70%, at least 80%, at least 90%, at least 95%, or more.

Other screening techniques for determining the epitope bound by antibodies disclosed herein include, for example, x-ray analysis of crystals of antigen:antibody complexes, which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

To determine the isotype of purified antibodies, isotype ELISAs can be performed using reagents specific for antibodies of a particular isotype.

Anti-α-synuclein antibodies can be further tested for reactivity with the α-synuclein antigen by Western blotting. Briefly, cell extracts from cells expressing α-synuclein can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-α-synuclein antibodies include standard assays known in the art, for example, Biacore™ surface plasmon resonance (SPR) analysis using a Biacore™ 2000 SPR instrument (Biacore AB, Uppsala, Sweden).

Anti-α-synuclein antibodies can also be tested for their preferential binding to α-synuclein oligomers over α-synuclein monomers. The "monomer/PFF binding ratio" is used herein as an index to describe the binding behavior of anti-α-synuclein antibodies to PFF and α-synuclein monomers. Ratios greater than 1 indicate a greater preference for binding to PFF than α-synuclein monomers. For example, if an antibody binds to monomeric α-synuclein with an EC50 of 291 nM and PFF with an EC50 of 0.16 nM by ELISA, e.g., as described in Example 3, the monomer/PFF binding ratio of that antibody would be 291/0.16=1819. In some embodiments, PFF is prepared according to the method described in Example 3.

Anti-α-synuclein antibodies can be tested for their ability to clear aggregates of α-synuclein oligomers in the brain using, e.g., the assays described in Example 11, or the oligomer ELISAs described in Example 12. The antibodies can also be tested for their ability to reduce or inhibit α-synuclein oligomer (PFF)-induced phosphorylation of S129 of α-synuclein using, e.g., the methods described in Examples 10 and 11, or the ability to deplete the molecular species that produces insoluble α-synuclein aggregates (e.g., serine-129 phosphorylated α-synuclein aggregates) from PFF and/or brain lysate prepared from patients with pathological aggregates of α-synuclein in the brain (e.g., brain lysates prepared from patients with synucleinopathies, e.g., MSA).

X. Immunoconjugates, Antibody Derivatives and Diagnostics

Antibodies described herein can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Preferably, conjugation methods result in linkages which are substantially (or nearly) non-immunogenic, e.g., peptide- (i.e. amide-), sulfide-, (sterically hindered), disulfide-, hydrazone-, and ether linkages. These linkages are nearly non-immunogenic and show reasonable stability within serum (see e.g. Senter, P. D., Curr. Opin. Chem. Biol. 13 (2009) 235-244; WO 2009/059278; WO 95/17886).

Depending on the biochemical nature of the moiety and the antibody, different conjugation strategies can be employed. In case the moiety is naturally occurring or recombinant of between 50 to 500 amino acids, there are standard procedures in text books describing the chemistry for synthesis of protein conjugates, which can be easily followed by the skilled artisan (see e.g. Hackenberger, C. P. R., and Schwarzer, D., Angew. Chem. Int. Ed. Engl. 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, J., Org. Biomol. Chem. 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., ChemBioChem. 10 (2009) 425-427). It is also possible to obtain a desired amino acid modification by utilizing the specific enzymatic reactivity of certain enzymes with a natural amino acid in a given sequence context (see, e.g., Taki, M. et al., Prot. Eng. Des. Sel. 17 (2004) 119-126; Gautier, A. et al. Chem. Biol. 15 (2008) 128-136; and Protease-catalyzed formation of C—N bonds is used by Bordusa, F., Highlights in Bioorganic Chemistry (2004) 389-403).

Site specific reaction and covalent coupling can also be achieved by the selective reaction of terminal amino acids with appropriate modifying reagents.

The reactivity of an N-terminal cysteine with benzonitrils (see Ren, H. et al., Angew. Chem. Int. Ed. Engl. 48 (2009) 9658-9662) can be used to achieve a site-specific covalent coupling.

Native chemical ligation can also rely on C-terminal cysteine residues (Taylor, E. Vogel; Imperiali, B, Nucleic Acids and Molecular Biology (2009), 22 (Protein Engineering), 65-96).

EP 1 074 563 describes a conjugation method which is based on the faster reaction of a cysteine within a stretch of negatively charged amino acids with a cysteine located in a stretch of positively charged amino acids.

The moiety may also be a synthetic peptide or peptide mimic. In case a polypeptide is chemically synthesized, amino acids with orthogonal chemical reactivity can be incorporated during such synthesis (see e.g. de Graaf, A. J. et al., Bioconjug. Chem. 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry may be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

In one embodiment the moiety attached to an anti-α-synuclein antibody is selected from the group consisting of a binding moiety, a labeling moiety, and a biologically active moiety.

Antibodies described herein may also be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO: 128), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference.

Anti-α-synuclein antibodies, e.g., those described herein, may also be used for detecting α-synuclein, such as human α-synuclein, e.g., human α-synuclein in tissues or tissue samples. The antibodies may be used, e.g., in an ELISA assay or in flow cytometry. In certain embodiments, an anti-α-synuclein antibody is contacted with cells, e.g., cells in a tissue, for a time appropriate for specific binding to occur, and then a reagent, e.g., an antibody that detects the anti-α-synuclein antibody, is added. The anti-α-synuclein antibody may be a fully human antibody, or it may be a chimeric antibody, such as an antibody having human variable regions and murine constant regions or a portion thereof. Exemplary methods for detecting α-synuclein, e.g., human α-synuclein, in a sample (cell or tissue sample) comprise (i) contacting a sample with an anti-α-synuclein antibody, for a time sufficient for allowing specific binding of the anti-α-synuclein antibody to α-synuclein in the sample, and (2) contacting the sample with a detection reagent, e.g., an antibody, that specifically binds to the anti-α-synuclein antibody, such as to the Fc region of the anti-α-synuclein antibody, to thereby detect α-synuclein bound by the anti-α-synuclein antibody. Wash steps may be included after the incubation with the antibody and/or detection reagent. Anti-α-synuclein antibodies for use in these methods do not have to be linked to a label or detection agents, as a separate detection agent can be used.

XI. Bispecific Molecules

Antibodies described herein may be used for forming bispecific molecules. An anti-α-synuclein antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. For example, an anti-α-synuclein antibody may be linked to an antibody or scFv that binds specifically to any protein that may be used as potential targets for combination treatments, such as the proteins described herein. The antibody described herein may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for α-synuclein and a second binding specificity for a second target epitope. In an embodiment described herein in which the bispecific molecule is multispecific, the molecule can further include a third binding specificity.

In one embodiment, the bispecific molecules described herein comprise as a binding specificity at least one antibody, or an antibody fragment thereof, including, e.g., an Fab, Fab', F(ab')$_2$, Fv, or a single chain Fv (scFv). The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies which can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

In some embodiments, the bispecific molecules described herein have a second binding specificity that increases the transport of the molecule into the brain, e.g., across the blood-brain-barrier.

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb×(scFv)$_2$, Fab×F(ab')$_2$ or ligand×Fab fusion protein. A bispecific antibody may comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

XII. Compositions

Further provided are compositions, e.g., pharmaceutical compositions, containing one or a combination of anti-α- synuclein antibodies or combination with antibodies to other targets, or antigen-binding portion(s) thereof, described herein, formulated together with a pharmaceutically acceptable carrier. Such compositions may include one or a combination of (e.g., two or more different) antibodies, or immunoconjugates or bispecific molecules described herein. For example, a pharmaceutical composition described herein can comprise a combination of antibodies (or immunoconjugates or bispecifics) that bind to different epitopes on the target antigen or that have complementary activities.

In certain embodiments, a composition comprises an anti-α-synuclein antibody at a concentration of at least 1 mg/ml, 5 mg/ml, 10 mg/ml, 50 mg/ml, 100 mg/ml, 150 mg/ml, 200 mg/ml, 1-300 mg/ml, or 100-300 mg/ml.

Pharmaceutical compositions described herein also can be administered in combination therapy, i.e., combined with other agents (either in the same composition or separate compositions). Examples of therapeutic agents that can be used in combination therapy include, e.g., levodopa, amantadine (Symmetrel), anticholinergics (trihexyphenidyl, benztropine mesylate, procyclidine, artane, cogentin), bromocriptidine (Parlodel), pergolide (Permax), ropinirol (Requip), pramipexole (Mirapex), monoaminoxidase-B inhibitors (MAO) such as selegiline (Diprenyl or Eldepryl), catechol-O-methyltransferase inhibitors (COMT) such as entocapone, tasmar, or tolcapone, cholinesterase inhibitors, D2 receptor antagonists, DA agonists, anti-sense oligonucleotides, (e.g., anti-sense oligonucleotides directed against α-synuclein), kinase inhibitors, and leucine-rich repeat kinase 2 (LRRK2) inhibitors. Additional agents include, for example, therapeutics targeting molecules known to be involved in the pathology of synucleinopathies, such as PINK, PARKIN, DJ1, glucocerebrosidase (GBA), and agents that target reactive oxygen species.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein may also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 or 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. In some embodiments, an anti-α-synuclein antibody may be administered at a flat dose (flat dose regimen).

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-α-synuclein antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-α-synuclein antibodies described herein can be formulated to ensure proper distribution in vivo. For example, the blood-brain barrier (BBB) excludes many highly hydrophilic compounds. To ensure that the therapeutic compounds described herein cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

XIII. Kits

Also provided are kits comprising the anti-α-synuclein antibodies, bispecific antibodies, or immunoconjugates disclosed herein, optionally contained in a single vial or container, and include, e.g., instructions for use in treating or diagnosing a disease associated with the presence of Lewy bodies or aggregates of α-synuclein in the brain. The kits may include a label indicating the intended use of the contents of the kit. The term label includes any writing, marketing materials or recorded material supplied on or with the kit, or which otherwise accompanies the kit. Such kits may comprise the antibody, bispecific antibodies, or immunoconjugate in unit dosage form, such as in a single dose vial or a single dose pre-loaded syringe.

XIV. Uses and Methods

Provided herein are methods of treating subjects (e.g., human patients) with diseases characterized by the presence of Lewy bodies or pathological aggregates of α-synuclein in the brain, as well as methods for prophylaxis of these diseases.

Accordingly, in one aspect, provided herein are methods of treating a disease characterized by the presence of Lewy bodies or pathological aggregates of α-synuclein in the brain comprising administering to a subject with the disease an effective amount of an anti-α-synuclein antibody, or antigen-binding portion, described herein.

In another aspect, provided herein are methods of lessening the severity of a disease characterized by the presence of Lewy bodies or pathological aggregates of α-synuclein in the brain comprising administering to a subject with the disease an effective amount of an anti-α-synuclein antibody, or antigen-binding portion, described herein.

In another aspect, provided herein are methods of delaying the progression of a disease characterized by the presence of Lewy bodies or pathological aggregates of α-synuclein in the brain comprising administering to a subject with the disease an effective amount of an anti-α-synuclein antibody, or antigen-binding portion, described herein.

In another aspect, provided herein are methods of reducing the risk of developing a disease characterized by the presence of Lewy bodies or pathological aggregates of α-synuclein in the brain comprising administering to a subject at risk of developing the disease an effective amount of an anti-α-synuclein antibody, or antigen-binding portion, described herein.

In another aspect, provided herein are methods of delaying the onset of a disease characterized by the presence of Lewy bodies or pathological aggregates of α-synuclein in the brain comprising administering to a subject at risk of developing the disease an effective amount of an anti-α-synuclein antibody, or antigen-binding portion, described herein.

In some embodiments, subjects to be treated exhibit symptoms (signs) of synucleinopathies, such as neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia), and other signs and symptoms (fatigue, diplopia, blurred vision, seborrhea, weight loss/gain).

In some embodiments, subjects to be treated do not exhibit symptoms of the disease, but are known to have a genetic risk for developing a disease characterized by the presence of Lewy bodies or pathological aggregates of α-synuclein in the brain. For instance, such individuals may have relatives with the disease, or their risk is determined by analysis of genetic or biochemical markers. For example, mutations in SNCA (PARK1, encoding α-synuclein), including A30P, E46K, H50Q, G51D, and A53T, as well as duplications and triplications of the entire SNCA gene cause autsomal dominat forms of PD. Mutations in LRRK2 (PARKS, Leucine-rich repeat kinase 2) and mutations in VPS35 (PARK17, vacuolar protein sorting 35) also cause autosomal dominant forms of PD (Hernandez et al., (2016) Genetics in Parkinson disease: Mendelial versus non-Medndelian inheritance. *Journal of Neurochemistry* 10.1111/jnc.13593). Mutations in PINK1 (PARK6, PTEN-induced kinase 1), DJ-1 (PARK7), Parkin (PARK2), ATP13A2 (PARK9, ATPase type 13A2), FBXO7 (PARK15, F-box only protein 7), and PLA2 GB (PARK14, phospholipase A2, group VI) have been shown to cause autosomal recessive PD/parkinonism. In addition, 28 different genetic risk loci associated with PD and related synucleinopathies have been identified including SNCA, LRRK2, GBA/SYT11, MAPT, HLA-DRB5, GAK, GCH1, NUCKS1/RAB7L1, SLC41A1, BST1, SIPA1L2, ACMSD/TMEM163, STK39, MCCC1, TMEM175/GAK/DGKQ, FAM47E/SCARB2, GPNMB, FGF20, INPP5F, MIR4697, CCDC62, GCH1, VPS13C, BCKDK/STX1B, SREBF/RA11, RIT2 and DDRGK1 (Nails et al. (2014) Large-scale meta-analysis of genome-wide association data identifies six new risk loci for Parkinson's disease. *Nature Genetics* 46(9): 989-993). Accordingly, in prophylactic applications, the antibodies described herein, or pharmaceutical compositions comprising the same, are administered to a patient susceptible to, or otherwise at risk of the disease in a regime (dose, frequency and route of administration) effective to reduce the risk, lessen the severity, or delay the onset of at least one sign or symptom of the disease. In some prophylactic applications, the regime is effective to inhibit or delay accumulation of α-synuclein in the brain, and/or inhibit or delay its toxic effects and/or inhibit or delay development of behavioral deficits in the patient.

In some embodiments, the methods described above generate a beneficial therapeutic response in a patient (e.g., reduction of α-synuclein aggregates in the brain, improved cognitive function, and/or reversing, treating or preventing cognitive decline) in the subject. Accordingly, in some embodiments, the antibodies described herein are administered to a patient suspected of, or already suffering from a disease characterized by the presence of Lewy bodies or pathological aggregates of α-synuclein in the brain in a regime (dose, frequency and route of administration) effective to ameliorate or at least inhibit further deterioration of at least one sign or symptom of the disease. In some therapeutic applications, the regime is effective to reduce or at least inhibit further increase of levels of α-synuclein, associated toxicities, and/or behavioral deficits. In certain embodiments, the treatments can result in, e.g., a reduction of α-synuclein aggregates in the brain by 10% or more, 20% or more, 30% or more, 40% or more, 50% or more, 60% or more, 70% or more, 80% or more, or 90% or more, relative to before initiating treatment or as compared to a population of untreated control patients.

In some embodiments, the disease characterized by the presence of Lewy bodies or pathological aggregates of α-synuclein in the brain is Parkinson's disease (including idiopathic Parkinson's disease), DLB, DLBD, LBVAD, pure autonomic failure, Lewy body dysphagia, incidental LBD, inherited LBD (e.g., mutations of SNCA (PARK1), LRRK2 (PARK8), VPS35 (PARK17), PINK1 (PARK6), DJ-1 (PARK7), Parkin (PARK2), ATP13A2 (PARK9), FBXO7 (PARK15) and PLA2 GB (PARK14)), or multiple system atrophy (MSA; e.g., olivopontocerebellar atrophy, striatonigral degeneration and Shy-Drageri syndrome).

Also provided are methods of inhibiting the generation of insoluble α-synuclein aggregates (e.g., serine-129 phosphorylated α-synuclein aggregates) in a cell (in vitro or in vivo) comprising contacting the cell with an effective amount of an anti-α-synuclein antibody, or antigen-binding portion thereof, described herein. In some embodiments, phosphorylation of serine-129 is induced by α-synuclein oligomers (e.g., PFF).

Also provided are methods for preserving or increasing synaptic density and/or dentritic density, as measured using markers of synapse formation (synaptophysin) and/or dendrites (MAP2). Accordingly, in some embodiments, subjects treated with the antibodies described herein exhibit an elevation of synaptic or dendritic density of 10% or more, 20% or more, 30% or more, 40% or more, or 50% or more, relative to before initiating treatment or as compared to a population of untreated control patients.

Antibodies disclosed herein also can be used to diagnose or prognose disease characterized by the presence of Lewy bodies or pathological aggregates of α-synuclein in the brain, for example, by contacting an antibody disclosed herein (e.g., ex vivo or in vivo) with cells from the subject, and measuring the level of binding to α-synuclein on the cells, wherein abnormally high levels of binding to α-synuclein indicate that the subject has a disease characterized by the presence of Lewy bodies or pathological aggregates of α-synuclein in the brain. For diagnostic or prognostic purposes, the antibodies described herein can be administered by intravenous injection into the body of the patient, or directly into the brain by intracranial injection or by drilling a hole through the skull. The dosage of reagent should be within the same ranges as for treatment methods. Suitable labels include, for example, fluorescent labels (e.g., for optical detection), paramagnetic labels (e.g., for tomographic detection without surgical intervention), and radioactive labels (e.g., for detection using PET or SPECT). Diagnosis is performed by comparing the number, size and/or intensity of labeled loci to corresponding baseline values. The baseline values can represent the mean levels in a population of undiseased individuals. Baseline values can also represent previous levels determined in the same patient. For example, baseline values can be determined in a patient before beginning treatment, and measured values thereafter compared with the baseline values. A decrease in values relative to baseline signals a positive response to treatment.

In one embodiment, provided herein is a method for diagnosing a disease characterized by the presence of Lewy bodies or pathological aggregates of α-synuclein in a subject comprising:

(a) contacting a sample from the subject with an antibody, or antigen-binding portion thereof, described herein such that an antibody-antigen complex is formed;

(b) measuring the amount of the complex formed; and (c) comparing the amount of the complex in the sample with the amount in a control wherein an elevated level of the complex in the sample relative to the control indicates the subject has a disease characterized by the presence of Lewy bodies or pathological aggregates of α-synuclein. In some embodiments, the sample is cerebrospinal fluid, brain tissue extract, urine, or blood. In some embodiments, the control is a population of healthy subjects who do not exhibit symptoms of the disease and are not genetically predisposed to the disease (e.g., synucleinopathies).

In preferred embodiments, an anti-α-synuclein antibody described herein is not significantly toxic. For example, an anti-α-synuclein antibody is not significantly toxic to an organ of a human, e.g., one or more of the liver, kidney, brain, lungs, and heart, as determined, e.g., in clinical trials. In certain embodiments, an anti-α-synuclein antibody does not significantly trigger an undesirable immune response, e.g., autoimmunity or inflammation.

The antibody can be administered alone or with another therapeutic agent that acts in conjunction with or synergistically with the antibody to treat the disease associated with Lewy bodies or aggregates of α-synuclein in the brain (e.g., multiple system atrophy).

Exemplary therapeutic agents suitable for use in combination with the antibodies described herein include, for example, levodopa, amantadine (Symmetrel), anticholinergics (trihexyphenidyl, benztropine mesylate, procyclidine, artane, cogentin), bromocriptidine (Parlodel), pergolide (Permax), ropinirol (Requip), pramipexole (Mirapex), monoaminoxidase-B inhibitors (MAO) such as selegiline (Diprenyl or Eldepryl), catechol-O-methyltransferase inhibitors (COMT) such as entocapone, tasmar, or tolcapone, cholinesterase inhibitors, D2 receptor antagonists, DA agonists, anti-sense oligonucleotides, (e.g., anti-sense oligonucleotides directed against α-synuclein), kinase inhibitors, and leucine-rich repeat kinase 2 (LRRK2) inhibitors. Additional agents include, for example, therapeutics targeting molecules known to be involved in the pathology of synucleinopathies, such as PINK, PARKIN, DJ1, glucocerebrosidase (GBA), and agents that target reactive oxygen species.

Additional therapeutic agents can be administered together (e.g., concurrently or sequentially) with the antibodies described herein, or separately (e.g., hours or days apart).

Also encompassed are methods for detecting the presence of human α-synuclein antigen in a sample, or measuring the amount of human α-synuclein antigen, comprising contacting the sample, and a control sample, with a monoclonal antibody, e.g., a human monoclonal antibody, or an antigen binding portion thereof, which specifically binds to human α-synuclein, under conditions that allow for formation of a complex between the antibody or portion thereof and human α-synuclein. The formation of a complex is then detected, wherein a difference complex formation between the sample compared to the control sample is indicative the presence of human α-synuclein antigen in the sample. In one embodiment, the anti-α-synuclein antibodies described herein can be used to purify human α-synuclein via immunoaffinity purification. In another embodiment, the anti-α-synuclein antibodies described herein can be used to detect the amount of α-synuclein proteins in a biological sample (e.g., a biopsy). In yet another embodiment, the anti-α-synuclein antibodies described herein can be used in in vitro assays (e.g., immunoassays such as Western blot, radioimmunoassays, ELISA) to detect α-synuclein proteins.

XV. Exemplary Embodiments

1. An isolated antibody, or antigen-binding portion thereof, which binds to α-synuclein and exhibits one or more of the following properties:
  (a) binds to mouse and rat α-synuclein;
  (b) binds to human β-synuclein and human γ-synuclein;
  (c) has a greater affinity for α-synuclein oligomers over α-synuclein monomers;
  (d) inhibits the generation of α-synuclein oligomer-induced insoluble serine-129 phosphorylated α-synuclein aggregates;
  (e) depletes the molecular species that produces soluble insoluble α-synuclein aggregates characterized by serine-129 phosphorylation from PFF and/or brain lysate prepared from patients with pathological aggregates of α-synuclein in the brain;
  (f) binds to all or a portion of amino acid positions 123-128 of human α-synuclein (SEQ ID NO: 1);
  (g) binds to all or a portion of amino acid positions 125-128 of human α-synuclein (SEQ ID NO: 1);
  (h) binds to all or a portion of amino acid positions 130-139 of human α-synuclein (SEQ ID NO: 1);
  (i) binds to all or a portion of amino acid positions 119-126 of human α-synuclein (SEQ ID NO: 1); and
  (j) binds to all or a portion of amino acid positions 130-138 of human α-synuclein (SEQ ID NO: 1).

2. The antibody, or antigen-binding portion thereof, of embodiment 1, wherein the α-synuclein oligomer is PFF.

3. The antibody, or antigen-binding portion thereof, of embodiment 2, wherein the PFF is prepared as described in Example 3.

4. The antibody, or antigen-binding portion thereof, of any of embodiments 1-3, wherein the α-synuclein oligomers are soluble α-synuclein oligomers.

5. The antibody, or antigen-binding portion thereof, of any of embodiments 1-3, wherein the α-synuclein oligomers are insoluble α-synuclein oligomers.

6. The antibody, or antigen-binding portion thereof, of any of embodiments 1-5, wherein the greater affinity for α-synuclein PFF over α-synuclein monomers is measured using an α-synuclein monomer/α-synuclein PFF binding ratio, as determined by a luminescence-based binding assay (e.g., as described in Example 3).

7. The antibody, or antigen-binding portion thereof, of embodiment 6, wherein the antibody, or antigen-binding portion thereof, has a α-synuclein monomer/α-synuclein PFF binding ratio of 100 or greater.

8. The antibody, or antigen-binding portion thereof, of embodiment 7, wherein the monomer/PFF binding ratio is 500 or greater.

9. The antibody, or antigen-binding portion thereof, of embodiment 8, wherein the monomer/PFF binding ratio is 700 or greater.

10. The antibody, or antigen-binding portion thereof, of embodiment 9, wherein the monomer/PFF binding ratio is 1500 or greater.

11. The antibody, or antigen-binding portion thereof, of embodiment 10, wherein the monomer/PFF binding ratio is 3000 or greater.

12. The antibody, or antigen-binding portion thereof, of embodiment 11, wherein the monomer/PFF binding ratio is 5000 or greater.

13. The antibody, or antigen-binding portion thereof, of any of the preceding embodiments, wherein the antibody, or antigen-binding portion thereof, binds to monomeric α-synuclein with an EC50 of 100 nM or greater, and binds to PFF with an EC50 of 2 nM or less, as measured by ELISA.

14. The antibody, or antigen-binding portion thereof, of embodiment 13, wherein the antibody, or antigen-binding portion thereof, binds to monomeric α-synuclein with an EC50 of 500 nM or greater, and binds to PFF with an EC50 of 0.5 nM or less.

15. The antibody, or antigen-binding portion thereof, of any of the preceding embodiments, wherein the antibody, or antigen-binding portion thereof, inhibits PFF-induced α-synuclein serine-129 phosphorylation with an $IC_{50}$ of 0.1 nM or less, as assessed using the assay described in Example 10.

16. An isolated monoclonal antibody, or antigen binding portion thereof, which specifically binds to α-synuclein and comprise the three variable heavy chain CDRs and the three variable light chain CDRs that are in the variable heavy chain and variable light chain pairs selected from the group consisting of:
  (a) SEQ ID NOs: 8 and 9;
  (b) SEQ ID NOs: 18 and 19;
  (c) SEQ ID NOs: 20 and 21;
  (d) SEQ ID NOs: 31 and 32;
  (e) SEQ ID NOs: 31 and 33;
  (f) SEQ ID NOs: 43 and 44;
  (g) SEQ ID NOs: 53 and 54;
  (h) SEQ ID NOs: 63 and 64;
  (i) SEQ ID NOs: 73 and 74;
  (j) SEQ ID NOs: 83 and 84;
  (k) SEQ ID NOs: 99 and 100;
  (l) SEQ ID NOs: 99 and 101;
  (m) SEQ ID NOs: 99 and 102; and
  (n) SEQ ID NOs: 113 and 114.

17. An isolated monoclonal antibody, or antigen binding portion thereof, which binds to α-synuclein, comprising:

(a) heavy chain variable region CDR1, CDR2, and CDR3 comprising SEQ ID NOs: 2-4, respectively, and the light chain variable region CDR1, CDR2, and CDR3 comprising SEQ ID NOs: 5-7, respectively;

(b) heavy chain variable region CDR1, CDR2, and CDR3 comprising SEQ ID NOs: 12-14, respectively, and the light chain variable region CDR1, CDR2, and CDR3 comprising SEQ ID NOs: 15-17, respectively;

(c) heavy chain variable region CDR1, CDR2, and CDR3 comprising SEQ ID NOs: 22-24, respectively, and the light chain variable region CDR1, CDR2, and CDR3 comprising SEQ ID NOs: 25-27, respectively;

(d) heavy chain variable region CDR1, CDR2, and CDR3 comprising SEQ ID NOs: 22-24, respectively, and the light chain variable region CDR1, CDR2, and CDR3 comprising SEQ ID NOs: 28-30, respectively;

(e) heavy chain variable region CDR1, CDR2, and CDR3 comprising SEQ ID NOs: 37-39, respectively, and the light chain variable region CDR1, CDR2, and CDR3 comprising SEQ ID NOs: 40-42, respectively;

(f) heavy chain variable region CDR1, CDR2, and CDR3 comprising SEQ ID NOs: 47-49, respectively, and the light chain variable region CDR1, CDR2, and CDR3 comprising SEQ ID NOs: 50-52, respectively;

(g) heavy chain variable region CDR1, CDR2, and CDR3 comprising SEQ ID NOs: 57-59, respectively, and the light chain variable region CDR1, CDR2, and CDR3 comprising SEQ ID NOs: 60-62, respectively;

(h) heavy chain variable region CDR1, CDR2, and CDR3 comprising SEQ ID NOs: 67-69, respectively, and the light chain variable region CDR1, CDR2, and CDR3 comprising SEQ ID NOs: 70-72, respectively;

(i) heavy chain variable region CDR1, CDR2, and CDR3 comprising SEQ ID NOs: 77-79, respectively, and the light chain variable region CDR1, CDR2, and CDR3 comprising SEQ ID NOs: 80-82, respectively;

(j) heavy chain variable region CDR1, CDR2, and CDR3 comprising SEQ ID NOs: 87-89, respectively, and the light chain variable region CDR1, CDR2, and CDR3 comprising SEQ ID NOs: 90-92, respectively;

(k) heavy chain variable region CDR1, CDR2, and CDR3 comprising SEQ ID NOs: 87-89, respectively, and the light chain variable region CDR1, CDR2, and CDR3 comprising SEQ ID NOs: 93-95, respectively;

(l) heavy chain variable region CDR1, CDR2, and CDR3 comprising SEQ ID NOs: 87-89, respectively, and the light chain variable region CDR1, CDR2, and CDR3 comprising SEQ ID NOs: 96-98, respectively; or (m) heavy chain variable region CDR1, CDR2, and CDR3 comprising SEQ ID NOs: 107-109, respectively, and the light chain variable region CDR1, CDR2, and CDR3 comprising SEQ ID NOs: 110-112, respectively.

18. An isolated monoclonal antibody, or antigen binding portion thereof, which binds to α-synuclein and comprises heavy and light chain variable regions, wherein the heavy chain variable region comprises an amino acid sequence which is at least 90% identical to the amino acid sequence selected from the group consisting of SEQ ID NOs: 8, 18, 31, 43, 53, 63, 73, 83, 99, and 113.

19. An isolated monoclonal antibody, or antigen binding portion thereof, which binds to α-synuclein and comprises heavy and light chain variable regions, wherein the light chain variable region comprises an amino acid sequence which is at least 90% identical to the amino acid sequence selected from the group consisting of SEQ ID NOs: 9, 19, 32, 33, 44, 54, 64, 74, 84, 100, 101, 102, and 114.

20. An isolated monoclonal antibody, or antigen binding portion thereof, which binds to α-synuclein and comprises heavy and light chain variable region sequences at least 90% identical to the amino acid sequences selected from the group consisting of:

(a) SEQ ID NOs: 8 and 9;
(b) SEQ ID NOs: 18 and 19;
(c) SEQ ID NOs: 31 and 32;
(d) SEQ ID NOs: 31 and 33;
(e) SEQ ID NOs: 43 and 44;
(f) SEQ ID NOs: 53 and 54;
(g) SEQ ID NOs: 63 and 64;
(h) SEQ ID NOs: 73 and 74;
(i) SEQ ID NOs: 83 and 84;
(j) SEQ ID NOs: 99 and 100;
(k) SEQ ID NOs: 99 and 101;
(l) SEQ ID NOs: 99 and 102; and
(m) SEQ ID NOs: 113 and 114.

21. The antibody, or antigen binding portion thereof, of embodiment 20, wherein the heavy and light chain variable regions comprise an amino acid sequence at least 95%, 98%, 99%, or 100% identical to the heavy and light chain variable regions selected from the group consisting of (a)-(m).

22. An isolated monoclonal antibody, or antigen binding portion thereof, which binds to α-synuclein and comprises heavy chain and light chain sequences at least 80%, 85%, 90%, 95%, 96%, 97%, 98%, 99%, or 100% identical to the amino acid sequences selected from the group consisting of:

(n) SEQ ID NOs: 10 and 11,
(o) SEQ ID NOs: 20 and 21,
(p) SEQ ID NOs: 34 and 35,
(q) SEQ ID NOs: 34 and 36,
(r) SEQ ID NOs: 45 and 46,
(s) SEQ ID NOs: 55 and 56,
(t) SEQ ID NOs: 65 and 66,
(u) SEQ ID NOs: 75 and 76,
(v) SEQ ID NOs: 85 and 86,
(w) SEQ ID NOs: 103 and 104,
(x) SEQ ID NOs: 103 and 105,
(y) SEQ ID NOs: 103 and 106, and
(z) SEQ ID NOs: 115 and 116.

23. The antibody, or antigen-binding portion thereof, of any of the preceding embodiments, wherein the antibody binds to all or a portion of amino acid positions 123-128 of human α-synuclein (SEQ ID NO: 1), as determined by peptide mapping (e.g., as described in Example 1).

24. The antibody, or antigen-binding portion thereof, of embodiment 23, wherein the antibody binds to all or a portion of amino acid positions 125-128 of human α-synuclein (SEQ ID NO: 1), as determined by peptide mapping (e.g., as described in Example 1).

25. The antibody, or antigen-binding portion thereof, of any of embodiments 1-22, wherein the antibody binds to all or a portion of amino acid positions 130-139 of human α-synuclein (SEQ ID NO: 1), as determined by peptide mapping (e.g., as described in Example 1).

26. The antibody, or antigen-binding portion thereof, of any of embodiments 1-22, wherein the antibody binds to all or a portion of amino acid positions 119-126 of human α-synuclein (SEQ ID NO: 1), as determined by peptide mapping (e.g., as described in Example 1).

27. The antibody, or antigen-binding portion thereof, of any of embodiments 1-22, wherein the antibody binds to all or a portion of amino acid positions 130-138 of human α-synuclein (SEQ ID NO: 1), as determined by peptide mapping (e.g., as described in Example 1).

28. The antibody, or antigen-binding portion thereof, of any of the preceding embodiments, wherein the antibody binds to rat and mouse α-synuclein.

29. The antibody, or antigen-binding portion thereof, of any of the preceding embodiments, wherein the antibody binds to human β-synuclein and human γ-synuclein.

30. The antibody, or antigen-binding portion thereof, of any of the preceding embodiments, wherein the antibody has greater affinity for α-synuclein PFF than α-synuclein monomers, as assessed by an α-synuclein monomer/α-synuclein PFF binding ratio (monomer:PFF binding ratio), as determined by a luminescence-based binding assay (e.g., as described in Example 3).

31. The antibody, or antigen-binding portion thereof, of embodiment 30, wherein the monomer:PFF binding ratio is 100 or greater, 500 or greater, 700 or greater, 1500 or greater, 3000 or greater, or 5000 or greater.

32. An antibody, or antigen-binding portion thereof, which binds to the same epitope as the antibody of embodiment 21.

33. An antibody, or antigen-binding portion thereof, which competes for binding to human α-synuclein with the antibody of embodiment 21.

34. The antibody, or antigen-binding portion thereof, of any of the preceding embodiments, wherein the antibody is selected from the group consisting of an IgG1, an IgG2, an IgG3, an IgG4, or a variant thereof.

35. The antibody, or antigen binding portion thereof, of embodiment 34, wherein the antibody is an IgG1 antibody.

36. The antibody, or antigen binding portion thereof, of any of the preceding embodiments, wherein the antibody comprises an Fc region with reduced or no effector function.

37. The antibody, or antigen binding portion thereof, of embodiment 36, wherein the antibody, or antigen binding portion thereof, comprises an effectorless IgG1 Fc that comprises the following mutations: L234A, L235E, and G257A.

38. The antibody, or antigen binding portion thereof, of any of the preceding embodiments, wherein the antibody, or antigen binding portion thereof, is a chimeric, humanized, or human antibody.

39. The antibody, or antigen-binding portion thereof, of any of the preceding embodiments, wherein the antibody is modified to reduce immunogenicity in humans.

40. The antibody, or antigen-binding portion thereof, of embodiment 39, wherein the antibody comprises heavy and light chain variable regions set forth in SEQ ID NOs: 18 and 19, respectively.

41. The antibody, or antigen-binding portion thereof, of any of the preceding embodiments, which is a monoclonal antibody.

42. A bispecific molecule comprising the antibody of any one of the preceding embodiments linked to a molecule having a second binding specificity.

43. The bispecific molecule of embodiment 42, wherein the second binding specificity increases transport of the molecule into the brain.

44. A nucleic acid encoding the heavy and/or light chain variable region of the antibody, or antigen binding portion thereof, or bispecific antibody, of any of embodiments 1-43.

45. An expression vector comprising the nucleic acid molecule of embodiment 44.

46. A cell transformed with an expression vector of embodiment 45.

47. An immunoconjugate comprising the antibody or bispecific antibody of any of embodiments 1-43, linked to a moiety.

48. The immunoconjugate of embodiment 47, wherein the moiety is a binding moiety, a labeling moiety, a biologically active moiety, or a therapeutic agent.

49. A composition comprising the antibody, or antigen binding portion thereof, bispecific molecule, or immunoconjugate, of any of embodiments 1-43, 47, and 48, and a pharmaceutically acceptable carrier.

50. A kit comprising the antibody, or antigen binding portion thereof, or bispecific molecule, or immunoconjugate of any of embodiments 1-43, 47, and 48, and instructions for use.

51. A method of preparing an anti-α-synuclein antibody, or antigen-binding portion thereof, comprising expressing the antibody, or antigen binding portion thereof, in the cell of embodiment 46 and isolating the antibody, or antigen binding portion thereof, from the cell.

52. A method of inhibiting the generation of insoluble serine-129 phosphorylated α-synuclein aggregates in a cell comprising contacting the cell with an effective amount of the antibody, or antigen-binding portion, bispecific antibody, or immunoconjugate of any of embodiments 1-43, 47, and 48.

53. The method of embodiment 52, wherein phosphorylation of serine-129 is induced by α-synuclein oligomers.

54. The method of embodiment 53, wherein the α-synuclein oligomers are pre-formed α-synuclein fibrils.

55. The method of embodiment 53, wherein the α-synuclein oligomers are derived from brain samples from patients with synucleinopathies.

56. A method of treating a disease characterized by the presence of Lewy bodies or pathological aggregates of α-synuclein in the brain comprising administering to a subject with the disease an effective amount of the antibody, or antigen-binding portion, bispecific antibody, or immunoconjugate of any of embodiments 1-43, 47, and 48.

57. A method of lessening the severity of a disease characterized by the presence of Lewy bodies or pathological aggregates of α-synuclein in the brain comprising administering to a subject with the disease an effective amount of the antibody, or antigen-binding portion, bispecific antibody, or immunoconjugate of any of embodiments 1-43, 47, and 48.

58. A method of delaying the progression of a disease characterized by the presence of Lewy bodies or pathological aggregates of α-synuclein in the brain comprising administering to a subject with the disease an effective amount of the antibody, or antigen-binding portion, bispecific antibody, or immunoconjugate of any of embodiments 1-43, 47, and 48.

59. A method of reducing the risk of developing a disease characterized by the presence of Lewy bodies or pathological aggregates of α-synuclein in the brain comprising administering to a subject at risk of developing the disease an effective amount of the antibody, or antigen-binding portion, bispecific antibody, or immunoconjugate of any of embodiments 1-43, 47, and 48.

60. A method of delaying the onset of a disease characterized by the presence of Lewy bodies or pathological aggregates of α-synuclein in the brain comprising administering to a subject at risk of developing the disease an effective amount of the antibody, or antigen-binding portion, bispecific antibody, or immunoconjugate of any of embodiments 1-43, 47, and 48.

61. A method of diagnosing a disease characterized by the presence of Lewy bodies or pathological aggregates of α-synuclein in a subject comprising:

(a) contacting a sample from the subject with the antibody, or antigen-binding portion thereof, bispecific antibody, or immunoconjugate of any of embodiments 1-43, 47, and 48 such that an antibody-antigen complex is formed;

(b) measuring the amount of the complex formed; and (c) comparing the amount of the complex in the sample with the amount in a control wherein an elevated level of the complex in the sample relative to the control indicates the subject has a disease characterized by the presence of Lewy bodies or pathological aggregates of α-synuclein.

62. The method of embodiment 61, wherein the sample is cerebrospinal fluid, brain tissue extract, urine, or blood.

63. The method of any of embodiment 56-62, wherein the disease is Parkinson's disease, Parkinson's disease dementia, dementia with Lewy bodies, Lewy body disease, multiple system atrophy, or pure autonomic failure.

64. The method of any of embodiment 56-63, comprising administering one or more additional therapeutics.

65. A method for detecting α-synuclein in a sample comprising contacting the sample with the antibody, or antigen-binding portion thereof, bispecific antibody, or immunoconjugate of any of embodiments 1-43, 47, and 48 under conditions that allow for formation of a complex between the antibody, or antigen-binding portion thereof, and α-synuclein, and detecting the formation of the complex.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publications WO 09/045957, WO 09/073533, WO 09/073546, WO 09/054863 and PCT/US2013/072918, and U.S. Patent Publication No. 2011/0150892 are expressly incorporated herein by reference.

EXAMPLES

Commercially available reagents referred to in the Examples below were used according to manufacturer's instructions unless otherwise indicated. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., PCR Protocols: *A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

Example 1: Generation of Anti-Alpha-Synuclein (Anti-αSyn) Antibodies

This Example describes the generation of fully human anti-αSyn monoclonal antibodies (mAbs) that bind preferentially to preformed fibrils (PFF), composed of human recombinant wild type αSyn, over αSyn monomer.

Human anti-αSyn monoclonal antibodies were generated in the HCo42 strain of HuMAb® transgenic mice ("HuMAb" is a Trade Mark of Medarex, Inc., Princeton, N.J.) and KM mice (the KM Mouse® strain contains the SC20 transchromosome as described in PCT Publication WO 02/43478).

Recombinant human αSyn WT or αSyn A53T-PFF mutant protein and crosslinked αSyn WT or A53T PFF were used to immunize recombinant human transgenic mice. Mice used in Fusion 5448 were immunized via intraperitoneal (IP) and subcutaneous (SC) injections of 25 µg per mouse of αSyn A53T-PFF in Ribi adjuvant. HCo42 mice used in Fusion 5450 were immunized IP+Sc+Hock with 25 µg per mouse of a mixture (1:1:1:1) of αSyn WT-PFF, αSyn A53T-PFF, αSyn WT-PFF crosslinked, and αSyn A53T-PFF crosslinked. A stock PFF antigen mix was made by mixing 200 µL of each 1 mg/mL stock PFF (WT, A53T, and crosslinked WT and A53T). Antigens were suspended in Ribi adjuvant. Mice selected for fusion and hybridoma generation received an additional intravenous/intraperitoneal (1V/IP) boost of antigen in Dulbecco's phosphate-buffered saline (DPBS) 3 days prior to fusion.

Following fusions of splenocytes or lymph nodes with P3×63Ag8.653 cells, fusion plates were screened for antigen-specific antibodies by testing for the presence of human gamma/human kappa mAbs. Cells from fusion plates were tested for binding specificity to αSyn PFF or native αSyn monomers. αSyn PFF-positive hybridomas selected from functional screening were subcloned by single cell subcloning to ensure cell line stability and hybridoma monoclonality. Each subclone was tested again by ELISA for antigen-specific binding (i.e., αSyn PFF binding), yielding the following subclones: 11H11-1, 11H11-2, 15A5, 7A10, 36A3, 44B11, and 21A3. Isotype analysis revealed all 6 antibodies to be human IgG1/kappa by ELISA. The amino acid and nucleotide sequences of the heavy and light chains, heavy and light chain variable regions, and heavy and light chain CDR1-3 are provided in Table 22.

The heavy and light chain variable regions of 7A10 consist of amino acid sequences 8 and 9, respectively. The heavy and light chain variable regions of 11H11-1 consist of amino acid sequences 28 and 29, respectively. The heavy and light chain variable regions of 11H11-2 consist of amino acid sequences 28 and 29, respectively. The heavy and light chain variable regions of 15A5 consist of amino acid sequences 38 and 39, respectively. The heavy and light chain variable regions of 21A3 consist of amino acid sequences 48 and 49, respectively. The heavy and light chain variable regions of 36A3 consist of amino acid sequences 58 and 59, respectively. The heavy and light chain variable regions of 44B11 consist of amino acid sequences 68 and 69, respectively. The heavy and light chain variable regions of 2E2 consist of amino acid sequences 78 and 79, respectively. The heavy and light chain variable regions of 23H8-1 consist of amino acid sequences 94 and 95, respectively. The heavy and light chain variable regions of 23H8-2 consist of amino acid sequences 94 and 96, respectively. The heavy and light chain variable regions of 23H8-3 consist of amino acid sequences 94 and 97, respectively. The heavy and light chain variable regions of 1E8 consist of amino acid sequences 106 and 107, respectively.

Effector function-less versions of the anti-αSyn antibodies described above were also generated. As used herein, hIgG1f refers to an allotype of IgG1 having the amino acid sequence set forth in SEQ ID NO: 117, and hIgG1.3f refers to a triple mutant version of hIgG1f (L234A, L235E, G237A) which lacks Fc gamma receptor binding and effector function. hIgG1.3f has the amino acid sequence set forth in SEQ ID NO: 119.

Example 2: Epitope Mapping of Anti-αSyn Antibodies

Epitope binding sites of the anti-αSyn antibodies described in Example 1 were determined by using a series of overlapping αSyn peptides.

A series of overlapping peptides with 10 a.a. of human αSyn sequence were generated with an N-terminal biotin group and a PEG4 linker and a C-terminal CONH2 (Table 1). Peptides were solubilized in DPBS at 1 mg/ml. For mapping studies, 100 µL of 0.25 µg/ml α-synuclein peptides in DPBS were added to a NeutrAvidin coated high capacity 96-well plate (Thermo Fisher Scientific, Waltham, Mass.) and incubated at RT for 2 h (or overnight at 4° C.). Plates were washed 3 times with ~300 µL of wash buffer (0.05% Tween in DPBS). Plates were then blocked with 150 µl of 3% BSA (Sigma-Aldrich, St. Louis, Mo.) in DPBS at RT for ~2h (or overnight at 4° C.). 100 µL of test samples diluted in sample buffer (0.1% BSA/0.05% Tween/dPBS, 2 pellets of protease inhibitor-(Roche complete, Sigma-Aldrich, St. Louis, Mo.) in 50 ml buffer were incubated on the plates at RT for 2 h. Plates were washed 3 times. 100 µL of secondary antibody diluted 1:1000 in PBSTB (1% BSA/0.2% Tween/ DPBS) was added and incubated at RT for 1 hr. Plates were washed 3 times for 5-10 min each wash. 100 µL of AP substrate (Tropix CDP Star Ready-to-Use with Sapphire II, Thermo Fisher Scientific, Waltham, Mass.) was added and developed at RT for 30 min. Luminescence counts were read with a Perkin Elmer EnVision (2102 Multilabel Reader, PerkinElmer, Waltham, Mass.). The plates were kept under constant shaking (Titer plate shaker) during the assay. The secondary antibodies used included alkaline phosphatase-affinipure donkey anti-human IgG, (Jackson ImmunoResearch, West Grove, Pa.), alkaline phosphatase-affinipure donkey anti-rabbit IgG, (Jackson ImmunoResearch, West Grove, Pa.), alkaline phosphatase-affinipure donkey anti-mouse IgG, (Jackson ImmunoResearch, West Grove, Pa.). All secondary antibodies were diluted to 50% glycerol final concentration.

An initial experiment determined that all antibodies recognized epitopes located within the C-terminal region of αSyn. The overlapping peptides shown in Table 1 were used to further refine the epitope binding sites of each antibody.

TABLE 1

Epitope mapping peptides

| αSyn region[a] (a.a.) | Sequence (SEQ ID NO) |
|---|---|
| 105-115 | EGAPQEGILED (130) |
| 106-116 | GAPQEGILEDM (131) |
| 107-117 | APQEGILEDMP (132) |
| 108-118 | PQEGILEDMPV (133) |
| 109-119 | QEGILEDMPVD (134) |
| 110-120 | EGILEDMPVDP (135) |
| 111-121 | GILEDMPVDPD (136) |
| 112-122 | ILEDMPVDPDN (137) |
| 113-123 | LEDMPVDPDNE (138) |
| 114-124 | EDMPVDPDNEA (139) |
| 115-125 | DMPVDPDNEAY (140) |
| 116-126 | MPVDPDNEAYE (141) |
| 117-127 | PVDPDNEAYEM (142) |
| 118-128 | VDPDNEAYEMP (143) |
| 119-129 | DPDNEAYEMPS (144) |
| 120-130 | PDNEAYEMPSE (145) |
| 121-131 | DNEAYEMPSEE (146) |
| 122-132 | NEAYEMPSEEG (147) |
| 123-133 | EAYEMPSEEGY (148) |
| 124-134 | AYEMPSEEGYQ (149) |
| 125-135 | YEMPSEEGYQD (150) |
| 126-136 | EMPSEEGYQDY (151) |
| 127-137 | MPSEEGYQDYE (152) |
| 128-138 | PSEEGYQDYEP (153) |
| 129-139 | SEEGYQDYEPE (154) |
| 130-140 | EEGYQDYEPEA (155) |

[a]Overlapping peptides with 10 a.a. of human αSyn sequence were generated with an N-terminal biotin group and a PEG4 linker and a C-terminal CONH2.

The results of epitope mapping are shown in FIG. 1. The data shows that 7A10, 21A3, 15A5, 36A3, and 1E8 bind within amino acids 123-128 of αSyn, corresponding to the amino acid sequence EAYEMP (SEQ ID NO: 121); 11H11-1 binds within amino acids 125-128 of αSyn, corresponding to the amino acid sequence YEMP (SEQ ID NO: 122); 44B11 binds within amino acids 130-139 of αSyn, corresponding to the amino acid sequence EEGYQDYEPE (SEQ ID NO: 124); 2E2 binds within amino acids 119-126 of αSyn, corresponding to the amino acid sequence DPDNEAYE (SEQ ID NO: 125); and 23H8 binds within amino acids 130-138 of αSyn, corresponding to the amino acid sequence EEGYQDYEP (SEQ ID NO: 123).

Example 3: Selectivity of Anti-αSyn Antibodies for αSyn-PFF Over αSyn Monomers

This Example demonstrates that the anti-αSyn antibodies preferentially bind to αSyn-PFF over αSyn monomers.

Recombinant wild type human αSyn (rPeptide, Bogart, Ga.) and human αSyn containing the A53T mutation (rPeptide, Bogart, Ga.) were reconstituted to 1 mg/ml in 20 mM Tris/HCl, 100 mM NaCl, PH7.4. PFF was generated using a standard protocol (Luk et al., PNAS 2007; 106:20051-6). Briefly, monomers were incubated in 2 ml safe-luck Eppendorf tubes (~1 ml/vial) at 37° C. with constant shaking (Titer plate shaker) for 4 days and then centrifuged at 100,000 g at RT for 20 min. The pellets were re-suspended with PBS for a final PFF concentration of 1 mg/ml.

Fibrillization of αSyn was monitored by a Thioflavin T binding assay, denaturing (SDS-PAGE) and non-denaturing (native) gel electrophoresis, and size exclusion chromatography (SEC-HPLC). For thioflavin-T assay, samples were diluted to 0.5 mg/ml in PBS and were added to an equal volume of 25 µM Thioflavin-T. Samples were then measured using an Envision multilabel plate reader (PerkinElmer, Waltham, Mass.) with the excitation and emission wavelengths set at 485 and 535 nm, respectively. Total protein levels were assessed with both a Micro BCA Protein Assay Kit (Thermo Fisher Scientific, Waltham, Mass.) and imperial protein stain assay (Thermo Fisher Scientific, Waltham, Mass.).

For SDS-PAGE analysis, PFF samples in NuPAGE sample reducing agent (Thermo Fisher Scientific, Waltham, Mass.) were incubated in heat block (70° C.) for 10 min, separated by SDS-PAGE (1 µg/10 µl/lane) using 4-12% Bis-Tris gel (Thermo Fisher Scientific, Waltham, Mass.) with MES SDS running buffer (Thermo Fisher Scientific, Waltham, Mass.) at constant voltage of 200V, and then transferred to nitrocellulose membrane (0.45 um pore size, Thermo Fisher Scientific, Waltham, Mass.) using Tris/glycine buffer (Thermo Fisher Scientific, Waltham, Mass.) containing 10% methanol at constant voltage 50V, 1.5h. For Native-PAGE, PFF samples were separated by NativePAGE (1 µg/10 µl/lane) using 3-12% Bis-Tris protein gel (Thermo Fisher Scientific, Waltham, Mass.) with NativePAGE running buffer (Thermo Fisher Scientific, Waltham, Mass.) at constant voltage 150 V and then transferred to PVDF membrane (0.45 um pore size, Thermo Fisher Scientific, Waltham, Mass.) using NuPAGE transfer buffer (Thermo Fisher Scientific, Waltham, Mass.) at constant voltage 50V, 1.5h. PVDF membranes were pretreated with methanol for 30 sec, dH2O for 2 min and transfer buffer for 10 min. Membranes were blocked with 5% non-fat dry milk (Thermo Fisher Scientific, Waltham) in 0.1% Tween/TBS at RT for 2h, then incubated with the primary antibody 4B12 (BioLegend, San Diego, Calif.) 1:1000 diluted in 1% BSA/

0.1% Tween/TBS at 4° C. overnight. Membranes were then washed 3 times (5-10 min each wash) with 0.1% Tween/TBS, and then incubated with anti-mouse IgG (Jackson ImmunoResearch, West Grove, Pa., peroxidase conjugated affinity purified Fab2) 1:10,000 diluted in 1% BSA/0.1% Tween/TBS at RT for 1 h. Membranes were then washed 3 times as above and then incubated for 5 min with SuperSignal West Femto Maximum Sensitivity Substrate (Thermo Fisher Scientific, Waltham, Mass.). Detection was performed using the GE Amersham imager 600. MagicMark™ XP Western Protein Standard (Thermo Fisher Scientific, Waltham, Mass.) and SeeBlue plus 2 (Thermo Fisher Scientific, Waltham, Mass.) were used for SDS-PAGE. Native-Mark Unstained Protein Standard (Invitrogen) was used for native gels. Wash buffer (TBST) consisted 0.1% Tween-20 in Tris buffered saline For the binding assay, 96 well plates (high bind microplate) were coated with 100 μL of 1 μg/ml αSyn WT PFF in DPBS at RT for 2h (or overnight at 4° C.). Plates were washed 3 times with ~300 μL of wash buffer (0.05% Tween in DPBS). Plates were blocked with 150 μl of 3% BSA/DPBS at RT for 2 h (or overnight at 4° C.). 3-fold serial dilutions of PFF (starting from 2 μg/ml) and α-syn WT monomer (starting from 20 μg/ml) were prepared in sample buffer (0.1% BSA/0.05% Tween/DPBS, 2 pellets of protease inhibitor (Roche complete, Sigma-Aldrich, St. Louis, Mo.) in 50 ml buffer). For antibody incubations, equal volumes of 2-fold assay concentration of αSyn PFF or monomer were mixed with 2-fold assay concentration of antibodies in BD falcon low binding plates and incubated at RT for ~2h. 100 μL of mixtures of antibody and PFF or monomer were added to PFF coated plates and incubated at RT for 10 min. Plates were washed 3 times. 100 μL of donkey anti-human IgG (Jackson ImmunoResearch, West Grove, Pa., with 50% glycerol) diluted 1:1000 in PBSTB (1% BSA/0.2% Tween/dPBS) was added and plates incubated at RT for 1 hr. Plates were washed 3 times for 5~10 min per wash. 100 μL of AP substrate (Tropix CDP Star Ready-to-Use with Sapphire II, Thermo Fisher Scientific, Waltham, Mass.) was added and developed at RT for 30 min. Luminescence counts were read with a Perkin Elmer EnVision (2102 Multilabel Reader, PerkinElmer, Waltham, Mass.). PFF was sonicated with 15 times 1 sec pulses before coating or mixing with antibodies. Plates were kept under constant shaking (Titer plate shaker) during the assay.

Figure 1A:
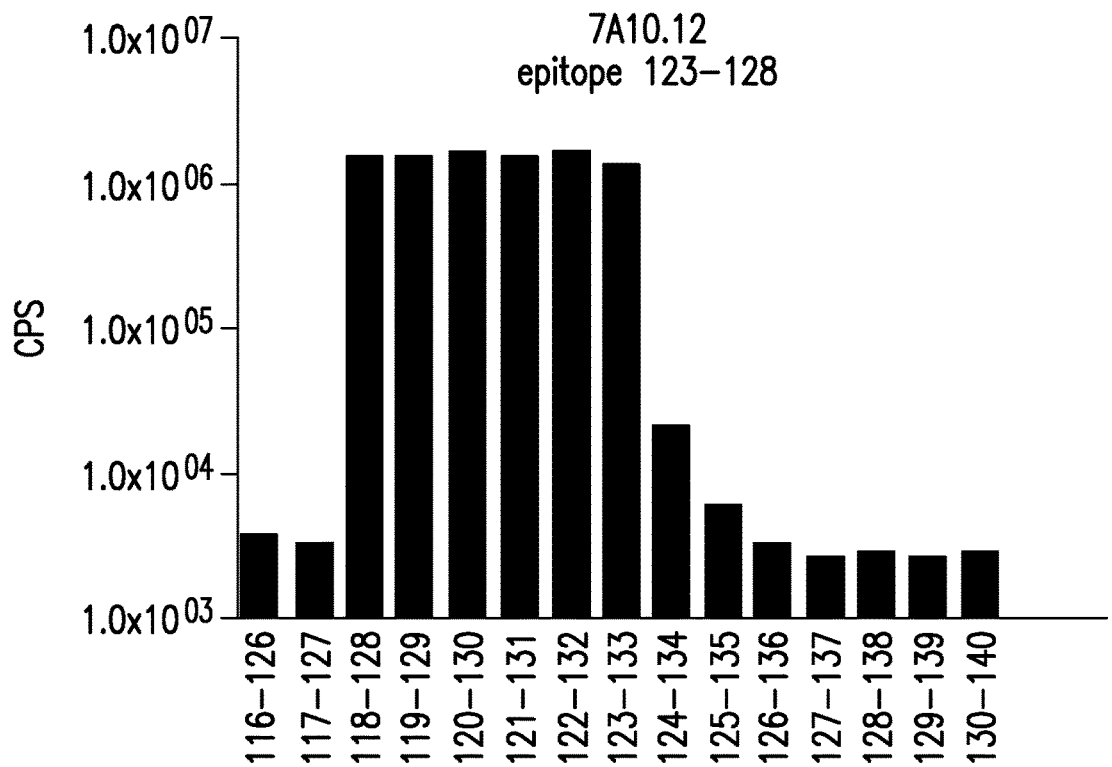
FIG. 1 is a series of graphs showing epitope binding data for 7A10, 21A3, 15A5, 36A3, 11H11-1, 44B11, 1E8, 2E2, and 23H8 which were incubated on plates coated with different αSyn peptides. Bound antibodies were measured by 1-sided ELISA. Data represents single determinations.
Figure 1B:
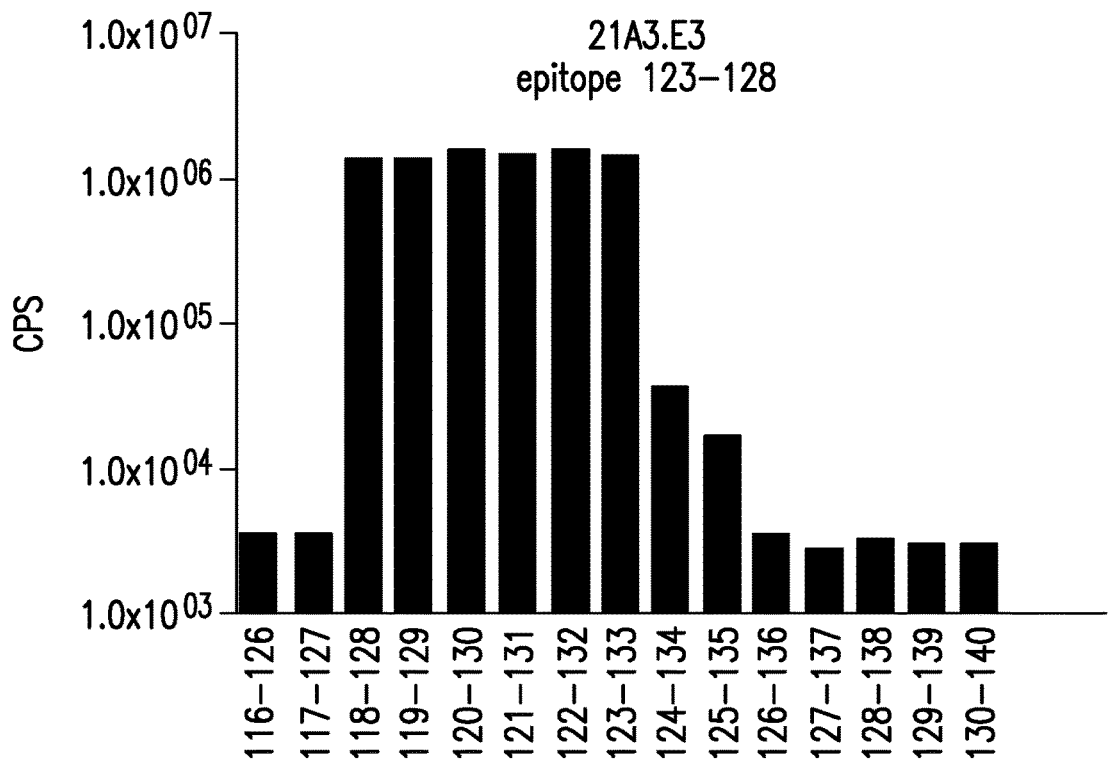
Figure 1C:
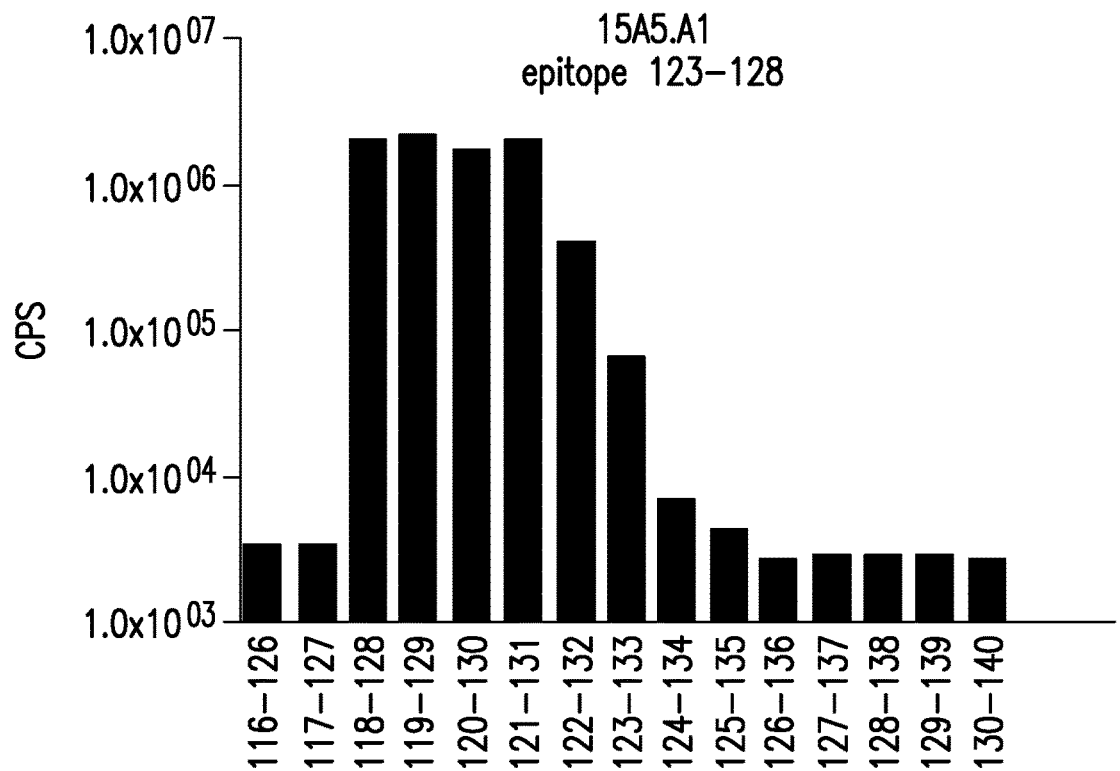
Figure 1D:
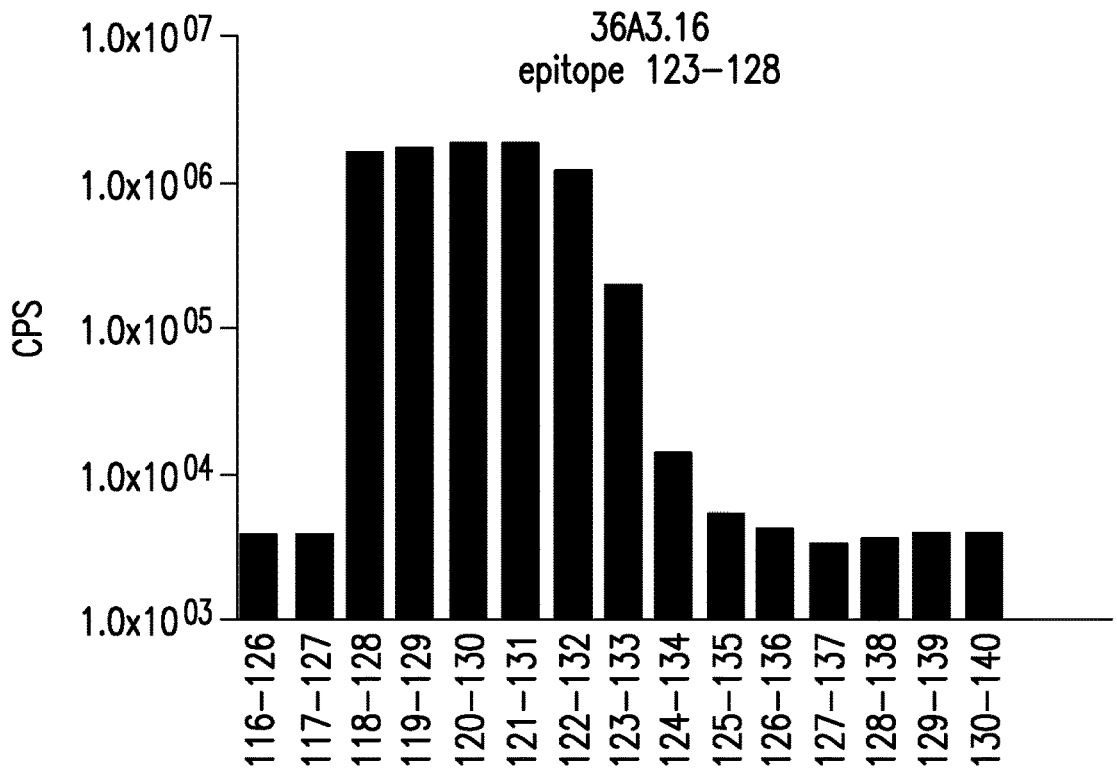
Figure 1E:
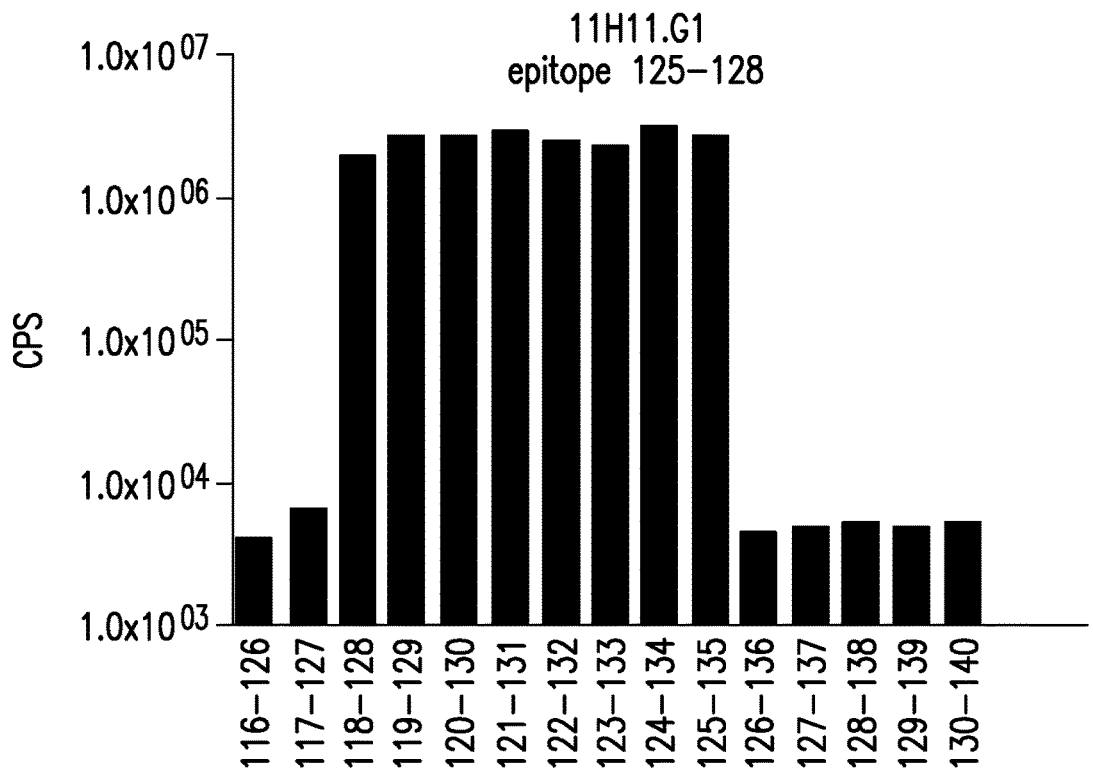
Figure 1F:
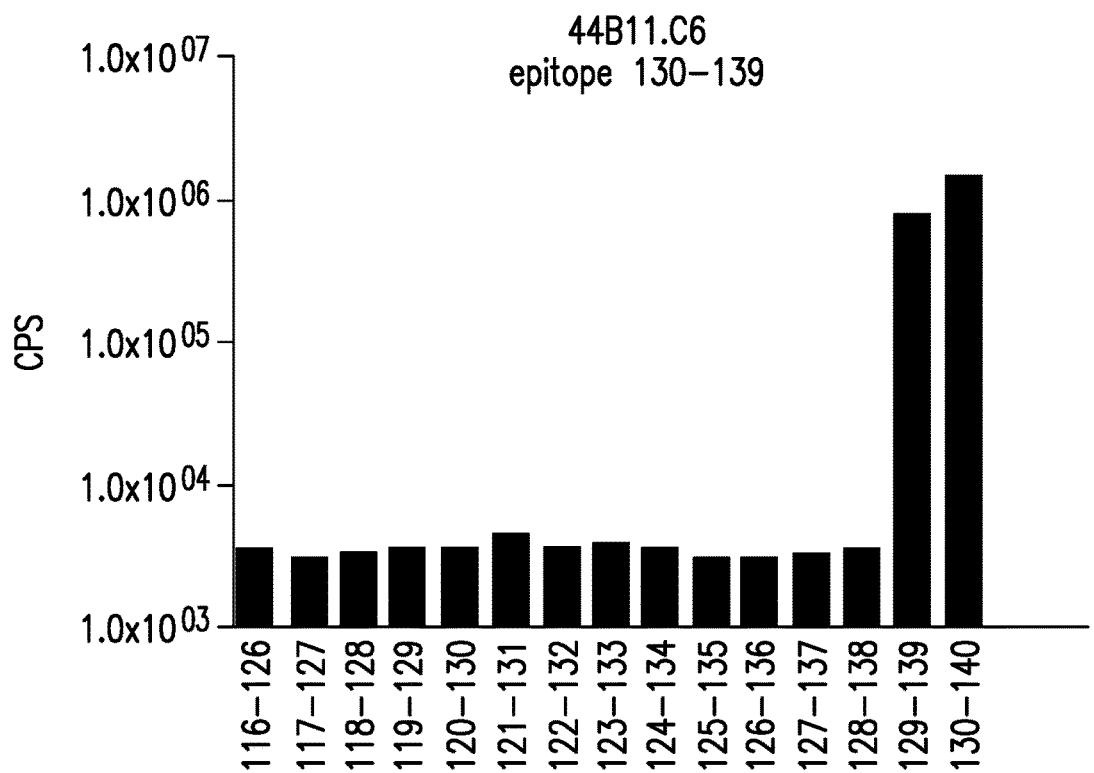
Figure 1G:
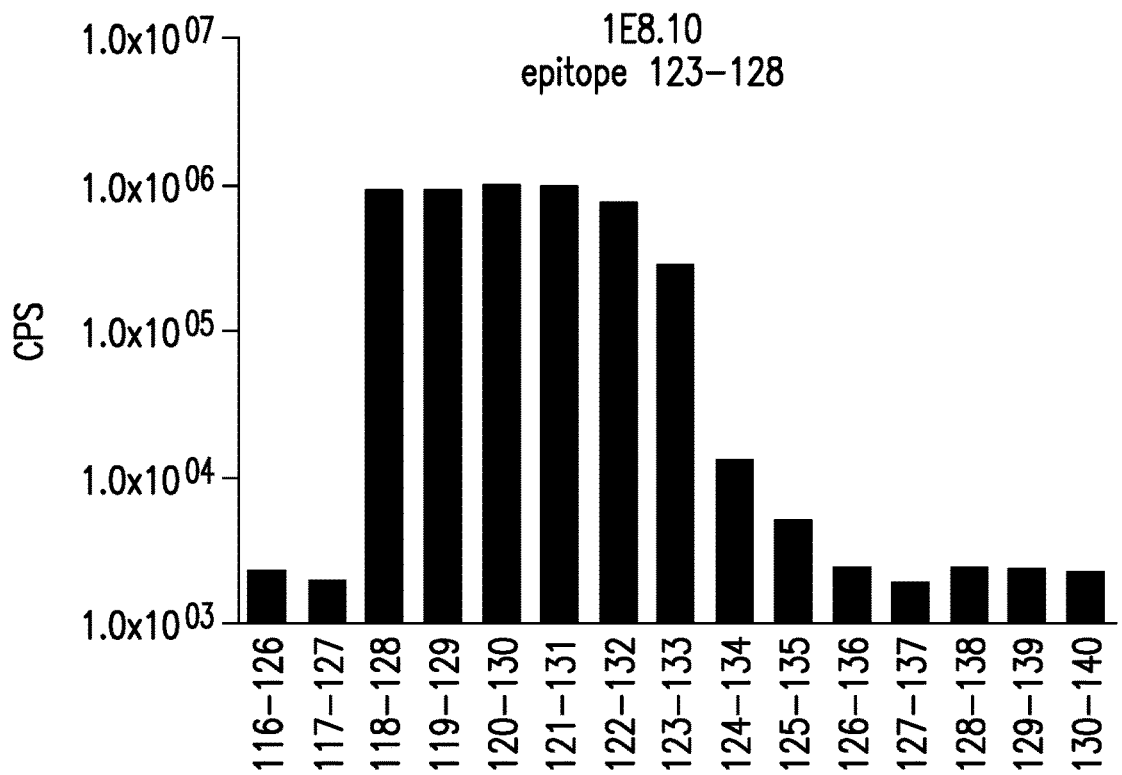
Figure 1H:
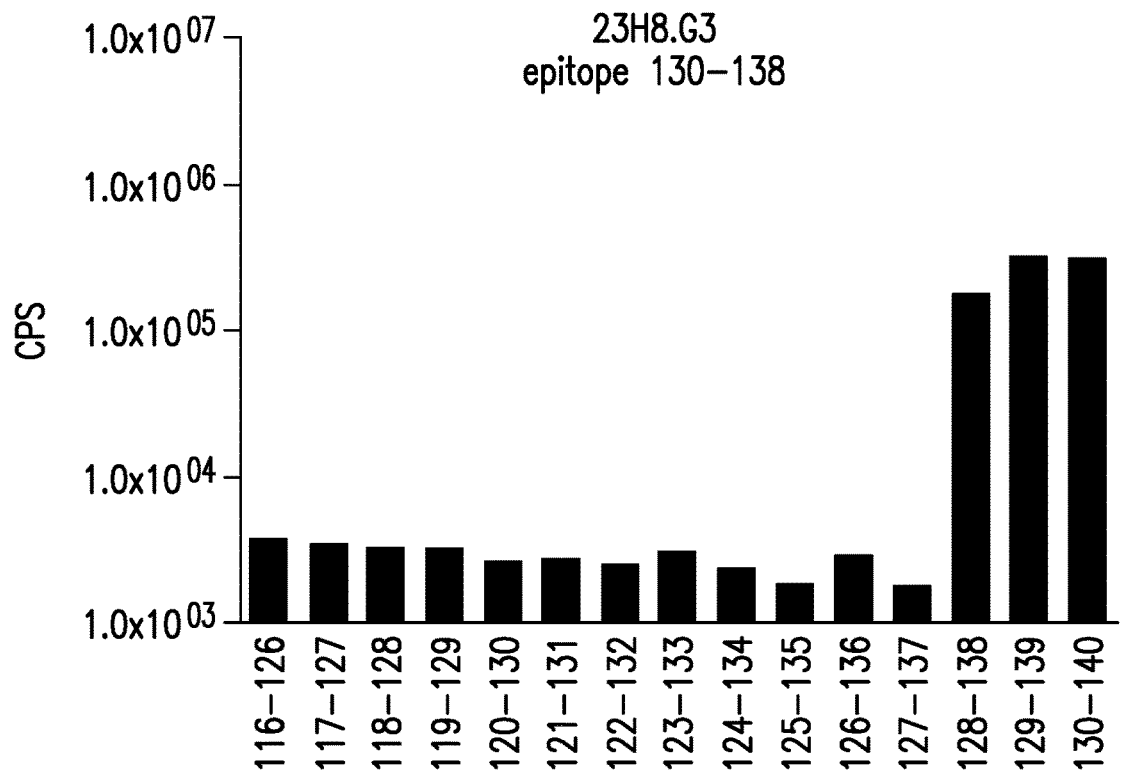
Figure 1I:
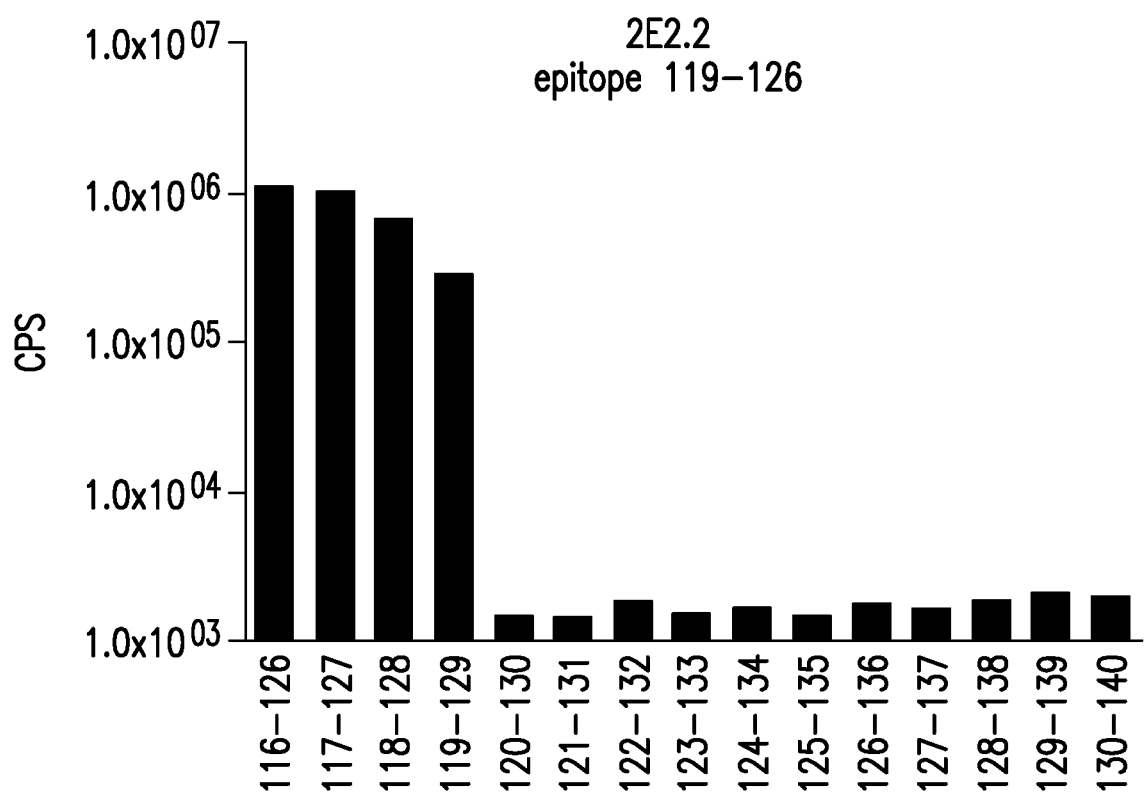
Figures 2A, 2B:
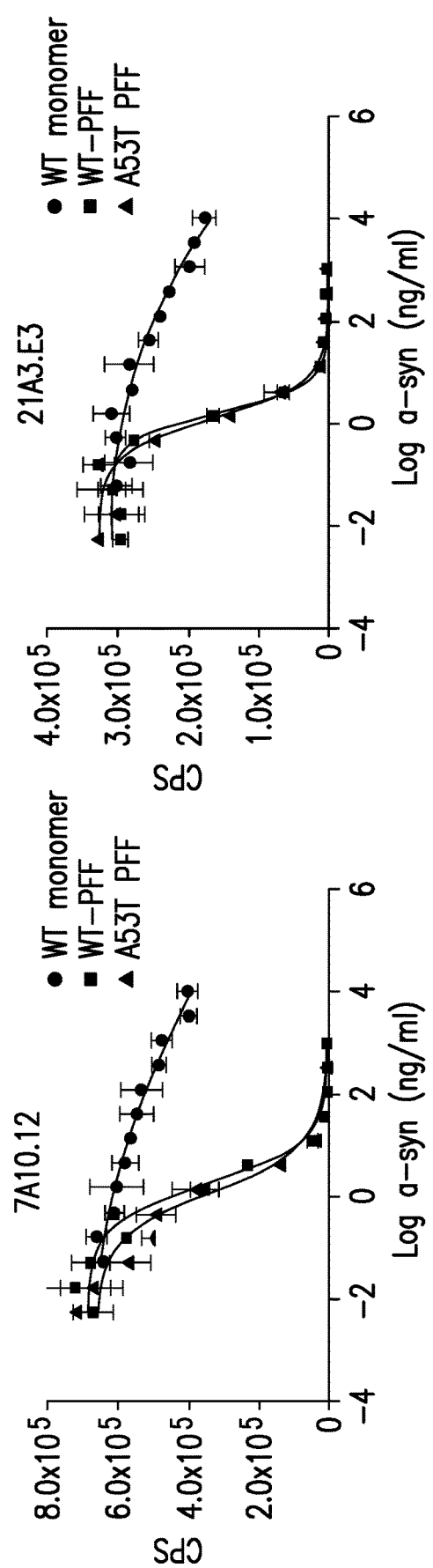
FIG. 2 is a series of graphs of the binding of 7A10, 21A3, 15A5, 36A3, 11H11-1, and 44B11 to full-length human recombinant wild-type αSyn monomer, αSyn PFF or A53T αSyn PFF. Antibodies were incubated in solution with increasing concentrations of αSyn monomer, αSyn PFF or A53T αSyn PFF. Unbound antibodies were captured on PFF-coated plates and measured by 1-sided ELISA. Data represents mean±sd for duplicate determinations.
Figures 2C, 2D:
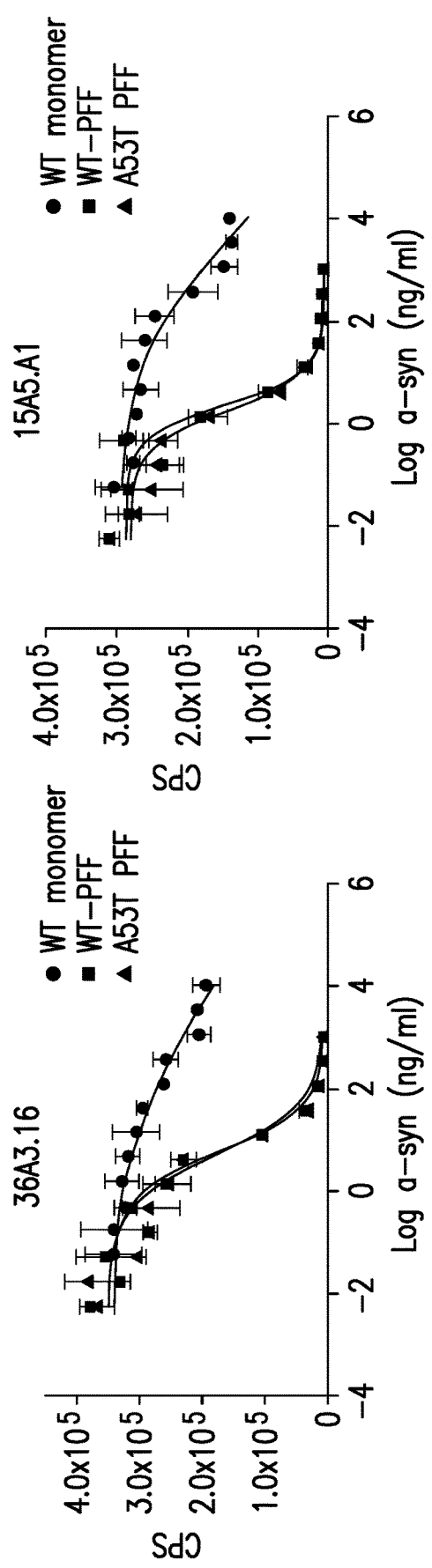
Figure 3:
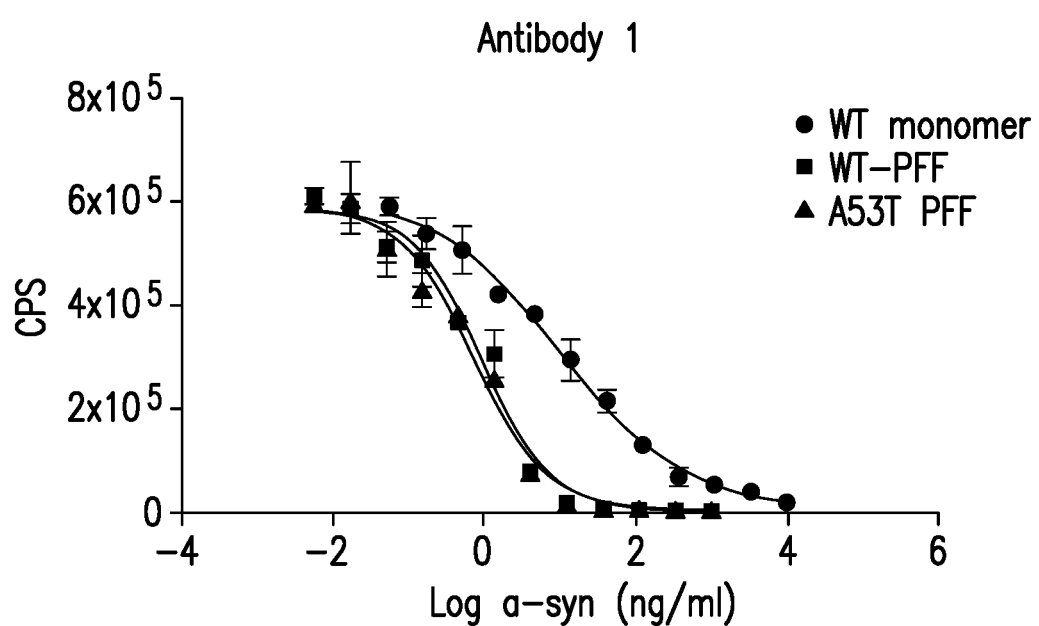
FIG. 3 is a graph showing the binding of Antibody 1 (an antibody known to bind to αSyn) to full-length human recombinant wild-type αSyn monomer, αSyn PFF or A53T αSyn PFF. Unbound antibody was captured on PFF-coated plates and measured by 1-sided ELISA. Data represents mean±sd for duplicate determinations.

As shown in FIG. 2, anti-αSyn antibodies were evaluated for binding potency to αSyn monomer and to WT or A53T αSyn PFFs. Data for the control antibody 1 are also shown in FIG. 3. Similar binding to WT PFF and A53T PFF was observed for all antibodies tested. With the exception of control antibodies Antibody 1 and Antibody 2, all six anti-αSyn antibodies preferentially bind to αSyn PFFs over αSyn monomers, with M/P ratios of at least 500. A summary of the binding data is shown Table 2.

TABLE 2

Summary of binding assay results

| Antibody | Monomer binding (nM) | SD | PFF binding (nM) | SD | M/P ratio[a] | n |
|---|---|---|---|---|---|---|
| 21A03 | 291 | 481 | 0.16 | 0.05 | 1819 | 4 |
| 7A10 | 779 | 694 | 0.15 | 0.03 | 5193 | 5 |
| 15A5 | 582 | 795 | 0.18 | 0.06 | 3233 | 5 |
| 36A3 | 350 | 224 | 0.49 | 0.11 | 714 | 6 |
| 11H11-1 | >700 | | 1.38 | 0.41 | >500 | 5 |

TABLE 2-continued

Summary of binding assay results

| Antibody | Monomer binding (nM) | SD | PFF binding (nM) | SD | M/P ratio[a] | n |
|---|---|---|---|---|---|---|
| 44B11 | >700 | | 0.41 | 0.10 | >1700 | 6 |
| Antibody 1[b] | 0.86 | 0.11 | 0.077 | 0.009 | 11 | 19 |
| Antibody 2[b] | 17 | 1.3 | 5.18 | 0.53 | 3 | 3 |

[a]M/P = monomer/PFF binding ratio (lower ratio means higher preference for PFF)
[b]Antibody 1 and Antibody 2 are control antibodies Example 4: Deimmunization of Anti-αSyn Antibodies This Example determined the effect that deimmunizing a subset of anti-αSyn antibodies has on binding to αSyn monomers and αSyn PFFs.

In order to remove possible immunogenic hotspots through humanization, the sequences of the heavy and light chains of 7A10 were analyzed for immunogenicity. An analysis of 7A10 for binding to 27 commonly found HLAs in the world population alleles and identification of non-germline segments was carried out to determine possible immunogenic hotspots.

The binding to MHC-II alleles of a cognate peptide (formed as the by-product of endocytosis and degradation of the biologic by dendritic cells) followed by presentation on the surface of dendritic cells is critical for an adaptive immune response. In addition to binding to MHC-II alleles, however, the presented peptide must be non-indigenous (non-self) for the CD4+ T-cell receptors to bind to it (T-cell recognition) thus leading to activation and T-cell proliferation. In order to simulate these effects computationally and model the effects of diverse donors, the antibody is first broken up into 15-mer peptides starting from the N-terminus and systematically moving towards the C-terminus one amino acid at a time. Each of the 15-mer peptides obtained is evaluated for (i) binding to each of 27 commonly found HLAs in the world population, and (ii) perfect sequence matches to human immunoglobulin germline sequences. In the event of a perfect germline match, the 15-mer peptide is considered "self" and therefore not considered to be antigenic. On the other hand, if determined to be "non-self" (absence of perfect germline match), it is regarded as potentially antigenic if binding with sufficient affinity to some of the 27 alleles.

The peptide/MHCII binding affinity predictions were made using the IEDB (Immune Epitope Database) analysis resource consensus tool. The predicted affinities were reported as percentile ranks based on the consensus of five different peptide MHC-II binding prediction methods.

The immunogenicity analysis of the heavy and light chains of 7A10 is shown in FIG. 4. The results of the analysis show that the light chain (VK) is predicted to be mostly non-immunogenic, with the only hotspots lying in CDR3 which is typically involved in epitope binding. The heavy chain (VH) has two regions showing the hotspots to be spread over large regions, i.e., CDR2 (residues 49-65) and FW3-CDR3 (residues 90-98). Ignoring hotspots that are less than 8 stretches long, only two regions in the VH chain (49-65, 90-98) were considered for de-risking through mutagenesis.

The number below each amino acid in FIG. 4 denotes the proportion of alleles that bind a 15-mer peptide centered at that amino acid. For example, "5" at Y52 in 7A10_VH refers to the 15-mer peptide centered at Y52, i.e., LEWIGYI YYSGRTKY and denotes that (i) this peptide does not have a human germline match (therefore non-self), and (ii) between 50-60% of the 27 alleles show high binding affinity to this peptide. The numbers are assigned a color on a scale from light grey (least likely to be immunogenic) to dark grey (most likely immunogenic hotspot). The 3 bold arrows show the positions for the mutant selections: R56S, K58N, and T93A.

The human immunogenicity risk was assessed for 7A10 and de-immunized 7A10-T93A using an in vitro human PBMC proliferation assay. Avastin and αIL-21R mAb were used as negative and positive assay controls as their clinical immunogenicity correlates positively with in vitro immunogenicity assay results. PBMC from healthy volunteers were isolated by Ficoll (GE Healthcare) gradient centrifugation and human leukocyte antigen (HLA) Class II was characterized utilizing polymerase chain reaction amplification and hybridization with oligonucleotide probes (ProImmune). A panel of 40 PBMC donors composed of HLA Class II types closely matching the world population frequencies was used for each assay run. PBMC were labeled with CFSE (Carboxyfluorescein succinimidyl ester, Invitrogen) to monitor proliferation and plated in 96 well plates in 6 replicates at 200,000 cells per well in RPMI (Lonza) containing 10% human AB serum (Bioreclamation), non-essential amino acids (Gibco), and penicillin-streptomycin (Gibco). α Synuclein antibodies and control proteins were cultured with PBMC at 1 µM for 7 days after which media was washed away and cells were labeled with an anti-human CD4 mAb conjugated to APC (Allophycocyanin, BD Biosciences). After removal of the unbound anti-CD4 mAb with a wash step, the remaining cells were fixed with 3.7% formalin (Sigma) in PBS and analyzed by flow cytometry to determine the percentage of proliferating CD4+ T cells. A donor is considered positive when the percentage of proliferating CD4+ T cells for a particular antibody is greater than the percentage of proliferating CD4+ T cells with media only plus two standard deviations. Data is presented as the percentage of the 40 donors that showed a positive proliferation signal.

Figure 5A:
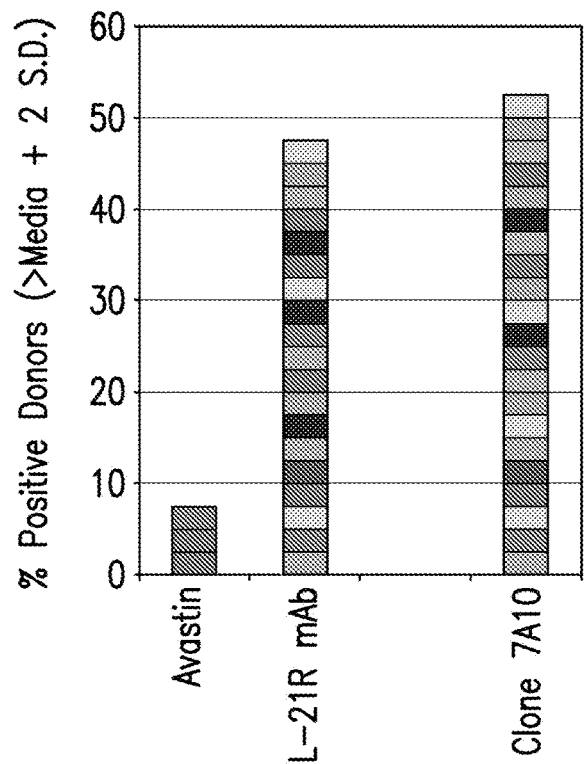
FIGS. 5A and 5B are graphs of the percentage of healthy volunteer human PBMC donors with a positive CD4+ proliferation response after 7 days of exposure to test antibodies. Each horizontal bar represent one positive donor. 7A10 and 7A10 T93A were tested in different assay runs. Avastin is an anti VEGF A monoclonal antibody and used as a negative control. αIL-21R mAb is a fully human anti-IL-21R monoclonal antibody and used as a positive control.
Figure 5B:
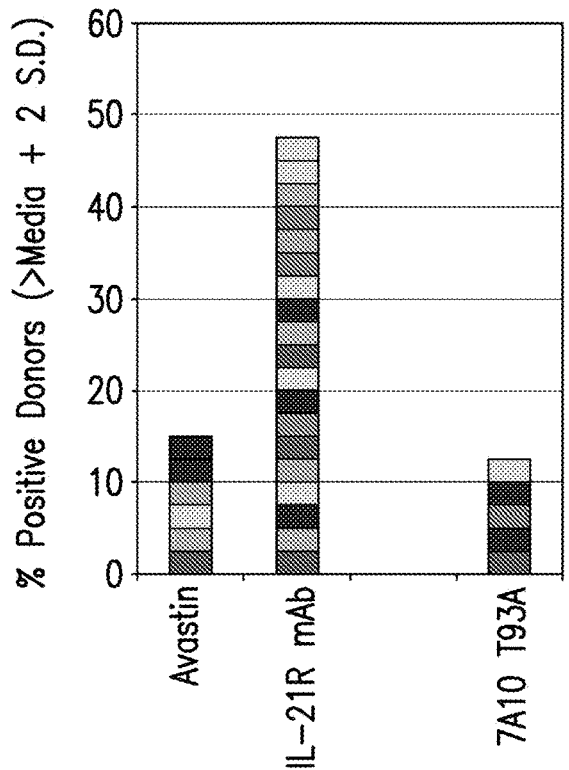

The percentage of donors showing a significant CD4+ T cell proliferation response after incubation with these antibodies is in shown in FIG. 5. 7A10 produced a proliferative response in 21 out of 40 (52.5%) of the PBMC donors, and 7A10-T93A showed a proliferative response in 5 of 40 donors (12.5%).

Example 5: Binding of De-Immunized Anti-αSyn Antibodies to αSyn Monomers and αSyn PFFs This Example assessed the binding of the de-immunized version of 7A10 described in Example 4, as well as a de-immunized version of 21A3, i.e., 21A3-V82L, to αSyn monomers and αSyn PFFs by ELISA, as described in Example 3.

As shown in Table 3, the 7A10-T93A and 21A3-V82L reversions exhibited PFF binding potencies within 2-fold of the potencies measured for the parent antibodies; monomer binding values were more variable due to the difficulty of generating accurate concentration-response curves for these relatively weak potencies. The K58Y-T93A reversion was >10× weaker for PFF binding compared to 7A10 parent, while the PFF binding potencies of R56S-T93A and R56S-K58N-T93A were within 2× of 7A10.

TABLE 3

Binding summary of de-immunized αSyn variants

| Antibody[a] | assay conc (ng/ml)[b] | Monomer binding (nM) | SD | PFF binding (nM) | SD | n |
|---|---|---|---|---|---|---|
| 7A10-Vh-R56S-T93A-hHC-IgG1.3f | 30 | 23 | 15 | 0.290 | 0.099 | 3 |
| 7A10-Vh-K58Y-T93A-hHC-IgG1.3f | 10 | 43 | 22 | 2.595 | 0.285 | 3 |
| 7A10-Vh-R565-K58N-T93A-IgG1.3f | 100 | 1046 | 174 | 0.335 | 0.035 | 3 |
| 7A10-Vh-T93A-hHC-IgG1.3f | 1 | 3851 | 661 | 0.367 | 0.043 | 3 |
| 21A3-Vh-V82L-hHC-IgG1.3f | 1 | 192 | 58 | 0.120 | 0.005 | 3 |
| 7A10-hIgG1.3f | 1 | 764 | 163 | 0.171 | 0.009 | 3 |
| 21A3-hIgG1.3f | 1 | 700 | 0.0 | 0.073 | 0.013 | 3 |
| Antibody 1 | 1 | 1.02 | 0.07 | 0.067 | 0.008 | 3 |

[a]Data shown is for the Fc inert human isotype IgG1.3 as indicated
[b]Concentration of antibody needed to generate acceptable control signal Example 6: Cross-Species Reactivity of Anti-αSyn Antibodies with Rat, Mouse, and Human αSyn In order to evaluate species cross-reactivity, anti-αSyn antibodies were tested for binding to peptides representing a.a. 111-140 of rat, mouse and human αSyn (Table 4). αSyn sequences at positions 121-122 differ between human, rat and mouse. The binding assay was performed as described in Example 3.

TABLE 4

Human, rat, and mouse αSyn 111-140 peptides

| Peptide | Sequence |
|---|---|
| mouse 111-140 | H-RRR GILEDMPVDP GSEAYEMPSE EGYQDYEPEA-NH2 |
| rat 111-140 | H-RRR GILEDMPVDP SSEAYEMPSE EGYQDYEPEA-NH2 |
| human 111-140 | H-RRR GILEDMPVDP DNEAYEMPSE EGYQDYEPEA-NH2 |

*mouse 111-140 (SEQ ID NO: 156), rat 111-140 (SEQ ID NO: 157), human 111-140 (SEQ ID NO: 158)

Figure 6A:
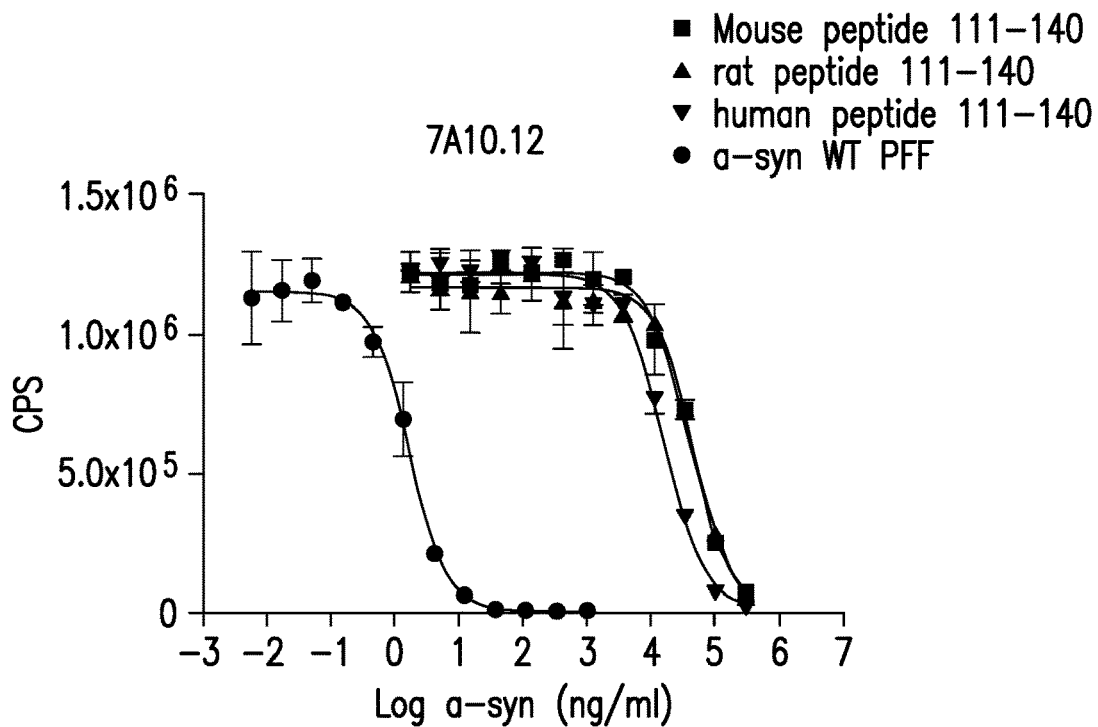
FIGS. 6A and 6B are graphs showing the binding of 7A10 (FIG. 6A) and 7A10-T93A (FIG. 6B) to increasing concentration of mouse, rat, and human αSyn peptides, and WT PFF. Unbound antibody was captured on PFF-coated plates and measured by 1-sided ELISA. Data represents mean±sd for duplicate determinations.
Figure 6B:
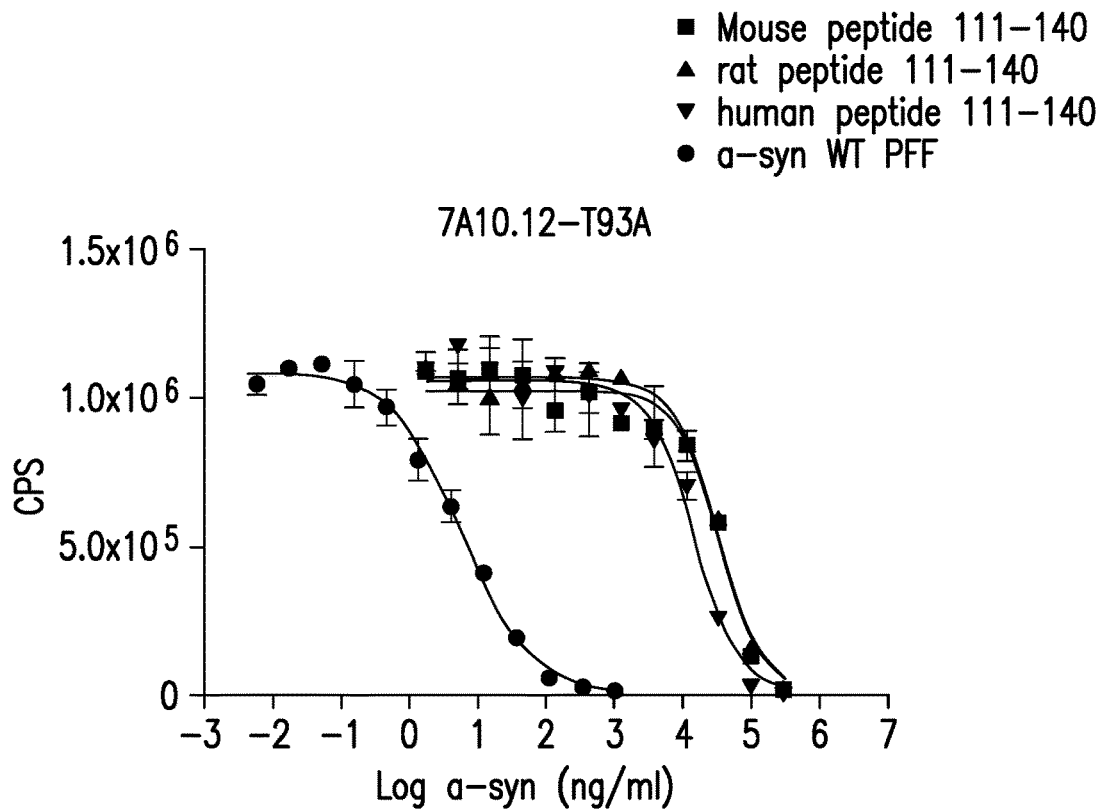

Anti-αSyn antibodies exhibited similar binding to rat and mouse αSyn 111-140 peptides as compared to the corresponding human peptide (FIG. 6). A summary of peptide binding results is shown in Table 5. Overall, anti-αSyn antibodies exhibited 2-3-fold weaker potency for binding to the rodent 111-140 peptide compared to the corresponding human peptide.

Analyses used an ACQUITY UPLC/Waters Synapt G2 Mass Spectrometer. Samples were reduced by DTT (100 mM) at 1 mg/mL. UPLC/MS Conditions: 1 μg sample injection onto BEH C4 RP column, 2.1×150 mm, 300 Å, 1.7 mm particle at 60° C., 20 min gradient: 10% to 38% (Mobile phase B) in 10 min, LC flow rate 200 μL/min, positive MS ion mode. This method was used for glycosylation profile analysis as well.

TABLE 5

Summary of binding to human, rat, and mouse αSyn 111-140 peptides

|  | PFF binding (nM) | SD | Mouse 111-140 (nM) | SD | Rat 111-140 (nM) | SD | Human 111-140 (nM) | SD |
|---|---|---|---|---|---|---|---|---|
| 36A3 | 0.416 | 0.062 | 8892 | 2888 | 8884 | 3591 | 3890 | 1207 |
| 15A5 | 0.144 | 0.012 | 9190 | 3505 | 8262 | 3195 | 3161 | 1658 |
| 44B11 | 0.389 | 0.038 | 93485 | 39183 | 78582 | 37897 | 75569 | 43663 |
| 11H11-1 | 2.675 | 1.196 | 5752 | 1708 | 5706 | 2338 | 3398 | 1149 |
| 7A10-Vh-T93A-hHC-IgG1.3f | 0.423 | 0.024 | 8932 | 1350 | 9268 | 1492 | 4693 | 950 |
| 21A3-Vh-V82L-hHC-IgG1.3f | 0.086 | 0.007 | 6656 | 3133 | 6413 | 3057 | 3702 | 2951 |
| 7A10-hIgG1.3f | 0.135 | 0.020 | 11393 | 534 | 10964 | 809 | 4760 | 521 |
| 21A3-hIgG1.3f | 0.095 | 0.016 | 13782 | 4139 | 12251 | 3248 | 6496 | 1939 |

Example 7: Cross-Reactivity of Anti-αSyn Antibodies with Human αSyn, βSyn, and γSyn In this Example, anti-αSyn antibodies were tested for binding and cross-reactivity to human βSyn and human γSyn by ELISA, as described in Example 3.

Figure 7B:
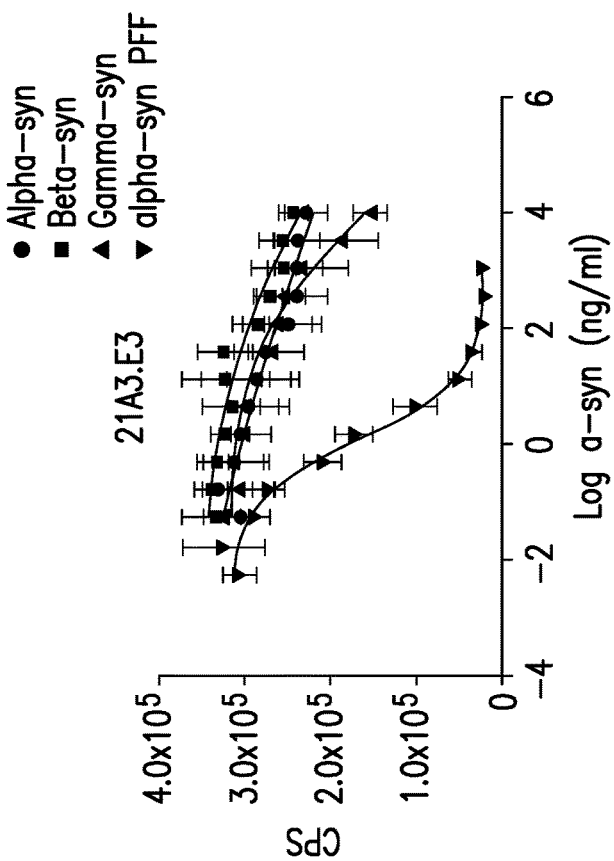
FIG. 7 is a series of graphs showing the binding of 7A10, 21A3, 15A5, 36A3, 11H11-1, and 44B11 to full-length human recombinant wild-type αSyn, βSyn, γSyn monomers; αSyn PFF was included as a positive control. Unbound antibody was captured on PFF-coated plates and measured by 1-sided ELISA. Data represents mean±sd for duplicate determinations.
Figure 7A:
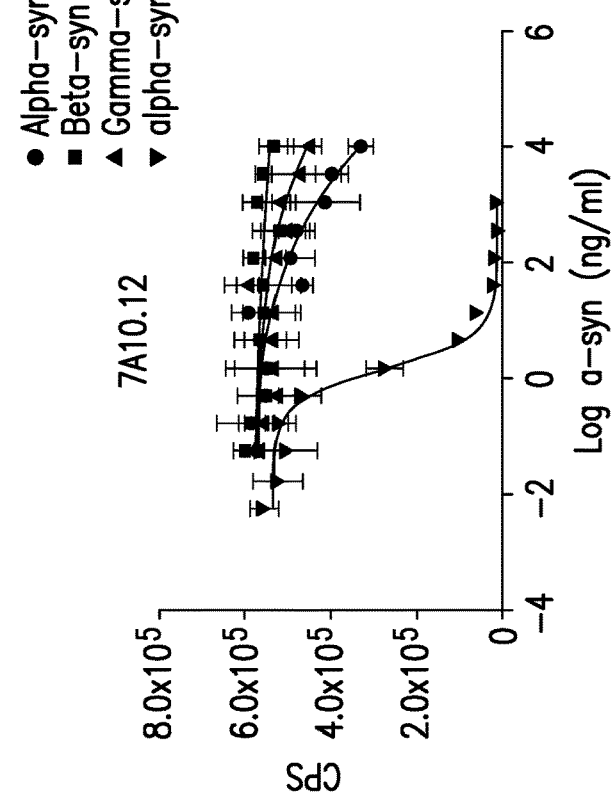
Figures 7E, 7F:
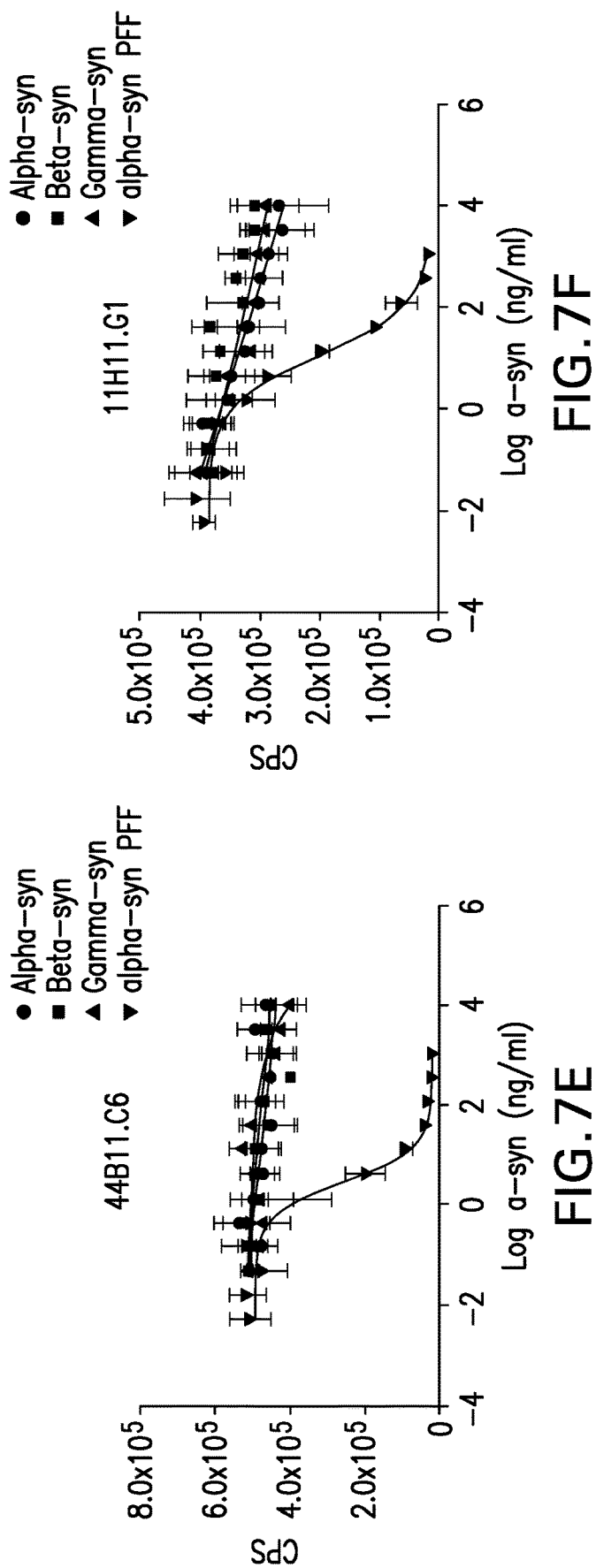

As shown in FIG. 7, antibodies did not distinguish between human αSyn, βSyn, or γSyn. Binding to PFF was included as a positive control.

Example 8: Biophysical Characterization of Anti-αSyn Antibodies

This Example describes the characterization of biophysical properties of anti-αSyn antibodies using various methods. The results of thermal stability, molecular weight, pI, hydrophobicity analyses are summarized in Table 6.

TABLE 6

Biophysical properties

| Method | Result | 7A10-IgG1f | 7A10-IgG1.3f | 7A10-T93A-IgG1.3f |
|---|---|---|---|---|
| Mass Spec | LC Intact Mass | Confirms Identity | Confirms Identity | Confirms Identity |
| Mass Spec | HC Intact Mass | Confirms Identity | Confirms Identity | Confirms Identity |
| Mass Spec | Glycosylation Profile | G0F 56% G1F 39% G2F 5% | G0F 48% G1F 46% G2F 6% | G0F 50% G1F 45% G2F 5% |
| Thermal Stability (DSC) | Tm1 | 70.2 | 67.6 | 66.3 |
|  | Tm2 | 83.3 | 83.3 | 83.2 |
|  | Tm3 | 86.6 | 86.6 | 87.1 |
| Analytical SEC | % HMW | 0 | 0 | 0 |
|  | % LMW | 1.4 | 0 | 0 |
| iCIEF | pI (measured) | 9.22 | 9.09 | 9.09 |
|  | % main | 84.9 | 87.2 | 84.4 |
|  | % acidic | 10.7 | 10.9 | 12.5 |
|  | % basic | 4.3 | 2.0 | 3.1 |
| Hydrophobicity (HIC) | % main | 100 | 100 | 100 |

For differential scanning calorimetry (DSC), samples were scanned up in temperate at 60° C./hr at 1 mg/ml antibody. As shown in Table 6, all 7A10 antibodies showed favorable folding stability.

The identities of all three 7A10 antibodies shown in Table 6 were assessed by intact mass spectroscopy (MS) analysis.

The identities of all three 7A10 antibodies were confirmed by intact mass spectroscopy (MS) analysis based on agreement between measured masses and masses theoretically predicted from amino acid sequence. Additionally, the glycosylation profiles were determined and found to be typical for mAbs glycosylated at N297.

Next, charge homogeneities were measured by iCIEF with the following conditions: ProteinSimple iCE3 instrument; 1 min 1500V pre-focus, 10 min 3000V focus, samples run at 0.2 mg/mL in 0.35% Methyl Cellulose, 2.0 M Urea, 1% v/v Pharmalyte 5-8, and 3% v/v Pharmalyte 8-10.5. pI Markers 5.8 and 10.10. Table 6 shows measured pI values near 9, and 84-87% as main peak, with 11-13% acidic variants, and remainder basic.

The homogeneity of the antibodies were also probed by hydrophobic interaction chromatography (HIC), using the following conditions: Tosoh TSKgel Butyl NPR column, Mobile phase A: 0.1M sodium phosphate pH 7.0, 2M ammonium sulfate, Mobile phase B: 0.1M sodium phosphate pH 7.0, Flow rate: 1.0 ml/min. As shown in Table 6, all three antibodies exhibited 100% as main peak.

In order to assess whether the antibodies aggregate or are truncated, analytical SEC was conducted with the following conditions: Shodex K403-4F column, buffer=100 mM Sodium Phosphate 150 mM Sodium Chloride, pH7.3, flow rate=0.3 mL/min. As shown in Table 6, all versions of 7A10 showed no detectable HMW species.

The stability of 7A10-IgG1f, 7A10-IgG1.3f, and 7A10-T93A-IgG1.3f were also tested under forced stability conditions, including high concentration and high temperature. The antibodies were concentrated to over 100 mg/ml in 20 mM histidine, 250 mM sucrose, pH 6.0 and stored for 4 weeks at 4° C. The antibodies were then analyzed for increases in HMW or LMW species. As shown in Table 7, there was little increase in either type of species, indicating that 7A10 has very favorable concentratability behavior.

The antibodies were also dialyzed into the same histidine buffer at a final antibody concentration of 10 mg/ml, and incubated at 40° C. for 4 weeks to force any potential chemical or physical degradation. As shown in Table 7, there was no increase in HMW species for any of the three 7A10 antibodies examined. There was an appearance of a small amount of LMW species (2.5-5%).

The charge profile of the antibodies was also measured by CIEF. The antibodies showed typical distributions of mostly main peak, with acidic species as the next largest population, and basic being the smallest. The changes in proportions of these charged species upon exposure to 40° C. for 4 weeks is also typical for antibodies.

TABLE 7

Forced stability

| Method | Result | 7A10-IgG1f | 7A10-IgG1.3f | 7A10-T93A-IgG1.3f | 7A10-T93A-IgG1f |
|---|---|---|---|---|---|
| Concentratability | Concentration Tested | 126 mg/ml | 119 mg/ml | 140 mg/ml | TBD |
| | % HMW T = 0 | 0 | 0.0 | 0.0 | TBD |
| | % HMW after 4 weeks 4° C. | 0 | 0.1 | 0.1 | TBD |
| | % LMW T = 0 | 0 | 0.0 | 0.0 | TBD |
| | % LMW after 4 weeks 4° C. | 0 | 0.0 | 0.0 | TBD |
| High Temperature (40° C.) | aSEC ΔHMW | 0% | 0% | 0% | TBD |
| | aSEC ΔLMW | 5% | 2.5% | 2.5% | TBD |
| | CIEF main T = 0 | ND | 87.2 | 84.4 | TBD |
| | CIEF main 4 weeks at 40° C. | ND | 59.7 | 55.2 | TBD |
| | CIEF acidic T = 0 | ND | 10.9 | 12.5 | TBD |
| | CIEF acidic 4 weeks at 40° C. | ND | 30.7 | 34.1 | TBD |
| | CIEF basic T = 0 | ND | 2.0 | 3.1 | TBD |
| | CIEF basic 4 weeks at 40° C. | ND | 9.6 | 10.7 | TBD |

Example 9: Binding Avidity of Anti-αSyn Antibodies to Preformed αSyn Fibrils

This Example describes the αSyn_binding behaviour of 7A10 using surface plasmon resonance (SPR).

Figure 8A:
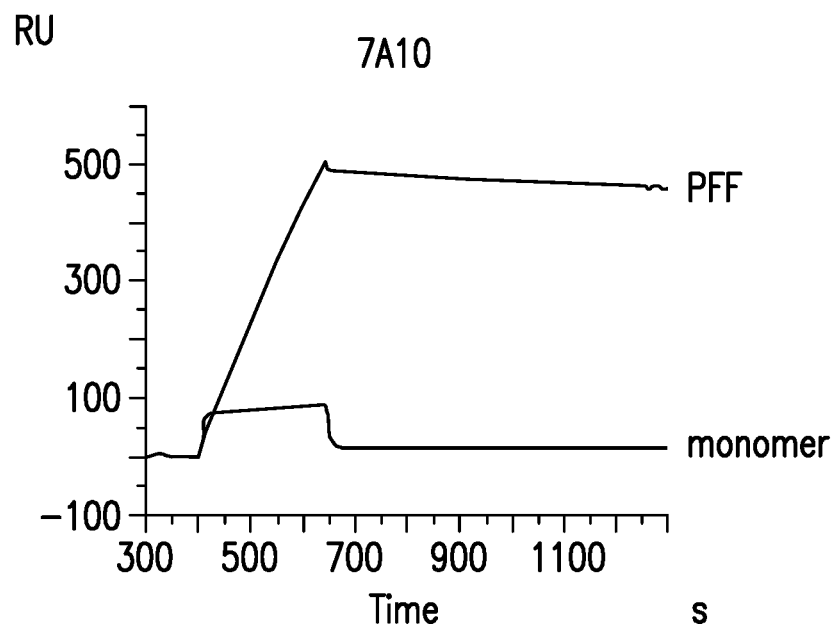
FIGS. 8A and 8B are graphs showing surface plasmon resonance (SPR) analysis of the binding of 7A10 and Antibody 1 to wild-type monomeric αSyn or PFF.
Figure 8B:
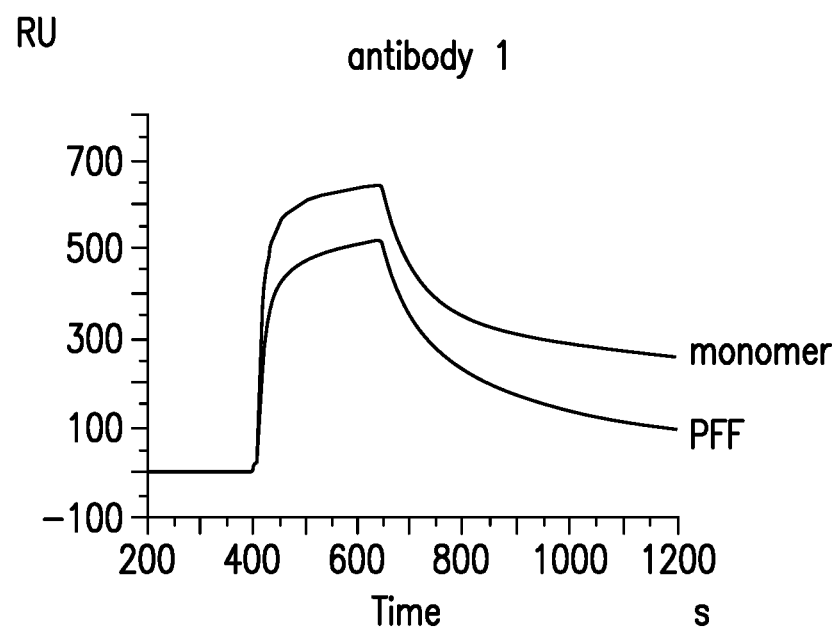

FIG. 8 shows binding behavior with the antibody captured on the surface and the wild type monomeric αSyn in solution. This format allows monovalent affinity to be measured. Wild type αSyn_showed very low and weak binding. In contrast, when PFF was tested as the solution analyte, a much larger mass of αSyn was observed to bind. This is consistent with an increase in tightness due to bivalent avidity of the multivalent PFF. A control anti-human αSyn antibody 1 was also tested. As shown in FIG. 8, Antibody 1 binds monomeric and PFF αSyn with similar association and dissociation rates, suggesting there is no detectable binding enhancement from bivalency/avidity with this antibody.

Next, the format of the SPR assay was optimized to facilitate an estimation of binding avidity. Note that PFF is multimeric and 7A10 is a normal bivalent monoclonal antibody. Thus, the binding data reflects an enhancement in binding affinity due to avidity effects (see FIG. 8).

Figure 9A:
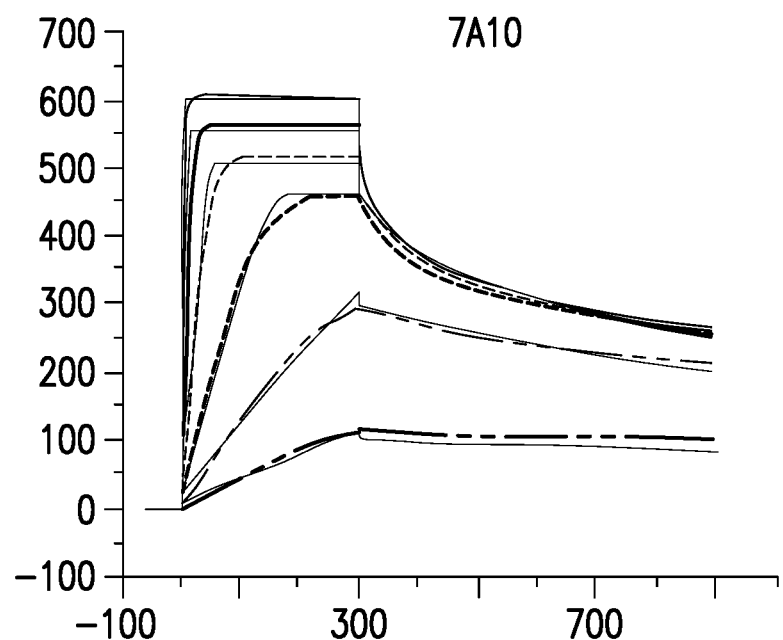
FIGS. 9A and 9B are graphs showing the results of a refined SPR assay to estimate the avidity of 7A10 and 7A10-T93A to PFF.
Figure 9B:
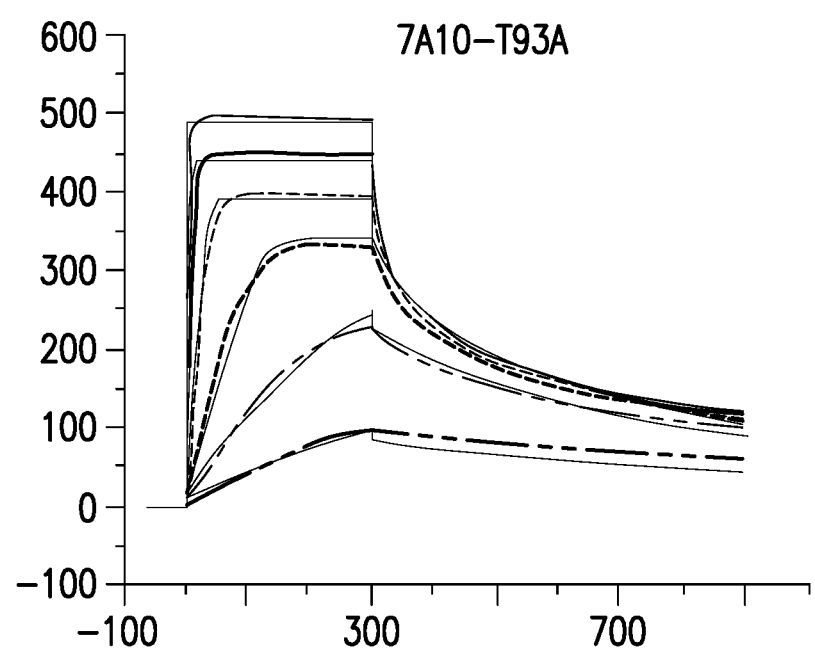

As shown in FIG. 9, 7A10 and 7A10-T93A bind with similar avidity to PFF immobilized on the surface (7A10: ka (1/Ms): 5.811E+7, kd (1/s): 0.009834, $K_D$: 1.692E-10 M; 7A10-T93A: ka (1/Ms): 8.946E+7, kd (1/s): 0.03873, $K_D$: 4.329E-10 M). The association kinetics for both were found to be very rapid. Nevertheless, the two data sets were analyzed as precisely as possible to a 1:1 binding model to determine if there is a discernable difference in avidity in this assay format. Based on curve-fitting, it appears that the antibodies bind with avidities that are within a factor of 4-fold to PFF immobilized to a surface.

Example 10: Blocking Induction of Insoluble, Aggregated αSyn by Anti-αSyn Antibodies In Vitro This Example describes the ability of anti-αSyn antibodies to block the generation of intracellular, detergent insoluble, phosphorylated (pS129) aggregates of αSyn by PFF or MSA brain lysates to induce the in vitro.

Intracellular, detergent insoluble, phosphorylated (pS129) aggregates of αSyn can be induced in cultured cells following treatment with PFF or MSA brain lysates (Prusiner et al., PNAS 2015:112:E5308-17; Luk et al., PNAS 2007; 106: 20051-6). A similar system was developed using rat hippocampal neurons by overexpressing human A53T αSyn and measuring the induction of insoluble pS129 αSyn after exposing cells for 11 days with either PFF or MSA brain lysate samples.

Methods a. Preparation of PFFs and Analysis of Fibrillization

PFFs were prepared and analyzed using the method described in Example 3.

b. Preparation of Human Brain Lysates

Cortical brain samples were obtained from Banner Health Research Institute (Sun City, Ariz.). MSA brain tissue from patients 12-18, 01-03 and 04-51 were used for immunodepletion experiments. Brain samples were sonicated in filtered PBS (1 ml PBS/100 mg tissue wet weight) with KONTES Micro Ultrasonic Cell Disrupter (output 40, Tune 50) for 2×10 sec. Samples were placed in 2 ml Eppendorf tubes and the tubes were kept on wet ice during sonication. Brain lysates were centrifuged at 3,000 g, 4° C. for 5 min. Supernatant aliquots were frozen in liquid nitrogen and stored at −80° C. QC assays including αSyn ELISAs (total & pS129) were performed. To isolate high-speed-spin pellets, brain homogenates previously prepared at 100 mg/ml in PBS were diluted 3-fold to 33.3 mg/ml in ice cold PBS followed by centrifugation at 100,000×g for 30 minutes at 4° C. The supernatant was removed and discarded. The pellet was resuspended in ice cold PBS in the same volume as the starting sample.

c. Primary Cell Culture Isolation

Primary rat hippocampal neuronal cultures were prepared weekly from ~7 litters at embryonic day 19 (E19) using the Papain Dissociation System, according to manufacturer's instructions (Worthington Biochemical). Rat hippocampal cells were plated on PDL coated 96 well BD imaging plates (~16 plates per week) at 30,000/well in neuronal culture medium, containing Neural Basal Medium (ThermoFisher Scientific, Waltham, Mass.) and 0.5 mM GlutaMax (ThermoFisher Scientific, Waltham, Mass.), supplemented with 1×B-27 (ThermoFisher Scientific, Waltham, Mass.).

d. Immunoprecipitation

Previously prepared brain homogenate (100 mg/ml) was diluted 150-fold in complete Neurobasal Medium (NBM) (Neurobasal medium containing pen/strep, Glutamax, and B-27 supplement) (ThermoFisher Scientific, Waltham, Mass.). A concentration response function of synuclein antibodies was tested by adding the test concentration of antibody to an aliquot of diluted brain homogenate. The sample was incubated at 4° C. with end over end incubation for 2 hours followed by the addition of washed and blocked Protein A/G agarose bead slurry at 1:10 dilution to the sample followed by overnight incubation at 4° C. with end over end incubation. Protein A/G agarose beads (ThermoFisher Scientific, Waltham, Mass.) were washed once with PBS+0.05% tween-20, 3-times with PBS, then blocked in PBS+1% BSA for 2 hours at 4° C.; 2 bead volumes for each step; final bead sample slurry was 1:1 with PBS:bead pellet. After incubation, the samples were centrifuged at 1500 g for 2 minutes to pellet the beads. The depleted supernatant was removed and used for treatment in the immunofluorescence assay.

e. Immunofluorescence Assay

On day in vitro (DIV) 4, rat hippocampal neurons were transduced with an adeno-associated viral vector, AAV1 containing the cDNA for human αSyn harboring the A53T mutation (GeneDetect, Bradenton, Fla.) at an MOI of 3,000. On DIV 7 cells were treated with test samples (6 wells per treatment). All treatments were done by half medium exchange. Each plate contained a negative control (no treatment condition), a positive control (10 nM PFF) and a non-depleted inducer control. On DIV 18 (11 days post treatment), cells were fixed and stained for insoluble αSyn. For fixation, a solution containing 4% paraformaldehyde and 4% sucrose and 1% triton was added for 15 min. Following fixation, cells were washed three time with wash buffer containing DPBS plus 0.05% tween. Cells were then blocked by 3% BSA and 0.3% triton in DPBS for 1-2 hr to block a non-specific signal. Following the blocking step, cells were treated with primary antibody overnight in blocking buffer. Primary antibodies used were, anti-Syn and beta Synuclein (EP1646Y, Millipore/Abcam; Cambridge, UK; N-terminal rabbit monoclonal, 1:100 dilution), anti-αSyn, phospho S129 (81A, Covance/Biolegend, Bogart, Ga. mouse monoclonal, 1:1000 dilution), and anti-MAP2 (ab5392, Abcam; Cambridge, UK; chicken polyclonal, 1:10,000 dilution). The following day, plates were washed 3 times with DPBS containing 0.05% tween followed by a 1 hour incubation with fluorescent-conjugated secondary antibodies. The secondary antibodies used were, Alexa Fluor 647 goat anti-mouse IgG, 1:500 dilution; Alexa Fluor 488 goat anti-rabbit IgG, 1:500 dilution, Alexa Fluor 568 goat anti-chicken IgG, 1:500 dilution and Hoechst, 1:800 dilution. All secondary antibodies were obtained from Invitrogen. Plates were then washed 3 times for 15 minutes each with DPBS plus 0.05% tween, with the final wash in DPBS alone.

f. High Content Immunofluorescent Analysis

Images were acquired on ArrayScan™ VTi automated microscopy and image analysis system (Cellomics Inc., Pittsburgh, Pa.) with ×10 objective. Imaged plates were analyzed with the High Content Studio 3.0 software package (Cellomics, USA) using the neuronal profiling application. Cells were identified with Hoechst fluorescence which defines the nuclear area, and neurites were identified by MAP2 staining. The cell soma was identified by overlapping nuclear and MAP2 staining. The total insoluble αSyn and total phosphorylated αSyn at S129 (pS129) were identified by the fluorescence intensities in two additional channels. Induction was quantified by the total pS129 spot intensity colocalized in neurites. Fold induction was determined by normalizing to the mean of the negative control wells. A toxicity index was calculated by multiplying the normalized nuclei count, normalized neuronal count, and normalized neurite length, with each well normalized to the respective mean values of the negative control wells. Wells with toxicity scores lower than 0.6 were excluded from analysis. Fold induction values for each antibody test concentration were normalized to the mean of the wells treated with the undepleted inducer. Concentration response curves were generated by a least-squares fit in Prism (GraphPad) using the equation $Y = Bottom + (Top - Bottom)/(1 + 10^{((X - \log IC50)}))$ and IC50s calculated for each experiment.

Results

Figure 10C:
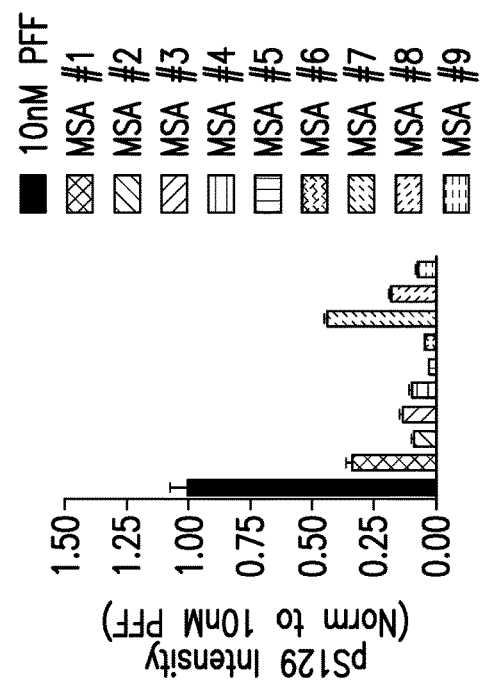
FIG. 10C is a graph showing induction of pS129 (normalized to 10 nM PFF control) following 11 days of treatment of transduced (3K MOI AAV-hA53T-αSyn) rat hippocampal neurons with lysates from 9 different MSA-patient derived brain samples. Bars from left to right correspond to 10 nM PFF, MSA #1, MSA #2, MSA #3, MSA #4, MSA #5, MSA #6, MSA #7, MSA #8, and MSA #9.
Figure 10B:
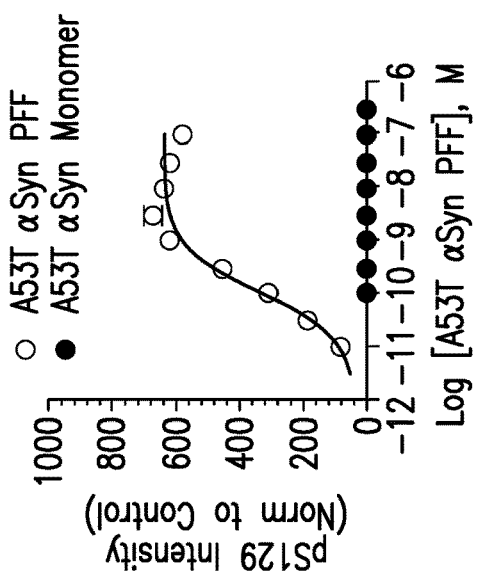
FIG. 10B is a graph showing concentration response curves for induction of pS129 (normalized to untreated control) in transduced (3K MOI AAV-hA53T αSyn) rat hippocampal neurons treated with either hA53T-αSyn PFF (upper (rising) line) or monomer (lower (flat) line) for 11 days.
Figure 10A:
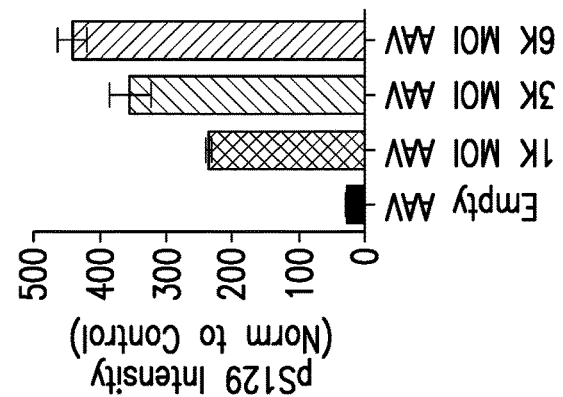
FIG. 10A is a graph showing induction of pS129 (normalized to untreated control) following 11 days of treatment with 10 nM PFF in rat hippocampal neurons transduced with increasing AAV-hA53T-αSyn MOI.
Figure 10D:
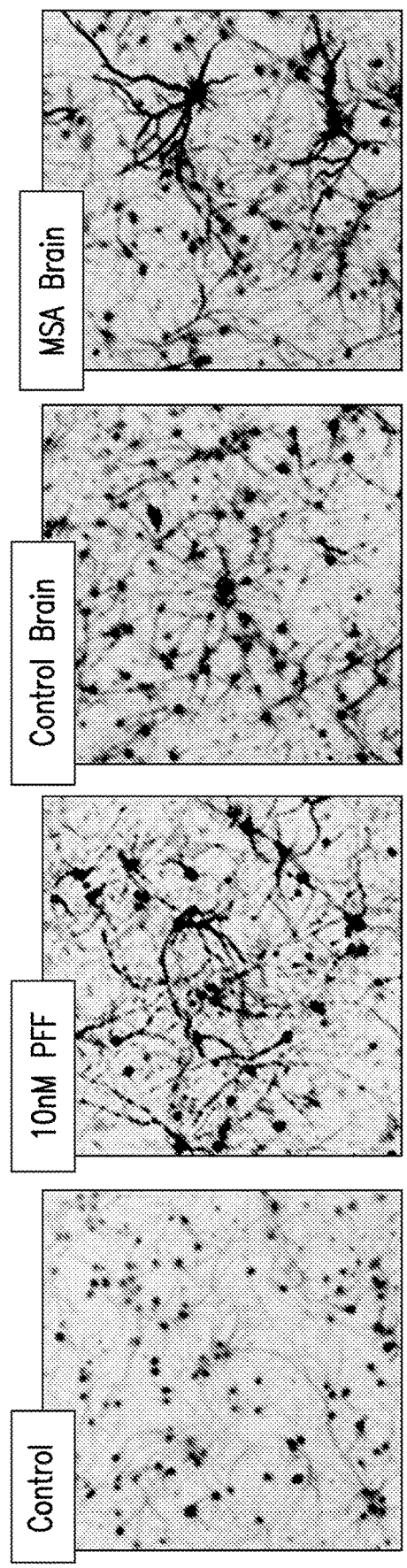
FIG. 10D shows immunofluorescent images of induced pS129 signal in transduced (3K MOI AAV-hA53T-αSyn) rat hippocampal neurons 11 days after treatment with either buffer, 10 nM PFF, lysate from a control brain, or lysate from a MSA brain. Brain lysates were applied at a 1:300 dilution.
Figure 10F:
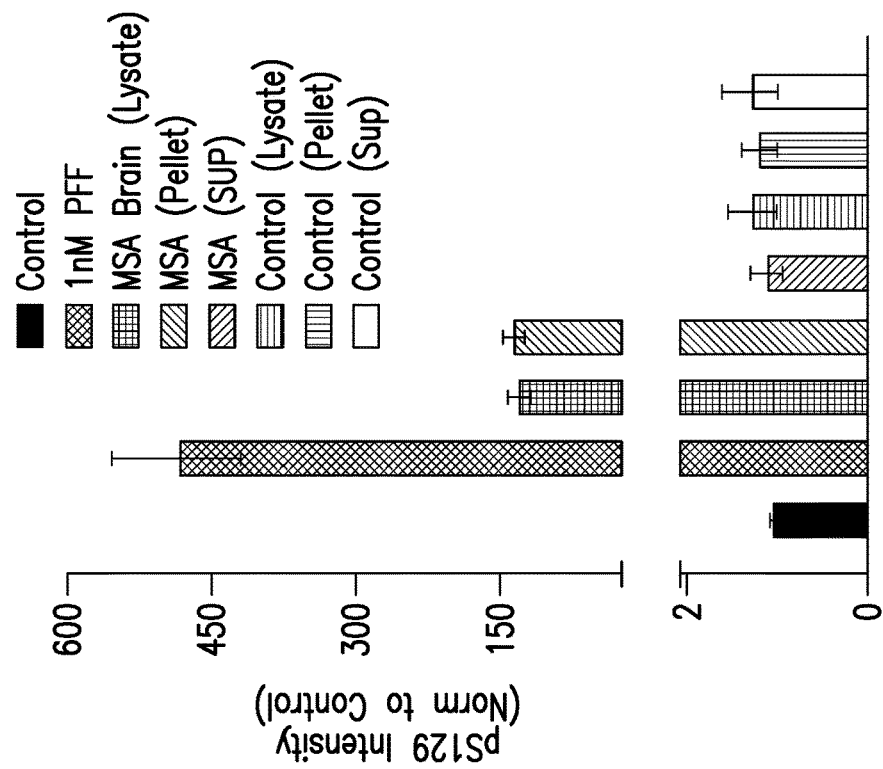
FIG. 10F is a graph showing induction of pS129 αSyn (normalized to untreated control), in transduced (3K MOI AAV-hA53T-αSyn) rat hippocampal neurons following 11 days of treatment with PFF, MSA and control brain lysates and the isolated high-speed centrifugation pellets and remaining supernatants from MSA and control brain lysates. Bars from left to right correspond to Control, 1 nM PFF, MSA Brain (lysate), MSA (Pellet), MSA (Sup), Control (Lysate), Control (Pellet), and Control (Sup).
Figure 10E:
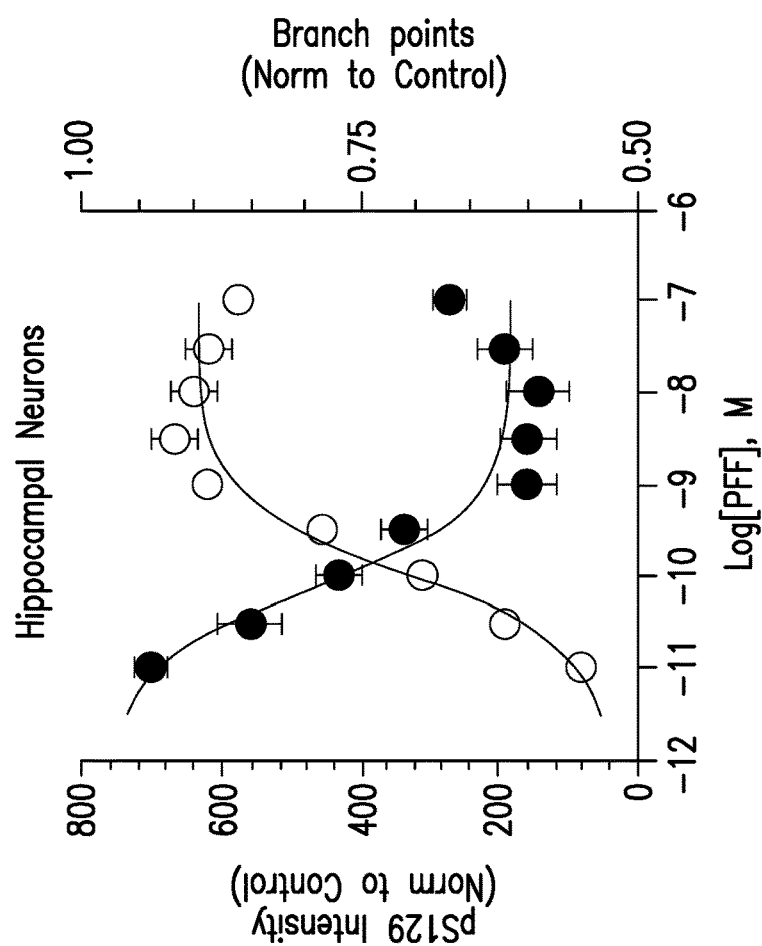
FIG. 10E is a graph showing the inverse correlation between pS129 αSyn induction (normalzied to untreated control; rising line) and branch points (normalzied to untreated control; descending line) in transduced (3K MOI AAV-hA53T-αSyn) rat hippocampal neurons following 11 days of treatment with increasing concentrations of PFF.

As shown in FIG. 10A, overexpression of A53T αSyn using AAV-hA53T-αSyn resulted in a robust increase in the PFF-induced pS129 signal as measured by high content immunofluorescent analysis. The PFF-induced pS129 signal was dose dependent, and could not be elicited with various concentrations of hA53T-αSyn monomer up to 300 nM (FIG. 10B). Additionally, treatment with 9 different MSA brain lysate samples also induced pS129 signal (FIG. 10C); however, induction was not observed with control brain lysates (FIG. 10D). PFF-dependent increases in pS129 signal correlated with decreased branch points of MAP2-positive neurons (FIG. 10E). The inducing activity in the MSA lysates could be isolated by high-speed centrifugation (FIG. 10F) suggesting that the inducer in these samples is a high molecular weight aggregate. In addition, a time-dependent increase in pS129 signal was seen following treatment with the MSA pellet (7d incubation: 0.22±0.06 of 10 nM PFF, n=6; 14d incubation: 0.32±0.05 of 10 nM PFF, n=6; 18d incubation: 0.52±0.08 of 10 nM PFF, n=6) (FIG. 10G). Finally, similar to the induced pathology seen with hA53T-aSyn PFF, a reduction in branch points was also observed following treatment with MSA brain lysate samples (10 nM PFF: 0.50±0.16, n=4300; MSA: 0.58±0.17, n=1842; FIG. 10H).

Figure 11:
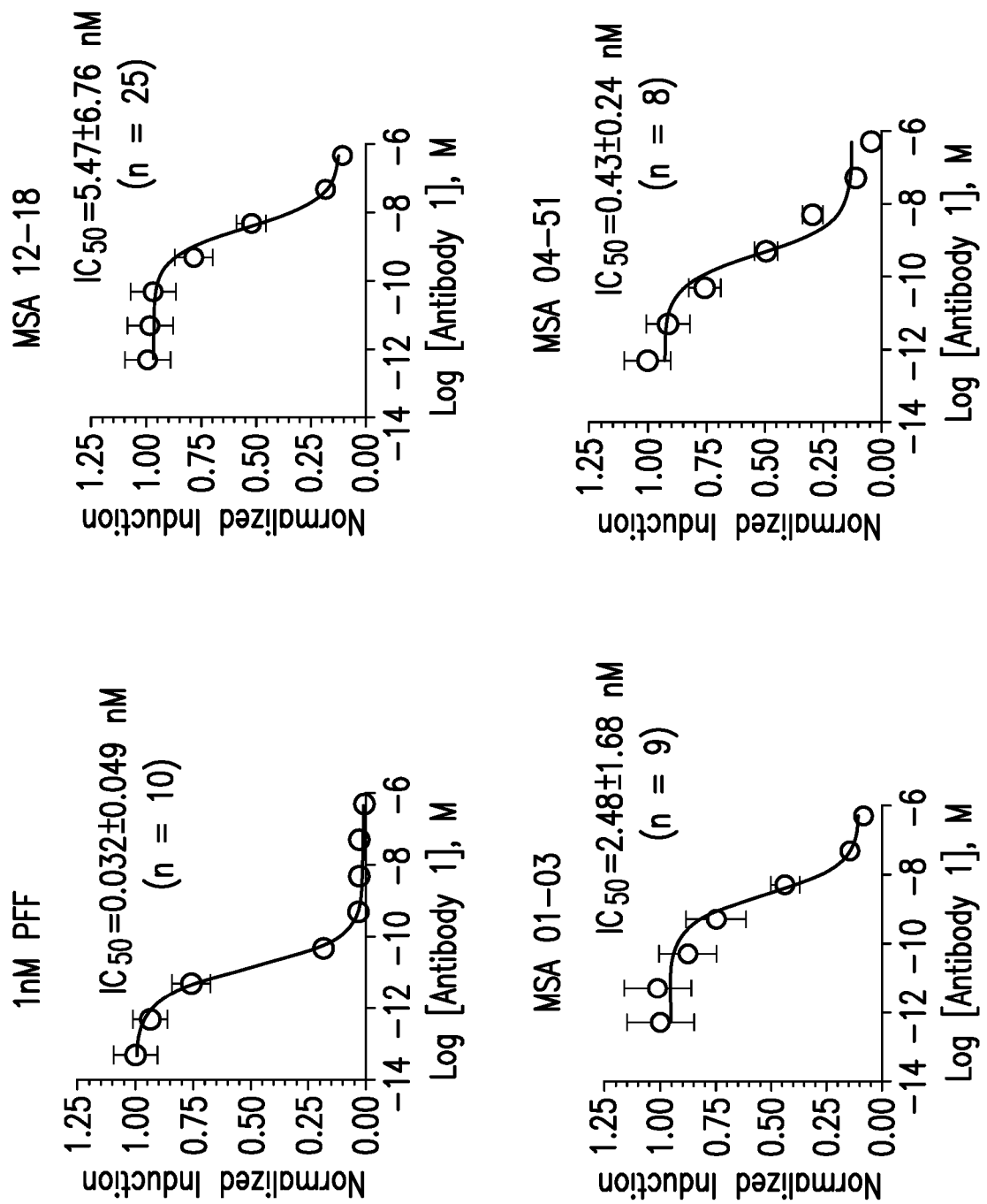
FIG. 11 is a series of graphs showing cumulative concentration response curves for Antibody 1 immunodepletion of PFF and brain lysates generated from three different MSA patients (12-18, 01-03, 04-51). Immunodepleted samples were tested for induction of pS129 in rat hippocampal neurons transduced with 3K MOI hA53T αSyn AAV. Y-axis values represent pS129 intensity normalized to undepleted samples. Data points (mean±95% CI) and fitted curves generated using cumulative data set. IC50s calculated for each experiment and mean±sd shown.
Figure 12:
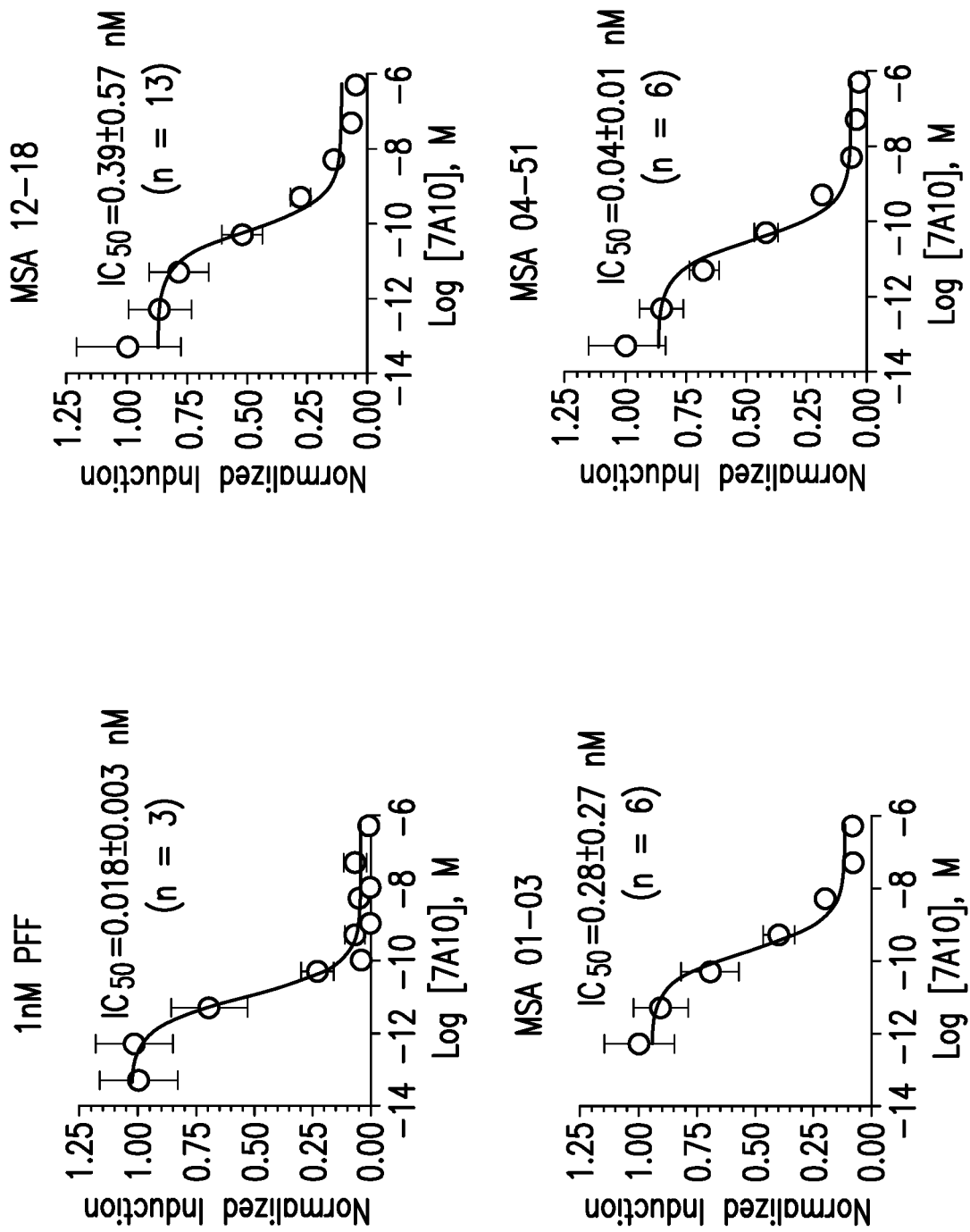
FIG. 12 is a series of graphs showing cumulative concentration response curves for 7A10 immunodepletion of PFF and brain lysates generated from three different MSA patients (12-18, 01-03, 04-51). Immunodepleted samples were tested for induction of pS129 in rat hippocampal neurons transduced with 3K MOI hA53T αSyn AAV. Y-axis values represent pS129 intensity normalized to undepleted samples. Data points (mean±95% CI) and fitted curves generated using cumulative data set. IC50s calculated for each experiment and mean±sd shown.
Figure 13:
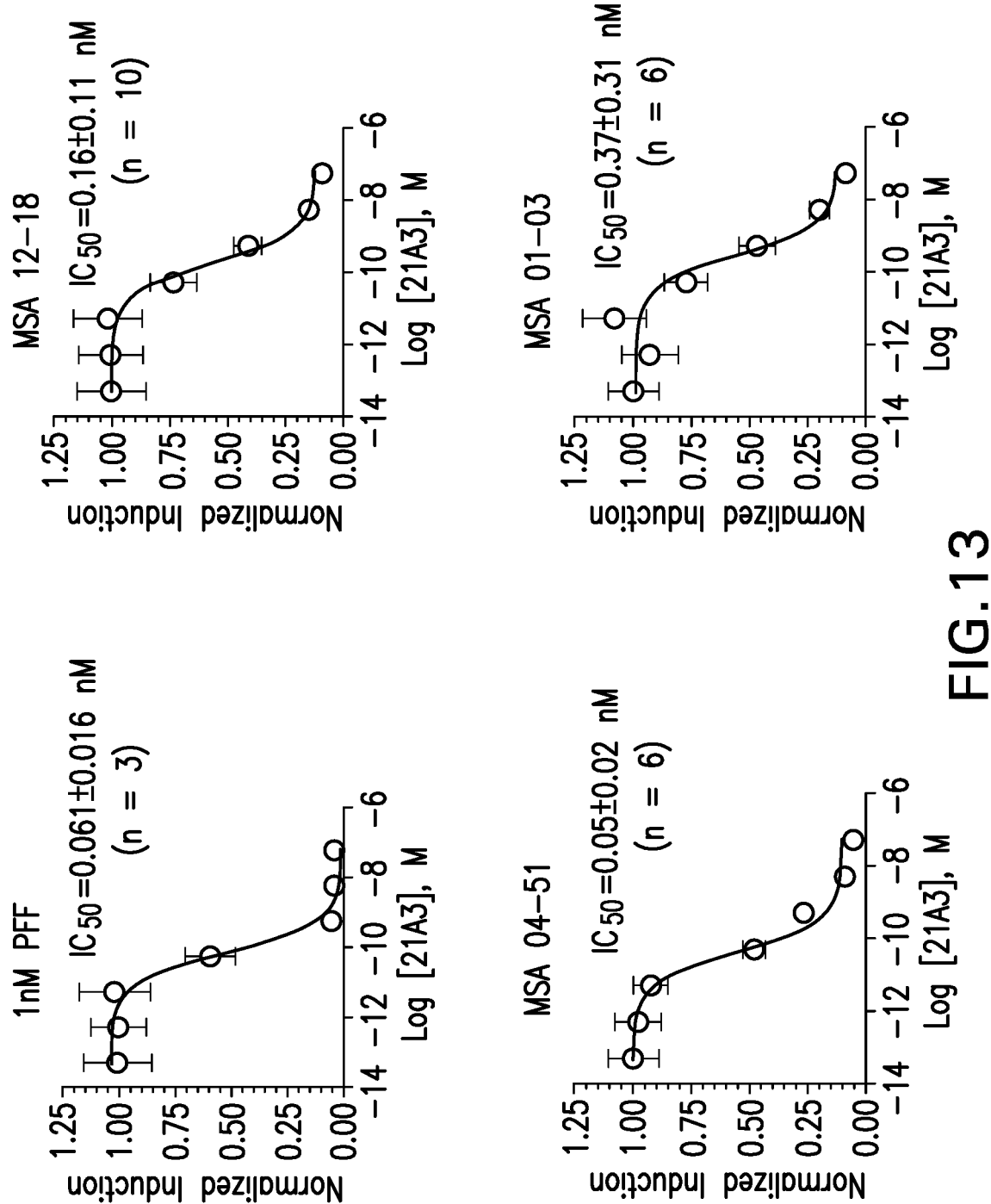
FIG. 13 is a series of graphs showing cumulative concentration response curves for 21A3 immunodepletion of PFF and brain lysates generated from three different MSA patients (12-18, 01-03, 04-51). Immunodepleted samples were tested for induction of pS129 in rat hippocampal neurons transduced with 3K MOI hA53T αSyn AAV. Y-axis values represent pS129 intensity normalized to undepleted samples. Data points (mean±95% CI) and fitted curves generated using cumulative data set. IC50s calculated for each experiment and mean±sd shown.
Figure 14:
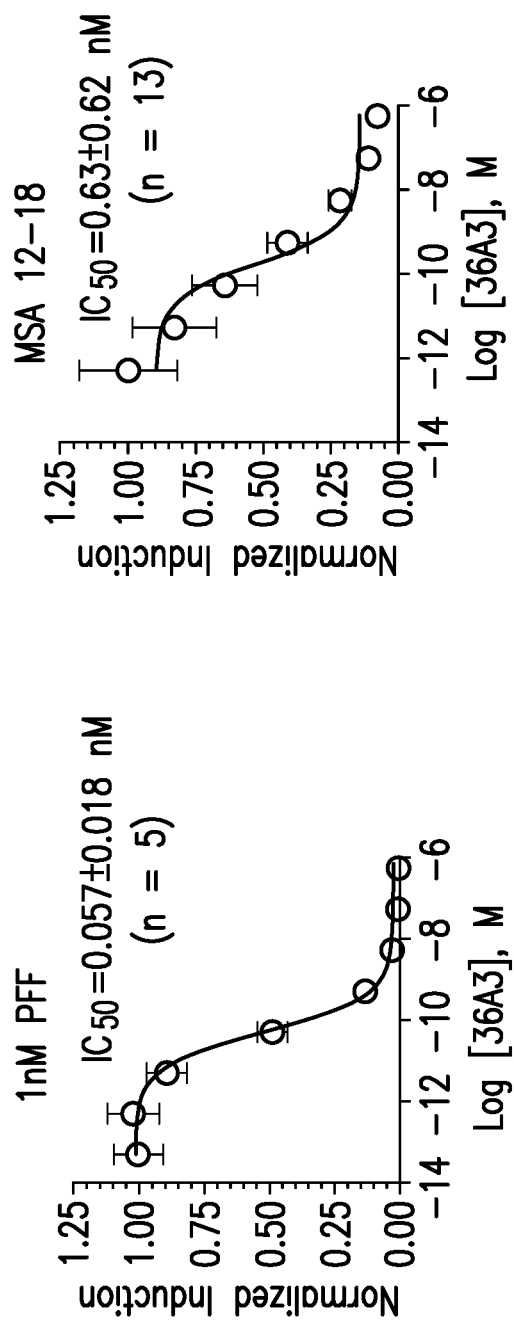
FIG. 14 is a series of graphs showing cumulative concentration response curves for 36A3 immunodepletion of PFF and brain lysates generated from three different MSA patients (12-18, 01-03, 04-51). Immunodepleted samples were tested for induction of pS129 in rat hippocampal neurons transduced with 3K MOI hA53T αSyn AAV. Y-axis values represent pS129 intensity normalized to undepleted samples. Data points (mean±95% CI) and fitted curves generated using cumulative data set. IC50s calculated for each experiment and mean±sd shown.
Figure 14:
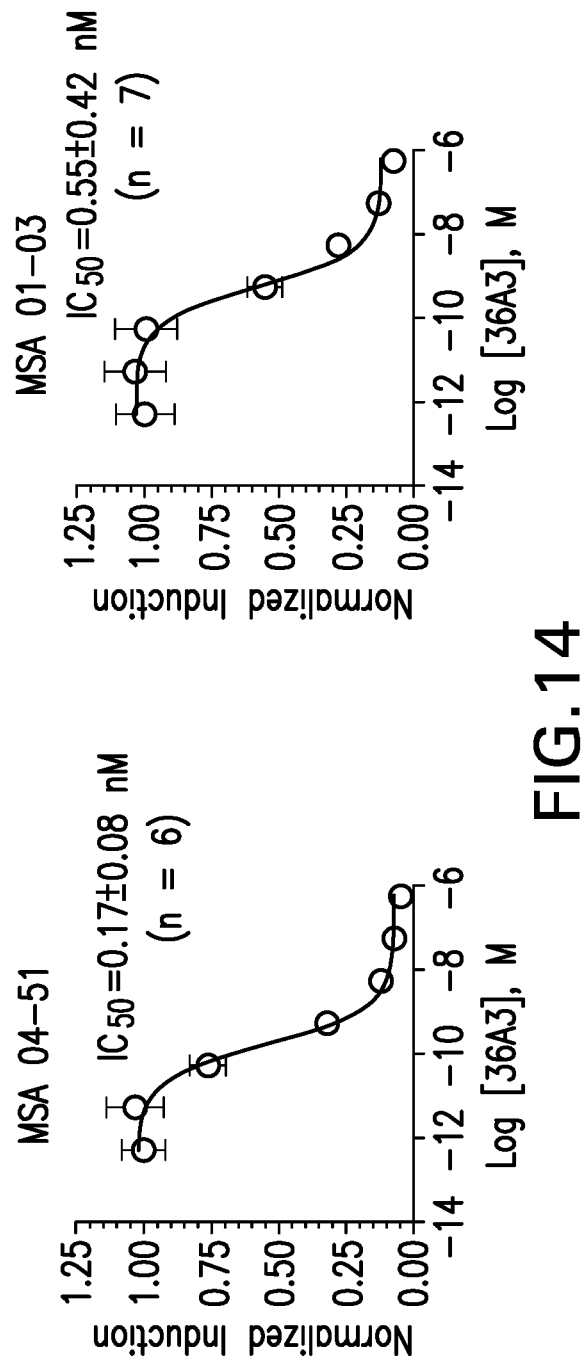
Figure 15:
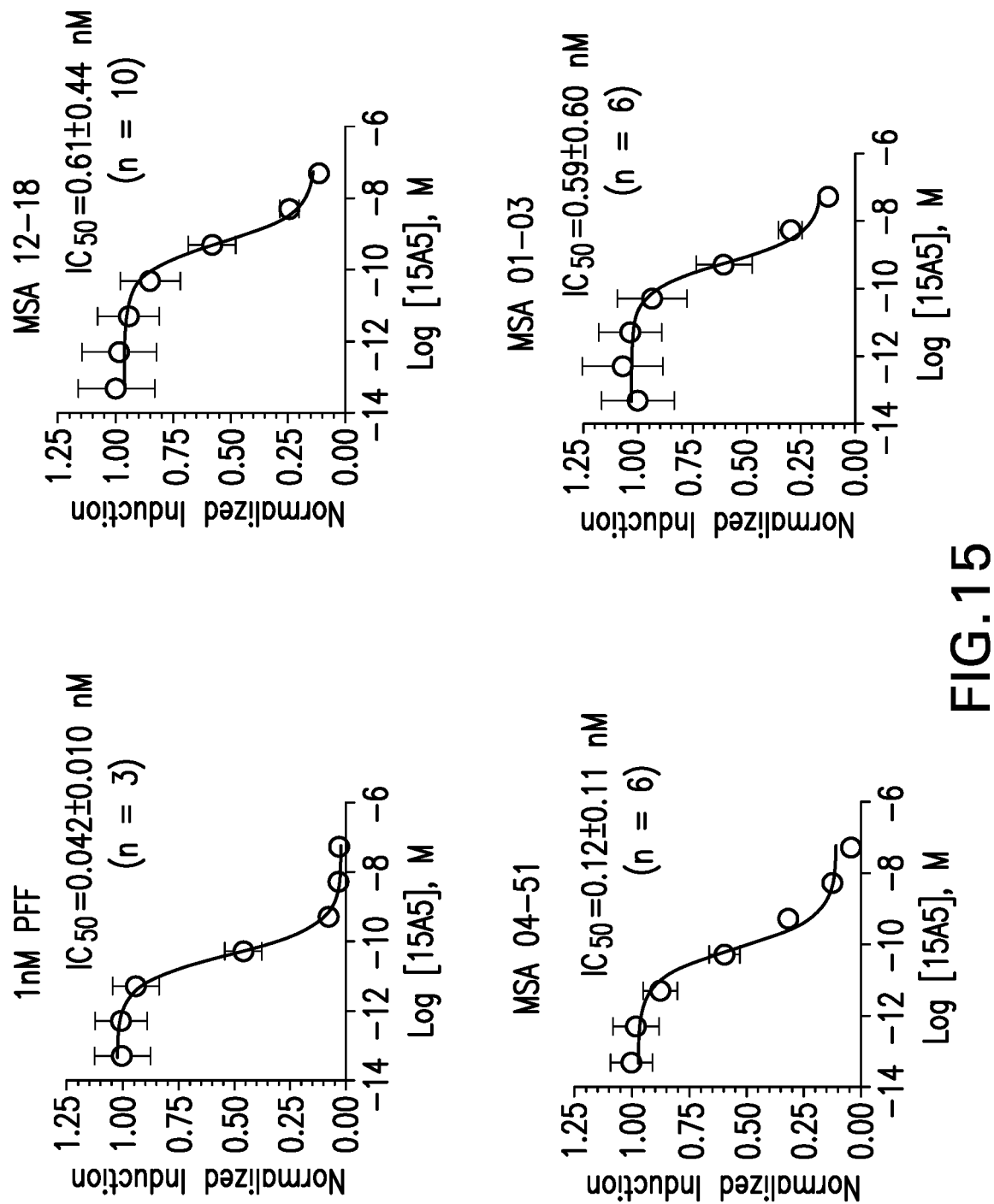
FIG. 15 is a series of graphs showing cumulative concentration response curves for 15A5 immunodepletion of PFF and brain lysates generated from three different MSA patients (12-18, 01-03, 04-51). Immunodepleted samples were tested for induction of pS129 in rat hippocampal neurons transduced with 3K MOI hA53T αSyn AAV. Y-axis values represent pS129 intensity normalized to undepleted samples. Data points (mean±95% CI) and fitted curves generated using cumulative data set. IC50s calculated for each experiment and mean±sd shown.
Figure 16:
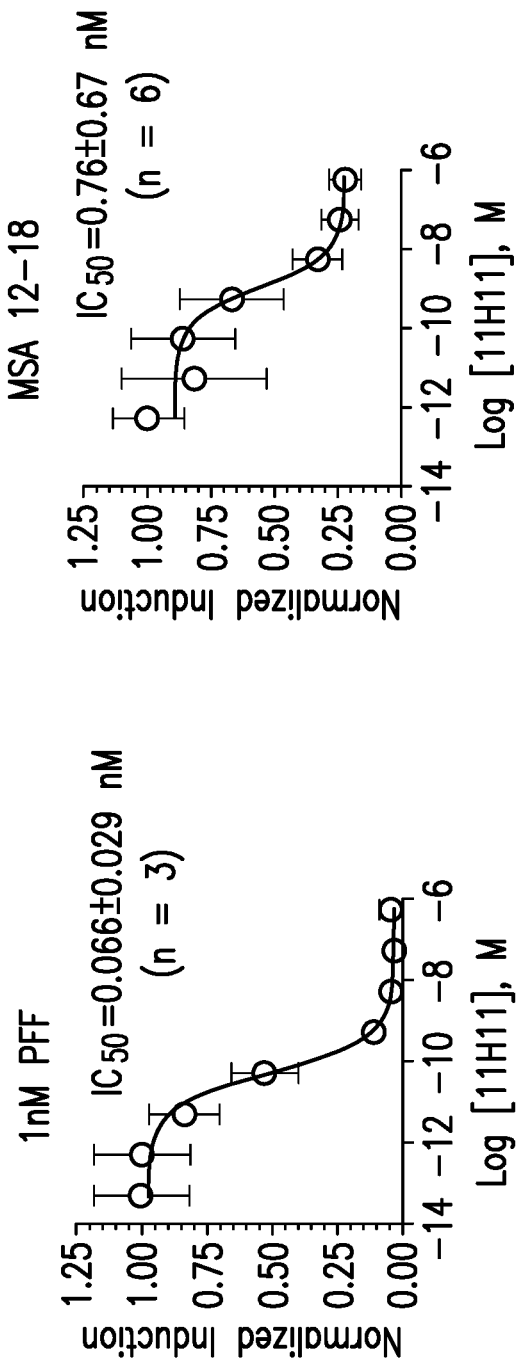
FIG. 16 is a series of graphs showing cumulative concentration response curves for 11H11-1 immunodepletion of PFF and brain lysates generated from three different MSA patients (12-18, 01-03, 04-51). Immunodepleted samples were tested for induction of pS129 in rat hippocampal neurons transduced with 3K MOI hA53T αSyn AAV. Y-axis values represent pS129 intensity normalized to undepleted samples. Data points (mean±95% CI) and fitted curves generated using cumulative data set. IC50s calculated for each experiment and mean±sd shown.
Figure 16:
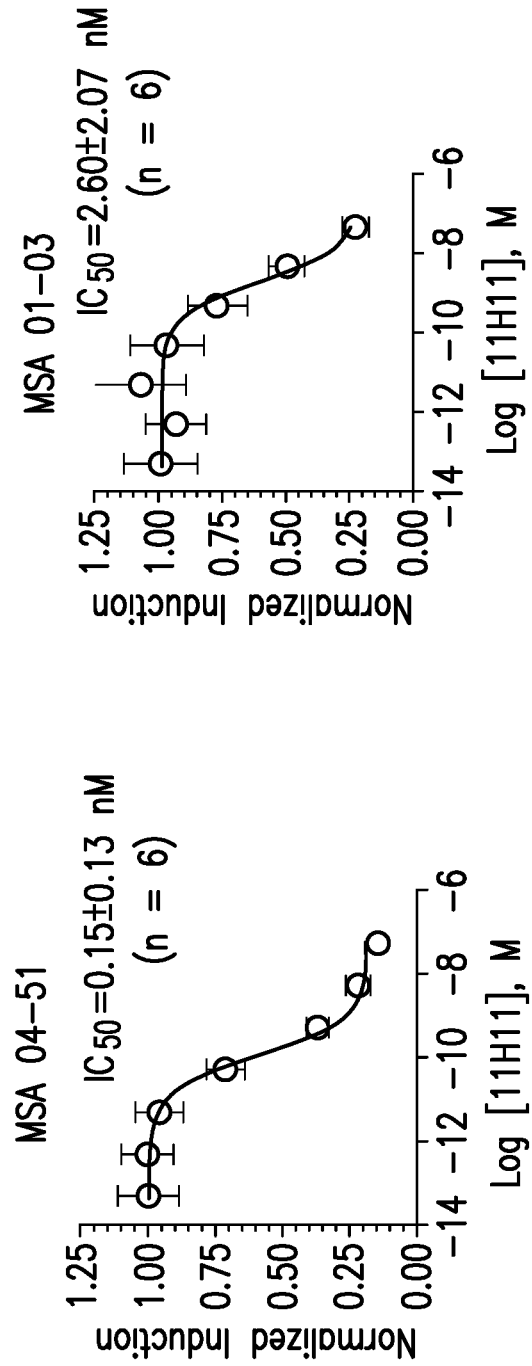
Figure 17:
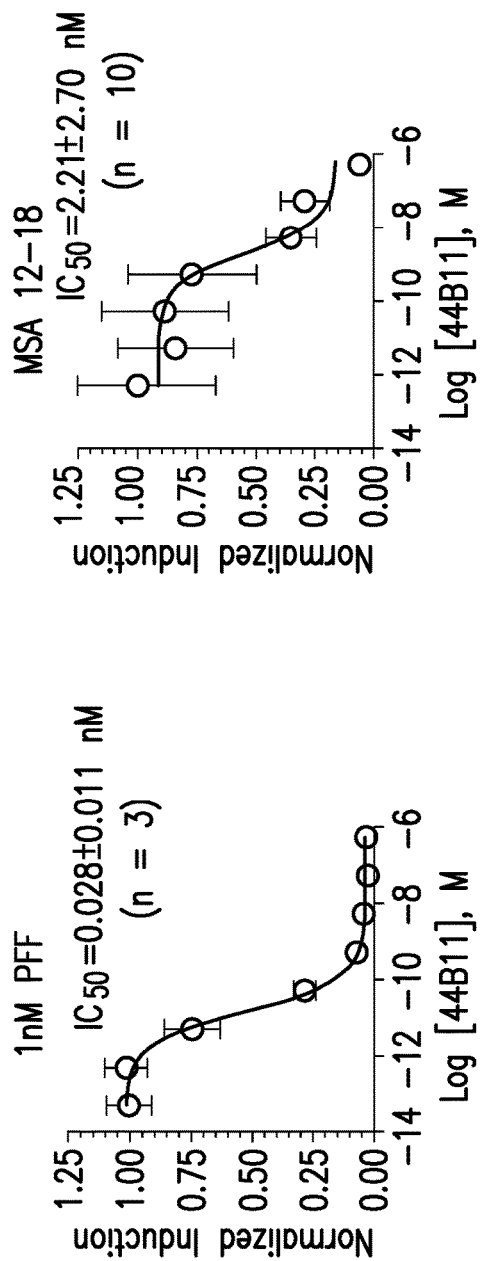
FIG. 17 is a series of graphs showing cumulative concentration response curves for 44B11 immunodepletion of PFF and brain lysates generated from three different MSA patients (12-18, 01-03, 04-51). Y-axis values represent pS129 intensity normalized to undepleted samples. Immunodepleted samples were tested for induction of pS129 in rat hippocampal neurons transduced with 3K MOI hA53T αSyn AAV. Data points (mean±95% CI) and fitted curves generated using cumulative data set. IC50s calculated for each experiment and mean±sd shown.
Figure 17:
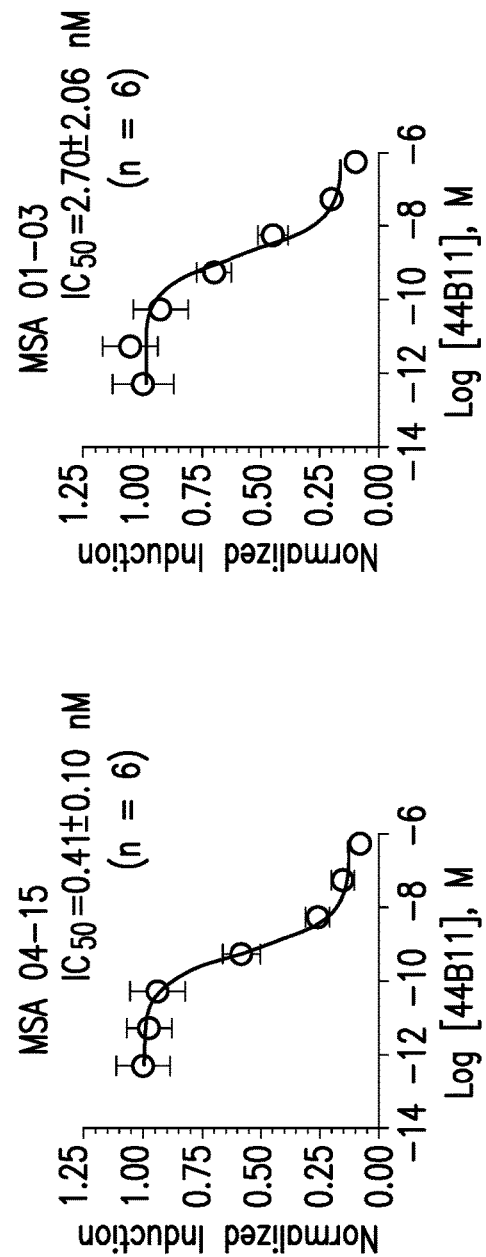
Figure 17:
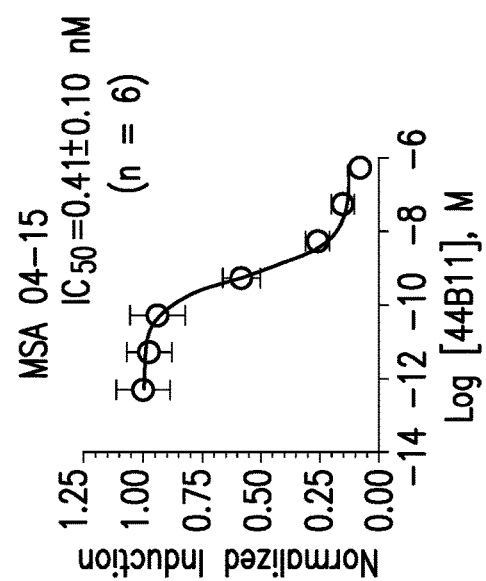

The high content assay was next used to evaluate the ability of different αSyn antibodies to immunodeplete the inducing activity (i.e., PFF-induced phosphorylation of S129) from PFF and MSA brain lysate samples. Lysates made from 3 different MSA patients, 12-18, 01-03, 04-51, were tested. For immunodepletion, samples were incubated overnight with a range of antibody concentrations. Immunocomplexes were then removed and the depleted samples incubated with neuronal cultures for 11d. Induction was measured by pS129 intensity normalized to the mean of the undepleted control wells. Exemplary concentration response curves for immunodepletion with the benchmark anti-αSyn antibody Antibody 1 are shown in FIG. 11, and IC50s are summarized in Tables 8-11. Antibody 1 exhibited potent and complete depletion of the inducer from both PFF and MSA brain lysates. These results confirm that the inducing activity in the MSA lysate is dependent on αSyn. Antibody 1 was more potent for depleting the inducing activity from PFF (0.032 nM, Table 8) compared to MSA lysates (5.47 nM, 2.48 nM and 0.43 nM, Tables 9-11) suggesting that there may be differences in the levels or conformation of these inducing species.

Next, antibodies 7A10, 21A3, 36A3, 15A5, 11H11-1, and 44B11 were tested for immunodepletion of the inducing activity from PFF and MSA brain lysates. Exemplary concentration response curves for 7A10, 21A3, 36A3, 15A5, 11H11-1, and 44B11 are shown in FIGS. 12-17, respectively. A summary of the mean IC50 values for PFF, MSA 12-18, MSA 01-03, MSA 04-51 are summarized in Tables 8-11, respectively. Similar to Antibody 1, all 6 antibodies depleted the inducing activity from PFF in a concentration-dependent manner (FIGS. 12-17). Mean IC50s ranged from 0.018 nM to 0.066 nM and were not significantly different from the IC50 for Antibody 1 (Table 8). All 6 antibodies also completely depleted the MSA lysates in a concentration-dependent manner; however, in contrast to the results with PFF, some of the antibodies were significantly more potent than Antibody 1 (Tables 9-11). For example, 7A10 was significantly more potent than Antibody 1 for depleting the inducing activity from all 3 MSA lysates: 7A10 was 14-fold more potent than Antibody 1 for depleting MSA 12-18 ($p<0.001$, Table 9), 9-fold for MSA 01-03 ($p<0.05$, Table 10) and 12-fold for MSA 04-51 ($p<0.01$, Table 11). Similarly, 21A3 was 34-fold more potent than Antibody 1 for MSA 12-18 ($p<0.01$, Table 9), 7-fold for MSA 01-03 (not significant, Table 10), and 10-fold for MSA 04-51 ($p<0.01$). Related antibodies 15A5 and 36A3 exhibited similar trends (Tables 9-11). 11H11-1 exhibited less robust differences in potency compared to Antibody 1 (Tables 9-11). 44B11, which binds a distinct epitope, was 3-fold more potent than 9E4 for immunodepletion of MSA lysate 12-18 ($p<0.05$, Table 9) and equipotent to Antibody 1 for depleting MSA lysate 01-03 (Table 10) and MSA lysate 04-51 (Table 11). The relative differences in potency observed could be linked to differences in the conformation or strain of the inducer which impact the exposure or accessibility of antibody epitopes.

TABLE 8

Summary of PFF IC50 data

| Antibody | IC50 (nM)[a] | Std | n | Fold Antibody 1 |
|---|---|---|---|---|
| Antibody 1 | 0.032 | 0.049 | 10 | |
| 7A10 | 0.018 | 0.003 | 3 | 1.8 |
| 44B11 | 0.028 | 0.011 | 3 | 1.1 |
| 15A5 | 0.042 | 0.010 | 3 | 0.8 |
| 36A3 | 0.057 | 0.018 | 5 | 0.6 |
| 21A3 | 0.061 | 0.016 | 3 | 0.5 |
| 11H11-1 | 0.066 | 0.029 | 3 | 0.5 |

[a]Statistics relative to Antibody 1 and based on paired t-test. ns: $p > 0.05$; * $p < 0.05$; $p < 0.01$; *$p < 0.001$. t-test results are ns unless indicated otherwise

TABLE 9

Summary of IC50 data for MSA 12-18 lysate

| Antibody | IC50 (nM)[a] | Std | n | Fold Antibody 1 |
|---|---|---|---|---|
| Antibody 1 | 5.47 | 6.76 | 25 | |
| 21A3 | 0.16** | 0.11 | 10 | 34.1 |
| 7A10 | 0.39*** | 0.57 | 13 | 14.2 |
| 15A5 | 0.61* | 0.44 | 10 | 8.9 |
| 36A3 | 0.63*** | 0.62 | 13 | 8.7 |
| 11H11-1 | 0.76* | 0.67 | 6 | 7.2 |

TABLE 9-continued

Summary of IC50 data for MSA 12-18 lysate

| Antibody | IC50 (nM)[a] | Std | n | Fold Antibody 1 |
|---|---|---|---|---|
| 44B11 | 2.21* | 2.70 | 10 | 2.5 |

[a]Statistics relative to Antibody 1 and based on paired t-test. ns: $p > 0.05$; *$p < 0.05$; $p < 0.01$; *$p < 0.001$. t-test results are ns unless indicated otherwise

TABLE 10

Summary of IC50 data for MSA 01-03 lysate

| Antibody | IC50 (nM)[a] | Std | n | Fold Antibody 1 |
|---|---|---|---|---|
| Antibody 1 | 2.48 | 1.68 | 9 | |
| 7A10 | 0.28* | 0.27 | 6 | 8.8 |
| 21A3 | 0.37 | 0.31 | 6 | 6.7 |
| 36A3 | 0.55 | 0.42 | 7 | 4.5 |
| 15A5 | 0.59* | 0.60 | 6 | 4.2 |
| 11H1-1 | 2.60 | 2.07 | 6 | 1.0 |
| 44B11 | 2.70 | 2.06 | 6 | 0.9 |

[a]Statistics relative to Antibody 1 and based on paired t-test. ns: $p > 0.05$; *$p < 0.05$; $p < 0.01$; *$p < 0.001$. t-test results are ns unless indicated otherwise

TABLE 11

Summary of IC50 data for MSA 04-51 lysate

| Antibody | IC50 (nM)[a] | Std | n | Fold Antibody 1 |
|---|---|---|---|---|
| Antibody 1 | 0.43 | 0.24 | 8 | |
| 7A10 | 0.04** | 0.01 | 6 | 12.0 |
| 21A3 | 0.05** | 0.02 | 6 | 9.5 |
| 15A5 | 0.12** | 0.11 | 6 | 3.6 |
| 11H11-1 | 0.15* | 0.13 | 6 | 2.9 |
| 36A3 | 0.17* | 0.08 | 6 | 2.5 |
| 44B11 | 0.41 | 0.10 | 6 | 1.1 |

[a]Statistics relative to Antibody 1 and based on paired t-test. ns: $p > 0.05$; *$p < 0.05$; $p < 0.01$; *$p < 0.001$. t-test results are ns unless indicated otherwise Deimmunized variants of 7A10 and 21A3 were also tested for immunodepletion of MSA 12-18 extract to assess the impact of the amino acid modifications on antibody activity. As shown in Table 12, 7A10-T93A exhibited similar potency for depleting the inducing activity from MSA 12-18 (0.66 nM) compared to the 7A10 parent antibody (0.52 nM); in contrast, other 7A10 variants were 10-100-fold weaker than the 7A10 parent. The V82L variant of 21A3 exhibited similar potency as the 21A3 parent (Table 12). Taken together these results suggest that the modifications in 7A10-T93A and 21A3-V82L do not impact overall antibody activity.

TABLE 12

Summary of IC50 data with MSA 12-18 lysate

| Antibody | IC50 (nM)[a] | Std | n |
|---|---|---|---|
| 7A10 hIgG1.3f (parent) | 0.52 | 0.28 | 3 |
| 7A10-Vh-T93A-IgG1.3f | 0.66 | 0.53 | 3 |
| 7A10 Vh-R56S-T93A-hIgG1.3f | 9.00 | 3.15 | 3 |
| 7A10-Vh-K58Y-T93A-IgG1.3f | 4.65 | 2.62 | 2 |
| 7A10-Vh-R56S-K58N-T93A-IgG1.3f | 51.05 | 38.54 | 2 |
| 21A3-hIgG1.3f (parent) | 0.19 | 0.22 | 3 |
| 21A3-Vh-V82L-IgG1.3f | 0.11 | 0.03 | 3 |

[a]Statistics relative to 7A10 or 21A3 parents and based on paired t-test. ns: $p > 0.05$; *$p < 0.05$; $p < 0.01$; *$p < 0.001$. t-test results are ns unless indicated otherwise In conclusion, 7A10, 21A3, 36A3, 15A5, 11H11-1, and 44B11 exhibited potent and complete depletion of the aggregate-inducing activity from PFF and 3 different MSA lysates. These results, in conjunction with results from the previous Examples, suggest that the antibodies preferentially bind to a form of αSyn found in these disease brain extracts that may be responsible for spreading of pathology and thus may be effective in blocking the transmission of αSyn pathology in vivo.

Example 11: Blocking αSyn Pathology by Anti-αSyn Antibodies In Vivo

This Example describes the ability of anti-αSyn antibodies to inhibit the spreading and transmission of αSyn pathology in a mouse model.

Methods a. Mice

Mice used in the study were 2-3-month-old, male and female [PAC-Tg(SNCA$^{A53T}$)$^{+/+}$; Snca$^{-/-}$] (PAC-A53T) mice carrying the human A53T mutation on a mouse Snca knockout background (Kuo et al, *Human Molecular Genetics* 2010:19:1633-50) were used for in vivo efficacy studies. Mice were housed in groups of four in a temperature controlled housing rooms with food and water available ad-libitum.

b. Antibody Treatment and Stereotaxic Surgery

Approximately 40 μl blood was collected from a subset of male and female PAC-A53T mice via retro-orbital bleed to set the baseline for antibody and anti-drug-antibody (ADA) levels. The entire cohort of mice was divided into two groups: control and treatment groups. Mice in the control group were given an intraperitoneal (i.p) saline injection prior to PBS injection into the striatum and 4 additional weekly saline injections until completion of the experiment (n=8). The second group of mice were divided into 9 sub-treatment groups: saline (n=11), Antibody 1 (n=12), 7A10 (n=12), 11AH11 (n=12), 15A5 (n=11), 21A3 (n=11), 36A3 (n=11), 44B11 (n=12), and Antibody 3 (n=5). All mice in the second group were inoculated with recombinant A53T-PFFs following first i.p. dose of saline or selected antibody. Similar to the control group, treatment groups received 4 additional weekly i.p. injections of saline or selected antibody. Antibody dose in all treatment groups was 10 mg/kg. The selection of antibody dose was based on the outcome of Study I, where Antibody 3 antibody effectively reduced pSer129 pathology in PAC-A53T mice. Weekly antibody treatment was preceded by retro-orbital bleed in subset of mice in order to evaluate pharmacokinetics (PK) and possible ADA levels in all treatment groups. Mice were sacrificed 30 days post A53T-PFF inoculation and 24h from last antibody treatment.

Stereotaxic injections: For unilateral striatal injections mice were anesthetized via isoflurane (1-4%) inhalation and placed in a stereotaxic frame with an attached nose cone to maintain isoflurane-induced anesthesia throughout the procedure. The surgical site was prepared with betadine followed by 70% isopropyl alcohol and a 1-2 cm skin incision was made to expose the skull and reference landmark locations. Sterile cotton swabs were used to gently clean the skull. A sterile carbide micro-burr bit was used to drill a hole at a depth of 0.5-1 mm through the surface of the skull. Mice were injected unilaterally with either 10 ug A53T-PFFs or PBS (control group) into a lateral Striatum (AP 0.2, ML-2.0, DV-3.6). The material was injected via a Hamilton syringe at a rate of 0.25 μl per min (2.5 μl total per mice) with the needle in place for ≥10 min at target. Mice were transferred to their housing room once they were fully recovered from the surgery.

c. Immunohistochemistry (IHC)

Mice were sacrificed for evaluation of pathology 30 days post A53T-PFF injections. For histological studies brains were fixed in 4% Paraformaldehyde (PFA) for 48 hours followed by 24 h in 15% sucrose and then for 48 h (or until use) in 30% sucrose solution. Coronal, 40 μm serial brain sections were prepared on a sliding microtome (Leica Microsystems, Buffalo Grove, Ill.) and placed in cryoprotectant until IHC analysis. IHC procedure included the following steps: brain sections were moved into staining dishes and rinsed in Phosphate Buffered Saline (PBS, Thermo Fisher Scientific, Waltham, Mass.) 3 times (5 min/rinse). Sections then were postfixed for 10 min in 3.7% formaldehyde (in PBS). They were then rinsed twice in PBS (10 min/rinse). Next, sections were incubated in a fresh 3% $H_2O_2$, 10% Methanol in PBS for 30 min to get rid of endogenous peroxidase activity. Sections were rinsed 3 times in PBS (10 min/rinse) followed by one hour blocking step in 10% normal serum (using serum from the species of the secondary antibody) plus 0.3% Triton X-100 in PBS at a room temperature. Slices were then rinsed 3 times in PBS (10 min/rinse). Brain slices were incubated overnight in a primary antibody [Anti-alpha-syn pSer129 (Abcam, Cambridge, UK; ab51253) at 1:100,000 dilution] at 4° C. on a micro-titer plate shaker at a speed to gently, yet uniformly agitate sections. On the second day of IHC, brain sections were rinsed ×4 times in PBS (10 min/rinse) and then incubated in biotinylated 2° antibody (1:500 goat anti-rabbit in PBS, Vector BA-1000) for 60 min. Sections were then rinsed in PBS (4 times, 10 min/rinse) and subsequently incubated in ABC complex made in PBS for 60 min at a room temperature (Elite ABC kit, Vector laboratories, Burlingame, Calif.). After rinsing in PBS (4 times, 10 min/rinse), sections were incubated for 10 min in peroxidase substrate (Vector Cat. # SK-4100, Vector laboratories, Burlingame, Calif.). Lastly, brain sections were rinsed in PBS (4 times, 10 min/rinse) and mounted on a Superfrost Plus Micro Slides (VWR, Randor, Pa.). Slides were air-dried and subsequently counterstained in Hemotoxylin and Scott's blue solutions followed by series of ethanol rinses. Slides were finally cover slipped using Permount and micro cover glass (VWR, Randor, Pa.) and allowed to dry for scanning and MC quantification analysis.

IHC quantification: Brain sections mounted onto glass slides were imaged using Aperio AT2 slide scanners. All slides within each study were imaged using identical illumination power and camera exposure. Approximately 2 slides from each animal were analyzed, each with ~20 mounted coronal brain sections. Following image acquisition, brain sections containing region of interests (ROI), a) Primary Cortex along with Cingulate Gyrus region (interaural 5.48 mm-2.96 mm, bregma 1.69 mm-0.83 mm, 6-10 sections) and b) Amygdala regions (interaural 2.72 mm-1.76 mm, bregma 1.07 mm-2.03 mm, 4-6 sections) were identified for each animal using HALO image analysis software. ROI was outlined for overall area occupied by pS129 stain on ipsi-lateral side (side of injection) and corresponding contra-lateral side for both the regions. The average stain from all ROI outlined sections for each animal was then quantified using Algorithm (Indica Labs)—Area Quantification. All images were analyzed simultaneously using identical threshold settings to identify positively stained regions. Tissue area (μm$^2$), total stain Area (μm$^2$), stain weak area & strong Area (μm$^2$), % stain positive tissue, % stain weak and % stain strong positive tissue were analyzed. ONE Way ANOVA followed by Dunnett's post-test was used to determine treatment effects.

d. Measurement of Antibody Levels in Plasma and Brain

ELISA plates (Costar 3925) were coated with 100 µl of 1 PFF (prepared from α-synuclein WT, PROTEOS) diluted in PBS (GIBCO cat #14190) 2 hours at room temperature (RT). PFF was sonicated 15 sec with a pause every second before coating. The plates were washed four times with 0.05% Tween in Dulbecco's PBS (Life Technologies, #14040-117) and blocked with 150 µl of 3% BSA (bovine serum albumin, protease free, Fraction V, Roch Diagnostic #03117332001) in DPBS for 2~3 h at RT or overnight at 4° C. Standards, plasma and brain samples were diluted in 1% BSA/0.05% Tween/DPBS containing Roche protease inhibitor (Roche 11836145001, 1 pellet/25 ml). Samples (3~4 dilutions) 100 µL/well were loaded in duplicate and incubated for ~2 hours at RT. After plates were washed four times with 0.05% Tween/DPBS, 100 µl of secondary antibodies (Alkaline phosphatase-affinipure donkey anti-human IgG, JacksonImmuno #709-055-149, with 50% glycerol) 1:1000 diluted in 1% BSA/0.2% Tween/DPBS were added and incubated for 1 hour at RT. Following four washes, the plates were developed with 100 µL of alkaline phosphatase substrate (Tropix CDP Star Ready-to-Use with Sapphire II, T-2214, Life Technologies) for 30 minutes. Luminescence counts were measured with Perkin Elmer EnVision (2102 Multilabel Reader). The plates were kept constantly shaking (Titer plate shaker, speed 3) during the assay.

e. Measurement of Anti-Drug Antibodies (ADAs)

A non-quantitative immunogenicity assay was developed in order to detect the possible development of Antibody 1, anti-7A10 antibody, anti-11AH11 antibody, anti-15A5 antibody, anti-21A3 antibody, anti-36A3 antibody, anti-44B11 antibody, and Antibody 3 in mice treated with Antibody 1, 7A10, 11AH11, 15A5, 21A3, 36A3, 44B11 and Antibody 3. In this enzyme-linked immunosorbent assay, Antibody 1, 7A10, 11AH11, 15A5, 21A3, 36A3, 44B11 and Antibody 3 were coated on a Maxisorp flat-bottom 96-well plate overnight at 4° C. Serum samples diluted at 1:100 were incubated overnight at room temperature to capture potential anti-drug antibodies (ADAs). Captured antibodies were detected with a goat anti-mouse immunoglobulin G (IgG) and immunoglobulin M (IgM) horseradish peroxidase enzyme (HRP) conjugated antibody. A goat anti-human immunoglobulin G (IgG) and immunoglobulin M (IgM) horseradish peroxidase enzyme (HRP) conjugated antibody was used as a positive control. Tetramethylbenzidine (TMB) was added as a colorimetric substrate for HRP that produces optical density (OD450) in proportion to the amount of Antibody 1, anti-7A10 antibody, anti-11AH11 antibody, anti-15A5 antibody, anti-21A antibody 3, anti-36A3 antibody, anti-44B11 antibody, and Antibody 3 present in the serum samples.

f. Measurement of αSyn Levels in Brain Tissue

Briefly, ELISA plates (Costar 3925) were coated with 100 µl of respective capture antibodies diluted in BupH carbonate-bicarbonate buffer, pH 9.4 (Thermo Fisher Scientific #28382) overnight at 4° C. Capture antibody MJFR1 (Abcam ab138501) was used at a concentration of 0.1 µg/ml (total α-synuclein assay) or 0.35 µg/ml (pS129 assay), MJFR14-6-4-2 (Abcam ab209538) at 0.1 µg/ml, and 1E8 (BMS 5446.1E8.10) at 0.3 µg/ml. The plates were washed four times with Dulbecco's PBS (Thermo Fisher Scientific, #14040-117) and blocked with 3% BSA (bovine serum albumin, protease free, Fraction V, Thermo Fisher Scientific) in DPBS for 2~3 h at room temperature (RT) or overnight at 4° C. Standards, brain samples and QC samples were diluted with 1% BSA/0.05% Tween/DPBS containing Roche protease inhibitor (Thermo Fisher Scientific, 1 pellet/25 ml) and Phosphatase Inhibitor 2&3 (Sigma Aldrich, P5726 & P0044, 1:100). Standards are α-synuclein WT (rPeptide S-1001), pS129 (aa89-140, AATGFVKKDQLGKNEEGAPQEG-ILEDMPVDPDNEAYEMP-pS-EEGYQDYE-PEAHHHHHH-CONH2; SEQ ID NO: 129) or PFF (prepared from α-synuclein WT, PROTEOS). Samples 50 µL/well were loaded in duplicate and incubated for overnight at 4° C. After plates were equilibrated to RT, 50 µl detection antibodies 1:4000 diluted in 1% BSA/0.1% Tween/DPBS were added and co-incubated with samples at RT for ~2 hours. Detection antibodies (4B12 from BioLegend SIG39730, MBJR13 from Abcam ab168381, 2E2, and 23H8) were pre-conjugated with alkaline phosphatase (AP kit from Novus Biologicals #702-0010). Plates were then washed four times with 0.05% Tween/PBS and developed with 100 µL of alkaline phosphatase substrate (Tropix CDP Star Ready-to-Use with Sapphire II, T-2214, Thermo Fisher Scientific) for 30 minutes. Luminescence counts were measured with Perkin Elmer EnVision (2102 Multilabel Reader). The plates were kept constant shaking (Titer plate shaker, speed 3) during the assay.

Results

PFF-inoculated mice were dosed weekly by IP injection for 4 weeks with PBS (n=11) or Antibody 1 (n=12), 7A10 (n=12), 11AH11 (n=12), 15A5 (n=11), 21A3 (n=11), 36A3 (n=11), 44B11 (n=12), and Antibody 3(n=5). PBS-inoculated mice were dosed by IP injection with PBS (n=8) as a negative control. All antibodies were dosed at 10 mg/kg. Weekly antibody treatment was preceded by retro-orbital bleeds in subset of mice in order to evaluate pharmacokinetics (PK) and possible ADA levels. Mice were harvested 30 days post inoculation and 24 hr following the last antibody treatment. Antibody levels were measured in brain tissue from a subset of mice. pS129 αSyn pathology was measured in select brain regions by immunohistochemistry.

Figure 18:
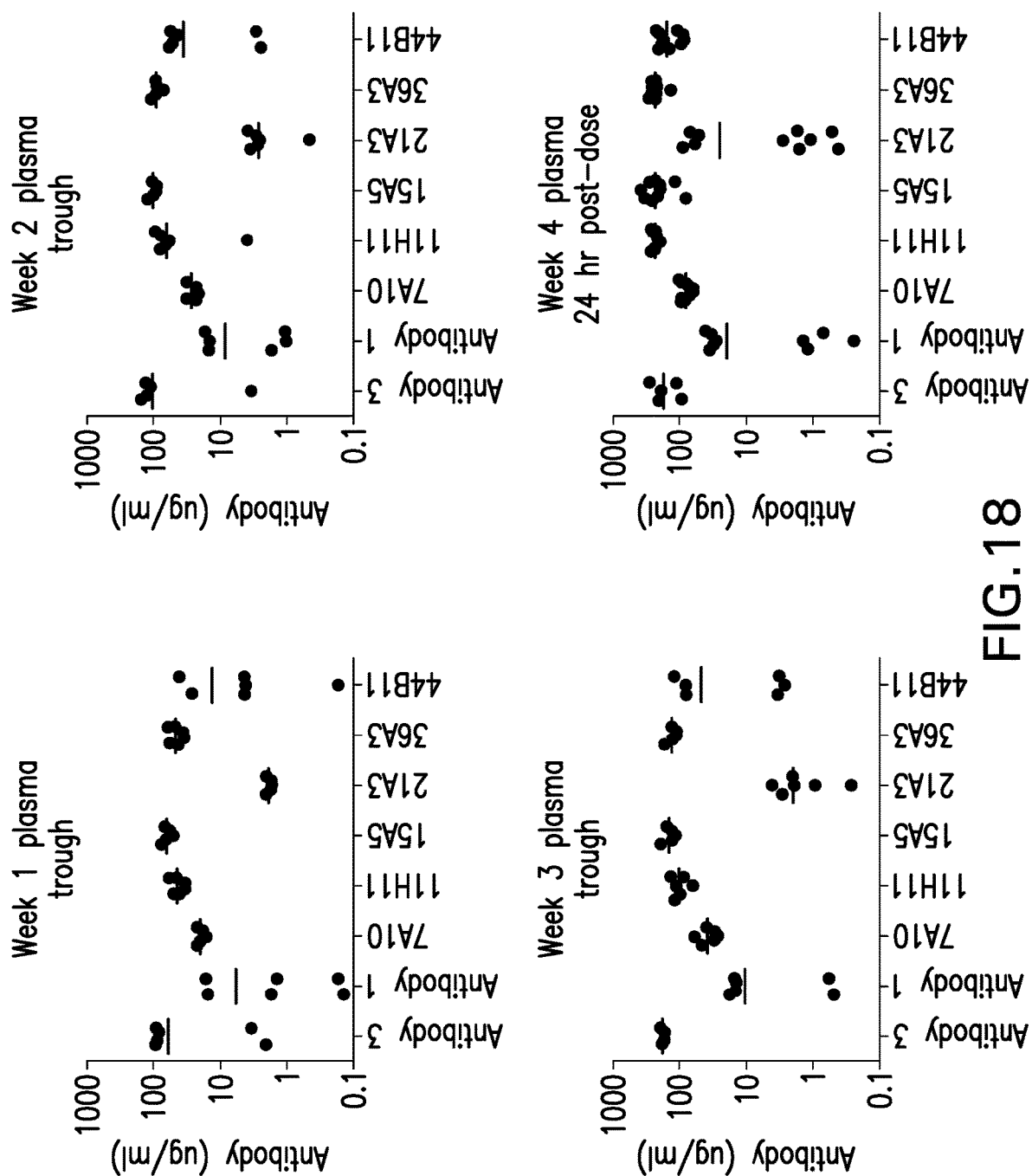
FIG. 18 is a series of graphs showing plasma concentrations of Antibody 3 (an antibody known to bind to αSyn), Antibody 1, 7A10, 11H11-1, 15A5, 21A3, 36A3, and 44B11 in plasma samples taken at trough on weeks 1-3 and at harvest 24 hr post-dose on week 4. Upper left (week 1 plasma trough), Upper right (week 2 plasma trough), Lower left (week 3 plasma trough), and Lower right (week 4 plasma 24 hour post-dose).
Figure 19:
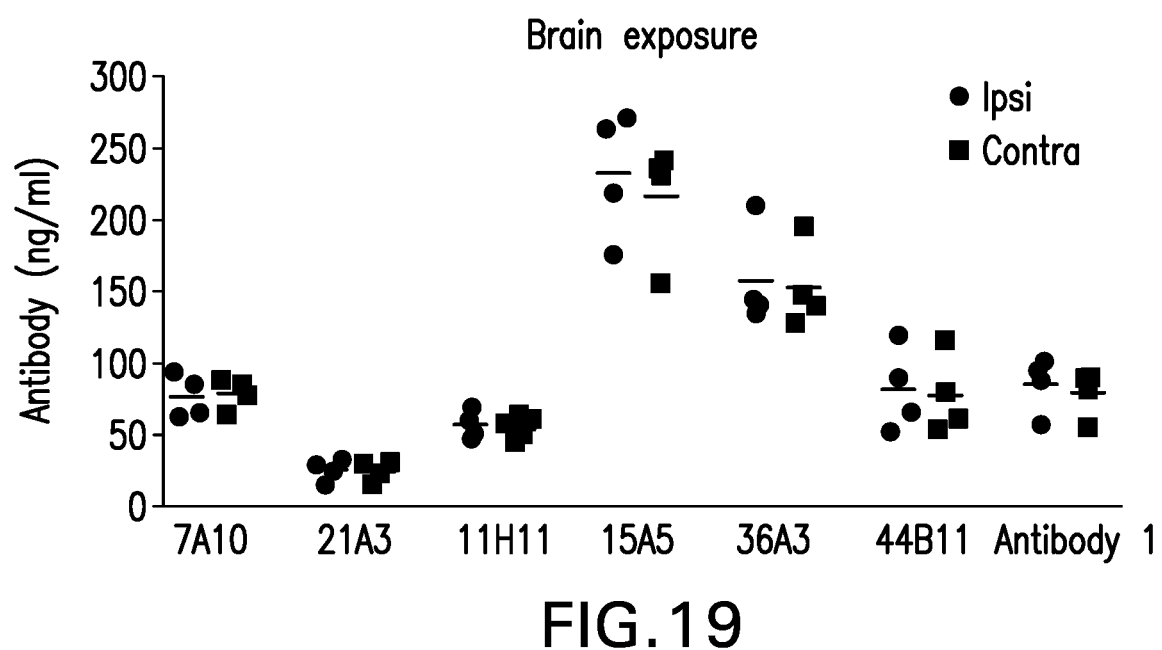
FIG. 19 is a graph showing brain concentrations of 7A10, 21A3, 11H11-1, 15A5, 36A3, 44B11, and Antibody 1, ipsi-lateral and contra-lateral to the PFF injection site.
Figure 20:
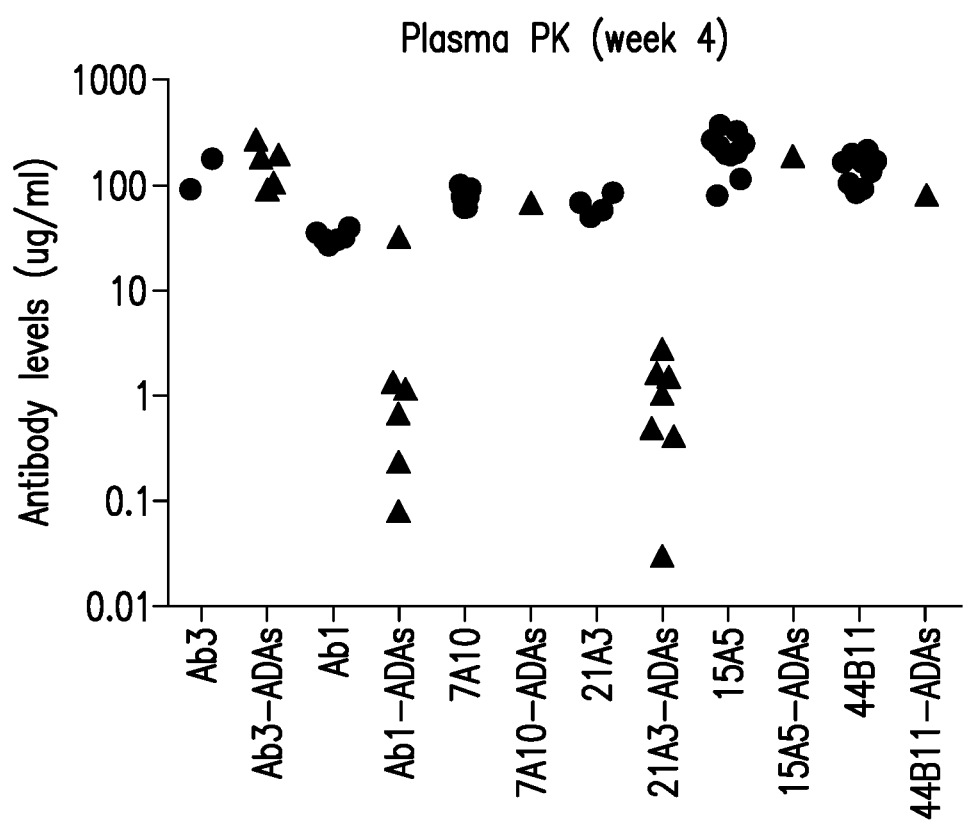
FIG. 20 is a graph showing plasma levels of Antibody 3, Antibody 1, 7A10, 21A3, 15A5, and 44B11 on week 4 for samples without (circles) and with (triangles) ADA activity.

Plasma antibody exposures are summarized in FIG. 18. Plasma exposures varied ~100-fold between antibodies and ranged from 1 µg/ml to 100 µg/ml. The low exposure of some antibodies (e.g. 21A3 and Antibody 1) was likely due to ADAs. Plasma concentrations of the Antibody 3 control antibody were similar to levels observed in the first treatment study. Antibody levels in brain tissue extracts are shown in FIG. 19. Brain exposures varied ~10-fold between antibodies and ranged from ~25 ng/ml to 250 ng/ml. Similar antibody levels were observed in brain hemispheres ipsilateral and contra-lateral to the injection site. ADAs were measured in plasma samples (Tables 13 and 14). ADAs were observed in some animals for Antibody 3 (n=3), Antibody 1 (n=6), 7A10 (n=1), 21A3 (n=7), 15A5 (n=1), 36A3 (n=1), and 44B11 (n=1). ADAs were not observed with antibody 11H11-1. Lower plasma antibody levels were associated with ADAs for Antibody 1- and 21A3-treated (FIG. 20). In contrast, plasma antibody levels were not adversely affected by the presence of ADAs for Antibody 3, 7A10, 15A5 and 44B11.

TABLE 13

Anti-drug antibody activity in plasma samples[a]

| 7A10 ID#[b] | OD[c] | 15A5 ID# | OD | 21A3 ID# | OD | 36A3 ID# | OD | 44B11 ID# | OD |
|---|---|---|---|---|---|---|---|---|---|
| wk4-44 | 0.230 | wk4-57 | 0.497 | wk4-71 | 0.663 | wk2-88 | 0.429 | wk2-102 | 0.487 |
| | | | | wk4-72 | 0.827 | | | wk3-102 | 0.764 |
| | | | | wk4-73 | 4.000 | | | wk4-102 | 1.410 |
| | | | | wk4-77 | 0.574 | | | | |
| | | | | wk3-78 | 0.743 | | | | |
| | | | | wk4-78 | 3.667 | | | | |
| | | | | wk2-79 | 0.207 | | | | |
| | | | | wk3-79 | 3.010 | | | | |
| | | | | wk4-79 | 4.000 | | | | |
| | | | | wk3-80 | 0.220 | | | | |
| Cutoff[d] | 0.186 | | 0.255 | | 0.187 | | 0.241 | | 0.257 |

[a]Only samples with significant ADA activity are shown. ADAs were not observed for 11H11-1
[b]ID# indicates week of sample collection (wk1, wk2, wk3 or wk4) and animal ID#
[c]Optical density measurement of colorimetric substrate at 450 nm.
[d]Cutoff based on 2X the average OD of the vehicle control samples. OD values above the cutoff limit are considered significant. Cutoffs calculated for each assay plate are shown.

TABLE 14

Anti-drug antibody activity for Antibody 1 and Antibody 3 control antibodies[a]

| Antibody 3 ID#[b] | OD[c] | Antibody 1 ID# | OD |
|---|---|---|---|
| wk1-105 | 2.099 | wk1-22 | 0.234 |
| wk2-105 | 0.435 | wk4-22 | 0.522 |
| wk3-105 | 2.051 | wk1-24 | 0.298 |
| wk4-105 | 2.854 | wk4-24 | 2.712 |
| wk4-106 | 0.524 | wk1-25 | 0.382 |
| wk4-108 | 0.277 | wk4-25 | 3.658 |
| | | wk4-26 | 3.410 |
| | | wk2-31 | 0.371 |
| | | wk3-31 | 2.715 |
| | | wk4-31 | 3.553 |
| | | wk3-32 | 0.372 |
| | | wk4-32 | 2.298 |
| Cutoff[d] | 0.196 | | 0.216 |

Figure 21:
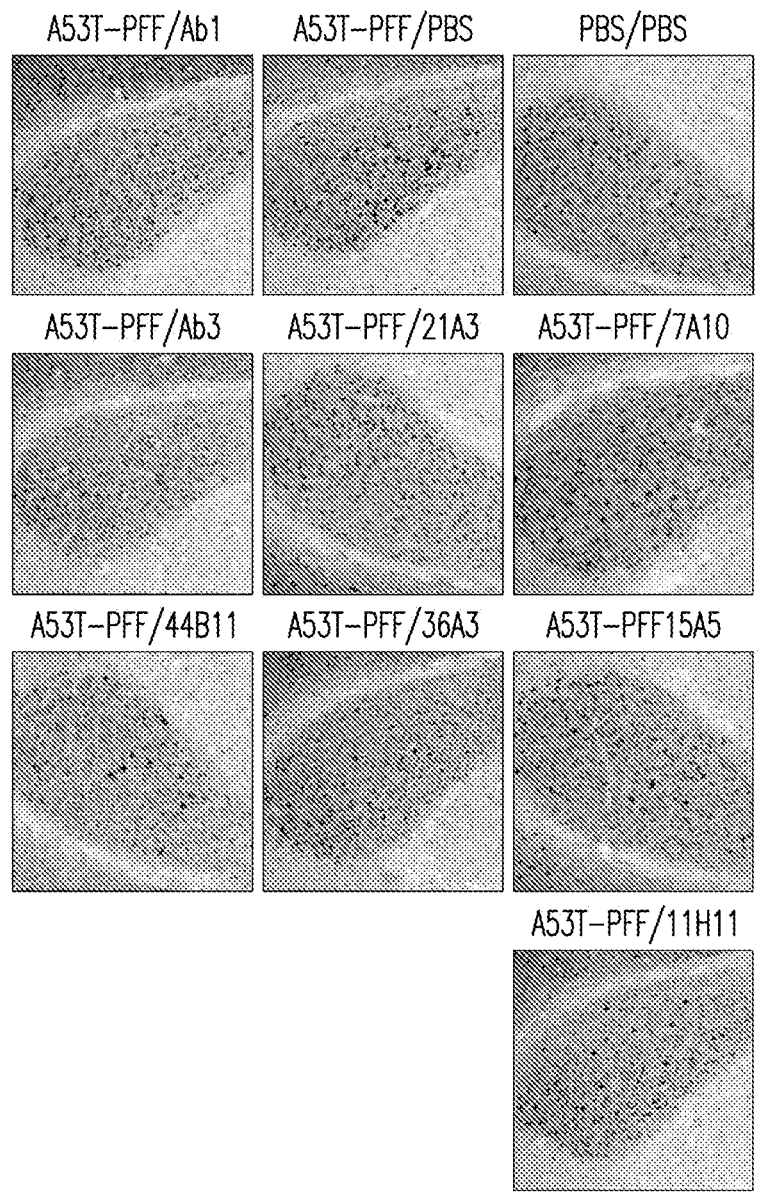
FIG. 21 shows representative immunohistochemical images demonstrating induction of pS129 αSyn pathology in ipsilateral amygdala of mice. Mice were inoculated with PBS or A53T-PFF and then dosed weekly for 4 weeks with PBS or the following antibodies at 10 mg/kg: Antibody 1, 7A10, 21A3, Antibody 3, 15A5, 36A3, 44B11 and 11H11-1. Brain sections were stained for pS129 αSyn. Arrows highlight examples of pS129 αSyn aggregates detected in the A53T-PFF control section. Images were acquired using a 10× objective.
Figure 22A:
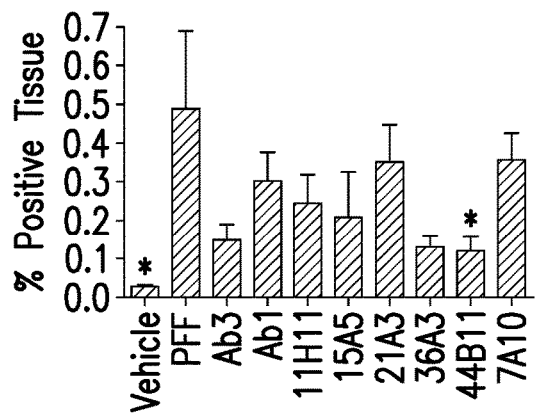
FIGS. 22A-22D are graphs showing the number of cells positive for pS129 staining in motor cortex (FIGS. 22A and 22B) and amygdala (FIGS. 22C and 22D) ipsilateral to the striatal A53T-PFF injection site. Group averages and statistical significance (FIGS. 22A and 22C) and individual animal data (FIGS. 22B and 22D) are shown. Statistical analysis based on 1-way ANOVA with Dunnett's post-test using PFF group as control (*p<0.05, p<0.01, *p<0.001).
Figure 22B:
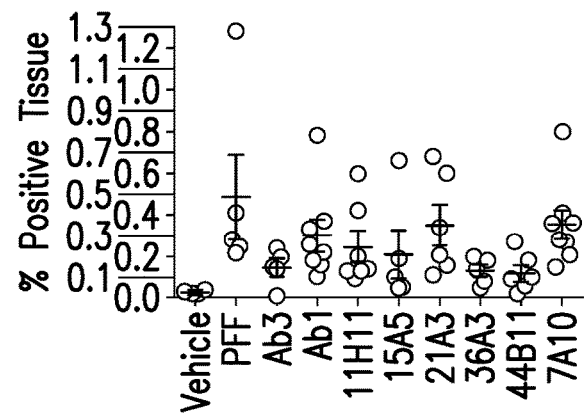
Figure 22C:
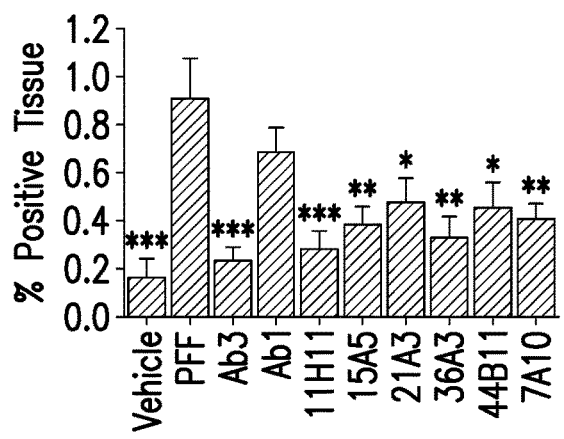
Figure 22D:
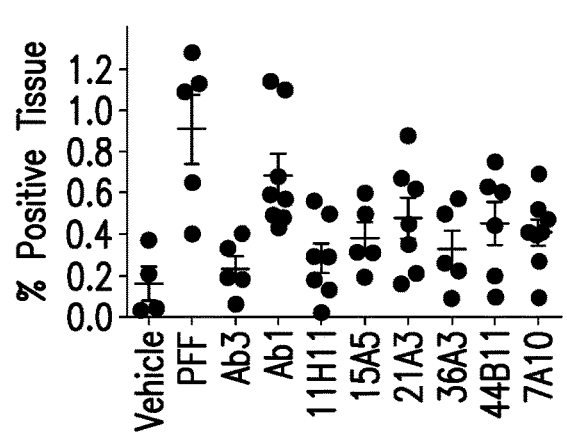
Figure 23A:
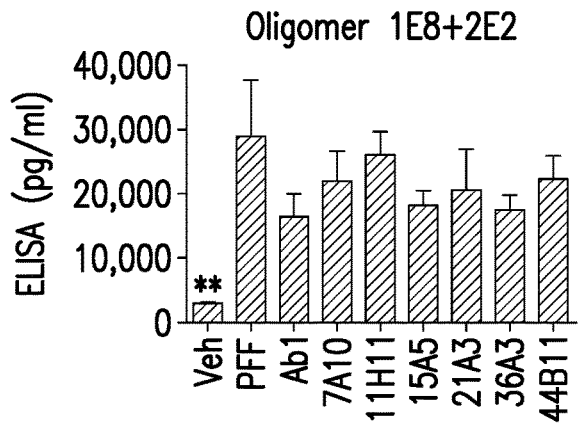
FIGS. 23A-23D are graphs showing αSyn oligomer levels measured in brain tissue using two independent ELISA assays. Soluble extracts from brain hemispheres contra-lateral and ipsi-lateral to the site of injection were analyzed. Group averages and statistical significance (FIGS. 23A and 23C) and individual animal data (FIGS. 23B and 23D) are shown. Statistical analysis based on 1-way ANOVA with Dunnett's post-test using PFF group as control p<0.01, *p<0.001).
Figure 23B:
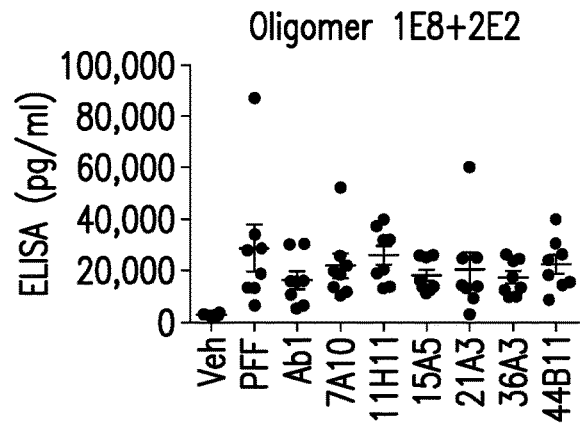
Figure 23C:
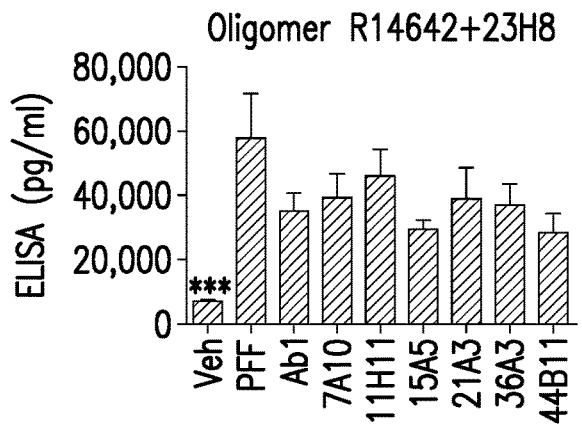
Figure 23D:
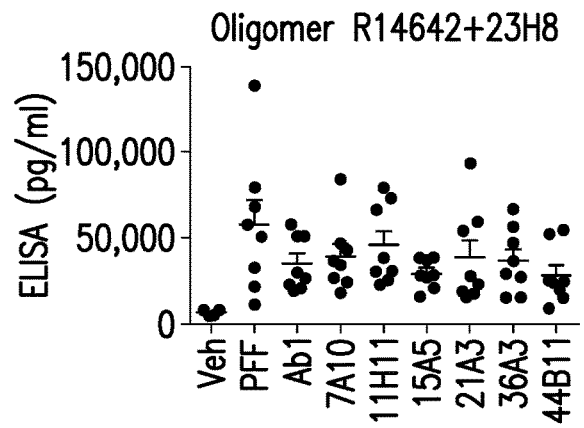
Figure 24A:
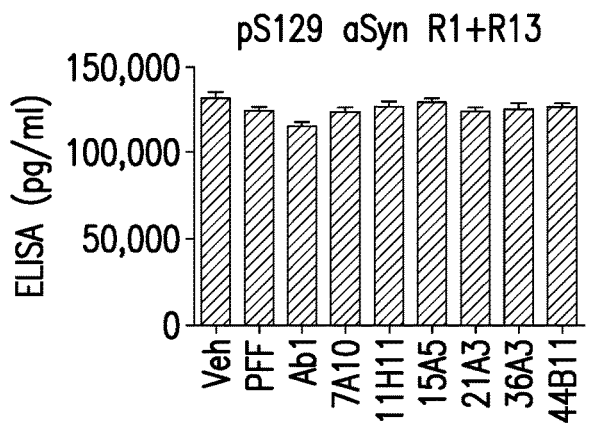
FIGS. 24A-24D is a series of graphs showing levels of pS129 aSyn (FIGS. 24A and 24B) and total aSyn (FIGS. 24C and 24D) were measured in brain tissue using ELISAs. Soluble extracts from brain hemispheres contra-lateral and ipsi-lateral to the site of injection were analyzed. Group averages (FIGS. 24A and 24C) and individual animal data (FIGS. 24B and 24D) are shown. There were no statistically significant differences between groups (statistical analysis based on 1-way ANOVA with Dunnett's post-test using PFF group as control).
Figure 24B:
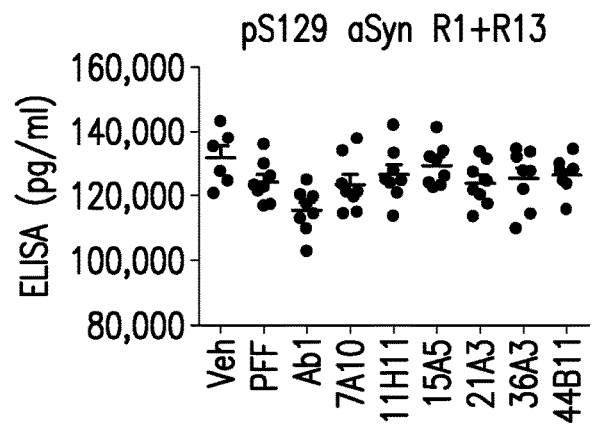
Figure 24C:
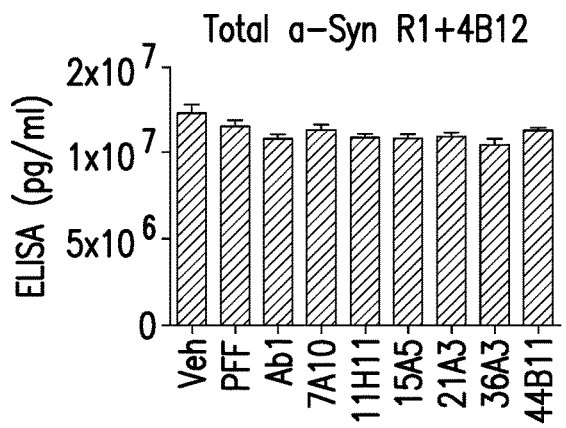
Figure 24D:
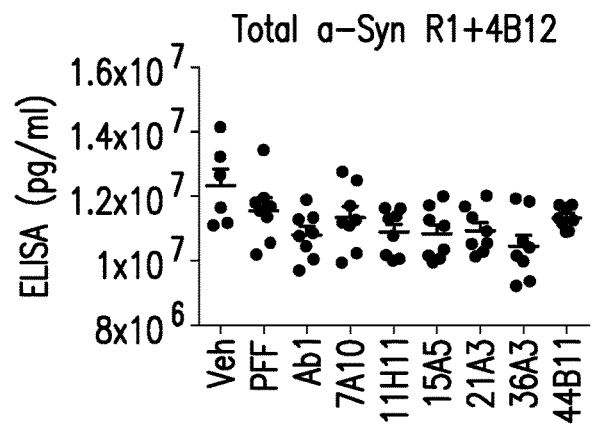

[a]Only samples with significant ADA activity are shown.
[b]ID# indicates week of sample collection (wk1, wk2, wk3 or wk4) and animal ID#
[c]Optical density measurement of colorimetric substrate at 450 nm.
[d]Cutoff based on 2X the average OD of the vehicle control samples. OD values above the cutoff limit are considered significant. Cutoffs calculated for each assay plate are shown In order to evaluate the effect of passive immunization on transmission and spreading of pathology, aSyn pS129 was measured in motor cortex and amygdala by immunohistochemistry. Representative images are shown in FIG. 21, and graphical summaries in FIG. 22. PAC mice injected with A53T-PFFs exhibited a significant increase in pS129 pathology in both motor cortex (1-way ANOVA, p<0.05) and amygdala (1-way ANOVA, p<0.001) compared to PBS controls (FIG. 22). Passive immunization with the control antibody Antibody 3 resulted in a significant reduction of pathology in the ipsi-lateral amygdala (1-way ANOVA, p<0.001) and a trend for reduced pathology in the ipsi-lateral motor cortex. In addition to Antibody 3, other antibodies with significant reductions of pathology in the amygdala were 7A10 (p<0.01), 11H11-1 (p<0.001), 15A5 (p<0.01), 21A3 (p<0.05), 36A3 (p<0.01), and 44B11 (p<0.05). Only Antibody 1 did not exhibit a significant reduction of pathology in the amydala. In the motor cortex, only ^^B11 exhibited a significant reduction iii pathology (p<0.05) while the other antibodies showed a trend for reduction. The lack of significant effects in the motor cortex are likely due to the variable PFF-mediated induction observed.

Next, the effect of passive immunization on the soluble levels of αSyn in brain extracts was determined. Brain extracts were measured for aSyn oligomers, pS129 αSyn, and total αSyn levels by ELISA and are shown in FIGS. 23 and 24. Significant increases in αSyn oligomers were observed in animals inoculated with A53T-PFF compared to PBS (Veh) controls; similar results were obtained with two independent αSyn oligomer ELISAs (1E8+2E2 and MJFR14642+23H8, both of which are described in Example 12) (FIG. 23). A trend for reduced oligomer levels compared to the A53T-PFF group was observed for all of the antibody treated animals. In contrast to the oligomer results, pS129 αSyn and total αSyn levels were not affected by inoculation with A53T-PFF or passive immunization (FIG. 24). The changes in pS129 signal observed by IHC are not likely to be detected with the pS129 ELISA due to the relatively high level of background pS129 present in the extracts.

In a second study of 90 days duration using the methods described in Example 11, 7A10-Vh-T93A-IgG1.3f was administered via intraperitoneal injection at doses of 3, 10, and 30 mg/kg weekly. For clarity, the antibody tested in Example 11 was 7A10 hIgG1.3f. In the second study, using 7A10-Vh-T93A-IgG1.3f, the presence of anti-drug antibodies were detected in 44% of the treated animals. The results of this study were highly variable and no significant effect on pathology was observed.

In summary, anti-αSyn antibodies 7A10, 11H11-1, 15A5, 21A3, 36A3 and 44B11 are effective for blocking the transmission of αSyn pathology in vivo.

Example 12: Evaluation of αSyn Oligomer Levels in Brain Extracts and CSF Using Oligomer-Specific ELISAs The Example describes the development of oligomer-specific ELISAs to measure αSyn oligomer levels in human brain lysates and CSF.

Methods a. Epitope Mapping

αSyn peptides for epitope mapping studies were purchased from InnoPep (San Diego, Calif.). Two sets of overlapping peptides of human αSyn sequence were generated with an N-terminal biotin group and a PEG4 linker and a C-terminal. Peptides were solubilized in PBS at 1 mg/ml. For mapping studies, 100 µL of 0.25 µg/ml α-synuclein peptides in PBS were added to a NeutrAvidin coated high capacity 96 well plate (Thermo Fisher Scientific) and incubated at room temperature (RT) for 2 h (or 4° C. for overnight (O/N)). Plates were washed 3-times with ~300 µL of wash buffer (0.05% Tween in PBS). Plates were then blocked with 150 µl of 3% BSA in PBS at RT for ~2 h (or 4° C. for O/N). 100 µL of test samples diluted in sample buffer (0.1% BSA/0.05% Tween/PBS, 2 pellets of Roche protease inhibitor-in 50 ml buffer) were incubated on the plates at RT for 2 h. Plates were then washed 3 times. 100 µL of secondary antibody diluted 1:1000 in PBSTB (1% BSA/0.2% Tween/dPBS) was added and incubated at RT for 1 hr. Plates were washed 3 times for 5~10 min per wash. 100ꞏ of AP substrate (Tropix CDP Star Ready-to-Use with Sapphire II, Applied Biosystems; Cat # T-2214) was added and developed at RT for 30 min. Luminescence counts were read with a Perkin Elmer EnVision (2102 Multilabel Reader). The plates were kept under constant shaking (Titer plate shaker, speed 3) during the assay. The secondary antibodies used included Alkaline phosphatase-affinipure donkey anti-human IgG, (JacksonImmuno #709-055-149), Alkaline phosphatase-affinipure donkey anti-rabbit IgG, (JacksonImmuno #711-055-152), Alkaline phosphatase-affinipure donkey anti-mouse IgG, (JacksonImmuno #715-055-151). All secondary antibodies were diluted to 50% glycerol final concentration.

b. Preparation of PFFs and Analysis of Fibrilization

PFFs were prepared and analyzed using the method described in Example 3.

c. αSyn Binding Assay

Antibodies were tested for binding to human αSyn monomer, human βSyn monomer, human γSyn monomer, PFF generated from human αSyn, PFF generated from human A53T αSyn, and αSyn peptides a.a. 111-140 containing human, rat and mouse sequences. αSyn peptides a.a. 111-140 containing human, rat and mouse sequences were purchased from InnoPep (San Diego, Calif.). Human αSyn monomer, human βSyn monomer, and human γSyn monomer were purchased from rPeptide (Bogart, Ga.).

For the binding assay, 96 well plates (Costa #3925, high bind microplate) were coated with 100 µL of 1 µg/ml αSyn WT PFF in PBS at RT for 2 h (or 4° C. for O/N). Plates were washed 3-times with ~300 µL of wash buffer (0.05% Tween in dPBS). Plates were blocked with 150 µl of 3% BSA/PBS at RT for 2h (or 4° C. for O/N). 3-fold serial dilutions of PFF (starting from 2 µg/ml) and α-syn WT monomer (starting from 20 µg/ml) were prepared in sample buffer (0.1% BSA/0.05% Tween/PBS, 2 pellets of Roche complete protease inhibitor-in 50 ml buffer). For antibody incubations, equal volumes of 2-fold assay concentration of αSyn PFF or monomer were mixed with 2-fold assay concentration of antibodies in BD falcon low binding plates and incubated at RT for ~2 h. 100 µL of mixtures of antibody and PFF or monomer were added to PFF coated plates and incubated at RT for 10 min. Plates were washed 3-times. 100 µL of donkey anti-human IgG (JacksoImmuno #709-055-149, with 50% glycerol) diluted 1:1000 in PBSTB (1% BSA/0.2% Tween/dPBS) was added and plates incubated at RT for 1 hr. Plates were washed 3-times for 5~10 min per wash. 100 µL of AP substrate (Tropix CDP Star Ready-to-Use with Sapphire II, Applied Biosystems) was added and plates developed at RT for 30 min. Luminescence counts were measured using a Perkin Elmer EnVision (2102 Multilabel Reader). PFF was sonicated with 15-times 1 sec pulses before coating or mixing with antibodies. Plates were kept under constant shaking (Titer plate shaker, speed 3) during the assay.

d. ELISA

ELISA plates (Costar) were coated with 100 µl of respective capture antibodies diluted in BupH carbonate-bicarbonate buffer, pH 9.4 (Thermo Fisher Scientific) overnight at 4° C. Capture antibody MJFR1 (Abcam) was used at a concentration of 0.1 µg/ml (total α-synuclein assay) or 0.35 µg/ml (pS129 assay), MJFR14642 (Abcam) at 0.1 µg/ml and 1E8 at 0.3m/ml. The plates were washed 4-times with Dulbecco's PBS (Thermo Fisher Scientific) and blocked with 3% BSA (bovine serum albumin, protease free, Fraction V) in PBS for 2~3h at RT or overnight at 4° C. Standards, brain samples and QC samples were diluted with 1% BSA/0.05% Tween/PBS containing Roche complete protease inhibitor (1 pellet/25 ml) and Phosphatase Inhibitor 2&3 (Sigma Aldrich, 1:100). Standards are α-synuclein WT (rPeptide), pS129 (aa89-140, AATGFVKKDQLGK-NEEGAPQEGILEDMPVDPDNEAYEMP-pS-EE-GYQDYEPEAHHHHHH-CONH2; SEQ ID NO: 129) or PFF. Sonication of PFF and monomer was performed using a KONTES Micro Ultrasonic Cell Disrupter (output 40, Tune. 50). Samples were sonicated 15-times 1 sec/pulse. Samples 50 µL/well were loaded in duplicate and incubated for O/N at 4° C. After plates were equilibrated to RT, 50 µl detection antibodies 1:4000 diluted in 1% BSA/0.1% Tween/DPBS were added and co-incubated with samples at RT for ~2 hours. Detection antibodies (4B12 from Covance, MBJR13 from Abcam, 2E2, and 23H8) were pre-conjugated with alkaline phosphatase (AP kit from Novus Biologicals). Plates were then washed 4-times with 0.05% Tween/PBS and developed with 100 µL of alkaline phosphatase substrate (Tropix CDP Star Ready-to-Use with Sapphire II, T-2214, Thermo Fisher Scientific) for 30 minutes. Luminescence counts were measured with Perkin Elmer EnVision (2102 Multilabel Reader). The plates were kept constant shaking (Titer plate shaker, speed 3) during the assay. Data was analyzed using GraphPad Prism.

e. Preparation of Human Brain Lysates

Brain samples were sonicated in filtered PBS (Gibco, #70011, 1 ml PBS/100 mg tissue wet weight) with KONTES Micro Ultrasonic Cell Disrupter (output 40, Tune 50) for 2×10 sec/pulse. Samples were placed in 2 ml Eppendorf tubes and the tubes were kept on wet ice during sonication. Brain lysates were spun at 3,000 g, 4° C. for 5 min. Supernatant aliquots were frozen in liquid nitrogen and stored at −80° C. QC assays including αSyn ELISAs (total & pS129) and BCA were performed.

To isolate high-speed-spin pellets, brain homogenates previously prepared at 100 mg/ml in 1×PBS were diluted 3-fold to 33.3 mg/ml in ice cold 1×PBS followed by centrifugation at 100,000×g for 30 minutes at 4° C. The supernatant was removed and discarded. The pellet was re-suspended in ice cold 1×PBS in the same volume as the starting sample.

f. Immunoprecipitation of Brain Extracts

Pooled human brain extracts were prepared by combining the following samples in equal proportions: PD (PD1, PD3 and PD5), MSA (12-18, 01-03 and 14-49), and DLB (13-37, 05-31 and 08-26). Pooled samples were diluted 100-fold with PBSTB buffer (1% BSA+0.05% Tween+PBS). For immunoprecipitation, brain extracts were incubated with antibody at 4° C. for 2 hours with end over end rotation. Protein A/G agarose beads (Thermo Fisher Scientific) were then added and samples incubated overnight at 4° C. To prepare Protein A/G beads, 1.2 ml bead slurry was centrifuged at 1000×g for 2 minutes at 4° C. Storage buffer was removed and the beads washed 1-time with 0.6 ml PBS containing 0.05% tween-20, centrifuged as above and beads washed 3-times with 0.6 ml PBS. After the final spin, beads were blocked by addition of 0.6 ml 1% BSA in PBS and incubated at 4° C. with end over end incubation for 2 hours. After blocking, beads were isolated by centrifugation and re-suspended in 0.6 ml PBS to a final volume of 1.2 ml. Bead slurry was added to each brain extract at a 1:10 (vol:vol) dilution. Following overnight immunoprecipitation, samples were centrifuged to remove the beads and the depleted brain samples isolated and evaluated by ELISA. The following antibodies were used for immunoprecipitation: 26D6 (mouse IgG control antibody specific for human Abeta (a.a. 1-12), MJFR-14642 (Abcam), LB509 (Covance), Clone 42 (BD), 7A10, and 1E8.

g. Primary Cell Culture Isolation

Primary rat hippocampal neurons were prepared as described in Example 10.

h. Immunofluorescence Assay

Immunofluorescence was performed as described in Example 10.

i. High Content Immunofluorescent Assay

The high content immunofluorescent assay was performed as described in Example 10.

j. SDS-PAGE/Immunoblot Analysis

Brain homogenates from MSA and PD brain tissue were generated as described above. 200 µl of each brain homogenate was brought to a total volume of 400 µl by addition of PBS (Thermo Fisher Scientific). Diluted samples were centrifuged at 100,000×g for 30 minutes at 4° C. to isolate high molecular weight aggregates. Pellets were re-suspended in 200 µl PBS. 50 µl of 4× NuPAGE loading dye (Thermo Fisher Scientific) and 20 µl of NuPAGE 10× reducing agent (Thermo Fisher Scientific) were added to 130 µl of pellet homogenate. Samples were denatured by incubation at 95° C. for 5 min and then 10 µl of sample fractionated on 4-12% NuPAGE Bis-Tris gels with 1×MES running buffer (Thermo Fisher Scientific). Gels were run at 200 V for 50 minutes followed by transfer to 0.4 µm nitrocellulose (Thermo Fisher Scientific) at 30 V for 1 hour. Blots were then blocked in 5% milk in TBST (TBS with 0.1% Tween-20 (Promcga)). Blots were then probed overnight at 4° C. with shaking with the following antibodies diluted 1:5000 in 1% BSA (BioRad) in TBST: 4B12 (BioLegend), 4D6 (BioLegend), Syn-303 (BioLegend), 81A (BioLegend), EP1536Y (Abcam), LB509 (BioLegend), mouse IgG (Thermo Fisher Scientific), anti-actin (Sigma). All antibodies were conjugated to HRP using BioRad EZ-link conjugation kit. Following overnight incubation, blots were washed with TBST. HRP-labeled antibodies were detected using Supersignal West Femto Maximum (Thermo Fisher Scientific) detection reagent and images captured using the GE A1600 CCD camera.

k. SEC-HPLC Analysis

100 µl of MSA brain homogenate 11-46 and control brain homogenate 11-49, was added to 400 µl of PBS and samples centrifuged at 100,000×g for 30 minutes at 4° C. Supernatants (sup) were saved and remaining pellets resuspended in 120 µl PBS. For size exclusion chromatography, 100 µl of either sup or pellet was injected onto a BioSec-5 300 Å SEC column (7.8 mm diameter×300 mm, Agilent) on an Agilent 1100 HPLC. 1 ml fractions were collected across the 20 ml run time. The mobile phase used was PBS. The column was run at 1 ml/minute and 37° C. column temp. To concentrate the SEC fractions, samples were subjected to solid phase extraction (SPE) using Waters Oasis SPE HLB cartridge. 1 ml of each SEC fraction was diluted with 1000 µl 4% phosphoric acid. SPE columns were conditioned with 1 ml methanol and then equilibrated with 1 ml H2O. Acidified samples were then added. Loaded columns were washed with 1 ml 5% methanol and sample eluted with 1 ml 100% methanol. Eluates were dried overnight in a speed vac. The SPE purified SEC-HPLC fractions were stored at −20° C. dried until SDS-PAGE/immunoblot analysis.

Results a. Characterization of Antibodies

A summary of the antibodies used in this study is provided in Table 15.

TABLE 15

Antibody summary

| Antibody | Isotype | Source | Immunogen | Epitope (aa) |
|---|---|---|---|---|
| 1E8 | Human IgG1 | | PFF | 123-128[a] |
| 2E2 | Human IgG1 | | PFF | 119-126[a] |
| 23H8 | Human IgG1 | | PFF | 130-138[a] |
| MJFR14642 | Rabbit IgG | abcam | filament | 130-140[a] |
| MJFR1 | Rabbit IgG | abcam | full-length peptide | 118-123[b] |
| 4D6 | Mouse IgG1 | Biolegend | full-length peptide | 124-128[a] |
| 4B12 | Mouse IgG1 | Biolegend | full-length peptide | 103-108[b] |
| Syn303 | Mouse IgG1 | Biolegend | Oxidized full-length | 1-5[c] |
| LB509 | Mouse IgG1 | Biolegend | Lewy bodies | 115-121[d] |
| MJFR13 | Rabbit IgG | abcam | pS129 peptide | pS129[b] |
| EP1536Y | Rabbit IgG | abcam | pS129 peptide | pS129[b] |
| 81A | Mouse IgG2a | Biolegend | pS129 peptide | pS129[e] |

[a]Epitope mapped in a similar manner as described in Example 2; see FIG. 1.
[b]Epitope provided by vendor
[c]J Duda, et al., Ann Neurol 2002; H Tran, et al., Cell Reports, 2014
[d]M Baba, et al., Am J Path 1998; R Jakes, et al., Neurosci Letts 1999
[e]Waxman and B Giasson, J Neuropath Exp Neurol 2008

Figure 25:
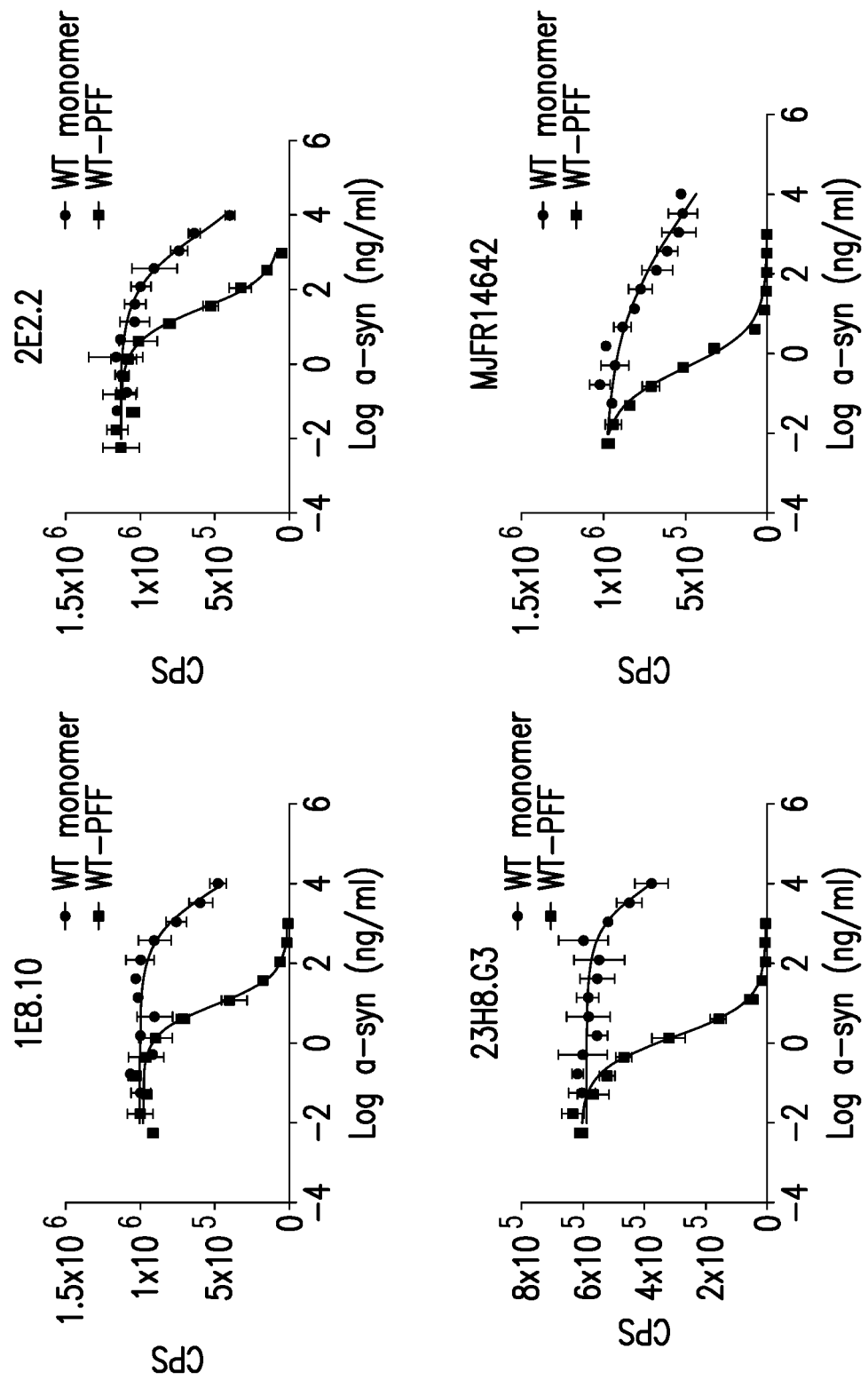
FIG. 25 is a series of graphs showing the binding of the indicated antibodies to a titration of αSyn monomer or αSyn PFF. Unbound antibodies were captured on PFF-coated plates and measured by 1-sided ELISA. Data represents mean±sd for duplicate determinations.
Figure 26:
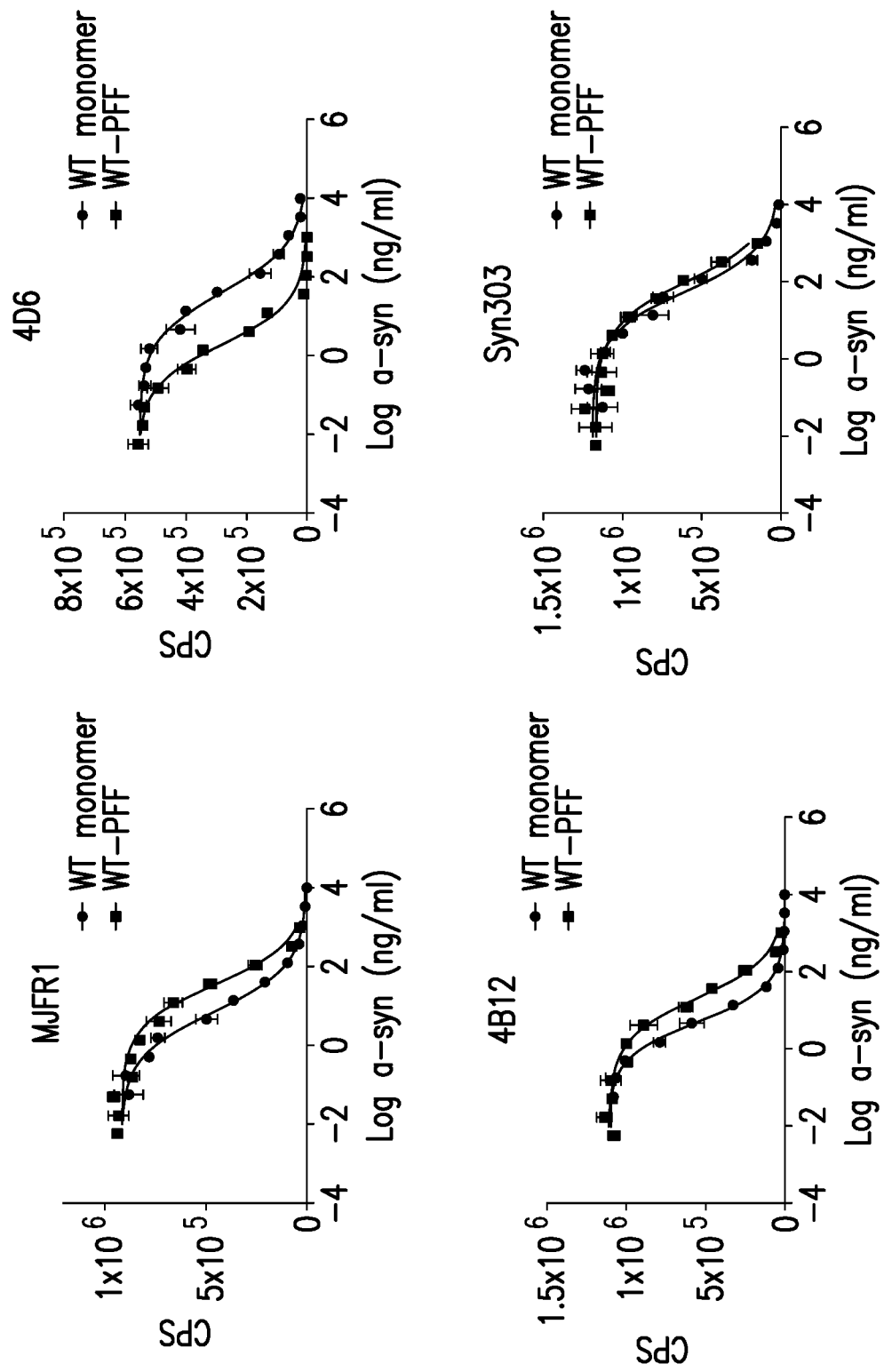
FIG. 26 is a series of graphs showing the binding of the indicated antibodies to a titration of αSyn monomer or αSyn PFF. Unbound antibodies were captured on PFF-coated plates and measured by 1-sided ELISA. Data represents mean±sd for duplicate determinations.

The antibodies described above were evaluated for binding potency to αSyn monomers and αSyn PFF. Antibodies were incubated in solution with increasing concentrations of either αSyn monomers or PFF. Unbound antibody was captured on plates coated with PFF and antibody levels measured by 1-sided ELISA. As shown in FIG. 25, antibodies 1E8, 2E2, 23H8, and MJFR14642 exhibited more potent binding to PFF compared to monomer, with monomer-PFF binding potency ratios of 902, 236, 3258 and 7234, respectively (Table 16). In contrast, antibodies MJFR1, 4B12, and Syn303 were more potent for binding to monomer compared to PFF (FIG. 26), with monomer-PFF binding potency ratios of 0.27, 0.24 and 0.47, respectively (Table 16). Antibodies 4D6 and LB509 were modestly PFF-selective with monomer-PFF binding potency ratios of 26 and 34, respectively. Taken together these results indicate that antibodies 1E8, 2E2, 23H8, and MJFR14642 are highly PFF/oligomer-selective.

TABLE 16

Antibody binding summary

| Antibody | monomer (ng/ml) | SD | n | PFF (ng/ml) | SD | n | Mono/PFF Ratio |
|---|---|---|---|---|---|---|---|
| 1E8 | 6464 | 872 | 4 | 7.2 | 2.0 | 4 | 903 |
| 2E2 | 6226 | 6690 | 4 | 26.4 | 6.5 | 4 | 236 |
| 23H8 | 5808 | 10834 | 4 | 1.8 | 0.3 | 4 | 3258 |
| MJFR 14642 | 3658 | 1981 | 5 | 0.51 | 0.10 | 5 | 7234 |

TABLE 16-continued

Antibody binding summary

| Antibody | monomer (ng/ml) | SD | n | PFF (ng/ml) | SD | n | Mono/PFF Ratio |
|---|---|---|---|---|---|---|---|
| MJFR1 | 8.0 | 1.28 | 2 | 29.2 | 7.0 | 2 | 0.27 |
| 4D6 | 54.2 | 17.6 | 2 | 2.1 | 0.2 | 2 | 26 |
| 4B12 | 5.6 | 1.15 | 2 | 23.3 | 3.2 | 2 | 0.24 |
| Syn303 | 51.2 | 9.1 | 2 | 109.3 | 6.6 | 2 | 0.47 |
| LB509 | 62 | 24 | 2 | 1.6 | 0.1 | 2 | 38 | b. Development of Oligomer-Specific ELISAs

Based on the monomer and PFF binding data described above, various antibody pair combinations were developed and evaluated in sandwich ELISAs for detection of aSyn monomers and aSyn PFF/oligomers; a summary of the optimal ELISA pairs identified and specificities of those assays are shown in Table 17.

TABLE 17

ELISA summary

| Capture Antibody | Epitope (aa) | Detection Antibody[a] | Epitope (aa) | Monomer LLQ (pg/ml)[b] | PFF LLQ (pg/ml)[b] |
|---|---|---|---|---|---|
| 1E8.10 | 123-128 | 2E2.2 | 119-126 | >10,000 | 33 |
| MJFR14642 | 130-140 | 23H8.G3 | 130-138 | >10,000 | 34 |
| MJFR1 | 118-123 | Syn303 | 1-5 | 23 | 45 |
| MJFR1 | 118-123 | 4B12 | 103-108 | 8 | 23 |
| MJFR1 | 118-123 | 4D6 | 124-128 | 27 | 19 |
| MJFR1 | 118-123 | MJFR13 | pS129 | >3,000 | >3,000 |

[a]Detection antibodies were conjugated with alkaline phosphatase (AP)
[b]LLQ (lowest level of quantitation) is defined by 2-times the assay background. Monomer LLQ based on results for sonicated monomer; similar results were observed with non-sonicated monomer. PFF LLQ based on results for sonicated PFF. LLQ for pS129 ELISA (MJFR1 + MJFR13) is 2 pg/ml (pS129 peptide).

Figure 27:
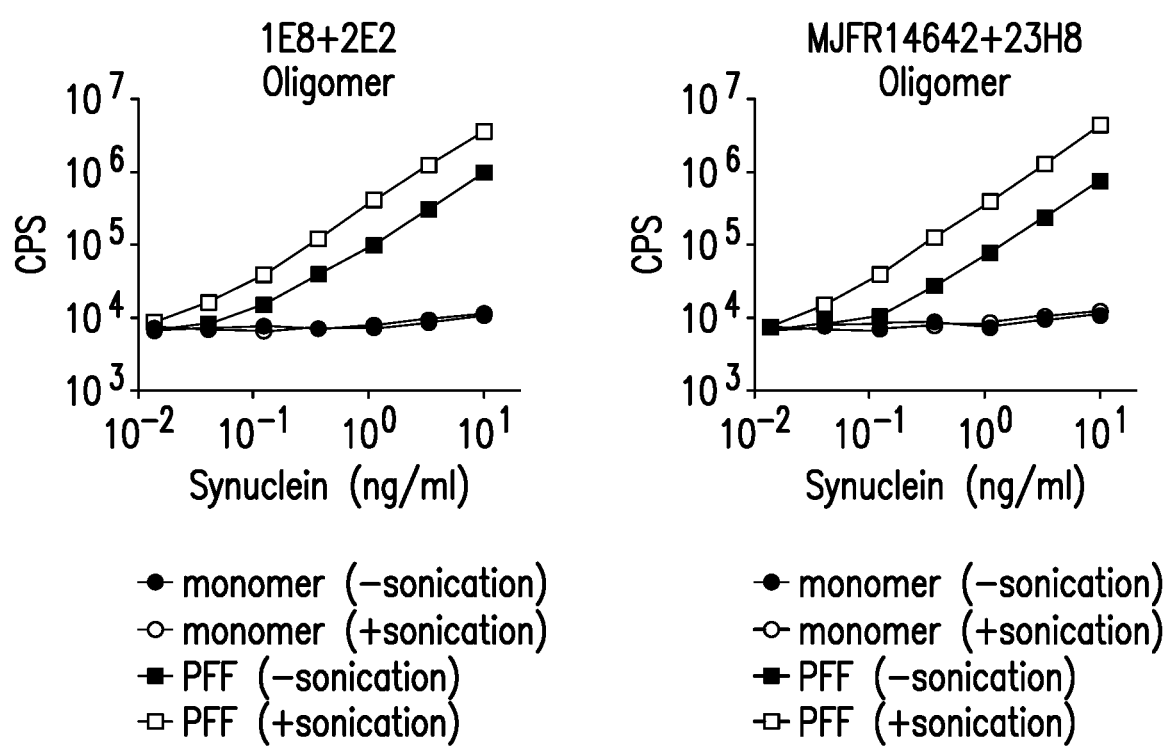
FIG. 27 is a series of graphs showing the detection of aSyn monomer and PFF by ELISAs 1E8.10+2E2.2 (1E8 capture antibody, 2E2 detection antibody) and MJFR14642+23H8.G3 (MJFR14642 capture antibody, 231-18 detection antibody). Example concentration response curves shown. Monomer and PFF samples were pretreated with sonication prior to ELISA. Monomer and PFF synuclein levels are expressed as monomer equivalent ng/ml. Data represents mean±sd from triplicate determinations. CPS=counts per sec.

ELISA pairs 1E8.10+2E2.2 and MJFR14642+23H8.G3 exhibited sensitive and specific detection of PFF/oligomers but not αSyn monomers (Table 17; FIG. 27). Sonication of PFF enhanced the overall signal in both assays suggesting that the assays are sensitive to aggregate size and that sonication may expose additional antibody binding sites. In contrast, sonication did not have any impact on the ability of the antibodies to detect monomers. Both assays exhibited similar sensitivity of approximately 30 pg/ml (monomer equivalent) for detecting sonicated PFF. Only background signal was observed with monomer concentrations of up to 10 ng/ml, the highest concentration tested. Taken together these results establish that the ELISAs employing 1E8+2E2 and MJFR14642+23H8 are PFF/oligomer-specific.

Figure 28:
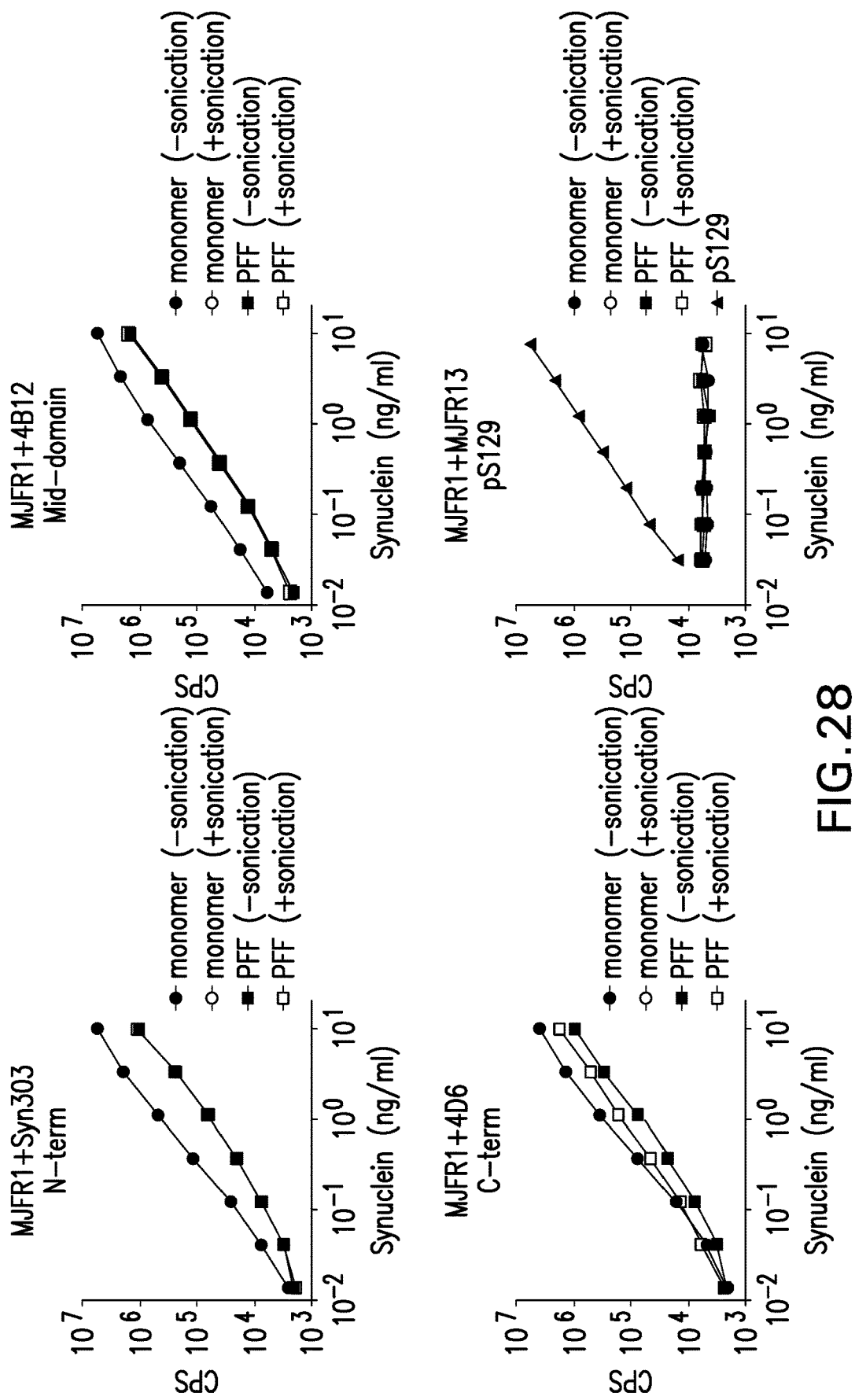
FIG. 28 is a series of graphs showing the detection of αSyn monomer and PFF by ELISA. Example concentration response curves shown. Capture antibody is the first antibody listed, the detection antibody the second listed. Monomer and PFF samples were pretreated with sonication prior to ELISA. Monomer and PFF synuclein levels are expressed as monomer equivalent ng/ml. Detection of pS129 αSyn peptide was evaluated with MJFR1+MJFR13 ELISA. Data represents mean±sd from triplicate determinations. CPS=counts per sec.

Additional ELISA pair combinations were also developed incorporating the same capture antibody (MJFR1) coupled with different detection antibodies including an antibody specific for the N-terminal domain (Syn303), the mid-domain (4B12), the C-terminal (4D6), and pS129 (MJFR13) of αSyn. ELISA pairs MJFR1+Syn303, MJFR1+4B12 and MJFR1+4D6 exhibited sensitive detection of both αSyn monomer and αSyn PFF (Table 17; FIG. 28). All three assays detected sonicated PFF with sensitives similar to the oligomer ELISAs (Table 17). Unlike the oligomer assays, detection of PFF by MJFR1+Syn303 and MJFR1+4B12 was not affected by sonication, suggesting that exposure of these epitopes is less sensitive to aggregate size. Interestingly, sonication did enhance detection of PFF by MJFR1+4D6, potentially related to the fact that 4D6 binds to a C-terminal epitope, similar to the oligomer-selective antibodies. In contrast to the oligomer-specific assays, MJFR1+Syn303, MJFR1+4B12 and MJFR1+4D6 exhibited sensitive detection of αSyn monomer with LLQs of 23, 8, and 27 pg/ml, respectively. Detection of monomer was not affected by sonication. The MJFR1+MJFR13 ELISA demonstrated sensitive and specific detection of the pS129 αSyn peptide only confirming its pS129 specificity.

Figure 29:
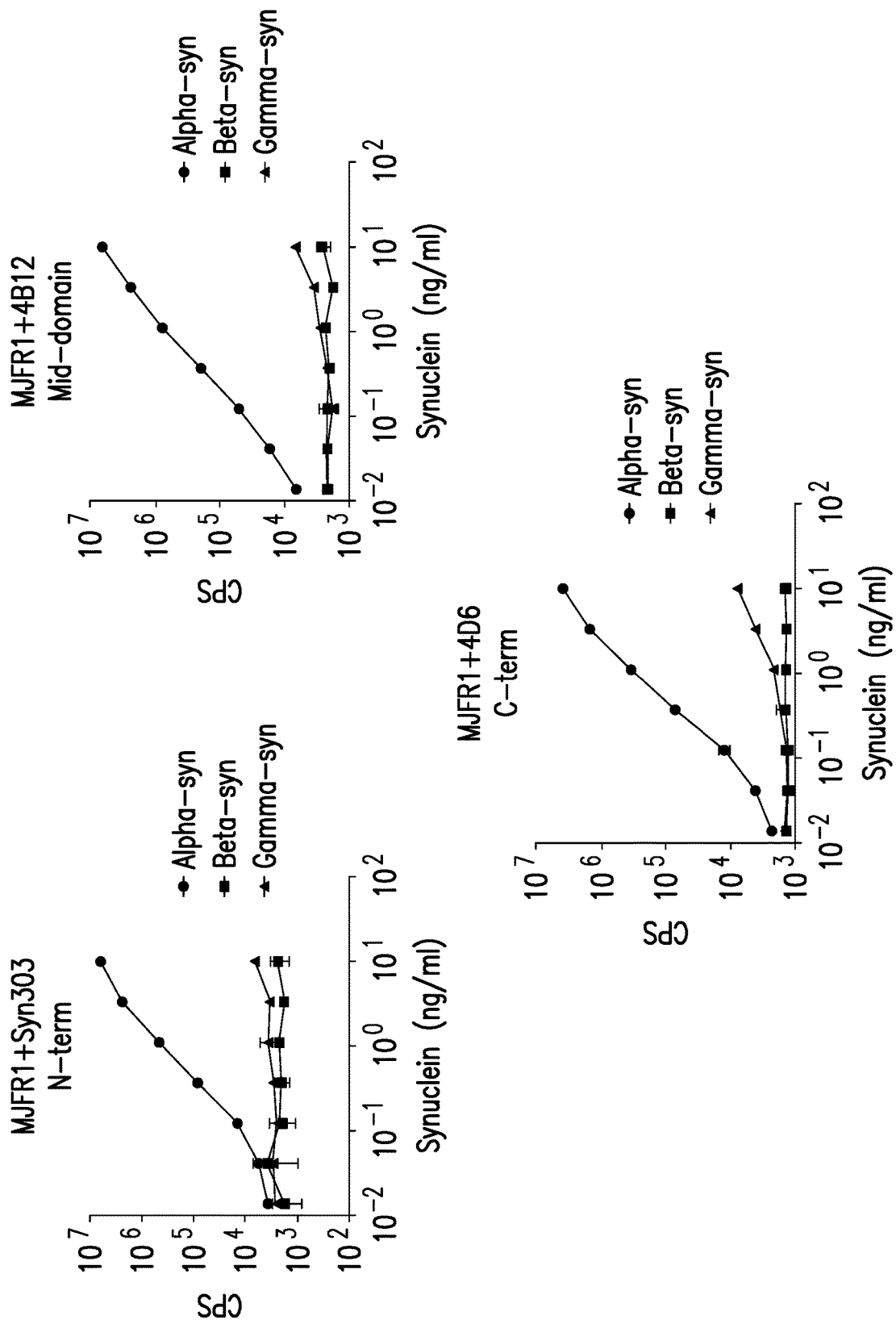
FIG. 29 is a series of graphs showing the detection of αSyn and αSyn family members β-synuclein and γ-synuclein by ELISA. Capture antibody is the first antibody listed, the detection antibody the second listed. Example concentration response curves shown. Data represents mean±sd from duplicate determinations. CPS=counts per sec.

To further evaluate specificity, MJFR1+Syn303, MJFR1+4B12, and MJFR1+4D6 were also tested for detection of the αSyn family members, β-synuclein and γ-synuclein. As shown in FIG. 29, all three assays exhibited little cross-reactivity with β-synuclein or γ-synuclein confirming their αSyn specificity. Taken together, these results indicate that MJFR1+Syn303, MJFR1+4B12 and MJFR1+4D6 are specific for αSyn and can detect both monomer and oligomer supporting their utility as "total" αSyn assays.

c. Measurement of αSyn Levels in Brain Extracts

Figure 30:
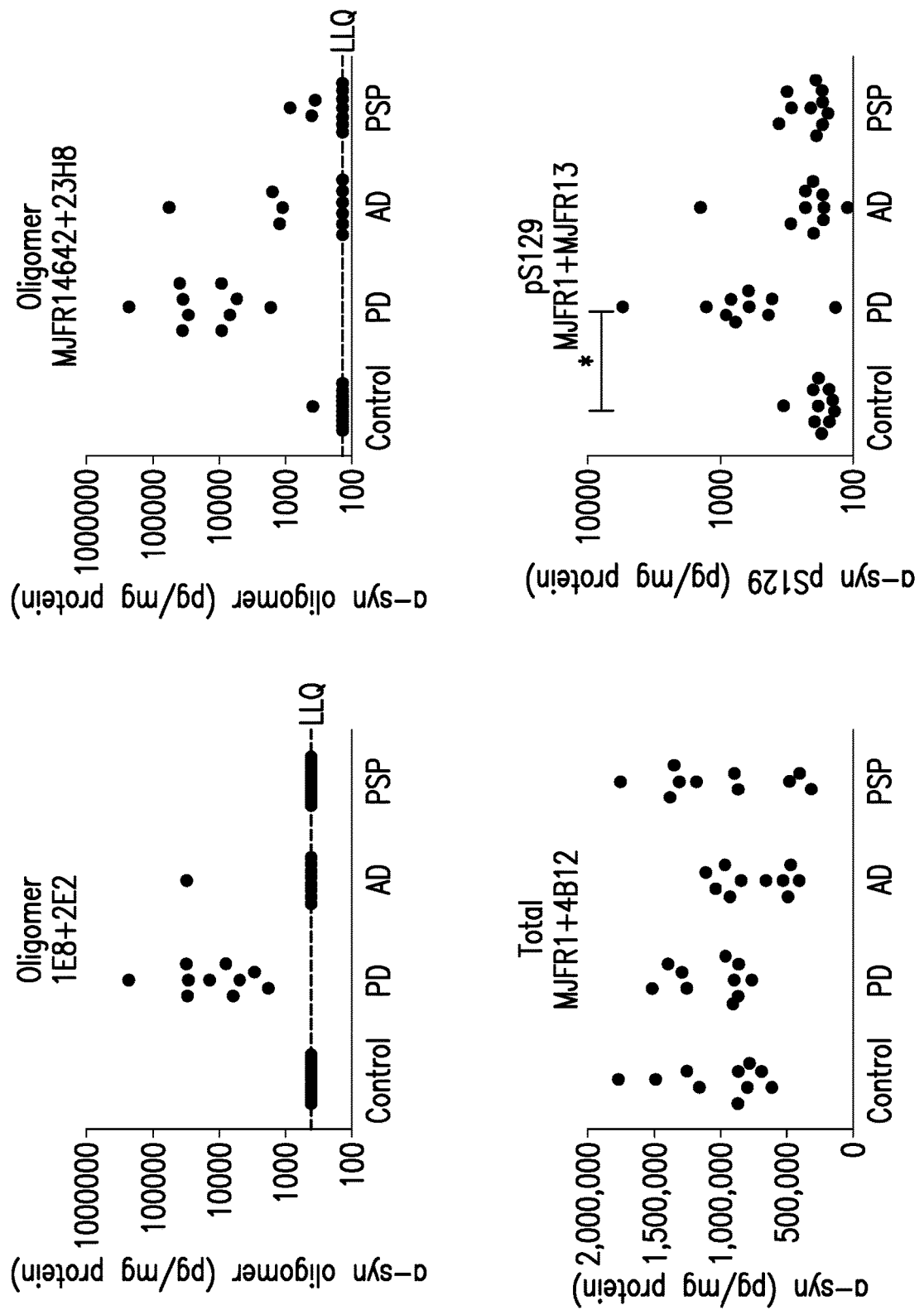
FIG. 30 is a series of graphs showing αSyn levels measured in control, PD, AD and PSP extracts using 1E8.10+2E2.2 oligomer ELISA, MJFR14642+23H8.G3 oligomer ELISA, MJFR1+4B12 total ELISA and MJFR1+MJFR13 (pS129) ELISA. Capture antibody is the first antibody listed, the detection antibody the second listed. Levels are expressed as αSyn monomer equivalent or pS129 peptide equivalent (MJFR1+MJFR13) normalized to total protein (pg/mg protein). Statistics based on 1-way ANOVA with Dunnett's multiple comparisons relative to the control group. Note that statistics were not performed on oligomer assay results since the majority of control samples were <LLQ. *p<0.05.

ELISAs were used to measure oligomer, pS129, and total αSyn levels in brain extracts generated from control and disease tissue (AD, PSP, MSA, PD, DLB). Brain extract ELISA signal specificity was confirmed by dilution-linearity and immunodepletion studies. As shown in FIG. 30, robust levels of αSyn oligomer (1E8+2E2 and MJFR14642+23H8) were detected in PD brain extracts compared to extracts from other neurodegenerative diseases (AD, PSP) and controls. Average oligomer levels in PD extracts were 36 ng/mg total protein in the 1E8+2E2 ELISA and 40 ng/mg total protein in the MJFR14642+23H8.G2 ELISA (Table 18). Oligomer levels were <LLQ for the majority of AD, PSP and control extracts. In contrast to the oligomer results, similar levels of total αSyn were observed across all of the extracts as measured using the MJFR1+4B12 assay (FIG. 30; Table 18). pS129 αSyn was detected in all extracts but levels were elevated in PD and significantly higher compared to controls (FIG. 30; Table 18).

TABLE 18

Summary of αSyn levels in control, PD, AD and PSP brain extracts

| Assay[a] | Control AVE | Control SD | PD AVE | PD SD | AD AVE | AD SD | PSP AVE | PSP SD |
|---|---|---|---|---|---|---|---|---|
| 1E8 + 2E2 oligomer | NA | | 35,990 | 69,696 | NA | | NA | |

TABLE 18-continued

Summary of αSyn levels in control, PD, AD and PSP brain extracts

| Assay[a] | Control AVE | Control SD | PD AVE | PD SD | AD AVE | AD SD | PSP AVE | PSP SD |
|---|---|---|---|---|---|---|---|---|
| MJFR14642 + 23H8 oligomer | NA | | 39,890 | 67,158 | NA | | NA | |
| MJFR1 + 4B12 total | 1,026,776 | 377,889 | 1,070,430 | 265,630 | 741,702 | 263,191 | 993,685 | 483,847 |
| MJFR1 + MJFR13 pS129 | 184 | 56 | 1,143 | 1,554 | 316 | 387 | 221 | 73 |
| Total protein (mg/ml) | 3.3 | 0.3 | 3.3 | 0.5 | 3.0 | 0.5 | 3.3 | 0.9 |

[a]Data normalized to total protein and expressed as monomer equivalent (pg/mg total protein) or pS129 peptide equivalent (pg/mg total protein). Total protein levels expressed as mg/ml To determine if αSyn oligomers are also present in brain tissue from other synucleinopathy patients, extracts were also generated from MSA and DLB and analyzed using the oligomer ELISAs. As shown in FIG. 31, similar and robust levels of oligomer were detected in all three synucleinopathy brain extracts (MSA, DLB and PD) while levels in control extracts were ≤LLQ; similar results were observed in both oligomer assays. In contrast, levels of total αSyn as measured using MJFR1+4B12 were similar across all extracts, including the controls (FIG. 31). pS129 levels were also elevated to a similar extent in the synucleinopathy extracts, and were significantly higher (MSA, DLB) or trending higher (PD) compared to controls (FIG. 31). Total αSyn levels were also measured using the ELISAs sensitive to the N-terminal region (MJFR1+Syn303) and C-terminal region (MJFR1+4D6). As shown in FIG. 32, no differences in total αSyn levels were observed. ELISA results are summarized in Table 19.

(MJFR1+MJFR13) were also highly correlated with oligomer levels. In contrast, total αSyn levels as measured in the MJFR1+4B12 assay were not significantly correlated with either oligomer levels or pS129 levels (FIG. 33, Table 20). However, total αSyn levels in the MJFR1+4B12 assay were significantly correlated with levels in the MJFR1+4D6 assay and showed a trend for correlation with levels measured in the MJFR1+Syn303 assay (FIG. 34, Table 21). These results provide additional confirmation of signal specificity in the different assays. The correlation between the oligomer-specific ELISAs and the pS129 ELISA suggests that the oligomeric species is likely to be phosphorylated.

TABLE 19

Summary of aSyn levels in control, MSA, DLB, and PD extracts

| Assay[a] | Control AVE | Control SD | MSA AVE | MSA SD | DLB AVE | DLB SD | PD AVE | PD SD |
|---|---|---|---|---|---|---|---|---|
| 1E8 + 2E2 oligomer | NA | | 19,491 | 1,442 | 36,937 | 10,465 | 14,278 | 6,880 |
| MJFR14642 + 23H8 oligomer | NA | | 31,237 | 16,953 | 57,456 | 13,458 | 18,501 | 13,487 |
| MJFR1 + 4B12 total | 642,881 | 108,670 | 814,335 | 172,628 | 546,145 | 98,753 | 745,521 | 251,293 |
| MJFR1 + MJFR13 pS129 | 322 | 63 | 1,335 | 393 | 1,713 | 31 | 801 | 246 |
| MJFR1 + Syn303 N-term | 456,572 | 81,475 | 371,498 | 232,720 | 314,518 | 104,705 | 530,481 | 121,371 |
| MJFR1 + 4D6 C term | 772,985 | 97,069 | 907,132 | 148,462 | 622,223 | 79,754 | 929,488 | 242,206 |
| Total protein (mg/ml) | 4.4 | 1.1 | 3.7 | 0.6 | 4.0 | 0.8 | 3.5 | 0.3 |

[a]Data normalized to total protein and expressed as monomer equivalent (pg/mg total protein) or pS129 peptide equivalent (pg/mg total protein). Total protein levels expressed as mg/ml.

Oligomer levels measured in the 1E8+2E2 and MJFR14642+23H8 ELISAs were highly correlated across the different synucleinopathy brain extracts (MSA, DLB, PD) (FIG. 33, Table 20). Absolute oligomer levels were comparable in the two oligomer assays. Levels of pS129

TABLE 20

Correlation of oligomer levels[a]

|  | MJFR14642 + 23H8 | MJFR1 + MJFR13 | MJFR1 + 4B12 |
|---|---|---|---|
| 1E8 + 2E2 | 0.95 | 0.92 | NS |
| MJFR14642 + 23H8 |  | 0.96 | NS |
| MJFR1 + MJFR13 |  |  | NS |

[a]Data from analysis of MSA, DLB and PD brain extracts. Pearson r values for significant correlations (p < 0.001) shown. NS represents p > 0.05

TABLE 21

Correlation of total aSyn levels[a]

|  | MJFR1 + MJFR13 | MJFR1 + Syn303 | MFJR1 + 4D6 |
|---|---|---|---|
| MJFR1 + 4612 | NS | NS | 0.97 |
| MJFR1 + MJFR13 |  | NS | NS |
| MJFR1 + Syn303 |  |  | NS |

[a]Data from analysis of control, MSA, DLB and PD brain extracts. Pearson r values for significant correlations (p < 0.001) shown. NS represents p > 0.05 d. Biochemical Characterization of Oligomers in Brain Extracts

High-speed centrifugation can be used to purify aSyn PFF and has been used to isolate high molecular weight aggregates of the tau protein from brain extracts. A similar strategy was employed to help isolate and characterize the αSyn aggregates present in the synucleinopathy brain extracts. Control, MSA, DLB, and PD brain extracts were subjected to high-speed centrifugation and the soluble (supe) and insoluble (pellet) material isolated and analyzed by oligomer ELISA. As shown in FIG. 35, oligomer was detected in brain extract pellets, including extracts generated from control brain tissues. The specificity of these ELISA signals was confirmed by dilution linearity. Similar results were observed with both oligomer ELISAs. The overall recovery of oligomer in the pellet relative to levels in the starting extract ranged from 20-80% (FIG. 35). In contrast, oligomer was not detected in the supernatants from any of the brain extracts. These findings suggest that oligomers are present as high molecular weight aggregates and also indicate that oligomers are present in control brain extracts but at lower levels compared to disease extracts.

To further characterize the high molecular aggregates in brain extracts, pellet, and supernatant fractions isolated from a control and MSA brain extract were subjected to size exclusion chromatography and fractions analyzed by SDS-PAGE/immunblot. As shown in FIG. 36, the majority of aSyn in the supernatant SEC fractions, from both the control and MSA extracts, eluted in fraction 10, corresponding to a molecular radius of ~60 kDa and suggesting that this species is a tetramer. This tetramer resolved into a monomer and lower molecular weight cleavage fragment when analyzed by SDS-PAGE/immunoblot. In contrast, the majority of the aSyn isolated in the pellet fractions eluted in the void volume by SEC (fraction 6), corresponding to a molecular radius of >670 kDa. Similar results were observed for both the control and MSA samples confirming the presence of aggregates in the control extracts: These high molecular weight aggregates also resolved into monomer and cleavage fragments by SDS-PAGE/immunoblot. In addition, aSyn from the pellet isolate was also detected in fraction 6 suggesting that the high molecular weight aggregate is in rapid equilibrium with the tetramer species. Taken together, these results confirm the presence of high-molecular weight aggregates in both MSA and control extracts, indicate that the aggregates are >670 kDa in size and that the aggregates are disrupted under denaturing conditions (SDS with boiling).

To further investigate potential difference in the high molecular weight aggregates, extract pellets isolated from control, MSA, DLB and PD were analyzed by SDS-PAGE/immunoblot using different aSyn antibodies. Results are shown for molecular weight ranges of <20 kDA (FIG. 37), 30-40 kDa (FIG. 38), and 60-100 kDa (FIG. 39). aSyn signal specificity was confirmed using an IgG antibody control. As shown in FIG. 37, comparable levels of aSyn migrating as a monomer (~14 kDa) were detected across all of the brain extract pellets (4B12, 4D6). However, the level and extent of cleavage products appeared to be higher in the MSA and DLB pellets compared to PD and control (4B12). Results with the 4D6 antibody, which recognizes the C-terminal domain of aSyn, indicates that the cleavage fragments lack this C-terminal region. pS129 signal (EP1536Y) was highest in DLB>MSA>PD>>control. Actin was present in the pellet isolates and levels were comparable across the samples. Nonspecific reactivity with the IgG control antibody was not observed, confirming aSyn specificity within this molecular weight region.

A prominent species of 30-40 kDa was detected at comparable levels in all extract pellets and likely corresponds to a dimer of aSyn (FIG. 38). Results with antibodies Syn 303 and 4D6 indicate that this species contains intact N- and C-terminal domains, respectively. Interestingly, the prominent dimer was not readily detected using antibody 4B12 although a low level of reactivity was present in the DLB pellets. These results indicate that the 4B12 epitope is masked in the dimer species and suggest that 4B12 reactivity may be a sensitive indicator of dimer conformation. Results with antibody 81A indicate that the dimer species is phosphorylated at S129 and that the highest levels are observed in the DLB pellets.

Multiple species were detected in the 60-100 kDa molecular weight range (FIG. 39). Potential aSyn aggregates of ~60 kDa (Syn303, 4B12, 4D6) and ~80-100 kDa (4B12, LB509, 4D6) were detected. Overall, the pattern of immunoreactivity observed with the different aSyn antibodies was similar across all of the brain extract pellets.

e. Induction of Insoluble, pS129 aSyn Aggregates in Cells

αSyn PFF and extracts isolated from synucleinopathy patient brain tissue induced formation of insoluble, highly phosphorylated aggregates of αSyn when added to primary neurons in culture. Moreover, induction was dependent on high molecular weight species of αSyn present in the brain extracts. These findings support the idea that αSyn pathology can be transmitted in a prion-like manner and suggest that the transmissible species is an aggregate of αSyn. High molecular weight aggregates isolated in the pellet fraction from control, MSA, DLB and PD extracts were evaluated for induction of insoluble, pS1290 αSyn in primary neurons overexpressing human A53T aSyn. Robust induction of insoluble pS129 was observed following treatment with MSA brain extract pellets for 11 days; in contrast, 10-fold lower levels of induction were observed with PD and DLB extract pellets and only background signal was observed with the control extract pellets (FIG. 40). Induction was not related to the levels of oligomer present in the pellet isolates. These results suggest that the robust induction observed with the MSA extract pellets may be related to differences in conformation and/or modifications of the MSA high molecular weight species compared to PD, DLB and control and that these differences likely affect uptake and/or the ability to initiate templated aggregation within the recipient cell.

f. Measurement of aSyn Levels in Human CSF

The aSyn oligomer ELISAs 1E8+2E2 and MJFR14642+23H8 were used to evaluate CSF from MSA synucleinopathy patients and controls; the total αSyn ELISA MJFR1+4B12 was also included for comparison. Dilution linearity and spike recovery analysis were used to validate the assays for human CSF and to identify the optimal dilution. As shown in FIG. 41, oligomer levels were <LLQ for all of the CSF samples in cohort 1, including MSA, progressive supranuclear palsy (PSP) and controls. Similar results were observed in both the 1E8+2E2 and MJFR14642+23H8 ELISAs. In contrast, total aSyn levels of ~1000 pg/ml were observed in the MJFR1+4B12 assay and levels were similar between MSA, PSP and controls. A second cohort of MSA and control CSF samples were analyzed (FIG. 42). As observed for cohort 1, oligomer levels in the majority of samples were <LLQ; however, quantifiable oligomer levels were detected for 7 CSF samples (6 MSA and 1 control) in the 1E8+2E2 ELISA. Total aSyn levels, measured with MJFR1+4B12, were similar between MSA and control CSF samples and were ~1000 pg/ml, consistent with results from cohort 1.

TABLE 22

Summary of Sequences

| SEQ ID | Description | Sequence |
|---|---|---|
| 1 | Human α-synuclein | MDVFMKGLSKAKEGVVAAAEKTKQGVAEAAGKTKEGVLYVGSKTKEGVVHG VATVAEKTKEQVTNVGGAVVTGVTAVAQKTVEGAGSIAAATGFVKKDQLGK NEEGAPQEGILEDMPVDPDNEAYEMPSEEGYQDYEPEA |
| 2 | 7A10 VH CDR1 | SGRYYWS |
| 3 | 7A10 VH CDR2 | YIYYSGRTKYNPSLKS |
| 4 | 7A10 VH CDR3 | ERGYLDY |
| 5 | 7A10 VL CDR1 | RASQSVSSSYLA |
| 6 | 7A10 VL CDR2 | GASSRAT |
| 7 | 7A10 VL CDR3 | QQYGSSPLT |
| 8 | 7A10 VH | QVQLQESGPGLVKPSETLSLTCTVSGGVSSGRYYWSWIRQPPGKGLEWIG YIYYSGRTKYNPSLKSRVTISVDTSKNQFSLKLSSVTAADTAVYYCTRERG YLDYWGQGTLVTVSS |
| 9 | 7A10 VL | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIK |
| 10 | 7A10 HC | QVQLQESGPGLVKPSETLSLICTVSGGSVSSGRYYWSWIRQPPGKGLEWIG YIYYSGRTKYNPSLKSRVTISVDTSKNQFSLKLSSVTAADTAVYYCTRERG YLDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCDKTHTCPPCPAPEAEGAPSVFLFPPKPKDTLMISR TPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYS KLTVDKSRWQQGNVFSCSVMHEALHNHYTQKSLSLSPG |
| 11 | 7A10 LC | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |

TABLE 22 -continued

Summary of Sequences

| SEQ ID | Description | Sequence |
|---|---|---|
| 12 | 7A10-T93A VH CDR1 | SGRYYWS |
| 13 | 7A10-T93A VH CDR2 | YIYYSGRTKYNPSLKS |
| 14 | 7A10-T93A VH CDR3 | ERGYLDY |
| 15 | 7A10-T93A VL CDR1 | RASQSVSSSYLA |
| 16 | 7A10-T93A VL CDR2 | GASSRAT |
| 17 | 7A10-T93A VL CDR3 | QQYGSSPLT |
| 18 | 7A10-T93A VH | QVQLQESGPGLVKPSETLSLTCTVSGGSVSSGRYYWSWIRQPPGKGLEWIG YIYYSGRTKYNPSLKSRVTISVDTSKNQFSLKLSSVTAADTAVYYCARERG YLDYWGQGTLVTVSS |
| 19 | 7A10-T93A VL | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIK |
| 20 | 7A10-T93A HC | QVQLQESGPGLVKPSETLSLTCTVSGGSVSSGRYYWSWIRQPPGKGLEWIG YIYYSGRTKYNPSLKSRVTISVDTSKNQFSLKLSSVTAADTAVYYCARERG YLDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCDKTHTCPPCPAPEAEGAPSVFLFPPKPKDTLMISR TPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYS KLTVDKSRWQQGNVFSCSVMHEALHNHYTQKSLSLSPG |
| 21 | 7A10-T93A LC | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| 22 | 11H11 VH CDR1 | SYAMH |
| 23 | 11H11 VH CDR2 | AIGTGGGTYYADSVKG |
| 24 | 11H11 VH CDR3 | GNWEFDY |
| 25 | 11H11 VL1 CDR1 | RASQSVSSSYLA |
| 26 | 11H11 VL1 CDR2 | GASSRAT |
| 27 | 11H11 VL1 CDR3 | QQYGSSPFT |
| 28 | 11H11 VL2 CDR1 | RASQGISSALA |
| 29 | 11H11 VL2 CDR2 | DASSLES |
| 30 | 11H11 VL2 CDR3 | QQFNSYP |
| 31 | 11H11 VH | EVQLVQSGGGLVHPGGSLRLSCAGSGFTFSSYAMHWVRQAPGKGLEWVSAI GTGGGTYYADSVKGRFTISRDNAKNSLYLQMNSLRAEDMAVYYCARGNWEF DYWGQGTLVTVSS |

TABLE 22-continued

Summary of Sequences

| SEQ ID | Description | Sequence |
|---|---|---|
| 32 | 11H11 VL1 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPFTFGPGTKVDIK |
| 33 | 11H11 VL2 | AIQLTQSPSSLSASVGDRVTITCRASQGISSALAWYQQKPGKAPKVPIYDASSLESGVPSRFSGSGSGTDFTLTISSLQPEDLATYYCQQFNSYPFGGGTKVEIK |
| 34 | 11H11 HC | EVQLVQSGGGLVHPGGSLRLSCAGSGFTFSSYAMHWVRQAPGKGLEWVSAIGTGGGTYYADSVKGRFTISRDNAKNSLYLQMNSLRAEDMAVYYCARGNWEFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 35 | 11H11 LC1 (SEQ ID NO: 33 + 34 = 11H11-1) | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPFTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 36 | 11H11 LC2 (SEQ ID NO: 33 + 35 = 11H11-2) | AIQLTQSPSSLSASVGDRVTITCRASQGISSALAWYQQKPGKAPKVPIYDASSLESGVPSRFSGSGSGTDFTLTISSLQPEDLATYYCQQFNSYPFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 37 | 15A5 VH CDR1 | SGSYYWC |
| 38 | 15A5 VH CDR2 | YIYYSGRTKYNPSLKS |
| 39 | 15A5 VH CDR3 | ERGRFDY |
| 40 | 15A5 VL CDR1 | RASQSVSSSYLA |
| 41 | 15A5 VL CDR2 | GASSRAT |
| 42 | 15A5 VL CDR3 | QQYGSSPLT |
| 43 | 15A5 VH | QVQLQESGPGLVKPSETLSLTCTVSGGSVSSGSYYWCWIRQPPGKGLEWIGYIYYSGRTKYNPSLKSRVTISVDTSKNQFSLKLSSVTAADTAVYYCARERGRFDYWGQGTLVTVSS |
| 44 | 15A5 VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGGGTKVEIK |

TABLE 22 -continued

Summary of Sequences

| SEQ ID | Description | Sequence |
|---|---|---|
| 45 | 15A5 HC | QVQLQESGPGLVKPSETLSLTCTVSGGSVSSGSYYWCWIRQPPGKGLEWIG YIYYSGRTKYNPSLKSRVTISVDTSKNQFSLKLSSVTAADTAVYYCARERG RFDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCDKTHTCPPCPAPEAEGAPSVFLFPPKPKDTLMISR TPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYS KLTVDKSRWQQGNVFSCSVMHEALHNHYTQKSLSLSPG |
| 46 | 15A5 LC | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| 47 | 21A3 VH CDR1 | NRNYYWS |
| 48 | 21A3 VH CDR2 | YIYYSGRTKYNPSLKS |
| 49 | 21A3 VH CDR3 | ERGRFDY |
| 50 | 21A3 VL CDR1 | RASQSVSSSYLA |
| 51 | 21A3 VL CDR2 | GASSRT |
| 52 | 21A3 VL CDR3 | QQYGSSPLT |
| 53 | 21A3 VH | QVQLQESGPGLVKPSETLSLTCTVSGGSVSNRNYYWSWIRQPPGKGLEWIG YIYYSGRTKYNPSLKSRVTISVDTSKNQFSLKVSSVTAADTAVYYCARERG RFDYWGQGTLVTVSS |
| 54 | 21A3 VL | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIK |
| 55 | 21A3 HC | QVQLQESGPGLVKPSETLSLTCTVSGGSVSNRNYYWSWIRQPPGKGLEWIG YIYYSGRTKYNPSLKSRVTISVDTSKNQFSLKVSSVTAADTAVYYCARERG RFDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCDKTHTCPPCPAPEAEGAPSVFLFPPKPKDTLMISR TPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYS KLTVDKSRWQQGNVFSCSVMHEALHNHYTQKSLSLSPG |

TABLE 22 -continued

Summary of Sequences

| SEQ ID | Description | Sequence |
|---|---|---|
| 56 | 21A3 LC | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| 57 | 36A3 VH CDR1 | SGSYYWS |
| 58 | 36A3 VH CDR2 | YIYYSGRTKYNPSLKS |
| 59 | 36A3 VH CDR3 | ERGWLDP |
| 60 | 36A3 VL CDR1 | RASQSVSSSYLA |
| 61 | 36A3 VL CDR2 | GASSRAT |
| 62 | 36A3 VL CDR3 | QQYGSSPLT |
| 63 | 36A3 VH | QVQLQESGPGLVKPSETLSLTCTVSGGSVSSGSYYWSWIRQPPGKGLEWIG YIYYSGRTKYNPSLKSRVTISVDTSRNQFSLKLSSVTAADTAVYYCARERG WLDPWGQGTLVTVSS |
| 64 | 36A3 VL | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGQG TRLEIK |
| 65 | 36A3 HC | QVQLQESGPGLVKPSETLSLTCTVSGGSVSSGSYYWSWIRQPPGKGLEWIG YIYYSGRTKYNPSLKSRVTISVDTSRNQFSLKLSSVTAADTAVYYCARERG WLDPWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCDKTHTCPPCPAPEAEGAPSVFLFPPKPKDTLMISR TPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYS KLTVDKSRWQQGNVFSCSVMHEALHNHYTQKSLSLSPG |
| 66 | 36A3 LC | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGQG TRLEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| 67 | 44B11 VH CDR1 | SKYMS |
| 68 | 44B11 VH CDR2 | VMYSGGRRYYADSVKG |
| 69 | 44B11 VH CDR3 | GDRGDY |
| 70 | 44B11 VL CDRI | RASQSVSSYLA |
| 71 | 44B11 VL CDR2 | DASNRAT |
| 72 | 44B11 VL CDR3 | QQRSNWPIT |

TABLE 22 -continued

Summary of Sequences

| SEQ ID | Description | Sequence |
|---|---|---|
| 73 | 44B11 VH | EVQLVESGGGLIQPGGSLRLSCAASGFTVS<u>SKYMS</u>WVRQAPGKGLEWVS<u>VMYSGGRRYYADSVKG</u>RFTISRDNSKNTLYLQMNSLRAEDTAVYYCAR<u>GDRGDYW</u>GQGTLVTVSS |
| 74 | 44B11 VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIK |
| 75 | 44B11 HC | EVQLVESGGGLIQPGGSLRLSCAASGFTVSSKYMSWVRQAPGKGLEWVSVMYSGGRRYYADSVKGRFTISRDNSKNTLYLQMNSTRAEDTAVYYCARGDRGDYWCQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 76 | 44B11 LC | EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 77 | 2E2 VH CDR1 | SYAMH |
| 78 | 2E2 VH CDR2 | VISYDGSNKYYADSVKG |
| 79 | 2E2 VH CDR3 | RGSGSYYNFDY |
| 80 | 2E2 VL CDR1 | RASQSVSSSYLA |
| 81 | 2E2 VL CDR2 | GASSRAT |
| 82 | 2E2 VL CDR3 | QQYGSSPT |
| 83 | 2E2 VH | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARRGSGSYYNFDYWGQGTLVTVSS |
| 84 | 2E2 VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPTFGQGTRLEIK |
| 85 | 2E2 HC | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARRGSGSYYNFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCDPCPAPEAEGAPSVFLFPPKPKDTLMISRTPEVTCVVVDVSHEDPEVKFNWYVDGVEVHNAKTKPREEQYNSTYRVV |

TABLE 22 -continued

Summary of Sequences

| SEQ ID | Description | Sequence |
|---|---|---|
| | | SVLTVLHQDWLNGKEYKCKVSNKALPAPIEKTISKAKGQPREPQVYTLPPS |
| | | REEMTKNQVSLTCLVKGFYPSDIAVEWESNGQPENNYKTTPPVLDSDGSFF |
| | | LYSKLTVDKSRWQQGNVFSCSVMHEALHNHYTQKSLSLSPG |
| 86 | 2E2 LC | EIVLTQSPGTLSLSPGERATLSCRASQSVSSSYLAWYQQKPGQAPRLLIYG |
| | | ASSRATGIPDRFSGSGSGTDFTLTISRLEPEDFAVYYCQQYGSSPTFGQGT |
| | | RLEIKRTVAAPSVFIFPPSDEQLKSGTASVVCLLNNFYPREAKVQWKVDNA |
| | | LQSGNSQESVTEQDSKDSTYSLSSTLTLSKADYEKHKVYACEVTHQGLSSP |
| | | VTKSFNRGEC |
| 87 | 23H8 VH CDR1 | SYGMN |
| 88 | 23H8 VH CDR2 | YISSSSSTIYYADSVKG |
| 89 | 23H8 VH CDR3 | WGSY |
| 90 | 23H8 VL1 CDR1 | RASQSVSRSYLA |
| 91 | 23H8 VL1 CDR2 | GASSRAT |
| 92 | 23H8 VL1 CDR3 | QQYGSSPLT |
| 93 | 23H8 VL2 CDR1 | RASQGVSSYLA |
| 94 | 23H8 VL2 CDR2 | DASNRAT |
| 95 | 23H8 VL2 CDR3 | QQRSNWHT |
| 96 | 23H8 VL3 CDR1 | RASQSVSSSYLA |
| 97 | 23H8 VL3 CDR2 | GASSRAT |
| 98 | 23H8 VL3 CDR3 | QQYGSSPT |
| 99 | 23H8 VH | EVQLVESGGGLVQPGGSLRLSCAASGFTFSSYGMNWVRQAPGKGLEWVSYI |
| | | SSSSSTIYYADSVKGRFTISRDNAKNSLYLQMNSLRDEDTAVYYCANWGSY |
| | | WGQGTLVTVSS |
| 100 | 23H8 VL1 | EIVLTQSPGTLSLSPGERATLSCRASQSVSRSYLAWYQQKLGQAPRLLIYG |
| | | ASSRATGIPDRFSGSGSGTDFTLTISRLEPEDFAVYYCQQYGSSPLTFGGG |
| | | TKVEIK |
| 101 | 23H8 VL2 | EIVLTQSPATLSLSPGERATLSCRASQGVSSYLAWYQQKPGQAPRLLIYDA |
| | | SNRATGIPARFSGSGPGTDFTLTISSLEPEDFAVYYCQQRSNWHTFGGGTK |
| | | VEIK |
| 102 | 23H8 VL3 | EIVLTQSPGTLSLSPGERATLSCRASQSVSSSYLAWYQQKPGQAPRLLIYG |
| | | ASSRATGIPDRFSGSGSGTDFTLTISRLEPEDFAVYYCQQYGSSPTFGGGT |
| | | KVEIK |
| 103 | 23H8 HC | EVQLVESGGGLVQPGGSLRLSCAASGFTFSSYGMNWVRQAPGKGLEWVSYI |
| | | SSSSSTIYYADSVKGRFTISRDNAKNSLYLQMNSLRDEDTAVYYCANWGSY |
| | | WGQGTLVTVSSASTKGPSVFPLAPSSKSTSGGTAALGCLVKDYFPEPVTVS |
| | | WNSGALTSGVHTFPAVLQSSGLYSLSSVVTVPSSSLGTQTYICNVNHKPSN |
| | | TKVDKRVEPKSCDKTHTCPPCPAPEAEGAPSVFLFPPKPKDTLMISRTPEV |

TABLE 22 -continued

Summary of Sequences

| SEQ ID | Description | Sequence |
|---|---|---|
| | | TCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSREEMTKN QVSLTCLVKGFYPSDIAVEWESNGQPENNYKTTPPVLDSDGSFFLYSKLTV DKSRWQQGNVFSCSVMHEALHNHYTQKSLSLSPG |
| 104 | 23H8 LC1 (SEQ ID NO: 102 + 103 = 23H8-1) | EIVLTQSPGTLSLSPGERATLSCRASQSVSRSYLAWYQQKLGQAPRLLIYG ASSRATGIPDRFSGSGSGTDFTLTISRLEPEDFAVYYCQQYGSSPLTFGGG TKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| 105 | 23H8 LC2 (SEQ ID NO: 102 + 104 = 23H8-2) | EIVLTQSPATLSLSPGERATLSCRASQGVSSYLAWYQQKPGQAPRLLIYDA SNRATGIPARFSGSGPGTDFTLTISSLEPEDFAVYYCQQRSNWHTFGGGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| 106 | 23118 LC3 (SEQ ID NO: 102 + 105 = 23H8-3) | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPTFGGGT KVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| 107 | 1E8VH CDR1 | SGSYYWS |
| 108 | 1E8VH CDR2 | YIYYSGRTKYNPSLKS |
| 109 | 1E8VH CDR3 | ERGWFDP |
| 110 | 1E8VL CDR1 | RASQSVSSSYLA |
| 111 | 1E8VL CDR2 | GASSRT |
| 112 | 1E8VL CDR3 | QQYGSSPLT |
| 113 | 1E8VH | QVQLQESGPGLVKPSETLSLTCTVSGGSVSSGSYYWSWIRQPPGKGLEWIG YIYYSGRTKYNPSLKSRVTISVDTSKNQFSLKLRSVTAADTAVYYCVRERG WFDPWGQGTLVTVSS |
| 114 | 1E8VL | EIVLTQSPGTLSLSPGERATLSCRASQSVSSSYLAWYQQKPGQAPRLLIYG ASSRATGIPDRFSGSGSGTDFTLTISRLEPEDFAVYYCQQYGSSPLTFGGG TKVEIK |
| 115 | 1E8HC | QVQLQESGPGLVKPSETLSLTCTVSGGSVSSGSYYWSWIRQPPGKGLEWIG YIYYSGRTKYNPSLKSRVTISVDTSKNQFSLKLRSVTAADTAVYYCWRERC WFDPWGQGTLVTVSSASTNGPSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCDKTHTCPPCPAPEAEGAPSVFLFPPKPKDTLMISR TPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREE |

TABLE 22 -continued

Summary of Sequences

| SEQ ID | Description | Sequence |
|---|---|---|
| | | MTKNQVSLTCLVKGFYPSDIAVEWESNGQPENNYKTTPPVLDSDGSFFLYS |
| | | KLTVDKSRWQQGNVFSCSVMHEALHNHYTQKSLSLSPG |
| 116 | 1E8LC | EIVLTQSPGTLSLSPGERATLSCRASQSVSSSYLAWYQQKPGQAPRLLIYG |
| | | ASSRATGIPDRFSGSGSGTDFTLTISRLEPEDFAVYYCQQYGSSPLTFGGG |
| | | TKVEIKRTVAAPSVFIFPPSDEQLKSGTASVVCLLNNFYPREAKVQWKVDN |
| | | ALQSGNSQESVTEQDSKDSTYSLSSTLTLSKADYEKHKVYACEVTHQGLSS |
| | | PVTKSFNRGEC |
| 117 | Human IgG1f constant domain | ASTKGPSVFPLAPSSKSTSGGTAALGCLVKDYFPEPVTVSWNSGALTSGVHTF |
| | | PAVLQSSGLYSLSSVVTVPSSSLGTQTYICNVNHKPSNTKVDKRVEPKSCDKT |
| | | HTCPPCPAPELLGGPSVFLFPPKPKDTLMISRTPEVTCVVVDVSHEDPEVKFN |
| | | WYVDGVEVHNAKTKPREEQYNSTYRVVSVLTVLHQDWLNGKEYKCKVSNKALP |
| | | APIEKTISKAKGQPREPQVYTLPPSREEMTKNQVSLTCLVKGFYPSDIAVEWE |
| | | SNGQPENNYKTTPPVLDSDGSFFLYSKLTVDKSRWQQGNVFSCSVMHEALHNH |
| | | YTQKSLSLSPG |
| 118 | Human IgG1za (allotypic variant) | ASTKGPSVFPLAPSSKSTSGGTAALGCLVKDYFPEPVTVSWNSGALTSGVHTF |
| | | PAVLQSSGLYSLSSVVTVPSSSLGTQTYICNVNHKPSNTKVDKKVEPKSCDKT |
| | | HTCPPCPAPELLGGPSVFLFPPKPKDTLMISRTPEVTCVVVDVSHEDPEVKFN |
| | | WYVDGVEVHNAKTKPREEQYNSTYRVVSVLTVLHQDWLNGKEYKCKVSNKALP |
| | | APIEKTISKAKGQPREPQVYTLPPSRDELTKNQVSLTCLVKGFYPSDIAVEWE |
| | | SNGQPENNYKTTPPVLDSDGSETLYSKLTVDKSRWQQGNVESCSVMHEALHNH |
| | | YTQKSLSLSPG |
| 119 | Human IgG1.3f | ASTKGPSVFPLAPSSKSTSGGTAALGCLVKDYFPEPVTVSWNSGALTSGVHTF |
| | | PAVLQSSGLYSLSSVVTVPSSSLGTQTYICNVNHKPSNTKVDKRVEPKSCDKT |
| | | HTCPPCPAPEAEGAPSVFLFPPKPKDTLMISRTPEVTCVVVDVSHEDPEVKFN |
| | | WYVDGVEVHNAKTKPREEQYNSTYRVVSVLTVLHQDWLNGKEYKCKVSNKALP |
| | | APIEKTISKAKGQPREPQVYTLPPSREEMTKNQVSLTCLVKGFYPSDIAVEWE |
| | | SNGQPENNYKTTPPVLDSDGSFELYSKLTVDKSRWQQGNVESCSVMHEALHNH |
| | | YTQKSLSLSPG |
| 120 | Human IgG1 kappa light chain constant region | RTVAAPSVFIFPPSDEQLKSGTASVVCLLNNFYPREAKVQWKVDNALQSGNSQESV |
| | | TEQDSKDSTYSLSSTLTLSKADYEKHKVYACEVTHQGLSSPVTKSFNRGEC |
| 121 | αSyn epitope (123-128) | EAYEMP |
| 122 | αSyn epitope (125-128) | YEMP |
| 123 | αSyn epitope (130-138) | EEGYQDYEP |
| 124 | αSyn epitope (130-139) | EEGYQDYEPE |
| 125 | αSyn epitope (119-126) | DPDNEAYE |
| 126 | αSyn epitope (130-138) | EEGYQDYEP |
| 127 | C-terminal sequence | LSPG |

TABLE 22 -continued

Summary of Sequences

| SEQ ID | Description | Sequence |
|---|---|---|
| 128 | Peptide linker | PVGVV |
| 129 | pS219 peptide | AATGFVKKDQLGKNEEGAPQEGILEDMPVDPDNEAYEMP-pS-EEGYQDYEPEAHHHHHH |
| 130 | αSyn 105-115 | EGAPQEGILED |
| 131 | αSyn 106-116 | GAPQEGILEDM |
| 132 | αSyn 107-117 | APQEGILEDMP |
| 133 | αSyn 108-118 | PQEGILZDMPV |
| 134 | αSyn 109-119 | QEGILEDMPVD |
| 135 | αSyn 110-120 | EGILEDMPVDP |
| 136 | αSyn 111-121 | GILEDMPVDPD |
| 137 | αSyn 112-122 | ILEDMPVDPDN |
| 138 | αSyn 113-123 | LEDMPVDPDNE |
| 139 | αSyn 114-124 | EDMPVDPDNEA |
| 140 | αSyn 115-125 | DMPvDPDNEAY |
| 141 | αSyn 116-126 | MPVDPDNEAYE |
| 142 | αSyn 117-127 | PVDPDNEAYEM |
| 143 | αSyn 118-128 | VDPDNEAYEMP |
| 144 | αSyn 119-129 | DPDNEAYEMPS |
| 145 | αSyn 120-130 | PDNEAYEMPSE |
| 146 | αSyn 121-131 | DNEAYEMPSEE |
| 147 | αSyn 122-132 | NEAYEMPSEEG |
| 148 | αSyn 123-133 | EAYEMPSEEGY |
| 149 | αSyn 124-134 | AYEMPSEEGYQ |
| 150 | αSyn 125-135 | YEMPSEEGYQD |
| 151 | αSyn 126-136 | EMPSEEGYQDY |
| 152 | αSyn 127-137 | MPSEEGYQDYE |
| 153 | αSyn 128-138 | PSEEGYQDYEP |
| 154 | αSyn 129-139 | SEEGYQDYEPE |
| 155 | αSyn 130-140 | EEGYQDYEPEA |
| 156 | mouse αSyn 111-140 peptide in Table 4 | RRRGILEDMPVDPGSEAYEMPSEEGYQDYEPEA |
| 157 | rat αSyn 111-140 peptide in Table 4 | RRRGILEDMPVDPSSEAYEMPSEEGYQDYEPEA |
| 158 | human αSyn 111-140 peptide in Table 4 | RRRGILEDMPVDPDNEAYEMPSEEGYQDYEPEA |
| 159 | 7A10-T93A-IgG1.3 HC DNA | ATGGAGGGCTGGATCTTCTTTCTGCTCTGCCTGGCCGGGAGAGCGCTCGCACAGGTGCAGCTGCAGGAGTCGGGCCCAGGACTGGTGAAGCCTTCGGAGACCCTGTCCCTCACCTGCACTGTCTCTGGTGGCTCCGTCAGCAGTGGTCGTTACTACTGGAGCTGGATCCGGCAGCCCCCAGGGAAGGGACTGGAGTGGATTGGGTATATCTATTACAGTGGGAGAACCAAGTACAACCCCTCCCTCAAGAGTCGA |

TABLE 22 -continued

Summary of Sequences

| SEQ ID | Description | Sequence |
|---|---|---|
| | | GTCACCATATCAGTAGACACGTCCAAGAACCAGTTCTCCCTGAAGCTGAGC |
| | | TCTGTGACCGCTGCGGACACGGCCGTGTATTACTGTGCGAGAGAGAGGGGG |
| | | TACCTTGACTACTGGGGCCAGGGAACCCTGGTCACCGTCTCCTCAGCTAGC |
| | | ACCAAGGGCCCATCGGTCTTCCCCCTGGCACCCTCCTCCAAGAGCACCTCT |
| | | GGGGGCACAGCGGCCCTGGGCTGCCTGGTCAAGGACTACTTCCCCGAACCG |
| | | GTGACGGTGTCGTGGAACTCAGGCGCCCTGACCAGCGGCGTGCACACCTTC |
| | | CCGGCTGTCCTACAGTCCTCAGGACTCTACTCCCTCAGCAGCGTGGTGACC |
| | | GTGCCCTCCAGCAGCTTGGGCACCCAGACCTACATCTGCAACGTGAATCAC |
| | | AAGCCCAGCAACACCAAGGTGGACAAGAGAGTTGAGCCCAAATCTTGTGAC |
| | | AAAACTCACACATGCCCACCGTGCCCAGCACCTGAAGCCGAAGGGGCCCCG |
| | | TCAGTCTTCCTCTTCCCCCCAAAACCCAAGGACACCCTCATGATCTCCCGG |
| | | ACCCCTGAGGTCACATGCGTGGTGGTGGACGTGAGCCACGAAGACCCTGAG |
| | | GTCAAGTTCAACTGGTACGTGGACGGCGTGGAGGTGCATAATGCCAAGACA |
| | | AAGCCGCGGGAGGAGCAGTACAACAGCACGTACCGTGTGGTCAGCGTCCTC |
| | | ACCGTCCTGCACCAGGACTGGCTGAATGGCAAGGAGTACAAGTGCAAGGTC |
| | | TCCAACAAAGCCCTCCCAGCCCCCATCGAGAAAACCATCTCCAAAGCCAAA |
| | | GGGCAGCCCCGAGAACCACAGGTGTACACCCTGCCCCCATCCCGGGAGGAG |
| | | ATGACCAAGAACCAGGTCAGCCTGACCTGCCTGGTCAAAGGCTTCTATCCC |
| | | AGCGACATCGCCGTGGAGTGGGAGAGCAATGGGCAGCCGGAGAACAACTAC |
| | | AAGACCACGCCTCCCGTGCTGGACTCCGACGGCTCCTTCTTCCTCTATAGC |
| | | AAGCTCACCGTGGACAAGAGCAGGTGGCAGCAGGGGAACGTCTTCTCATGC |
| | | TCCGTGATGCATGAGGCTCTGCACAACCACTACACGCAGAAGAGCCTCTCC |
| | | CTGTCCCCGGGTTGA |
| 160 | 7A10-LC DNA (for both 7A10 and 7A10-T93A); same LC sequence shared with 21A3 and 15A5 | ATGAGGGCTTGGATCTTCTTTCTGCTCTGCCTGGCCGGGCGCGCCTTGGCC |
| | | GAAATTGTGTTGACGCAGTCTCCAGGCACCCTGTCTTTGTCTCCAGGGGAA |
| | | AGAGCCACCCTCTCCTGCAGGGCCAGTCAGAGTGTTAGCAGCAGCTACTTA |
| | | GCCTGGTACCAGCAGAAACCTGGCCAGGCTCCCAGGCTCCTCATCTATGGT |
| | | GCATCCAGCAGGGCCACTGGCATCCCAGACAGGTTCAGTGGCAGTGGGTCT |
| | | GGGACAGACTTCACTCTCACCATCAGCAGACTGGAGCCTGAAGATTTTGCA |
| | | GTGTATTACTGTCAGCAGTATGGTAGCTCACCGCTCACTTTCGGCGGAGGG |
| | | ACCAAGGTGGAGATCAAACGTACGGTGGCTGCACCATCTGTCTTCATCTTC |
| | | CCGCCATCTGATGAGCAGTTGAAATCTGGAACTGCCTCTGTTGTGTGCCTG |
| | | CTGAATAACTTCTATCCCAGAGAGGCCAAAGTACAGTGGAAGGTGGATAAC |
| | | GCCCTCCAATCGGGTAACTCCCAGGAGAGTGTCACAGAGCAGGACAGCAAG |
| | | GACAGCACCTACAGCCTCAGCAGCACCCTGACGCTGAGCAAAGCAGACTAC |
| | | GAGAAACACAAAGTCTACGCCTGCGAAGTCACCCATCAGGGCCTGAGCTCG |
| | | CCCGTCACAAAGAGCTTCAACAGGGGAGAGTGTTAG |

TABLE 22 -continued

Summary of Sequences

| SEQ ID | Description | Sequence |
|---|---|---|
| 161 | 7A10 VH DNA | CAGGTGCAGCTGCAGGAGTCGGGCCCAGGACTGGTGAAGCCTTCGGAGACC CTGTCCCTCACCTGCACTGTCTCTGGTGGCTCCGTCAGCAGTGGTCGTTAC TACTGGAGCTGGATCCGGCAGCCCCCAGGGAAGGGACTGGAGTGGATTGGG TATATCTATTACAGTGGGAGAACCAAGTACAACCCCTCCCTCAAGAGTCGA GTCACCATATCAGTAGACACGTCCAAGAACCAGTTCTCCCTGAAGCTGAGC TCTGTGACCGCTGCGGACACGGCCGTGTATTACTGTACGAGAGAGAGGGGG TACCTTGACTACTGGGGCCAGGGAACCCTGGTCACCGTCTCCTCA |
| 162 | 7A10 VL DNA (for both 7A10 and 7A10-T93A); same VL sequence shared with 21A3 and 15A5 | GAAATTGTGTTGACGCAGTCTCCAGGCACCCTGTCTTTGTCTCCAGGGGAA AGAGCCACCCTCTCCTGCAGGGCCAGTCAGAGTGTTAGCAGCAGCTACTTA GCCTGGTACCAGCAGAAACCTGGCCAGGCTCCCAGGCTCCTCATCTATGGT GCATCCAGCAGGGCCACTGGCATCCCAGACAGGTTCAGTGGCAGTGGGTCT GGGACAGACTTCACTCTCACCATCAGCAGACTGGAGCCTGAAGATTTTGCA GTGTATTACTGTCAGCAGTATGGTAGCTCACCGCTCACTTTCGGCGGAGGG ACCAAGGTGGAGATCAAA |
| 163 | 7A10-T93A VH DNA | CAGGTGCAGCTGCAGGAGTCGGGCCCAGGACTGGTGAAGCCTTCGGAGACC CTGTCCCTCACCTGCACTGTCTCTGGTGGCTCCGTCAGCAGTGGTCGTTAC TACTGGAGCTGGATTCGGCAGCCCCCAGGGAAGGGACTGGAGTGGATTGGG TATATCTATTACAGTGGGAGAACCAAGTACAACCCCTCCCTCAAGAGTCGA GTCACCATATCAGTAGACACGTCCAAGAACCAGTTCTCCCTGAAGCTGAGC TCTGTGACCGCTGCGGACACGGCCGTGTATTACTGTGCGAGAGAGAGGGGG TACCTTGACTACTGGGGCCAGGGAACCCTGGTCACCGTCTCCTCA |
| 164 | 21A3 VH DNA | CAGGTGCAGCTGCAGGAGTCGGGCCCAGGACTGGTGAAGCCTTCGGAGACCCTGTC CCTCACCTGCACTGTCTCTGGTGGCTCCGTCAGCAATCGTAATTACTACTGGAGCT GGATCCGGCAGCCCCCAGGGAAGGGACTGGAGTGGATTGGGTATATCTATTACAGT GGGAGGACCAAGTACAACCCCTCCCTCAAGAGTCGAGTCACCATATCAGTAGACAC GTCCAAGAACCAGTTCTCCCTGAAGGTGAGCTCTGTGACCGCTGCGGACACGGCCG TGTATTACTGTGCGAGAGAGGGGGCGGTTTGACTACTGGGGCCAGGGAACCCTG GTCACCGTCTCCTCA |
| 165 | 21A3 VL DNA | GAAATTGTGTTGACGCAGTCTCCAGGCACCCTGTCTTTGTCTCCAGGGGAA AGAGCCACCCTCTCCTGCAGGGCCAGTCAGAGTGTTAGCAGCAGCTACTTA GCCTGGTACCAGCAGAAACCTGGCCAGGCTCCCAGGCTCCTCATCTATGGT CCATCCAGCAGGGCLACTGGCATCCCAGACAGGTTCAGTGGCAGTGGGTCT GGGACAGACTTCACTCTCACCATCAGCAGACTGGAGCCTGAAGATTTTGCA GTGTATTACTGTCAGCAGTATGGTAGCTCACCGCTCACTTTCGGCGGAGGG ACCAAGGTGGAGATCAAA |
| 165 | 1E8 VH DNA | CAGGTGCAGCTGCAGGAGTCGGGCCCAGGACTGGTGAAGCCTTCGGAGACC CTGTCCCTCACCTGCACTGTCTCTGGTGGCTCCGTCAGCAGTGGTAGTTAC TACTGGAGCTGGATCCGGCAGCCCCCAGGGAAGGGACTGGAGTGGATTGGG |

TABLE 22 -continued

Summary of Sequences

| SEQ ID | Description | Sequence |
|---|---|---|
| | | TATATCTATTACAGTGGGAGAACCAAGTACAACCCCTCCCTCAAGAGTCGA |
| | | GTCACCATATCAGTAGACACGTCCAAGAACCAGTTCTCCCTGAAGCTGAGG |
| | | TCTGTGACCGCTGCGGACACGGCCGTGTATTACTGTGTGAGAGAGAGGGGC |
| | | TGGTTCGACCCCTGGGGCCAGGGAACCCTGGTCACCGTCTCCTCA |
| 166 | 1E8 VL DNA | GAAATTGTGTTGACGCAGTCTCCAGGCACCCTGTCTTTGTCTCCAGGGGAA |
| | | AGAGCCACCCTCTCCTGCAGGGCCAGTCAGAGTGTTAGCAGCAGCTACTTA |
| | | GCCTGGTACCAGCAGAAACCTGGCCAGGCTCCCAGGCTCCTCATCTATGGT |
| | | GCATCCAGCAGGGCCACTGGCATCCCAGACAGGTTCAGTGGCAGTGGGTCT |
| | | GGGACAGACTTCACTCTCACCATCAGCAGACTGGAGCCTGAAGATTTTGCA |
| | | GTGTATTACTGTCAGCAGTATGGTAGCTCACCTCTCACTTTCGGCGGAGGG |
| | | ACCAAGGTGGAGATCAAA |
| 167 | 2E2 VH DNA | CAGGTGCAGCTGGTGGAGTCTGGGGGAGGCGTGGTCCAGCCTGGGAGGTCC |
| | | CTGAGACTCTCCTGTGCAGCCTCTGGATTCACCTTCAGTAGCTATGCTATG |
| | | CACTGGGTCCGCCAGGCTCCAGGCAAGGGGCTGGAGTGGGTGGCAGTTATA |
| | | TCATATGATGGAAGCAATAAATACTACGCAGACTCCGTGAAGGGCCGATTC |
| | | ACCATCTCCAGAGACAATTCCAAGAACACGCTGTATCTGCAAATGAACAGC |
| | | CTGAGAGCTGAGGACACGGCTGTGTATTACTGTGCGAGAAGGGGTTCGGGG |
| | | AGTTATTATAACTTTGACTACTGGGGCCAGGGAACCCTGGTCACCGTCTCC |
| | | TCA |
| 168 | 2E2 VL DNA | GAAATTGTGTTGACGCAGTCTCCAGGCACCCTGTCTTTGTCTCCAGGGGAA |
| | | AGAGCCACCCTCTCCTGCAGGGCCAGTCAGAGTGTTAGCAGCAGCTACTTA |
| | | GCCTGGTACCAGCAGAAACCTGGCCAGGCTCCCAGGCTCCTCATCTATGGT |
| | | GCATCCAGCAGGGCCACTGGCATCCCAGACAGGTTCAGTGGCAGTGGGTCT |
| | | GGGACAGACTTCACTCTCACCATCAGCAGACTGGAGCCTGAAGATTTTGCA |
| | | GTGTATTACTGTCAGCAGTATGGTAGCTCACCCACCTTCGGCCAAGGGACA |
| | | CGACTGGAGATTAAA |
| 169 | 23H8 VH DNA | GAGGTGCAGCTGGTGGAGTCTGGGGGAGGCTTGGTACAGCCTGGGGGGTCC |
| | | CTGAGACTCTCCTGTGCAGCCTCTGGATTCACCTTCAGTAGCTATGGCATG |
| | | AACTGGGTCCGCCAGGCTCCAGGGAAGGGGCTGGAGTGGGTTTCATACATT |
| | | AGTAGTAGTAGTAGTACCATATACTACGCAGACTCTGTGAAGGGCCGATTC |
| | | ACCATCTCCAGAGACAATGCCAAGAACTCACTGTATCTGCAAATGAACAGC |
| | | CTGAGAGACGAGGACACGGCTGTGTATTACTGTGCTAACTGGGGATCCTAC |
| | | TGGGGCCAGGGAACCCTGGTCACCGTCTCCTCA |
| 170 | 23H8 VL1 DNA | GAAATTGTGTTGACGCAGTCTCCAGGCACCCTGTCTTTGTCTCCAGGGGAA |
| | | AGAGCCACCCTCTCCTGCAGGGCCAGTCAGAGTGTTAGCAGAAGCTACTTA |
| | | GCCTGGTACCAGCAGAAACTTGGCCAGGCTCCCAGGCTCCTCATCTATGGT |
| | | GCATCCAGCAGGGCCACTGGCATCCCAGACAGGTTCAGTGGCAGTGGGTCT |

TABLE 22 -continued

Summary of Sequences

| SEQ ID | Description | Sequence |
|---|---|---|
| | | GGGACAGACTTCACTCTCACCATCAGCAGACTGGAGCCTGAAGATTTTGCA GTGTATTACTGTCAGCAGTATGGTAGCTCACCTCTCACTTTCGGCGGAGGG ACCAAGGTGGAGATCAAA |
| 171 | 23H8 VL2 DNA | GAAATTGTGTTGACACAGTCTCCAGCCACCCTGTCTTTGTCTCCAGGGGAA AGAGCCACCCTCTCCTGCAGGGCCAGTCAGGGTGTTAGCAGCTACTTAGCC TGGTACCAGCAGAAACCTGGCCAGGCTCCCAGGCTCCTCATCTATGATGCA TCCAACAGGGCCACTGGCATCCCAGCCAGGTTCAGTGGCAGTGGGCCTGGG ACAGACTTCACTCTCACCATCAGCAGCCTAGAGCCTGAAGATTTTGCAGTT TATTACTGTCAGCAGCGTAGCAACTGGCATACTTTCGGCGGAGGGACCAAG GTGGAGATCAAA |
| 172 | 23H8 VL3 DNA | GAAATTGTGTTGACGCAGTCTCCAGGCACCCTGTCTTTGTCTCCAGGGGAA AGAGCCACCCTCTCCTGCAGGGCCAGTCAGAGTGTTAGCAGCAGCTACTTA GCCTGGTACCAGCAGAAACCTGGCCAGGCTCCCAGGCTCCTCATCTATGGT GCATCCAGCAGGGCCACTGGCATCCCAGACAGGTTCAGTGGCAGTGGGTCT GGGACAGACTTCACTCTCACCATCAGCAGACTGGAGCCTGAAGATTTTGCA GTGTATTACTGTCAGCAGTATGGTAGCTCACCCACTTTCGGCGGAGGGACC AAGGTGGAGATCAAA |
| 173 | 11H11VH DNA | GAGGTTCAGCTGGTGCAGTCTGGGGGAGGCTTGGTACATCCTGGGGGGTCCCTGAG ACTCTCCTGTGCAGGCTCTGGATTCACCTTCAGTAGCTATGCTATGCACTGGGTTC GCCAGGCTCCAGGAAAAGGTCTGGAGTGGGTATCAGCTATTGGTACTGGTGGTGGC ACATACTATGCAGACTCCGTGAAGGGCCGATTCACCATCTCCAGAGACAATGCCAA GAACTCCTTGTATCTTCAAATGAACAGCCTGAGAGCCGAGGACATGGCTGTGTATT ACTGTGCAAGAGGGAACTGGGAATTTGACTACTGGGGCCAGGGAACCCTGGTCACC GTCTCCTCA |
| 174 | 11H11VL1 DNA | GAAATTGTGTTGACGCAGTCTCCAGGCACCCTGTCTTTGTCTCCAGGGGAAAGAGC CACCCTCTCCTGCAGGGCCAGTCAGAGTGTTAGCAGCAGCTACTTAGCCTGGTACC AGCAGAAACCTGGCCAGGCTCCCAGGCTCCTCATCTATGGTGCATCCAGCAGGGCC ACTGGCATCCCAGACAGGTTCAGTGGCAGTGGGTCTGGGACAGACTTCACTCTCAC CATCAGCAGACTGGAGCCTGAAGATTTTGCAGTGTATTACTGTCAGCAGTATGGTA GCTCACCATTCACTTTCGGCCCTGGGACCAAAGTGGATATCAAA |
| 175 | 11H11VL2 DNA | GCCATCCAGTTGACCCAGTCTCCATCCTCCCTGTCTGCATCTGTAGGAGACAGAGT CACCATCACTTGCCGGGCAAGTCAGGGCATTAGCAGTGCTTTAGCCTGGTATCAGC AGAAACCAGGGAAAGCTCCTAAGGTCCCGATCTATGATGCCTCCAGTTTGGAAAGT GGGGTCCCATCAAGGTTCAGCGGCAGTGGATCTGGGACAGATTTCACTCTCACCAT CAGCAGCCTGCAGCCTGAAGATCTTGCAACTTATTACTGTCAACAGTTTAATAGTT ACCCTTTCGGCGGAGGGACCAAGGTGGAGATCAAA |
| 176 | 15A5VH DNA | CAGGTGCAGCTGCAGGAGTCGGGCCCAGGACTGGTGAAGCCTTCGGAGACCCTGTC CCTCACCTGCACTGTCTCTGGTGGCTCCCTCAGCAGTGGTAGTTACTACTGGTGCT |

TABLE 22 -continued

Summary of Sequences

| SEQ ID | Description | Sequence |
|---|---|---|
| | | GGATCCGGCAGCCCCCAGGGAAGGGACTGGAGTGGATCGGGTATATCTATTACAGT |
| | | GGGCGCACCAAGTACAACCCCTCCCTCAAGAGTCGAGTCACCATATCAGTAGACAC |
| | | GTCCAAGAACCAGTTCTCCCTGAAGCTGAGCTCTGTGACCGCTGCGGACACGGCCG |
| | | TGTATTACTGTGCGAGAGAGAGGGGCGGTTTGACTACTGGGGCCAGGGAACCCTG |
| | | GTCACCGTCTCCTCA |
| 177 | 15A5VL DNA | GAAATTGTGTTGACGCAGTCTCCAGGCACCCTGTCTTTGTCTCCAGGGGAAAGAGC |
| | | CACCCTCTCCTGCAGGGCCAGTCAGAGTGTTAGCAGCAGCTACTTAGCCTGGTACC |
| | | AGCAGAAACCTGGCCAGGCTCCCAGGCTCCTCATCTATGGTGCATCCAGCAGGGCC |
| | | ACTGGCATCCCAGACAGGTTCAGTGGCAGTGGGTCTGGGACAGACTTCACTCTCAC |
| | | CATCAGCAGACTGGAGCCTGAAGATTTTGCAGTGTATTACTGTCAGCAGTATGGTA |
| | | GCTCACCGCTCACTTTCGGCGGAGGGACCAAGGTGGAGATCAAA |
| 178 | 36A3VH DNA | CAGGTGCAGCTGCAGGAGTCGGGCCCAGGACTGGTGAAGCCTTCGGAGACCCTGTC |
| | | CCTCACCTGCACTGTCTCTGGTGGCTCCGTCAGCAGTGGTAGTTACTACTGGAGCT |
| | | GGATCCGGCAGCCCCCAGGGAAGGGACTGGAGTGGATTGGGTATATCTATTACAGT |
| | | GGGAGAACCAAGTACAACCCCTCCCTCAAGAGTCGAGTCACCATATCAGTAGACAC |
| | | GTCCAGGAACCAGTTCTCCCTGAAGCTGAGCTCTGTGACCGCTGCGGACACGGCCG |
| | | TGTATTACTGTGCGAGAGAGAGGGGCTGGCTCGACCCCTGGGGCCAGGGAACCCTG |
| | | GTCACCGTCTCCTCA |
| 179 | 36A3VL DNA | GAAATTGTGTTGACACAGTCTCCAGCCACCCTGTCTTTGTCTCCAGGGGAAAGAGC |
| | | CACCCTCTCCTGCAGGGCCAGTCAGAGTGTTAGCAGCTACTTAGCCTGGTACCAAC |
| | | AGAAACCTGGCCAGGCTCCCAGGCTCCTCATCTATGATGCATCCAACAGGGCCACT |
| | | GGCATCCCAGCCAGGTTCAGTGGCAGTGGGTCTGGGACAGACTTCACTCTCACCAT |
| | | CAGCAGCCTAGAGCCTGAAGATTTTGCAGTTTATTACTGTCAGCAGCGTAGCAACT |
| | | GGTCACCTTCGGCCAAGGGACACGACTGGAGATTAAA |
| 180 | 44B11VH DNA | GAGGTGCAGTTGGTGGAGTCTGGAGGAGGCTTGATCCAGCCTGGGGGGTCCCTGAG |
| | | ACTCTCCTGTGCAGCCTCTGGGTTCACCGTCAGTAGCAAATACATGAGCTGGGTCC |
| | | GCCAGGCTCCAGGGAAGGGGCTGGAGTGGGTCTCAGTTATGTATAGCGGTGGTAGA |
| | | AGATACTATGCAGACTCCGTGAAGGGCCGATTCACCATCTCCAGAGACAATTCCAA |
| | | GAACACGCTGTATCTTCAAATGAACAGCCTGAGAGCCGAGGACACGGCCGTGTATT |
| | | ACTGTGCGAGAGGGGATCGGGGTGACTACTGGGGCCAGGGAACCCTGGTCACCGTC |
| | | TCCTCA |
| 181 | 44B11VL DNA | GAAATTGTGTTGACACAGTCTCCAGCCACCCTGTCTTTGTCTCCAGGGGAAAGAGC |
| | | CACCCTCTCCTGCAGGGCCAGTCAGAGTGTTAGCAGCTACTTAGCCTGGTACCAAC |
| | | AGAAACCTGGCCAGGCTCCCAGGCTCCTCATCTATGATGCATCCAACAGGGCCACT |
| | | GGCATCCCAGCCAGGTTCAGTGGCAGTGGGTCTGGGACAGACTTCACTCTCACCAT |
| | | CAGCAGCCTAGAGCCTGAAGATTTTGCAGTTTATTACTGTCAGCAGCGTAGCAACT |
| | | GGCCGATCACCTTCGGCCAAGGGACACGACTGGAGATTAAA |

EQUIVALENTS

Those skilled in the art will recognize, or be able to ascertain using no more than routine experimentation, many equivalents of the specific embodiments disclosed herein. Such equivalents are intended to be encompassed by the following claims.

---

We claim:

1. An isolated antibody comprising:
   a heavy chain variable region comprising the following CDRs:
   i. CDR1 having the amino acid sequence of SEQ ID NO:12;
   ii. CDR2 having the amino acid sequence of SEQ ID NO:13; and
   iii. CDR3 having the amino acid sequence of SEQ ID NO:14; and
   a light chain variable region comprising the following CDRs:
   i. CDR1 having the amino acid sequence of SEQ ID NO:15;
   ii. CDR2 having the amino acid sequence of SEQ ID NO:16; and
   iii. CDR3 having the amino acid sequence of SEQ ID NO:17;
   wherein the antibody binds to human α-synuclein (SEQ ID NO:1).

2. The isolated antibody of claim 1, wherein the antibody binds to at least one or more of amino acid residues 123-128 of SEQ ID NO: 1.

3. The isolated antibody of claim 1, wherein the antibody comprises heavy and light chain variable region sequences which are at least 95% identical to the amino acid sequences set forth in SEQ ID NOs: 18 and 19, respectively.

4. The isolated antibody of claim 1, wherein the antibody is selected from the group consisting of an IgG1, an IgG2, an IgG3, an IgG4, and a variant thereof.

5. The isolated antibody of claim 1, wherein the antibody comprises an Fc domain comprising the amino acid sequence set forth in SEQ ID NO: 119.

6. The isolated antibody of claim 1, wherein the antibody comprises heavy and light chain sequences which are at least 95% identical to the amino acid sequences set forth in SEQ ID NOs: 20 and 21, respectively.

7. The isolated antibody of claim 1, wherein the antibody is a chimeric, humanized, or human antibody.

8. An isolated bispecific antibody comprising the isolated antibody of claim 1.

9. A nucleic acid molecule encoding the heavy and/or light chain variable region of the isolated antibody of claim 1.

10. An expression vector comprising the nucleic acid molecule of claim 9.

11. A cell transformed with the expression vector of claim 10.

12. An immunoconjugate comprising the isolated antibody of claim 1, linked to a moiety.

13. A composition comprising the isolated antibody of claim 1, and a pharmaceutically acceptable carrier.

14. A method of preparing an anti-α-synuclein antibody comprising:
   culturing a host cell comprising the expression vector of claim 10, wherein the antibody is expressed; and
   isolating the antibody from the cell.

15. A method of inhibiting the generation of insoluble serine-129 phosphorylated α-synuclein aggregates in a cell comprising contacting the cell with an effective amount of the isolated antibody of claim 1.

16. A method of treating a disease or lessening the severity of a disease characterized by the presence of Lewy bodies or pathological aggregates of α-synuclein in neurons and/or glia comprising administering to a subject with the disease an effective amount of the isolated antibody of claim 1.

17. The method of claim 16, wherein the disease is Parkinson's disease, Parkinson's disease dementia, dementia with Lewy bodies, Lewy body disease, multiple system atrophy, or pure autonomic failure.

18. The method of claim 16, comprising administering one or more additional therapeutic agents.

19. A method for detecting α-synuclein in a sample comprising contacting the sample with the isolated antibody of claim 1 under conditions that allow for formation of a complex between the antibody and α-synuclein, and detecting the formation of the complex.

20. An isolated antibody comprising a heavy chain variable region comprising the amino acid sequence set forth in SEQ ID NO:18 and a light chain variable region comprising the amino acid sequence set forth in SEQ ID NO:19, wherein the antibody binds to human α-synuclein (SEQ ID NO:1).

21. An isolated antibody comprising a heavy chain comprising the amino acid sequence set forth in SEQ ID NO:20 and a light chain comprising the amino acid sequence set forth in SEQ ID NO:21, wherein the antibody binds to human α-synuclein (SEQ ID NO:1).

22. A method of inhibiting the generation of insoluble serine-129 phosphorylated α-synuclein aggregates in a cell comprising contacting the cell with an effective amount of the isolated antibody of claim 20.

23. A method of treating a disease or lessening the severity of a disease characterized by the presence of Lewy bodies or pathological aggregates of α-synuclein in neurons and/or glia comprising administering to a subject with the disease an effective amount of the isolated antibody of claim 20.

24. The method of claim 23, wherein the disease is Parkinson's disease, Parkinson's disease dementia, dementia with Lewy bodies, Lewy body disease, multiple system atrophy, or pure autonomic failure.

25. A method of inhibiting the generation of insoluble serine-129 phosphorylated α-synuclein aggregates in a cell comprising contacting the cell with an effective amount of the isolated antibody of claim 21.

26. A method of treating a disease or lessening the severity of a disease characterized by the presence of Lewy bodies or pathological aggregates of α-synuclein in neurons and/or glia comprising administering to a subject with the disease an effective amount of the isolated antibody of claim 21.

27. The method of claim 26, wherein the disease is Parkinson's disease, Parkinson's disease dementia, dementia with Lewy bodies, Lewy body disease, multiple system atrophy, or pure autonomic failure.

28. An isolated antibody comprising two heavy chains and two light chains, wherein each of the heavy chains comprises the amino acid sequence set forth in SEQ ID NO:20 and each of the light chains comprises the amino acid sequence set forth in SEQ ID NO:21, wherein the antibody binds to human α-synuclein (SEQ ID NO:1).

* * * * *

SEQUENCE LISTING

<160> NUMBER OF SEQ ID NOS: 182

<210> SEQ ID NO 1
<211> LENGTH: 140
<212> TYPE: PRT
<213> ORGANISM: Homo sapiens
<220> FEATURE:
<221> NAME/KEY: misc_feature
<223> OTHER INFORMATION: Human alpha-synuclein

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 7
<212> TYPE: PRT
<213> ORGANISM: Artificial Sequence
<220> FEATURE:
<223> OTHER INFORMATION: Synthetic: 7A10 VH CDR1

<400> SEQUENCE: 2

Ser Gly Arg Tyr Tyr Trp Ser
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic: 7A10 VH CDR2

<400> SEQUENCE: 3

Tyr Ile Tyr Tyr Ser Gly Arg Thr Lys Tyr Asn Pro Ser Leu Lys Ser
1               5                   10                  15

<210> SEQ ID NO 4
<211> LENGTH: 7
<212> TYPE: PRT

```
<213> ORGANISM: Artificial Sequence
<220> FEATURE:
<223> OTHER INFORMATION: Synthetic: 7A10 VH CDR3

<400> SEQUENCE: 4

Glu Arg Gly Tyr Leu Asp Tyr
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic: 7A10 VL CDR1

<400> SEQUENCE: 5

Arg Ala Ser Gln Ser Val Ser Ser Tyr Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic: 7A10 VL CDR2

<400> SEQUENCE: 6

Gly Ala Ser Ser Arg Ala Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic: 7A10 VL CDR3

<400> SEQUENCE: 7

Gln Gln Tyr Gly Ser Ser Pro Leu Thr
1               5

<210> SEQ ID NO 8
<211> LENGTH: 117
<212> TYPE: PRT
<213> ORGANISM: Artificial Sequence
<220> FEATURE:
<223> OTHER INFORMATION: Synthetic: 7A10 VH

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Arg Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Arg Gly Tyr Leu Asp Tyr Trp Gly Gln Gly Thr Leu
            100                 105                 110
```

-continued

```
Val Thr Val Ser Ser
        115

<210> SEQ ID NO 9
<211> LENGTH: 108
<212> TYPE: PRT
<213> ORGANISM: Artificial Sequence
<220> FEATURE:
<223> OTHER INFORMATION: Synthetic: 7A10 VL

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 10
<211> LENGTH: 446
<212> TYPE: PRT
<213> ORGANISM: Artificial Sequence
<220> FEATURE:
<223> OTHER INFORMATION: Synthetic: 7A10 HC

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Arg Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Arg Gly Tyr Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

-continued

```
Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 11
<211> LENGTH: 215
<212> TYPE: PRT
<213> ORGANISM: Artificial Sequence
<220> FEATURE:
<223> OTHER INFORMATION: Synthetic: 7A10 LC

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110
```

```
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 12
<211> LENGTH: 7
<212> TYPE: PRT
<213> ORGANISM: Artificial Sequence
<220> FEATURE:
<223> OTHER INFORMATION: Synthetic: 7A10-T93A VH CDR1

<400> SEQUENCE: 12

Ser Gly Arg Tyr Tyr Trp Ser
1               5

<210> SEQ ID NO 13
<211> LENGTH: 16
<212> TYPE: PRT
<213> ORGANISM: Artificial Sequence
<220> FEATURE:
<223> OTHER INFORMATION: Synthetic: 7A10-T93A VH CDR2

<400> SEQUENCE: 13

Tyr Ile Tyr Tyr Ser Gly Arg Thr Lys Tyr Asn Pro Ser Leu Lys Ser
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Synthetic: 7A10-T93A VH CDR3

<400> SEQUENCE: 14

Glu Arg Gly Tyr Leu Asp Tyr
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic: 7A10-T93A VL CDR1

<400> SEQUENCE: 15

Arg Ala Ser Gln Ser Val Ser Ser Ser Tyr Leu Ala
1               5                   10

<210> SEQ ID NO 16
<211> LENGTH: 7
<212> TYPE: PRT
<213> ORGANISM: Artificial Sequence
```

```
<220> FEATURE:
<223> OTHER INFORMATION: Synthetic: 7A10-T93A VL CDR2

<400> SEQUENCE: 16

Gly Ala Ser Ser Arg Ala Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic: 7A10-T93A VL CDR3

<400> SEQUENCE: 17

Gln Gln Tyr Gly Ser Ser Pro Leu Thr
1               5

<210> SEQ ID NO 18
<211> LENGTH: 117
<212> TYPE: PRT
<213> ORGANISM: Artificial Sequence
<220> FEATURE:
<223> OTHER INFORMATION: Synthetic: 7A10-T93A VH

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Arg Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Gly Tyr Leu Asp Tyr Trp Gly Gln Gly Thr Leu
            100                 105                 110

Val Thr Val Ser Ser
        115

<210> SEQ ID NO 19
<211> LENGTH: 108
<212> TYPE: PRT
<213> ORGANISM: Artificial Sequence
<220> FEATURE:
<223> OTHER INFORMATION: Synthetic: 7A10-T93A VL

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```

<210> SEQ ID NO 20
<211> LENGTH: 446
<212> TYPE: PRT
<213> ORGANISM: Artificial Sequence
<220> FEATURE:
<223> OTHER INFORMATION: Synthetic: 7A10-T93A HC

<400> SEQUENCE: 20

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Arg Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Gly Tyr Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 21
<211> LENGTH: 215
<212> TYPE: PRT
<213> ORGANISM: Artificial Sequence
<220> FEATURE:
<223> OTHER INFORMATION: Synthetic: 7A10-T93A LC

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 22
<211> LENGTH: 5
<212> TYPE: PRT
<213> ORGANISM: Artificial Sequence

```
<220> FEATURE:
<223> OTHER INFORMATION: Synthetic: 11H11 VH CDR1

<400> SEQUENCE: 22

Ser Tyr Ala Met His
1               5

<210> SEQ ID NO 23
<211> LENGTH: 16
<212> TYPE: PRT
<213> ORGANISM: Artificial Sequence
<220> FEATURE:
<223> OTHER INFORMATION: Synthetic: 11H11 VH CDR2

<400> SEQUENCE: 23

Ala Ile Gly Thr Gly Gly Gly Thr Tyr Tyr Ala Asp Ser Val Lys Gly
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Synthetic: 11H11 VH CDR3

<400> SEQUENCE: 24

Gly Asn Trp Glu Phe Asp Tyr
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic: 11H11 VL1 CDR1

<400> SEQUENCE: 25

Arg Ala Ser Gln Ser Val Ser Ser Ser Tyr Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic: 11H11 VL1CDR2

<400> SEQUENCE: 26

Gly Ala Ser Ser Arg Ala Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic: 11H11 VL1 CDR3

<400> SEQUENCE: 27

Gln Gln Tyr Gly Ser Ser Pro Phe Thr
1               5

<210> SEQ ID NO 28
<211> LENGTH: 11
<212> TYPE: PRT
<213> ORGANISM: Artificial Sequence
<220> FEATURE:
```

```
<223> OTHER INFORMATION: Synthetic: 11H11 VL2 CDR1

<400> SEQUENCE: 28

Arg Ala Ser Gln Gly Ile Ser Ser Ala Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic: 11H11 VL2 CDR2

<400> SEQUENCE: 29

Asp Ala Ser Ser Leu Glu Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic: 11H11 VL2 CDR3

<400> SEQUENCE: 30

Gln Gln Phe Asn Ser Tyr Pro
1               5

<210> SEQ ID NO 31
<211> LENGTH: 115
<212> TYPE: PRT
<213> ORGANISM: Artificial Sequence
<220> FEATURE:
<223> OTHER INFORMATION: Synthetic: 11H11 VH

<400> SEQUENCE: 31

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ser Ala Ile Gly Thr Gly Gly Gly Thr Tyr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Asn Trp Glu Phe Asp Tyr Trp Gly Gln Gly Thr Leu Val Thr
            100                 105                 110

Val Ser Ser
        115

<210> SEQ ID NO 32
<211> LENGTH: 108
<212> TYPE: PRT
<213> ORGANISM: Artificial Sequence
<220> FEATURE:
<223> OTHER INFORMATION: Synthetic: 11H11 VL1

<400> SEQUENCE: 32

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105
```

<210> SEQ ID NO 33
<211> LENGTH: 105
<212> TYPE: PRT
<213> ORGANISM: Artificial Sequence
<220> FEATURE:
<223> OTHER INFORMATION: Synthetic: 11H11 VL2

<400> SEQUENCE: 33

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Val Pro Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Phe Asn Ser Tyr Pro Phe
                85                  90                  95

Gly Gly Gly Thr Lys Val Glu Ile Lys
            100                 105
```

<210> SEQ ID NO 34
<211> LENGTH: 444
<212> TYPE: PRT
<213> ORGANISM: Artificial Sequence
<220> FEATURE:
<223> OTHER INFORMATION: Synthetic: 11H11 HC

<400> SEQUENCE: 34

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Asn Trp Glu Phe Asp Tyr Trp Gly Gln Gly Thr Leu Val Thr
```

```
            100                 105                 110
Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Ala Glu Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 35
<211> LENGTH: 215
<212> TYPE: PRT
<213> ORGANISM: Artificial Sequence
<220> FEATURE:
<223> OTHER INFORMATION: Synthetic: 11H11 LC1

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                    20                  25                  30
Tyr Leu Ala Trp Tyr Gln Gln Lys Pro Gly Gln Ala Pro Arg Leu Leu
                35                  40                  45
Ile Tyr Gly Ala Ser Ser Arg Ala Thr Gly Ile Pro Asp Arg Phe Ser
            50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Phe Thr Phe Gly Pro Gly Thr Lys Val Asp Ile Lys Arg Thr Val Ala
                100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 36
<211> LENGTH: 212
<212> TYPE: PRT
<213> ORGANISM: Artificial Sequence
<220> FEATURE:
<223> OTHER INFORMATION: Synthetic: 11H11 LC2

<400> SEQUENCE: 36

Ala Ile Gln Leu Thr Gln Ser Pro Ser Ser Leu Ser Ala Ser Val Gly
 1               5                  10                  15
Asp Arg Val Thr Ile Thr Cys Arg Ala Ser Gln Gly Ile Ser Ser Ala
                20                  25                  30
Leu Ala Trp Tyr Gln Gln Lys Pro Gly Lys Ala Pro Lys Val Pro Ile
                35                  40                  45
Tyr Asp Ala Ser Ser Leu Glu Ser Gly Val Pro Ser Arg Phe Ser Gly
            50                  55                  60
Ser Gly Ser Gly Thr Asp Phe Thr Leu Thr Ile Ser Ser Leu Gln Pro
 65                  70                  75                  80
Glu Asp Leu Ala Thr Tyr Tyr Cys Gln Gln Phe Asn Ser Tyr Pro Phe
                 85                  90                  95
Gly Gly Gly Thr Lys Val Glu Ile Lys Arg Thr Val Ala Ala Pro Ser
                100                 105                 110
Val Phe Ile Phe Pro Pro Ser Asp Glu Gln Leu Lys Ser Gly Thr Ala
            115                 120                 125
Ser Val Val Cys Leu Leu Asn Asn Phe Tyr Pro Arg Glu Ala Lys Val
        130                 135                 140
Gln Trp Lys Val Asp Asn Ala Leu Gln Ser Gly Asn Ser Gln Glu Ser
145                 150                 155                 160
Val Thr Glu Gln Asp Ser Lys Asp Ser Thr Tyr Ser Leu Ser Ser Thr
```

```
                    165                 170                 175
Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 37
<211> LENGTH: 7
<212> TYPE: PRT
<213> ORGANISM: Artificial Sequence
<220> FEATURE:
<223> OTHER INFORMATION: Synthetic: 15A5 VH CDR1

<400> SEQUENCE: 37

Ser Gly Ser Tyr Tyr Trp Cys
1               5

<210> SEQ ID NO 38
<211> LENGTH: 16
<212> TYPE: PRT
<213> ORGANISM: Artificial Sequence
<220> FEATURE:
<223> OTHER INFORMATION: Synthetic: 15A5 VH CDR2

<400> SEQUENCE: 38

Tyr Ile Tyr Tyr Ser Gly Arg Thr Lys Tyr Asn Pro Ser Leu Lys Ser
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: Synthetic: 15A5 VH CDR3

<400> SEQUENCE: 39

Glu Arg Gly Arg Phe Asp Tyr
1               5

<210> SEQ ID NO 40
<211> LENGTH: 12
<212> TYPE: PRT
<213> ORGANISM: Artificial Sequence
<220> FEATURE:
<223> OTHER INFORMATION: Synthetic: 15A5 VL CDR1

<400> SEQUENCE: 40

Arg Ala Ser Gln Ser Val Ser Ser Ser Tyr Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic: 15A5 VL CDR2

<400> SEQUENCE: 41

Gly Ala Ser Ser Arg Ala Thr
1               5

<210> SEQ ID NO 42
<211> LENGTH: 9
```

```
<212> TYPE: PRT
<213> ORGANISM: Artificial Sequence
<220> FEATURE:
<223> OTHER INFORMATION: Synthetic: 15A5 VL CDR3

<400> SEQUENCE: 42

Gln Gln Tyr Gly Ser Ser Pro Leu Thr
1               5

<210> SEQ ID NO 43
<211> LENGTH: 117
<212> TYPE: PRT
<213> ORGANISM: Artificial Sequence
<220> FEATURE:
<223> OTHER INFORMATION: Synthetic: 15A5 VH

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Cys Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Gly Arg Phe Asp Tyr Trp Gly Gln Gly Thr Leu
            100                 105                 110

Val Thr Val Ser Ser
        115

<210> SEQ ID NO 44
<211> LENGTH: 108
<212> TYPE: PRT
<213> ORGANISM: Artificial Sequence
<220> FEATURE:
<223> OTHER INFORMATION: Synthetic: 15A5 VL

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 45
<211> LENGTH: 446
<212> TYPE: PRT
```

<213> ORGANISM: Artificial Sequence
<220> FEATURE:
<223> OTHER INFORMATION: Synthetic: 15A5 HC

<400> SEQUENCE: 45

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Cys Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Gly Arg Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 46
<211> LENGTH: 215
<212> TYPE: PRT
<213> ORGANISM: Artificial Sequence
<220> FEATURE:
<223> OTHER INFORMATION: Synthetic: 15A5 LC

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 47
<211> LENGTH: 7
<212> TYPE: PRT
<213> ORGANISM: Artificial Sequence
<220> FEATURE:
<223> OTHER INFORMATION: Synthetic: 21A3 VH CDR1

<400> SEQUENCE: 47

Asn Arg Asn Tyr Tyr Trp Ser
1               5

<210> SEQ ID NO 48
<211> LENGTH: 16
```

```
<212> TYPE: PRT
<213> ORGANISM: Artificial Sequence
<220> FEATURE:
<223> OTHER INFORMATION: Synthetic: 21A3 VH CDR2

<400> SEQUENCE: 48

Tyr Ile Tyr Tyr Ser Gly Arg Thr Lys Tyr Asn Pro Ser Leu Lys Ser
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: Synthetic: 21A3 VH CDR3

<400> SEQUENCE: 49

Glu Arg Gly Arg Phe Asp Tyr
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic: 21A3 VL CDR1

<400> SEQUENCE: 50

Arg Ala Ser Gln Ser Val Ser Ser Ser Tyr Leu Ala
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic: 21A3 VL CDR2

<400> SEQUENCE: 51

Gly Ala Ser Ser Arg Ala Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic: 21A3 VL CDR3

<400> SEQUENCE: 52

Gln Gln Tyr Gly Ser Ser Pro Leu Thr
1               5

<210> SEQ ID NO 53
<211> LENGTH: 117
<212> TYPE: PRT
<213> ORGANISM: Artificial Sequence
<220> FEATURE:
<223> OTHER INFORMATION: Synthetic: 21A3 VH

<400> SEQUENCE: 53

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Asn Arg
            20                  25                  30

Asn Tyr Tyr Trp Ser Trp Ile Arg Gln Pro Pro Gly Lys Gly Leu Glu
```

```
                    35                  40                  45

Trp Ile Gly Tyr Ile Tyr Tyr Ser Gly Arg Thr Lys Tyr Asn Pro Ser
             50                  55                  60

Leu Lys Ser Arg Val Thr Ile Ser Val Asp Thr Ser Lys Asn Gln Phe
 65                  70                  75                  80

Ser Leu Lys Val Ser Ser Val Thr Ala Ala Asp Thr Ala Val Tyr Tyr
                 85                  90                  95

Cys Ala Arg Glu Arg Gly Arg Phe Asp Tyr Trp Gly Gln Gly Thr Leu
                100                 105                 110

Val Thr Val Ser Ser
            115

<210> SEQ ID NO 54
<211> LENGTH: 108
<212> TYPE: PRT
<213> ORGANISM: Artificial Sequence
<220> FEATURE:
<223> OTHER INFORMATION: Synthetic: 21A3 VL

<400> SEQUENCE: 54

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
            100                 105

<210> SEQ ID NO 55
<211> LENGTH: 446
<212> TYPE: PRT
<213> ORGANISM: Artificial Sequence
<220> FEATURE:
<223> OTHER INFORMATION: Synthetic: 21A3 HC

<400> SEQUENCE: 55

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Asn Arg
                 20                  25                  30

Asn Tyr Tyr Trp Ser Trp Ile Arg Gln Pro Pro Gly Lys Gly Leu Glu
             35                  40                  45

Trp Ile Gly Tyr Ile Tyr Tyr Ser Gly Arg Thr Lys Tyr Asn Pro Ser
             50                  55                  60

Leu Lys Ser Arg Val Thr Ile Ser Val Asp Thr Ser Lys Asn Gln Phe
 65                  70                  75                  80

Ser Leu Lys Val Ser Ser Val Thr Ala Ala Asp Thr Ala Val Tyr Tyr
                 85                  90                  95

Cys Ala Arg Glu Arg Gly Arg Phe Asp Tyr Trp Gly Gln Gly Thr Leu
                100                 105                 110
```

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 56
<211> LENGTH: 215
<212> TYPE: PRT
<213> ORGANISM: Artificial Sequence
<220> FEATURE:
<223> OTHER INFORMATION: Synthetic: 21A3 LC

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
              35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys Arg Thr Val Ala
             100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 57
<211> LENGTH: 7
<212> TYPE: PRT
<213> ORGANISM: Artificial Sequence
<220> FEATURE:
<223> OTHER INFORMATION: Synthetic: 36A3 VH CDR1

<400> SEQUENCE: 57

Ser Gly Ser Tyr Tyr Trp Ser
1               5

<210> SEQ ID NO 58
<211> LENGTH: 16
<212> TYPE: PRT
<213> ORGANISM: Artificial Sequence
<220> FEATURE:
<223> OTHER INFORMATION: Synthetic: 36A3 VH CDR2

<400> SEQUENCE: 58

Tyr Ile Tyr Tyr Ser Gly Arg Thr Lys Tyr Asn Pro Ser Leu Lys Ser
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Synthetic: 36A3 VH CDR3

<400> SEQUENCE: 59

Glu Arg Gly Trp Leu Asp Pro
1               5

<210> SEQ ID NO 60
<211> LENGTH: 12
<212> TYPE: PRT

-continued

<210> SEQ ID NO 60
<211> LENGTH: 10 (implied)
<212> TYPE: PRT
<213> ORGANISM: Artificial Sequence
<220> FEATURE:
<223> OTHER INFORMATION: Synthetic: 36A3 VL CDR1

<400> SEQUENCE: 60

Arg Ala Ser Gln Ser Val Ser Ser Tyr Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic: 36A3 VL CDR2

<400> SEQUENCE: 61

Gly Ala Ser Ser Arg Ala Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic: 36A3 VL CDR3

<400> SEQUENCE: 62

Gln Gln Tyr Gly Ser Ser Pro Leu Thr
1               5

<210> SEQ ID NO 63
<211> LENGTH: 117
<212> TYPE: PRT
<213> ORGANISM: Artificial Sequence
<220> FEATURE:
<223> OTHER INFORMATION: Synthetic: 36A3 VH

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Gly Trp Leu Asp Pro Trp Gly Gln Gly Thr Leu
            100                 105                 110

Val Thr Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: Synthetic: 36A3 VL

<400> SEQUENCE: 64

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Arg Leu Glu Ile Lys
            100                 105
```

<210> SEQ ID NO 65
<211> LENGTH: 446
<212> TYPE: PRT
<213> ORGANISM: Artificial Sequence
<220> FEATURE:
<223> OTHER INFORMATION: Synthetic: 36A3 HC

<400> SEQUENCE: 65

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Gly Trp Leu Asp Pro Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 66
<211> LENGTH: 215
<212> TYPE: PRT
<213> ORGANISM: Artificial Sequence
<220> FEATURE:
<223> OTHER INFORMATION: Synthetic: 36A3 LC

<400> SEQUENCE: 66

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 67
<211> LENGTH: 5
<212> TYPE: PRT
<213> ORGANISM: Artificial Sequence
<220> FEATURE:
<223> OTHER INFORMATION: Synthetic: 44B11 VH CDR1

<400> SEQUENCE: 67

Ser Lys Tyr Met Ser
1               5

<210> SEQ ID NO 68
<211> LENGTH: 16
<212> TYPE: PRT
<213> ORGANISM: Artificial Sequence
<220> FEATURE:
<223> OTHER INFORMATION: Synthetic: 44B11 VH CDR2

<400> SEQUENCE: 68

Val Met Tyr Ser Gly Gly Arg Arg Tyr Tyr Ala Asp Ser Val Lys Gly
1               5                   10                  15

<210> SEQ ID NO 69
<211> LENGTH: 6
<212> TYPE: PRT
<213> ORGANISM: Artificial Sequence
<220> FEATURE:
<223> OTHER INFORMATION: Synthetic: 44B11 VH CDR3

<400> SEQUENCE: 69

Gly Asp Arg Gly Asp Tyr
1               5

<210> SEQ ID NO 70
<211> LENGTH: 11
<212> TYPE: PRT
<213> ORGANISM: Artificial Sequence
<220> FEATURE:
<223> OTHER INFORMATION: Synthetic: 44B11 VL CDR1

<400> SEQUENCE: 70

Arg Ala Ser Gln Ser Val Ser Ser Tyr Leu Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Synthetic: 44B11 VL CDR2

<400> SEQUENCE: 71

Asp Ala Ser Asn Arg Ala Thr
1               5

<210> SEQ ID NO 72
<211> LENGTH: 9
<212> TYPE: PRT
<213> ORGANISM: Artificial Sequence
```

<220> FEATURE:
<223> OTHER INFORMATION: Synthetic: 44B11 VL CDR3

<400> SEQUENCE: 72

Gln Gln Arg Ser Asn Trp Pro Ile Thr
1               5

<210> SEQ ID NO 73
<211> LENGTH: 114
<212> TYPE: PRT
<213> ORGANISM: Artificial Sequence
<220> FEATURE:
<223> OTHER INFORMATION: Synthetic: 44B11 VH

<400> SEQUENCE: 73

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Lys
            20                  25                  30

Tyr Met Ser Trp Val Arg Gln Ala Pro Gly Lys Gly Leu Glu Trp Val
        35                  40                  45

Ser Val Met Tyr Ser Gly Gly Arg Arg Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Asp Arg Gly Asp Tyr Trp Gly Gln Gly Thr Leu Val Thr Val
            100                 105                 110

Ser Ser

<210> SEQ ID NO 74
<211> LENGTH: 107
<212> TYPE: PRT
<213> ORGANISM: Artificial Sequence
<220> FEATURE:
<223> OTHER INFORMATION: Synthetic: 44B11 VL

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 75
<211> LENGTH: 443
<212> TYPE: PRT
<213> ORGANISM: Artificial Sequence
<220> FEATURE:
<223> OTHER INFORMATION: Synthetic: 44B11 HC

<400> SEQUENCE: 75

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Lys
            20                  25                  30

Tyr Met Ser Trp Val Arg Gln Ala Pro Gly Lys Gly Leu Glu Trp Val
        35                  40                  45

Ser Val Met Tyr Ser Gly Gly Arg Arg Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Asp Arg Gly Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Ala Glu Gly Ala Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln 405                 410                 415
Gly Asn Val Phe Ser Cys Ser Val Met His Glu Ala Leu His Asn His
                420                 425                 430

Tyr Thr Gln Lys Ser Leu Ser Leu Ser Pro Gly
        435                 440

<210> SEQ ID NO 76
<211> LENGTH: 214
<212> TYPE: PRT
<213> ORGANISM: Artificial Sequence
<220> FEATURE:
<223> OTHER INFORMATION: Synthetic: 44B11 LC

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 77
<211> LENGTH: 5
<212> TYPE: PRT
<213> ORGANISM: Artificial Sequence
<220> FEATURE:
<223> OTHER INFORMATION: Synthetic: 2E2 VH CDR1

<400> SEQUENCE: 77

Ser Tyr Ala Met His
1               5

<210> SEQ ID NO 78
<211> LENGTH: 17
<212> TYPE: PRT
<213> ORGANISM: Artificial Sequence
<220> FEATURE:

<223> OTHER INFORMATION: Synthetic: 2E2 VH CDR2

<400> SEQUENCE: 78

Val Ile Ser Tyr Asp Gly Ser Asn Lys Tyr Tyr Ala Asp Ser Val Lys
1               5                   10                  15

Gly

<210> SEQ ID NO 79
<211> LENGTH: 11
<212> TYPE: PRT
<213> ORGANISM: Artificial Sequence
<220> FEATURE:
<223> OTHER INFORMATION: Synthetic: 2E2 VH CDR3

<400> SEQUENCE: 79

Arg Gly Ser Gly Ser Tyr Tyr Asn Phe Asp Tyr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic: 2E2 VL CDR1

<400> SEQUENCE: 80

Arg Ala Ser Gln Ser Val Ser Ser Ser Tyr Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic: 2E2 VL CDR2

<400> SEQUENCE: 81

Gly Ala Ser Ser Arg Ala Thr
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic: 2E2 VL CDR3

<400> SEQUENCE: 82

Gln Gln Tyr Gly Ser Ser Pro Thr
1               5

<210> SEQ ID NO 83
<211> LENGTH: 120
<212> TYPE: PRT
<213> ORGANISM: Artificial Sequence
<220> FEATURE:
<223> OTHER INFORMATION: Synthetic: 2E2 VH

<400> SEQUENCE: 83

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Gly Ser Gly Ser Tyr Tyr Asn Phe Asp Tyr Trp Gly Gln
                100                 105                 110

Gly Thr Leu Val Thr Val Ser Ser
            115                 120

<210> SEQ ID NO 84
<211> LENGTH: 107
<212> TYPE: PRT
<213> ORGANISM: Artificial Sequence
<220> FEATURE:
<223> OTHER INFORMATION: Synthetic: 2E2 VL

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Gln Gln Tyr Gly Ser Ser Pro
                85                  90                  95

Thr Phe Gly Gln Gly Thr Arg Leu Glu Ile Lys
            100                 105

<210> SEQ ID NO 85
<211> LENGTH: 449
<212> TYPE: PRT
<213> ORGANISM: Artificial Sequence
<220> FEATURE:
<223> OTHER INFORMATION: Synthetic: 2E2 HC

<400> SEQUENCE: 85

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Ala Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Arg Gly Ser Gly Ser Tyr Tyr Asn Phe Asp Tyr Trp Gly Gln
                100                 105                 110

Gly Thr Leu Val Thr Val Ser Ser Ala Ser Thr Lys Gly Pro Ser Val

```
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Ala Glu Gly Ala
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 86
<211> LENGTH: 214
<212> TYPE: PRT
<213> ORGANISM: Artificial Sequence
<220> FEATURE:
<223> OTHER INFORMATION: Synthetic: 2E2 LC

<400> SEQUENCE: 86

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 87
<211> LENGTH: 5
<212> TYPE: PRT
<213> ORGANISM: Artificial Sequence
<220> FEATURE:
<223> OTHER INFORMATION: Synthetic: 23H8 VH CDR1

<400> SEQUENCE: 87

Ser Tyr Gly Met Asn
1               5

<210> SEQ ID NO 88
<211> LENGTH: 17
<212> TYPE: PRT
<213> ORGANISM: Artificial Sequence
<220> FEATURE:
<223> OTHER INFORMATION: Synthetic: 23H8 VH CDR2

<400> SEQUENCE: 88

Tyr Ile Ser Ser Ser Ser Ser Thr Ile Tyr Tyr Ala Asp Ser Val Lys
1               5                   10                  15

Gly

<210> SEQ ID NO 89
<211> LENGTH: 4
<212> TYPE: PRT
<213> ORGANISM: Artificial Sequence
<220> FEATURE:
<223> OTHER INFORMATION: Synthetic: 23H8 VH CDR3

<400> SEQUENCE: 89

Trp Gly Ser Tyr
1

```
<210> SEQ ID NO 90
<211> LENGTH: 12
<212> TYPE: PRT
<213> ORGANISM: Artificial Sequence
<220> FEATURE:
<223> OTHER INFORMATION: Synthetic: 23H8 VL1 CDR1

<400> SEQUENCE: 90

Arg Ala Ser Gln Ser Val Ser Arg Ser Tyr Leu Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Synthetic: 23H8 VL1 CDR2

<400> SEQUENCE: 91

Gly Ala Ser Ser Arg Ala Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic: 23H8 VL1 CDR3

<400> SEQUENCE: 92

Gln Gln Tyr Gly Ser Ser Pro Leu Thr
1               5

<210> SEQ ID NO 93
<211> LENGTH: 11
<212> TYPE: PRT
<213> ORGANISM: Artificial Sequence
<220> FEATURE:
<223> OTHER INFORMATION: Synthetic: 23H8 VL2 CDR1

<400> SEQUENCE: 93

Arg Ala Ser Gln Gly Val Ser Ser Tyr Leu Ala
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Synthetic: 23H8 VL2 CDR2

<400> SEQUENCE: 94

Asp Ala Ser Asn Arg Ala Thr
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic: 23H8 VL2 CDR3

<400> SEQUENCE: 95

Gln Gln Arg Ser Asn Trp His Thr
1               5

<210> SEQ ID NO 96
```

```
<211> LENGTH: 12
<212> TYPE: PRT
<213> ORGANISM: Artificial Sequence
<220> FEATURE:
<223> OTHER INFORMATION: Synthetic: 23H8 VL3 CDR1

<400> SEQUENCE: 96

Arg Ala Ser Gln Ser Val Ser Ser Ser Tyr Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic: 23H8 VL3 CDR2

<400> SEQUENCE: 97

Gly Ala Ser Ser Arg Ala Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic: 23H8 VL3 CDR3

<400> SEQUENCE: 98

Gln Gln Tyr Gly Ser Ser Pro Thr
1               5

<210> SEQ ID NO 99
<211> LENGTH: 113
<212> TYPE: PRT
<213> ORGANISM: Artificial Sequence
<220> FEATURE:
<223> OTHER INFORMATION: Synthetic: 23H8 VH

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Asn Trp Gly Ser Tyr Trp Gly Gln Gly Thr Leu Val Thr Val Ser
            100                 105                 110

Ser

<210> SEQ ID NO 100
<211> LENGTH: 108
<212> TYPE: PRT
<213> ORGANISM: Artificial Sequence
<220> FEATURE:
<223> OTHER INFORMATION: Synthetic: 23H8 VL1

<400> SEQUENCE: 100
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Leu Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 101
<211> LENGTH: 106
<212> TYPE: PRT
<213> ORGANISM: Artificial Sequence
<220> FEATURE:
<223> OTHER INFORMATION: Synthetic: 23H8 VL2

<400> SEQUENCE: 101

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Thr
                85                  90                  95

Phe Gly Gly Gly Thr Lys Val Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Synthetic: 23H8 VL3

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro

Thr Phe Gly Gly Gly Thr Lys Val Glu Ile Lys
             85              90              95
                100             105

<210> SEQ ID NO 103
<211> LENGTH: 442
<212> TYPE: PRT
<213> ORGANISM: Artificial Sequence
<220> FEATURE:
<223> OTHER INFORMATION: Synthetic: 23H8 HC

<400> SEQUENCE: 103

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Asn Trp Gly Ser Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Arg Val Glu Pro Lys Ser Cys Asp Lys Thr His Thr Cys Pro Pro
210                 215                 220

Cys Pro Ala Pro Glu Ala Glu Gly Ala Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu

```
              340                 345                 350
Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 104
<211> LENGTH: 215
<212> TYPE: PRT
<213> ORGANISM: Artificial Sequence
<220> FEATURE:
<223> OTHER INFORMATION: Synthetic: 23H8 LC1

<400> SEQUENCE: 104

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Leu Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 105
<211> LENGTH: 213
<212> TYPE: PRT
<213> ORGANISM: Artificial Sequence
<220> FEATURE:
<223> OTHER INFORMATION: Synthetic: 23H8 LC2
```

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 106
<211> LENGTH: 214
<212> TYPE: PRT
<213> ORGANISM: Artificial Sequence
<220> FEATURE:
<223> OTHER INFORMATION: Synthetic: 23H8 LC3

<400> SEQUENCE: 106

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 107
<211> LENGTH: 7
<212> TYPE: PRT
<213> ORGANISM: Artificial Sequence
<220> FEATURE:
<223> OTHER INFORMATION: Synthetic: 1E8 VH CDR1

<400> SEQUENCE: 107

```
Ser Gly Ser Tyr Tyr Trp Ser
1               5
```

<210> SEQ ID NO 108
<211> LENGTH: 16
<212> TYPE: PRT
<213> ORGANISM: Artificial Sequence
<220> FEATURE:
<223> OTHER INFORMATION: Synthetic: 1E8VH CDR2

<400> SEQUENCE: 108

```
Tyr Ile Tyr Tyr Ser Gly Arg Thr Lys Tyr Asn Pro Ser Leu Lys Ser
1               5                   10                  15
```

<210> SEQ ID NO 109
<211> LENGTH: 7
<212> TYPE: PRT
<213> ORGANISM: Artificial Sequence
<220> FEATURE:
<223> OTHER INFORMATION: Synthetic: 1E8VH CDR3

<400> SEQUENCE: 109

```
Glu Arg Gly Trp Phe Asp Pro
1               5
```

<210> SEQ ID NO 110
<211> LENGTH: 12
<212> TYPE: PRT
<213> ORGANISM: Artificial Sequence
<220> FEATURE:
<223> OTHER INFORMATION: Synthetic: 1E8VL CDR1

<400> SEQUENCE: 110

```
Arg Ala Ser Gln Ser Val Ser Ser Ser Tyr Leu Ala
1               5                   10
```

<210> SEQ ID NO 111
<211> LENGTH: 7
<212> TYPE: PRT
<213> ORGANISM: Artificial Sequence
<220> FEATURE:
<223> OTHER INFORMATION: Synthetic: 1E8VL CDR2

<400> SEQUENCE: 111

Gly Ala Ser Ser Arg Ala Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic: 1E8VL CDR3

<400> SEQUENCE: 112

Gln Gln Tyr Gly Ser Ser Pro Leu Thr
1               5

<210> SEQ ID NO 113
<211> LENGTH: 117
<212> TYPE: PRT
<213> ORGANISM: Artificial Sequence
<220> FEATURE:
<223> OTHER INFORMATION: Synthetic: 1E8VH

<400> SEQUENCE: 113

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Val Arg Glu Arg Gly Trp Phe Asp Pro Trp Gly Gln Gly Thr Leu
            100                 105                 110

Val Thr Val Ser Ser
        115

<210> SEQ ID NO 114
<211> LENGTH: 108
<212> TYPE: PRT
<213> ORGANISM: Artificial Sequence
<220> FEATURE:
<223> OTHER INFORMATION: Synthetic: 1E8VL

<400> SEQUENCE: 114

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

```
Leu Thr Phe Gly Gly Gly Thr Lys Val Glu Ile Lys
            100                 105
```

<210> SEQ ID NO 115
<211> LENGTH: 446
<212> TYPE: PRT
<213> ORGANISM: Artificial Sequence
<220> FEATURE:
<223> OTHER INFORMATION: Synthetic: 1E8HC

<400> SEQUENCE: 115

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Arg Thr Lys Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Val Arg Glu Arg Gly Trp Phe Asp Pro Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 116
<211> LENGTH: 215
<212> TYPE: PRT
<213> ORGANISM: Artificial Sequence
<220> FEATURE:
<223> OTHER INFORMATION: Synthetic: 1E8LC

<400> SEQUENCE: 116

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 117
<211> LENGTH: 329
<212> TYPE: PRT
<213> ORGANISM: Homo sapiens
<220> FEATURE:
<221> NAME/KEY: misc_feature
<223> OTHER INFORMATION: Human IgG1f constant domain
```

<400> SEQUENCE: 117

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 118
<211> LENGTH: 329
<212> TYPE: PRT
<213> ORGANISM: Homo sapiens
<220> FEATURE:
<221> NAME/KEY: misc_feature
<223> OTHER INFORMATION: Human IgG1za (allotypic variant)

<400> SEQUENCE: 118

```
Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 119
<211> LENGTH: 329
<212> TYPE: PRT
<213> ORGANISM: Homo sapiens
<220> FEATURE:
<221> NAME/KEY: misc_feature
<223> OTHER INFORMATION: Human IgG1.3f

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                    325

<210> SEQ ID NO 120
<211> LENGTH: 107
<212> TYPE: PRT
<213> ORGANISM: Homo sapiens
<220> FEATURE:
<221> NAME/KEY: misc_feature
<223> OTHER INFORMATION: Human IgG1 kappa light chain constant region

<400> SEQUENCE: 120

Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu

```
                65                  70                  75                  80
Lys His Lys Val Tyr Ala Cys Glu Val Thr His Gln Gly Leu Ser Ser
                    85                  90                  95
Pro Val Thr Lys Ser Phe Asn Arg Gly Glu Cys
            100                 105
```

<210> SEQ ID NO 121
<211> LENGTH: 6
<212> TYPE: PRT
<213> ORGANISM: Artificial Sequence
<220> FEATURE:
<223> OTHER INFORMATION: Synthetic: alpha-Syn epitope (123-128)

<400> SEQUENCE: 121

```
Glu Ala Tyr Glu Met Pro
1               5
```

<210> SEQ ID NO 122
<211> LENGTH: 4
<212> TYPE: PRT
<213> ORGANISM: Artificial Sequence
<220> FEATURE:
<223> OTHER INFORMATION: Synthetic: alpha-Syn epitope (125-128)

<400> SEQUENCE: 122

```
Tyr Glu Met Pro
1
```

<210> SEQ ID NO 123
<211> LENGTH: 9
<212> TYPE: PRT
<213> ORGANISM: Artificial Sequence
<220> FEATURE:
<223> OTHER INFORMATION: Synthetic: alpha-Syn epitope (130-138)

<400> SEQUENCE: 123

```
Glu Glu Gly Tyr Gln Asp Tyr Glu Pro
1               5
```

<210> SEQ ID NO 124
<211> LENGTH: 10
<212> TYPE: PRT
<213> ORGANISM: Artificial Sequence
<220> FEATURE:
<223> OTHER INFORMATION: Synthetic: alpha-Syn epitope (130-139)

<400> SEQUENCE: 124

```
Glu Glu Gly Tyr Gln Asp Tyr Glu Pro Glu
1               5                   10
```

<210> SEQ ID NO 125
<211> LENGTH: 8
<212> TYPE: PRT
<213> ORGANISM: Artificial Sequence
<220> FEATURE:
<223> OTHER INFORMATION: Synthetic: alpha-Syn epitope (119-126)

<400> SEQUENCE: 125

```
Asp Pro Asp Asn Glu Ala Tyr Glu
1               5
```

<210> SEQ ID NO 126
<211> LENGTH: 9
<212> TYPE: PRT
<213> ORGANISM: Artificial Sequence
<220> FEATURE:

<223> OTHER INFORMATION: Synthetic: alpha-Syn epitope (130-138)

<400> SEQUENCE: 126

Glu Glu Gly Tyr Gln Asp Tyr Glu Pro
1               5

<210> SEQ ID NO 127
<211> LENGTH: 4
<212> TYPE: PRT
<213> ORGANISM: Artificial Sequence
<220> FEATURE:
<223> OTHER INFORMATION: Synthetic: C-terminal sequence

<400> SEQUENCE: 127

Leu Ser Pro Gly
1

<210> SEQ ID NO 128
<211> LENGTH: 5
<212> TYPE: PRT
<213> ORGANISM: Artificial Sequence
<220> FEATURE:
<223> OTHER INFORMATION: Synthetic: Peptide linker

<400> SEQUENCE: 128

Pro Val Gly Val Val
1               5

<210> SEQ ID NO 129
<211> LENGTH: 57
<212> TYPE: PRT
<213> ORGANISM: Artificial Sequence
<220> FEATURE:
<223> OTHER INFORMATION: Synthetic: pS219 peptide
<220> FEATURE:
<221> NAME/KEY: MOD_RES
<222> LOCATION: (40)..(40)
<223> OTHER INFORMATION: PHOSPHORYLATION

<400> SEQUENCE: 129

Ala Ala Thr Gly Phe Val Lys Lys Asp Gln Leu Gly Lys Asn Glu Glu
1               5                   10                  15

Gly Ala Pro Gln Glu Gly Ile Leu Glu Asp Met Pro Val Asp Pro Asp
                20                  25                  30

Asn Glu Ala Tyr Glu Met Pro Ser Glu Glu Gly Tyr Gln Asp Tyr Glu
            35                  40                  45

Pro Glu Ala His His His His His His
        50                  55

<210> SEQ ID NO 130
<211> LENGTH: 11
<212> TYPE: PRT
<213> ORGANISM: Artificial Sequence
<220> FEATURE:
<223> OTHER INFORMATION: Synthetic: alpha-Syn 105-115

<400> SEQUENCE: 130

Glu Gly Ala Pro Gln Glu Gly Ile Leu Glu Asp
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic: alpha-Syn 106-116

<400> SEQUENCE: 131

Gly Ala Pro Gln Glu Gly Ile Leu Glu Asp Met
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic: alpha-Syn 107-117

<400> SEQUENCE: 132

Ala Pro Gln Glu Gly Ile Leu Glu Asp Met Pro
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic: alpha-Syn 108-118

<400> SEQUENCE: 133

Pro Gln Glu Gly Ile Leu Glu Asp Met Pro Val
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic: alpha-Syn 109-119

<400> SEQUENCE: 134

Gln Glu Gly Ile Leu Glu Asp Met Pro Val Asp
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic: alpha-Syn 110-120

<400> SEQUENCE: 135

Glu Gly Ile Leu Glu Asp Met Pro Val Asp Pro
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic: alpha-Syn 111-121

<400> SEQUENCE: 136

Gly Ile Leu Glu Asp Met Pro Val Asp Pro Asp
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic: alpha-Syn 112-122

```
<400> SEQUENCE: 137

Ile Leu Glu Asp Met Pro Val Asp Pro Asp Asn
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Synthetic: alpha-Syn 113-123

<400> SEQUENCE: 138

Leu Glu Asp Met Pro Val Asp Pro Asp Asn Glu
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic: alpha-Syn 114-124

<400> SEQUENCE: 139

Glu Asp Met Pro Val Asp Pro Asp Asn Glu Ala
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic: alpha-Syn 115-125

<400> SEQUENCE: 140

Asp Met Pro Val Asp Pro Asp Asn Glu Ala Tyr
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic: alpha-Syn 116-126

<400> SEQUENCE: 141

Met Pro Val Asp Pro Asp Asn Glu Ala Tyr Glu
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic: alpha-Syn 117-127

<400> SEQUENCE: 142

Pro Val Asp Pro Asp Asn Glu Ala Tyr Glu Met
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic: alpha-Syn 118-128

<400> SEQUENCE: 143
```

```
Val Asp Pro Asp Asn Glu Ala Tyr Glu Met Pro
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic: alpha-Syn 119-129

<400> SEQUENCE: 144

Asp Pro Asp Asn Glu Ala Tyr Glu Met Pro Ser
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic: alpha-Syn 120-130

<400> SEQUENCE: 145

Pro Asp Asn Glu Ala Tyr Glu Met Pro Ser Glu
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic: alpha-Syn 121-131

<400> SEQUENCE: 146

Asp Asn Glu Ala Tyr Glu Met Pro Ser Glu Glu
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic: alpha-Syn 122-132

<400> SEQUENCE: 147

Asn Glu Ala Tyr Glu Met Pro Ser Glu Glu Gly
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic: alpha-Syn 123-133

<400> SEQUENCE: 148

Glu Ala Tyr Glu Met Pro Ser Glu Glu Gly Tyr
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Synthetic: alpha-Syn 124-134

<400> SEQUENCE: 149
```

```
Ala Tyr Glu Met Pro Ser Glu Glu Gly Tyr Gln
1               5                   10
```

<210> SEQ ID NO 150
<211> LENGTH: 11
<212> TYPE: PRT
<213> ORGANISM: Artificial Sequence
<220> FEATURE:
<223> OTHER INFORMATION: Synthetic: alpha-Syn 125-135

<400> SEQUENCE: 150

```
Tyr Glu Met Pro Ser Glu Glu Gly Tyr Gln Asp
1               5                   10
```

<210> SEQ ID NO 151
<211> LENGTH: 11
<212> TYPE: PRT
<213> ORGANISM: Artificial Sequence
<220> FEATURE:
<223> OTHER INFORMATION: Synthetic: alpha-Syn 126-136

<400> SEQUENCE: 151

```
Glu Met Pro Ser Glu Glu Gly Tyr Gln Asp Tyr
1               5                   10
```

<210> SEQ ID NO 152
<211> LENGTH: 11
<212> TYPE: PRT
<213> ORGANISM: Artificial Sequence
<220> FEATURE:
<223> OTHER INFORMATION: Synthetic: alpha-Syn 127-137

<400> SEQUENCE: 152

```
Met Pro Ser Glu Glu Gly Tyr Gln Asp Tyr Glu
1               5                   10
```

<210> SEQ ID NO 153
<211> LENGTH: 11
<212> TYPE: PRT
<213> ORGANISM: Artificial Sequence
<220> FEATURE:
<223> OTHER INFORMATION: Synthetic: alpha-Syn 128-138

<400> SEQUENCE: 153

```
Pro Ser Glu Glu Gly Tyr Gln Asp Tyr Glu Pro
1               5                   10
```

<210> SEQ ID NO 154
<211> LENGTH: 11
<212> TYPE: PRT
<213> ORGANISM: Artificial Sequence
<220> FEATURE:
<223> OTHER INFORMATION: Synthetic: alpha-Syn 129-139

<400> SEQUENCE: 154

```
Ser Glu Glu Gly Tyr Gln Asp Tyr Glu Pro Glu
1               5                   10
```

<210> SEQ ID NO 155
<211> LENGTH: 11
<212> TYPE: PRT
<213> ORGANISM: Artificial Sequence
<220> FEATURE:
<223> OTHER INFORMATION: Synthetic: alpha-Syn 130-140

<400> SEQUENCE: 155

```
Glu Glu Gly Tyr Gln Asp Tyr Glu Pro Glu Ala
```

<210> SEQ ID NO 156
<211> LENGTH: 33
<212> TYPE: PRT
<213> ORGANISM: Mus musculus
<220> FEATURE:
<221> NAME/KEY: misc_feature
<223> OTHER INFORMATION: mouse alpha-Syn 111-140 peptide in Table 4

<400> SEQUENCE: 156

Arg Arg Arg Gly Ile Leu Glu Asp Met Pro Val Asp Pro Gly Ser Glu
1               5                   10                  15

Ala Tyr Glu Met Pro Ser Glu Glu Gly Tyr Gln Asp Tyr Glu Pro Glu
            20                  25                  30

Ala

<210> SEQ ID NO 157
<211> LENGTH: 33
<212> TYPE: PRT
<213> ORGANISM: Rattus sp.
<220> FEATURE:
<221> NAME/KEY: misc_feature
<223> OTHER INFORMATION: rat alpha-Syn 111-140 peptide in Table 4

<400> SEQUENCE: 157

Arg Arg Arg Gly Ile Leu Glu Asp Met Pro Val Asp Pro Ser Ser Glu
1               5                   10                  15

Ala Tyr Glu Met Pro Ser Glu Glu Gly Tyr Gln Asp Tyr Glu Pro Glu
            20                  25                  30

Ala

<210> SEQ ID NO 158
<211> LENGTH: 33
<212> TYPE: PRT
<213> ORGANISM: Homo sapiens
<220> FEATURE:
<221> NAME/KEY: misc_feature
<223> OTHER INFORMATION: human alpha-Syn 111-140 peptide in Table 4

<400> SEQUENCE: 158

Arg Arg Arg Gly Ile Leu Glu Asp Met Pro Val Asp Pro Asp Asn Glu
1               5                   10                  15

Ala Tyr Glu Met Pro Ser Glu Glu Gly Tyr Gln Asp Tyr Glu Pro Glu
            20                  25                  30

Ala

<210> SEQ ID NO 159
<211> LENGTH: 1392
<212> TYPE: DNA
<213> ORGANISM: Artificial Sequence
<220> FEATURE:
<223> OTHER INFORMATION: Synthetic: 7A10-T93A-IgG1.3 HC DNA

<400> SEQUENCE: 159
atgagggctt ggatcttctt tctgctctgc ctggccggga gagcgctcgc acaggtgcag      60
ctgcaggagt cgggcccagg actggtgaag ccttcggaga ccctgtccct cacctgcact     120
gtctctggtg gctccgtcag cagtggtcgt tactactgga gctggattcg cagcccccca     180
gggaagggac tggagtggat tgggtatatc tattacagtg ggagaaccaa gtacaacccc     240
tccctcaaga gtcgagtcac catatcagta gacacgtcca agaaccagtt ctccctgaag     300

| | |
|---|---|
| ctgagctctg tgaccgctgc ggacacggcc gtgtattact gtgcgagaga gagggggtac | 360 |
| cttgactact ggggccaggg aaccctggtc accgtctcct cagctagcac caagggccca | 420 |
| tcggtcttcc ccctggcacc ctcctccaag agcacctctg ggggcacagc ggccctgggc | 480 |
| tgcctggtca aggactactt ccccgaaccg gtgacggtgt cgtggaactc aggcgccctg | 540 |
| accagcggcg tgcacaccct cccggctgtc ctacagtcct caggactcta ctccctcagc | 600 |
| agcgtggtga ccgtgccctc cagcagcttg ggcacccaga cctacatctg caacgtgaat | 660 |
| cacaagccca gcaacaccaa ggtggacaag agagttgagc ccaaatcttg tgacaaaact | 720 |
| cacacatgcc caccgtgccc agcacctgaa gccgaagggg cccgtcagt cttcctcttc | 780 |
| cccccaaaac ccaaggacac cctcatgatc tcccggaccc ctgaggtcac atgcgtggtg | 840 |
| gtggacgtga gccacgaaga ccctgaggtc aagttcaact ggtacgtgga cggcgtggag | 900 |
| gtgcataatg ccaagacaaa gccgcgggag gagcagtaca acagcacgta ccgtgtggtc | 960 |
| agcgtcctca ccgtcctgca ccaggactgg ctgaatggca aggagtacaa gtgcaaggtc | 1020 |
| tccaacaaag ccctcccagc ccccatcgag aaaaccatct ccaaagccaa agggcagccc | 1080 |
| cgagaaccac aggtgtacac cctgccccca tcccgggagg agatgaccaa gaaccaggtc | 1140 |
| agcctgacct gcctggtcaa aggcttctat cccagcgaca tcgccgtgga gtgggagagc | 1200 |
| aatgggcagc cggagaacaa ctacaagacc acgcctcccg tgctggactc cgacggctcc | 1260 |
| ttcttcctct atagcaagct caccgtggac aagagcaggt ggcagcaggg gaacgtcttc | 1320 |
| tcatgctccg tgatgcatga ggctctgcac aaccactaca cgcagaagag cctctccctg | 1380 |
| tccccgggtt ga | 1392 |

<210> SEQ ID NO 160
<211> LENGTH: 699
<212> TYPE: DNA
<213> ORGANISM: Artificial Sequence
<220> FEATURE:
<223> OTHER INFORMATION: Synthetic: 7A10-LC DNA (for both 7A10 and
7A10-T93A); same LC sequence shared with 21A3 and 15A5

<400> SEQUENCE: 160

| | |
|---|---|
| atgagggctt ggatcttctt tctgctctgc ctggccgggc gcgccttggc cgaaattgtg | 60 |
| ttgacgcagt ctccaggcac cctgtctttg tctccagggg aaagagccac cctctcctgc | 120 |
| agggccagtc agagtgttag cagcagctac ttagcctggt accagcagaa acctggccag | 180 |
| gctcccaggc tcctcatcta tggtgcatcc agcagggcca ctggcatccc agacaggttc | 240 |
| agtggcagtg ggtctgggac agacttcact ctcaccatca gcagactgga gcctgaagat | 300 |
| tttgcagtgt attactgtca gcagtatggt agctcaccgc tcactttcgg cggagggacc | 360 |
| aaggtggaga tcaaacgtac ggtggctgca ccatctgtct tcatcttccc gccatctgat | 420 |
| gagcagttga aatctggaac tgcctctgtt gtgtgcctgc tgaataactt ctatcccaga | 480 |
| gaggccaaag tacagtggaa ggtggataac gccctccaat cgggtaactc ccaggagagt | 540 |
| gtcacagagc aggacagcaa ggacagcacc tacagcctca gcagcaccct gacgctgagc | 600 |
| aaagcagact acgagaaaca caaagtctac gcctgcgaag tcacccatca gggcctgagc | 660 |
| tcgcccgtca caaagagctt caacagggga gagtgttag | 699 |

<210> SEQ ID NO 161
<211> LENGTH: 351
<212> TYPE: DNA
<213> ORGANISM: Artificial Sequence
<220> FEATURE:

<223> OTHER INFORMATION: Synthetic: 7A10 VH DNA

<400> SEQUENCE: 161

| caggtgcagc tgcaggagtc gggcccagga ctggtgaagc cttcggagac cctgtccctc | 60 |
| acctgcactg tctctggtgg ctccgtcagc agtggtcgtt actactggag ctggatccgg | 120 |
| cagcccccag ggaagggact ggagtggatt gggtatatct attacagtgg gagaaccaag | 180 |
| tacaacccct ccctcaagag tcgagtcacc atatcagtag acacgtccaa gaaccagttc | 240 |
| tccctgaagc tgagctctgt gaccgctgcg gacacggccg tgtattactg tacgagagag | 300 |
| aggggggtacc ttgactactg gggccaggga accctggtca ccgtctcctc a | 351 |

<210> SEQ ID NO 162
<211> LENGTH: 324
<212> TYPE: DNA
<213> ORGANISM: Artificial Sequence
<220> FEATURE:
<223> OTHER INFORMATION: Synthetic: 7A10 VL DNA (for both 7A10 and
      7A10-T93A); same VL sequence shared with 21A3 and 15A5

<400> SEQUENCE: 162

| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcaccgct cactttcggc | 300 |
| ggagggacca aggtggagat caaa | 324 |

<210> SEQ ID NO 163
<211> LENGTH: 351
<212> TYPE: DNA
<213> ORGANISM: Artificial Sequence
<220> FEATURE:
<223> OTHER INFORMATION: Synthetic: 7A10-T93A VH DNA

<400> SEQUENCE: 163

| caggtgcagc tgcaggagtc gggcccagga ctggtgaagc cttcggagac cctgtccctc | 60 |
| acctgcactg tctctggtgg ctccgtcagc agtggtcgtt actactggag ctggattcgg | 120 |
| cagcccccag ggaagggact ggagtggatt gggtatatct attacagtgg gagaaccaag | 180 |
| tacaacccct ccctcaagag tcgagtcacc atatcagtag acacgtccaa gaaccagttc | 240 |
| tccctgaagc tgagctctgt gaccgctgcg gacacggccg tgtattactg tgcgagagag | 300 |
| aggggggtacc ttgactactg gggccaggga accctggtca ccgtctcctc a | 351 |

<210> SEQ ID NO 164
<211> LENGTH: 351
<212> TYPE: DNA
<213> ORGANISM: Artificial Sequence
<220> FEATURE:
<223> OTHER INFORMATION: Synthetic: 21A3 VH DNA

<400> SEQUENCE: 164

| caggtgcagc tgcaggagtc gggcccagga ctggtgaagc cttcggagac cctgtccctc | 60 |
| acctgcactg tctctggtgg ctccgtcagc aatcgtaatt actactggag ctggatccgg | 120 |
| cagcccccag ggaagggact ggagtggatt gggtatatct attacagtgg ggagaccaag | 180 |
| tacaacccct ccctcaagag tcgagtcacc atatcagtag acacgtccaa gaaccagttc | 240 |

```
tccctgaagg tgagctctgt gaccgctgcg gacacggccg tgtattactg tgcgagagag    300
agggggcggt ttgactactg gggccaggga accctggtca ccgtctcctc a             351
```

<210> SEQ ID NO 165
<211> LENGTH: 324
<212> TYPE: DNA
<213> ORGANISM: Artificial Sequence
<220> FEATURE:
<223> OTHER INFORMATION: Synthetic: 21A3 VL DNA

<400> SEQUENCE: 165

```
gaaattgtgt tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccgct cactttcggc    300
ggagggacca aggtggagat caaa                                           324
```

<210> SEQ ID NO 166
<211> LENGTH: 324
<212> TYPE: DNA
<213> ORGANISM: Artificial Sequence
<220> FEATURE:
<223> OTHER INFORMATION: Synthetic: 1E8 VL DNA

<400> SEQUENCE: 166

```
gaaattgtgt tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctct cactttcggc    300
ggagggacca aggtggagat caaa                                           324
```

<210> SEQ ID NO 167
<211> LENGTH: 360
<212> TYPE: DNA
<213> ORGANISM: Artificial Sequence
<220> FEATURE:
<223> OTHER INFORMATION: Synthetic: 2E2 VH DNA

<400> SEQUENCE: 167

```
caggtgcagc tggtggagtc tgggggaggc gtggtccagc ctgggaggtc cctgagactc    60
tcctgtgcag cctctggatt caccttcagt agctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagaaggggt    300
tcggggagtt attataactt tgactactgg ggccagggaa ccctggtcac cgtctcctca    360
```

<210> SEQ ID NO 168
<211> LENGTH: 321
<212> TYPE: DNA
<213> ORGANISM: Artificial Sequence
<220> FEATURE:
<223> OTHER INFORMATION: Synthetic: 2E2 VL DNA

<400> SEQUENCE: 168

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacccac cttcggccaa   300
gggacacgac tggagattaa a                                             321
```

<210> SEQ ID NO 169
<211> LENGTH: 339
<212> TYPE: DNA
<213> ORGANISM: Artificial Sequence
<220> FEATURE:
<223> OTHER INFORMATION: Synthetic: 23H8 VH DNA

<400> SEQUENCE: 169

```
gaggtgcagc tggtggagtc tgggggaggc ttggtacagc ctggggggtc cctgagactc    60
tcctgtgcag cctctggatt caccttcagt agctatggca tgaactgggt ccgccaggct   120
ccagggaagg ggctggagtg ggtttcatac attagtagta gtagtagtac catatactac   180
gcagactctg tgaagggccg attcaccatc tccagagaca atgccaagaa ctcactgtat   240
ctgcaaatga acagcctgag agacgaggac acggctgtgt attactgtgc taactgggga   300
tcctactggg gccagggaac cctggtcacc gtctcctca                          339
```

<210> SEQ ID NO 170
<211> LENGTH: 324
<212> TYPE: DNA
<213> ORGANISM: Artificial Sequence
<220> FEATURE:
<223> OTHER INFORMATION: Synthetic: 23H8 VL1 DNA

<400> SEQUENCE: 170

```
gaaattgtgt tgacgcagtc tccaggcacc ctgtctttgt ctccagggga aagagccacc    60
ctctcctgca gggccagtca gagtgttagc agaagctact tagcctggta ccagcagaaa   120
cttggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctct cactttcggc   300
ggagggacca aggtggagat caaa                                          324
```

<210> SEQ ID NO 171
<211> LENGTH: 318
<212> TYPE: DNA
<213> ORGANISM: Artificial Sequence
<220> FEATURE:
<223> OTHER INFORMATION: Synthetic: 23H8 VL2 DNA

<400> SEQUENCE: 171

```
gaaattgtgt tgacacagtc tccagccacc ctgtctttgt ctccagggga aagagccacc    60
ctctcctgca gggccagtca gggtgttagc agctacttag cctggtacca gcagaaacct   120
ggccaggctc ccaggctcct catctatgat gcatccaaca gggccactgg catcccagcc   180
aggttcagtg gcagtgggcc tgggacagac ttcactctca ccatcagcag cctagagcct   240
gaagattttg cagtttatta ctgtcagcag cgtagcaact ggcatacttt cggcggaggg   300
accaaggtgg agatcaaa                                                 318
```

<210> SEQ ID NO 172
<211> LENGTH: 321
<212> TYPE: DNA
<213> ORGANISM: Artificial Sequence
<220> FEATURE:
<223> OTHER INFORMATION: Synthetic: 23H8 VL3 DNA

<400> SEQUENCE: 172

| | | |
|---|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcacccac tttcggcgga | 300 |
| gggaccaagg tggagatcaa a | 321 |

<210> SEQ ID NO 173
<211> LENGTH: 345
<212> TYPE: DNA
<213> ORGANISM: Artificial Sequence
<220> FEATURE:
<223> OTHER INFORMATION: Synthetic: 11H11VH DNA

<400> SEQUENCE: 173

| | | |
|---|---|---|
| gaggttcagc tggtgcagtc tgggggaggc ttggtacatc ctgggggtc cctgagactc | 60 |
| tcctgtgcag gctctggatt caccttcagt agctatgcta tgcactgggt tcgccaggct | 120 |
| ccaggaaaag gtctggagtg gtatcagct attggtactg gtggtggcac atactatgca | 180 |
| gactccgtga agggccgatt caccatctcc agagacaatg ccaagaactc cttgtatctt | 240 |
| caaatgaaca gcctgagagc cgaggacatg gctgtgtatt actgtgcaag agggaactgg | 300 |
| gaatttgact actggggcca gggaaccctg gtcaccgtct cctca | 345 |

<210> SEQ ID NO 174
<211> LENGTH: 324
<212> TYPE: DNA
<213> ORGANISM: Artificial Sequence
<220> FEATURE:
<223> OTHER INFORMATION: Synthetic: 11H11VL1 DNA

<400> SEQUENCE: 174

| | | |
|---|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcaccatt cactttcggc | 300 |
| cctgggacca agtggatat caaa | 324 |

<210> SEQ ID NO 175
<211> LENGTH: 315
<212> TYPE: DNA
<213> ORGANISM: Artificial Sequence
<220> FEATURE:
<223> OTHER INFORMATION: Synthetic: 11H11VL2 DNA

<400> SEQUENCE: 175

| | | |
|---|---|---|
| gccatccagt tgacccagtc tccatcctcc ctgtctgcat ctgtaggaga cagagtcacc | 60 |
| atcacttgcc gggcaagtca gggcattagc agtgctttag cctggtatca gcagaaacca | 120 |

```
gggaaagctc ctaaggtccc gatctatgat gcctccagtt tggaaagtgg ggtcccatca      180
aggttcagcg gcagtggatc tgggacagat ttcactctca ccatcagcag cctgcagcct      240
gaagatcttg caacttatta ctgtcaacag tttaatagtt acccttcgg cggagggacc       300 aaggtggaga tcaaa                                                       315
```

<210> SEQ ID NO 176
<211> LENGTH: 351
<212> TYPE: DNA
<213> ORGANISM: Artificial Sequence
<220> FEATURE:
<223> OTHER INFORMATION: Synthetic: 15A5VH DNA

<400> SEQUENCE: 176

```
caggtgcagc tgcaggagtc gggcccagga ctggtgaagc cttcggagac cctgtccctc       60
acctgcactg tctctggtgg ctccgtcagc agtggtagtt actactggtg ctggatccgg      120
cagcccccag ggaagggact ggagtggatc gggtatatct attacagtgg cgcaccaag      180 tacaacccct ccctcaagag tcgagtcacc atatcagtag acacgtccaa gaaccagttc      240
tccctgaagc tgagctctgt gaccgctgcg gacacggccg tgtattactg tgcgagagag      300 aggggcggt ttgactactg gggccaggga accctggtca ccgtctcctc a                351
```

<210> SEQ ID NO 177
<211> LENGTH: 324
<212> TYPE: DNA
<213> ORGANISM: Artificial Sequence
<220> FEATURE:
<223> OTHER INFORMATION: Synthetic: 15A5VL DNA

<400> SEQUENCE: 177

```
gaaattgtgt tgacgcagtc tccaggcacc ctgtctttgt ctccagggga aagagccacc       60
ctctcctgca gggccagtca gagtgttagc agcagctact tagcctggta ccagcagaaa      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcaccgct cactttcggc      300
ggagggacca aggtggagat caaa                                             324
```

<210> SEQ ID NO 178
<211> LENGTH: 351
<212> TYPE: DNA
<213> ORGANISM: Artificial Sequence
<220> FEATURE:
<223> OTHER INFORMATION: Synthetic: 36A3VH DNA

<400> SEQUENCE: 178

```
caggtgcagc tgcaggagtc gggcccagga ctggtgaagc cttcggagac cctgtccctc       60
acctgcactg tctctggtgg ctccgtcagc agtggtagtt actactggag ctggatccgg      120
cagcccccag ggaagggact ggagtggatt gggtatatct attacagtgg gagaaccaag     180
tacaacccct ccctcaagag tcgagtcacc atatcagtag acacgtccag gaaccagttc      240
tccctgaagc tgagctctgt gaccgctgcg gacacggccg tgtattactg tgcgagagag      300
aggggctggc tcgacccctg gggccaggga accctggtca ccgtctcctc a                351
```

<210> SEQ ID NO 179
<211> LENGTH: 317
<212> TYPE: DNA

```
<213> ORGANISM: Artificial Sequence
<220> FEATURE:
<223> OTHER INFORMATION: Synthetic: 36A3VL DNA

<400> SEQUENCE: 179
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggtcaccttc ggccaaggga   300
cacgactgga gattaaa                                                 317

<210> SEQ ID NO 180
<211> LENGTH: 342
<212> TYPE: DNA
<213> ORGANISM: Artificial Sequence
<220> FEATURE:
<223> OTHER INFORMATION: Synthetic: 44B11VH DNA

<400> SEQUENCE: 180
gaggtgcagt tggtggagtc tggaggaggc ttgatccagc ctgggggtc cctgagactc     60 tcctgtgcag cctctgggtt caccgtcagt agcaaataca tgagctgggt ccgccaggct   120
ccagggaagg ggctggagtg ggtctcagtt atgtatagcg gtggtagaag atactatgca   180
gactccgtga agggccgatt caccatctcc agagacaatt ccaagaacac gctgtatctt   240
caaatgaaca gcctgagagc cgaggacacg gccgtgtatt actgtgcgag aggggatcgg   300
ggtgactact ggggccaggg aaccctggtc accgtctcct ca                     342

<210> SEQ ID NO 181
<211> LENGTH: 321
<212> TYPE: DNA
<213> ORGANISM: Artificial Sequence
<220> FEATURE:
<223> OTHER INFORMATION: Synthetic: 44B11VL DNA

<400> SEQUENCE: 181
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgatcac cttcggccaa   300
gggacacgac tggagattaa a                                            321

<210> SEQ ID NO 182
<211> LENGTH: 351
<212> TYPE: DNA
<213> ORGANISM: Artificial Sequence
<220> FEATURE:
<223> OTHER INFORMATION: Synthetic: 1E8 VH DNA

<400> SEQUENCE: 182
caggtgcagc tgcaggagtc gggcccagga ctggtgaagc cttcggagac cctgtccctc    60
```

```
acctgcactg tctctggtgg ctccgtcagc agtggtagtt actactggag ctggatccgg    120
cagcccccag ggaagggact ggagtggatt gggtatatct attacagtgg gagaaccaag    180
tacaacccct ccctcaagag tcgagtcacc atatcagtag acacgtccaa gaaccagttc    240
tccctgaagc tgaggtctgt gaccgctgcg gacacggccg tgtattactg tgtgagagag    300
aggggctggt tcgaccctg gggccaggga accctggtca ccgtctcctc a              351
```